(12) United States Patent
Or et al.

(10) Patent No.: US 6,274,715 B1
(45) Date of Patent: *Aug. 14, 2001

(54) TRICYCLIC ERYTHROMYCIN DERIVATIVES

(75) Inventors: Yat Sun Or, Libertyville; Ly Tam Phan, Park City, both of IL (US); Daniel T. Chu, Santa Clara, CA (US); Kenneth P. Spina, Chicago, IL (US); Robert Hallas, Kenosha, WI (US); Richard L. Elliott, Grayslake; Michael Tufano, Chicago, both of IL (US)

(73) Assignee: Abbott Laboratories, Abbott Park, IL (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/779,786

(22) Filed: Jan. 7, 1997

Related U.S. Application Data

(63) Continuation-in-part of application No. 08/555,246, filed on Nov. 8, 1995, now abandoned.

(51) Int. Cl.[7] .......................... C07H 17/08; A61K 31/70; A61P 31/04

(52) U.S. Cl. .............................. 536/7.4; 536/7.2; 536/7.3

(58) Field of Search ................................ 536/7.2, 7.3, 7.4

(56) References Cited

U.S. PATENT DOCUMENTS

| 5,631,354 | * | 5/1997 | Asaka | 536/7.4 |
|---|---|---|---|---|
| 5,631,355 | * | 5/1997 | Asaka | 536/7.4 |

FOREIGN PATENT DOCUMENTS

| 0559896A | 9/1993 | (EP). |
|---|---|---|
| 0619319A | 10/1994 | (EP). |
| 0638585A | 2/1995 | (EP). |
| 6-247996 | * 9/1994 | (JP). |
| 97/17356 | 5/1997 | (WO). |

OTHER PUBLICATIONS

Chemical Abstracts, vol. 120 (1994) 218423h.
Chemical Abstracts, vol. 120 (1994) 77599f.
Chemical Abstracts, vol. 122 (1995) 240349b.
Chemical Abstracts, vol. 117 (1992) 251713p.

* cited by examiner

*Primary Examiner*—Mark L. Berch
(74) *Attorney, Agent, or Firm*—Dugal S. Sickert

(57) ABSTRACT

Compounds, or pharmaceutically acceptable salts and esters thereof, of the formula:

wherein A, B, D and E, $R^1$, $R^2$, and Z are specifically defined, having antibacterial activity, pharmaceutical compositions containing said compounds, treatment of bacterial infections with such compositions, and processes for the preparation of the compounds.

29 Claims, No Drawings

TRICYCLIC ERYTHROMYCIN DERIVATIVES

This application is a continuation-in-part of patent application Ser. No. 08/555,246, filed Nov. 8, 1995, abandoned.

TECHNICAL FIELD

The present invention relates to novel semisynthetic macrolides having antibacterial activity and useful in the treatment and prevention of bacterial infections. More particularly, the invention relates to tricyclic erythromycin derivatives, compositions containing such compounds and methods for using the same, as well as processes for making such compounds.

BACKGROUND OF THE INVENTION

Erythromycins A through D, represented by formula (E),

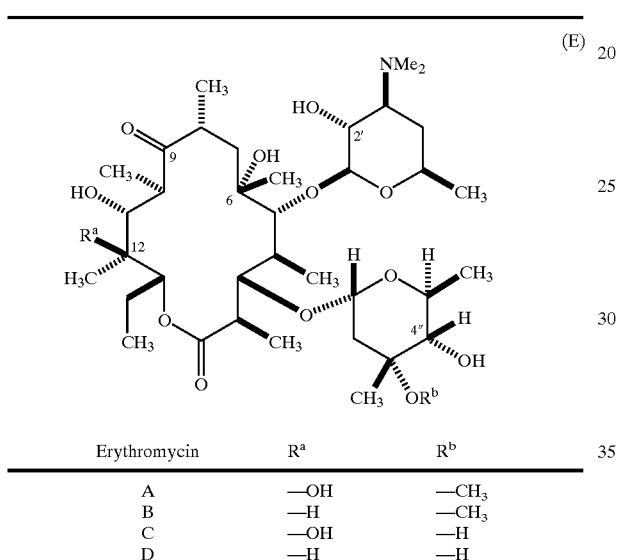

| Erythromycin | $R^a$ | $R^b$ |
|---|---|---|
| A | —OH | —CH$_3$ |
| B | —H | —CH$_3$ |
| C | —OH | —H |
| D | —H | —H | are well-known and potent antibacterial agents, used widely to treat and prevent bacterial infection. As with other antibacterials, however, bacterial strains having resistance or insufficient susceptibility to erythromycin have been identified. Also, erythromycin A has only weak activity against Gram-negative bacteria Therefore, there is a continuing need to identify new erythromycin derivative compounds which possess improved antibacterial activity, which have less potential for developing resistance, which possess the desired Gram-negative activity, or which possess unexpected selectivity against target microorganisms. Consequently, numerous investigators have prepared chemical derivatives of erythromycin in an attempt to obtain analogs having modified or improved profiles of antibiotic activity.

Kashimura, et al. have disclosed 6-O-methylerythromycin derivatives having a tricyclic basic nuclear structure in European Application 559896, published Nov. 11, 1991. Also, Asaka, et al. have disclosed 5-O-desoaminylerythronolide derivatives containing a tricyclic carbamate structure in PCT Application WO 93/21200, published Apr. 22, 1992.

SUMMARY OF THE INVENTION

The present invention provides a novel class of antibacterial tricyclic erythromycin compounds which possess antibacterial activity.

In one aspect of the present invention are disclosed novel tricyclic erytliromycin compounds selected from the group having the formulas:

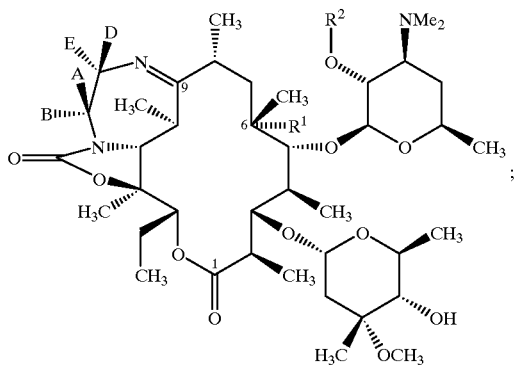

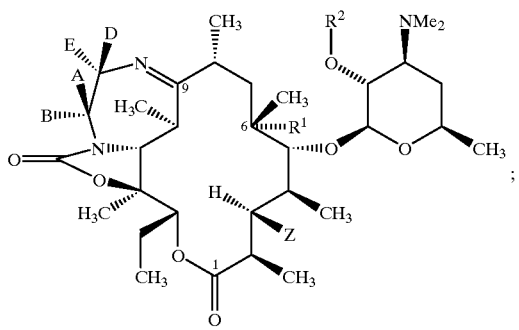

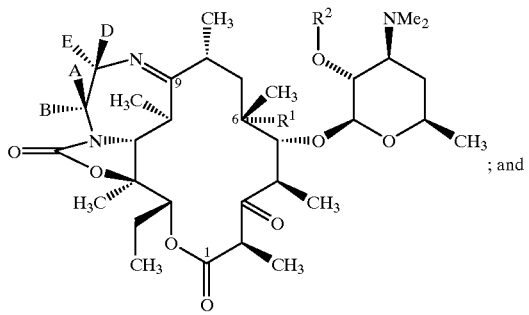

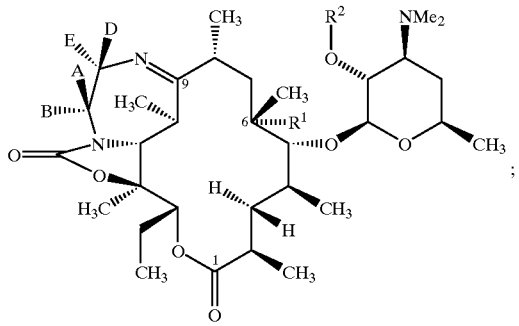

as well as the pharmaceutically acceptable salts and esters thereof. In formulas (I)–(IV) above, A, B, D and E are independently selected from the group consisting of:

(a) hydrogen;
(b) $C_1$–$C_6$-alkyl, as defined below, optionally substituted with one or more substituents selected from the group consisting of:
  (i) atyl;
  (ii) substituted-aryl;
  (iii) heteroaryl;
  (iv) substituted-heteroaryl;
  (v) heterocycloalkyl;
  (vi) hydroxy;
  (vii) $C_1$–$C_6$-alkoxy;
  (viii) halogen consisting of Br, Cl, F or I; and
  (ix) $NR^3R^4$, where $R^3$ and $R^4$ are independently selected from hydrogen and $C_1$–$C_6$-alkyl, or $R^3$ and $R^4$ are taken with the nitrogen atom to which they are connected to form a 3- to 7-membered ring optionally containing a hetero function consisting of —O—, —NH—, —N($C_1$–$C_6$-alkyl-)-, —N(aryl-$C_1$–$C_6$-alkyl-)-, —N(substituted-aryl-$C_1$–$C_6$-alkyl-)-, —N(heteroaryl-$C_1$–$C_6$-akyl-)-, —N(substituted-heteroaryl-$C_1$–$C_6$-alkyl-)-, —S— or —S(O)$_n$—, wherein n is 1 or 2;
(c) $C_3$–$C_7$-cycloalkyl;
(d) atyl;
(e) substituted-aryl;
(f) heteoaryl;
(g) substituted-heteroaryl;
(h) heterocycloalkyl; and
(i) a group selected from option (b) above further substituted with —M—$R^5$, wherein M is selected from the group consisting of:
  (aa) —C(O)—NH—;
  (bb) —NH—C(O)—;
  (cc) —NH—
  (dd) —N(CH$_3$)—
  (ee) —O—
  (ff) —S(O)$_n$—, wherein n is 0, 1 or 2;
  (gg) —C(=NH)—NH—;
  (hh) —C(O)—O—;
  (ii) —O—C(O)—;
  (jj) —O—C(O)—NH—;
  (kk) —NH—C(O)—O—; and
  (ll) —NH—C(O)—NH—;
and $R^5$ is selected from the group consisting of:
  (aaa) $C_1$–$C_6$-alkyl, optionally substituted with a substituent selected from the group consisting of:
    (i) aryl;
    (ii) substituted-aryl;
    (iii) heteroaryl; and
    (iv) substituted-heteroaryl;
  (bbb) aryl;
  (ccc) substituted-aryl;
  (ddd) heteroaryl;
  (eee) substituted-heteroaryl; and
  (fff) heterocycloalkyl; or
any one pair of substituents, consisting of AB, AD, AE, BD, BE or DE, is taken together with the atom or atoms to which they are attached to form a 3- to 7-membered ring optionally containing a hetero function consisting of:
—O—,
—NH—,
—N($C_1$–$C_6$-alkyl-)-,
—N(aryl-$C_1$–$C_6$-alkyl-)-,
—N(substituted-aryl-$C_1$–$C_6$-alkyl-)-,
—N(heteroaryl-$C_1$–$C_6$-alkyl-),
—N(substituted-heteroaryl-$C_1$–$C_6$-alkyl-)-,
—S— or —S(O)$_n$—, wherein n is 1 or 2;
—C(O)—NH—;
—C(O)—$NR^5$—, wherein $R^5$ is as described above;
—NH—C(O)—;
—$NR^5$—C(O)—, wherein $R^5$ is as described above; and
—C(=NH)—NH—;

$R^1$ is selected from the group consisting of:
  (a) hydrogen;
  (b) hydroxy;
  (c) —O—$C_1$–$C_3$-alkyl;
  (d) —O—$C_3$–$C_5$-cycloalkyl;
  (e) —O—$C_1$–$C_3$-alkyl-$C_3$–$C_5$-cycloalkyl;
  (f) —O—C(O)—$C_1$–$C_3$-alkyl;
  (g) —O—C(O)—O$C_1$–$C_3$-alkyl; and
  (h) —O—C(O)—NH—$C_1$–$C_3$-alkyl;

$R^2$ is hydrogen or a hydroxy-protecting group, as defined below; and

Z is hydroxy or protected-hydroxy;
with the provisos that when the compound is of Formulas (I), (II) or (III) then A, B, D, and E may not all be hydrogen, D and E may not be $C_1$–$C_3$-alkyl when A and B are hydrogen, nor may one of D and E be hydrogen and the other be $C_1$–$C_3$-alkyl when A and B are hydrogen.

In another aspect of the present invention are disclosed pharmaceutical compositions comprising a therapeutically effective amount of a compound of the invention in combination with a pharmaceutically acceptable carrier and treatment of bacterial infections with such compositions. Suitable carriers and methods of formulation are also disclosed. The compounds and compositions of the present invention have antibacterial activity.

In a furter aspect of the present invention are provided processes for the preparation of tricyclic macrolide derivatives of Formulas (I), (II), (III) and (IV) above.

DETAILED DESCRIPTION OF THE INVENTION

In one embodiment of the present invention are compounds selected from the group having Formula (I) above, wherein A, B, D, E, and $R^1$–$R^5$ are as described above.

In a second embodiment of the present invention are compounds selected from the group having Formula (II) above, wherein A, B, D, E, $R^1$–$R^5$ and Z are as described above.

In another embodiment of the present invention are compounds selected from the group having Formula (III) above, wherein A, B, D, E, and $R^1$–$R^5$ are as described above.

In yet another embodiment of the present invention are compounds selected from the group having Formula (IV) above, wherein A, B, D, E, and $R^1$–$R^5$ are as described above.

In one preferred embodiment of the present invention are compounds of Formula (III) above wherein $R^1$ is hydrogen, hydroxy or methoxy, $R^2$ is hydrogen, and A, B, D, E and $R^1$–$R^5$ are as described above.

In another preferred embodiment of the present invention are compounds of Formula (III) above wherein $R^1$ is hydrogen or methoxy, $R^2$ is hydrogen, and any three of the A, B, D and E groups are hydrogen and the other group is selected from a singly substituted $C_1$–$C_6$-alkyl group comprised of —(CH$_2$)$_m$$R^6$ where m=1, 2, 3 or 4 and $R^6$ is:
  (a) aryl;
  (b) substituted-aryl;
  (c) heteroaryl;

(d) substituted-heteroaryl;
(e) heterocycloalkyl;
(f) hydroxy;
(g) $C_1$–$C_6$-alkoxy
(h) $NR^3R^4$, where $R^3$ and $R^4$ are independently selected from hydrogen and $C_1$–$C_6$-alkyl, or $R^3$ and $R^4$ are taken with the nitrogen atom to which they are connected to form a 3- to 7-membered ring optionally containing a hetero function consisting of —O—, —NH—, —N($C_1$–$C_6$-alkyl-)-, —N(aryl-$C_1$–$C_6$-alkyl-)-, —N(substituted-aryl-$C_1$–$C_6$-alkyl-)-, —N(heteroaryl-$C_1$–$C_6$-alkyl-)-, —N(substituted-heteroaryl-$C_1$–$C_6$-alkyl-)-, —S— or —S(O)$_n$—, wherein n is 1 or 2;
(i) halogen consisting of Br, Cl, F or I;
(j) $C_1$–$C_3$ alkyl; or
(k) —(CH$_2$)$_r$—M—(CH$_2$)$_s$—$R^7$ wherein r=0, 1 or 2; s=0, 1 or 2 and M is
  (aa) —C(O)—NH—;
  (bb) —NH—C(O)—;
  (cc) —NH—
  (dd) —N(CH$_3$)—
  (ee) —O—
  (ff) —S(O)$_n$—, wherein n is 0, 1 or 2;
  (gg) —C(=NH)—NH—;
  (hh) —C(O)—O—;
  (ii) —O—C(O)—;
  (jj) —O—C(O)—NH—;
  (kk) —NH—C(O)—O—; and
  (ll) —NH—C(O)—NH—;
  and $R^7$ is selected from the group consisting of:
    (aaa) $C_1$–$C_3$-alkyl,
    (bbb) aryl;
    (ccc) substituted-aryl;
    (ddd) heteroaryl; and
    (eee) substituted-heteroaryl.

In yet another preferred embodiment of the present invention are compounds of Formula (III) above wherein $R^1$ is hydrogen or methoxy, $R^2$ is hydrogen, B=E=H, and A and D taken together is selected from the group consisting of:
(a) —CH$_2$—Z—CH$_2$—, wherein Z is
  (aa) —C(O)—NH—;
  (bb) —C(O)—NR$^5$—, wherein $R^5$ is selected from the group consisting of:
    (aaa) $C_1$–$C_6$-alkyl, optionally substituted with a substituent selected from the group consisting of:
      (i) aryl;
      (ii) substituted-aryl;
      (iii) heteroaryl; and
      (iv) substituted-heteroaryl;
    (bbb) aryl;
    (ccc) substituted-aryl;
    (ddd) heteroaryl;
    (eee) substituted-heteroayl; and
    (fff) heterocycloalkyl;
  (cc) —NH—C(O)—;
  (dd) —NR$^5$—C(O)—, wherein $R^5$ is as defined above;
  (ee) —NH—
  (ff) —N(CH$_3$)—
  (gg) —O—
  (hh) —S(O)$_n$—, wherein n is 0, 1 or 2; and
  (ii) —C(=NH)—NH—;
(b) —CH$_2$—N(—(CH$_2$)$_s$—$R^7$)—CH$_2$—, wherein s=0, 1 or 2, and $R^7$ is selected from the group consisting of:
  (aaa) $C_1$–$C_3$-alkyl,
  (bbb) aryl;
  (ccc) substituted-aryl;
  (ddd) heteroaryl; and
  (eee) substituted-heteroaryl;
(c) —CH$_2$—N(—(CH$_2$)$_r$—M—(CH$_2$)$_s$—$R^7$)—CH$_2$—, wherein r=0, 1 or 2; s=0, 1 or 2, and M and $R^7$ are as defined above; and
(d) —CH$_2$—(CH$_2$)$_r$—CH$_2$—, wherein r=0, 1 or 2.

In yet one more preferred embodiment of the present invention are compounds of Formula (III) above wherein $R^1$ is hydrogen or methoxy, $R^2$ is hydrogen, A=D=H, and B and E taken together is selected from the group consisting of:
(a) —CH$_2$—Z—CH$_2$—, wherein Z is:
  (aa) —C(O)—NH—;
  (bb) —C(O)—NR$^5$—, wherein $R^5$ is selected from the group consisting of:
    (aaa) $C_1$–$C_6$-alkyl, optionally substituted with a substituent selected from the group consisting of:
      (i) aryl;
      (ii) substituted-aryl;
      (iii) heteroaryl; and
      (iv) substituted-heteroaryl;
    (bbb) aryl;
    (ccc) substituted-aryl;
    (ddd) heteroaryl;
    (eee) substituted-heteroaryl; and
    (fff) heterocycloalkyl;
  (cc) —NH—C(O)—;
  (dd) —NR$^5$—C(O)—, wherein $R^5$ is as defined above;
  (ee) —NH—
  (ff) —N(CH$_3$)—
  (gg) —O—
  (hh) —S(O)$_n$—, wherein n is 0, 1 or 2; and
  (ii) —C(=NH)—NH—;
(b) —CH$_2$—N(—(CH$_2$)$_s$—$R^7$)—CH$_2$—, wherein s=0, 1 or 2, and $R^7$ is selected from the group consisting of:
  (aaa) $C_1$–$C_3$-alkyl,
  (bbb) aryl;
  (ccc) substituted-aryl;
  (ddd) heteroaryl; and
  (eee) substituted-heteroaryl;
(c) —CH$_2$—N(—(CH$_2$)$_r$M—(CH$_2$)$_s$—$R^7$)—CH$_2$—, wherein r=0, 1 or 2; s=0, 1 or 2, and M and $R^7$ are as defined above; and
(d) —CH$_2$—(CH$_2$)$_r$—CH$_2$—, wherein r=0, 1 or 2.

Representative of the compounds of the invention include:
Compound of Formula (IV): $R^1$=methoxy; $R^2$=hydrogen; A=B=D=E=hydrogen;
Compound of Formula (III): A=B=E=H, D=benzyl, $R^1$=methoxy, $R^2$=hydrogen;
Compound of Formula (III): A=B=D=H, E=benzyl, $R^1$=methoxy, $R^2$=hydrogen;
Compound of Formula (III): A=benzyl, B=D=E=H, $R^1$=methoxy, $R^2$=hydrogen;
Compound of Formula (III): B=benzyl, A=D=E=H, $R^1$=methoxy, $R^2$=hydrogen;
Compound of Formula (III): A=E=phenyl, B=D=H, $R^1$=methoxy, $R^2$=hydrogen;
Compound of Formula (III): A=methyl, B=D=E=H, $R^1$=methoxy, $R^2$=hydrogen;
Compound of Formula (III): B=methyl, A=D=E=H, $R^1$=methoxy, $R^2$=hydrogen;
Compound of Formula (III): A=D=methyl; B=E=H, $R^1$=methoxy, $R^2$=hydrogen;
Compound of Formula (III): A=E=methyl; B=D=H, $R^1$=methoxy, $R^2$=hydrogen;

Compound of Formula (III): B=D=H; A and E taken together is —CH$_2$CH$_2$CH$_2$—, R$^1$=methoxy, R$^2$=hydrogen;

Compound of Formula (III): B=E=H; A and D taken together is —CH$_2$CH$_2$CH$_2$CH$_2$—, R$^1$=methoxy, R$^2$=hydrogen;

Compound of Formula (I): A=B=D=E=hydrogen; R$^1$=hydrogen, R$^2$=hydrogen;

Compound of Formula (III): R$^1$=OCH3, R$^2$=H; A=B=D=H; E=—CH$_2$NH$_2$;

Compound of Formula (III): R$^1$=OCH3, R$^2$=H; A=B=E=H; D=—CH$_2$NH$_2$;

Compound of Formula (III): R$^1$=OCH3, R$^2$=H; B=E=H; A and D taken together is —CH$_2$CH$_2$CH$_2$—;

Compound of Formula (III): R$^1$=OCH3, R$^2$=H; B=E=H; A and D taken together is —CH$_2$OCH$_2$—;

Compound of Formula (III): R$^1$=OCH3, R$^2$=H; B=E=H; A and D taken together is —CH$_2$—NH—CH$_2$—;

Compound of Formula (III): R$^1$=OCH3, R$^2$=H; B=E=H; A and D taken together is —CH$_2$—N(Cbz)-CH$_2$—;

Compound of Formula (III): R$^1$=OCH3, R$^2$=H; B=E=H; A and D taken together is —CH$_2$—N(benzyl)-CH$_2$—;

Compound of Formula (III): R$^1$=OCH3, R$^2$=H; B=E=H; A and D taken together is —CH$_2$—N(benzoyl)-CH$_2$—;

Compound of Formula (III): R$^1$=OCH3, R$^2$=H; B=E=H; A and D taken together is —CH$_2$—N(phenyl-CH$_2$—CH$_2$—)—CH$_2$—;

Compound of Formula (III): R$^1$=OCH3, R$^2$=H; B=E=H; A and D taken together is —CH$_2$—N(4-Cl-phenyl-CH$_2$—)—CH$_2$—;

Compound of Formula (III): R$^1$=OCH3, R$^2$=H; B=E=H; A and D taken together is —CH$_2$—N(4-pyridyl-CH$_2$—)—CH$_2$—;

Compound of Formula (III): R$^1$=OCH3, R$^2$=H; B=E=H; A and D taken together is —CH$_2$—N(2-pyridyl-CH$_2$—)—CH$_2$—;

Compound of Formula (III): R$^1$=OCH3, R$^2$=H; B=E=H; A and D taken together is —CH$_2$—NH(3-pyridyl-CH$_2$—)—CH$_2$—;

Compound of Formula (III): R$^1$=OCH3, R$^2$=H; B=E=H; A and D taken together is —CH$_2$—N(4-quinolyl-CH$_2$—)—CH$_2$—;

Compound of Formula (III): R$^1$=OCH3, R$^2$=H; B=E=H; A=D=—CH$_2$—O—CH$_2$-phenyl;

Compound of Formula (III): R$^1$=OCH3, R$^2$=H; B=E=H; A=D=—CH$_2$—OH;

Compound of Formula (III): R$^1$=OCH3, R$^2$=H; B=E=H; A=D=—CH$_2$—O-phenyl;

Compound of Formula (III): R$^1$=OCH3, R$^2$=H; A=B=H; D and E taken together is —CH$_2$—CH$_2$—CH$_2$—CH$_2$—;

Compound of Formula (III): R$^1$=OCH3, R$^2$=H; A and B taken together is —CH$_2$—CH$_2$—CH$_2$—CH$_2$—; D=E=H;

Compound of Formula (III): R$^1$=OCH3, R$^2$=H; A=B=H; D and E taken together is —CH$_2$—O—CH$_2$—;

Compound of Formula (III): R$^1$=OCH3, R$^2$=H; A=D=E=H; B=—CH$_2$—CH$_2$-phenyl;

Compound of Formula (III): R$^1$=OCH3, R$^2$=H; A=D=E=H; B=—CH$_2$—CH$_2$—CH$_2$-phenyl;

Compound of Formula (III): R$^1$=OCH3, R$^2$=H; A=D=E=H; B=—CH$_2$—O—CH$_2$-phenyl;

Compound of Formula (III): R$^1$=OCH3, R$^2$=H; A=D=E=H; B=—CH$_2$—CH$_2$-(4-OCH$_3$-phenyl);

Compound of Formula (III): R$^1$=OCH3, R$^2$=H; A=—CH$_2$—CH$_2$-phenyl; B=D=E=H;

Compound of Formula (III): R$^1$=OCH3, R$^2$=H; A=—CH$_2$—CH$_2$—CH$_2$-phenyl; B=D=E=H;

Compound of Formula (III): R$^1$=OCH3, R$^2$=H; A=—CH$_2$—O—CH$_2$-phenyl; B=D=E=H;

Compound of Formula (III): R$^1$=OCH3, R$^2$=H; A=D=E=H; B=—CH$_2$—CH$_2$-(4-OCH$_3$-phenyl);

Compound of Formula (III): R$^1$=OCH3, R$^2$=H; A=B=D=H; E=—CH$_2$CH$_2$Ph;

Compound of Formula (III): R$^1$=OCH3, R$^2$=H; A=B=E=H; D=—CH$_2$CH$_2$Ph;

Compound of Formula (III): R$^1$=OCH3, R$^2$=H; A=B=D=H; E=—CH$_2$CH$_2$CH$_2$Ph;

Compound of Formula (III): R$^1$=OCH3, R$^2$=H; A=B=E=H; D=—CH$_2$CH$_2$CH$_2$Ph;

Compound of Formula (III): R$^1$=OCH3, R$^2$=H; A=—CH$_2$CH$_2$OPh; B=D=E=H;

Compound of Formula (III): R$^1$=OCH$_3$, R$^2$=H; A=—CH$_2$CH$_2$NH$_2$; B=D=E=H;

Compound of Formula (III): R1=OCH3, R2=H; A=—CH2CH2NH2; B=D=E=H;

Compound of Formula (III): R$^1$=OCH3, R$^2$=H; A=—CH$_2$CH$_2$OH; B=D=E=H;

Compound of Formula (III): R1=OCH3, R2=H; A=—CH2COOH; B=D=E=H;

Formula (III): R1=OCH3, R2=H; A=—CH2CH2OH; B=D=E=H;

Compound of Formula (III): R$^1$=OCH3, R$^2$=H; A=—CH$_2$CH$_2$NH(4'-Pyridyl-); B=D-E=H;

Compound of Formula (III): R$^1$=OCH3, R$^2$=H; A=B=D=H; E=—CH$_2$OH;

Compound of Formula (III): R$^1$=OCH$_3$, R$^2$=H; A=B=E=H; D=—CH$_2$OH;

Compound of Formula (III): R$^1$=OCH3, R$^2$=H; A=B=E=H; D=—CH$_2$NHBenzoyl;

Compound of Formula (III): R$^1$=OCH3, R$^2$=H; A=B=E=H; D=—CH$_2$NHBenzyl;

Compound of Formula (III): R$^1$=OCH3, R$^2$=H; A=B=D=H; E=—CH$_2$NHBenzoyl;

Compound of Formula (III): R$^1$=OCH3, R$^2$=H; A=B=D=H; E=—CH$_2$NHBenzyl;

Compound of Formula (III): R$^1$=OCH3, R$^2$=H; B=D=H; A=E=—CH$_2$OCH$_2$(4-Cl-phenyl-);

Compound of Formula (III): R$^1$=OCH3, R$^2$=H; A=B=E=H; D=—CH$_2$—N(CH$_3$)-Benzyl;

Compound of Formula (III): R$^1$=OCH3, R$^2$=H; A=B-D=H; E=—CH$_2$—N(CH$_3$)-Benzyl;

Compound of Formula (III): R$^1$=OCH3, R$^2$=H; A=B=D=H; E=—CH$_2$—NH-phenyl;

Compound of Formula (III): R$^1$=OCH3, R$^2$=H; A=B=E=H; D=—CH$_2$—NH-phenyl;

Compound of Formula (III): A=4-ethoxybenzyloxymethyl, B=D=E=H, R$^1$=methoxy, R$^2$=hydrogen;

Compound of Formula (III): A=hydroxymethyl, B=D=E=H, R$^1$=methoxy, R$^2$=hydrogen;

Compound of Formula (III): A=4-benzyloxybenzyl, B=D=E=H, R$^1$=methoxy, R$^2$=hydrogen;

Compound of Formula (III): A=4-hydroxybenzyl, B=D=E=H, R$^1$=methoxy, R$^2$=hydrogen;

Compound of Formula (III): A=S-benzylthioxymethyl, B=D=E=H, $R^1$=methoxy, $R^2$=hydrogen;

Compound of Formula (III): A=3-indolylmethyl, B=D=E=H, $R^1$=methoxy, $R^2$=hydrogen;

Compound of Formula (III): A=4-(CBZ-amino)benzyl, B=D=E=H, $R^1$=methoxy, $R^2$=hydrogen;

Compound of Formula (III): A=4-thiazolyhmethyl, B=D=E=H, $R^1$=methoxy, $R^2$=hydrogen;

Compound of Formula (III): A=4-iodobenzyl, B=D=E=H, $R^1$=methoxy, $R^2$=hydrogen;

Compound of Formula (III): A=4-fluorobenzyloxymethyl, B=D=E=H, $R^1$=methoxy, $R^2$=hydrogen;

Compound of Formula (III): A=3-fluorobenzyloxymethyl, B=D=E=H, $R^1$=methoxy, $R^2$=hydrogen;

Compound of Formula (III): A=2-fluorobenzyloxymethyl, B=D=E=H, $R^1$=methoxy, $R^2$=hydrogen;

Compound of Formula (III): A=B=E=H, D=(4-cyanobenzyloxy)methyl, $R^1$=methoxy, $R^2$=hydrogen;

Compound of Formula (III): A=B=E=H, D=(4-(t-butyloxycarbonyl)amino)benzyloxy)methyl, $R^1$=methoxy, $R^2$=hydrogen;

Compound of Formula (III): A=B=E=H, D=(4-(dimethylamino)benzyloxy)methyl, $R^1$=methoxy, $R^2$=hydrogen;

Compound of Formula (III): A=B=E=H, D=(4-pyridyl)methoxymethyl, $R^1$=methoxy, $R^2$=hydrogen;

Compound of Formula (III): A=B=E=H, D=(2-chloro)benzyloxymethyl, $R^1$=methoxy, $R^2$=hydrogen;

Compound of Formula (III): A=B=E=H, D=(4-chloro)benzyloxymethyl, $R^1$=methoxy, $R^2$=hydrogen;

Compound of Formula (III): A=B=E=H, D=(3-chloro)benzyloxymethyl, $R^1$=methoxy, $R^2$=hydrogen;

Compound of Formula (III): A=B=E=H, D=(2-pyridyl)methoxymethyl, $R^1$=methoxy, $R^2$=hydrogen;

Compound of Formula (III): A=B=E=H, D=(3-pyridyl)methoxymethyl, $R^1$=methoxy, $R^2$=hydrogen;

Compound of Formula (III): A=B=E=H, D=(4-methyl-2-quinolyl)methoxymethyl, $R^1$=methoxy, $R^2$=hydrogen;

Compound of Formula (III): A=B=E=H, D=(4-(methoxycarbonyl)benzyl)oxymethyl, $R^1$=methoxy, $R^2$=hydrogen;

Compound of Formula (III): A=B=E=H, D=(4-quinolyl)methoxymethyl, $R^1$=methoxy, $R^2$=hydrogen;

Compound of Formula (III): A=B=D=H, E=(4-pyridyl)methoxymethyl, $R^1$=methoxy, $R^2$=hydrogen;

Compound of Formula (III): A=B=E=H, D=(2-(N-morpholinyl)ethoxy)methyl, $R^1$=methoxy, $R^2$=hydrogen;

Compound of Formula (III): A=B=E=H, D=benzyloxymethyl, $R^1$=methoxy, $R^2$=hydrogen;

Compound of Formula (III): A=B=D=H, E=benzyloxymethyl, $R^1$=methoxy, $R^2$=hydrogen;

Compound of Formula (III): A=B=E=H, D=(4-methoxy)benzyloxymethyl, $R^1$=methoxy, $R^2$=hydrogen;

Compound of Formula (III): A=B=E=H, D=2-phenoxyethyl, $R^1$=methoxy, $R^2$=hydrogen;

Compound of Formula (III): A=B=E=H, D=2-(benzyloxy)ethyl, $R^1$=methoxy, $R^2$=hydrogen;

Compound of Formula (III): A=B=E=H, D=(4-methyl-1-piperazinyl)methyl, $R^1$=methoxy, $R^2$=hydrogen;

Compound of Formula (III): A=B=E=H, D=N-methyl-N-benzylaminomethyl, $R^1$=methoxy, $R^2$=hydrogen;

Compound of Formula (III): A=B=E=H, D=N-morpholinylmethyl, $R^1$=methoxy, $R^2$=hydrogen;

Compound of Formula (III): A=B=E=H, D=(1-piperidinyl)methyl, $R^1$=methoxy, $R^2$=hydrogen;

Compound of Formula (III): A=B=E=H, D=(N,N-dimethyl)aminomethyl, $R^1$=methoxy, $R^2$=hydrogen;

Compound of Formula (II): A=B=E=H, D=hydroxymethyl, $R^1$=methoxy, $R^2$=hydrogen;

Compound of Formula (III): A=B=E=H, D=(methylthioxy)methoxymethyl, $R^1$=methoxy, $R^2$=hydrogen;

Compound of Formula (III): A=B=E=H, D=3,5-dimethoxybenzyloxymethyl, $R^1$=methoxy, $R^2$=hydrogen;

Compound of Formula (III): A=B=E=H, D=4-fluorobenzyloxymethyl, $R^1$=methoxy, $R^2$=hydrogen;

Compound of Fonnula (III): A=B=E=H, D=2-fluorobenzyloxymethyl, $R^1$=methoxy, $R^2$=hydrogen;

Compound of Formula (III): A=B=E=H, D=4-bromobenzyloxymethyl, $R^1$=methoxy, $R^2$=hydrogen;

Compound of Formula (III): A=B=E=H, D=2-bromobenzyloxymethyl, $R^1$=methoxy, $R^2$=hydrogen;

Compound of Formula (III): A=B=E=H, D=3-bromobenzyloxymethyl, $R^1$=methoxy, $R^2$=hydrogen;

Compound of Formula (III): A=D=H; B and E taken together is —$CH_2CH_2CH_2CH_2$—, $R^1$=methoxy, $R^2$=hydrogen;

Compound of Formula (III): A=D=H; B and E taken together is —$CH_2CH_2CH_2$—, $R^1$=methoxy, $R^2$=hydrogen;

Compound of Formula (III): A=D=H; B and E taken together is —$CH_2OCH_2$—, $R^1$=methoxy, $R^2$=hydrogen;

Compound of Formula (III): A=D=H; B and E taken together is —$CH_2$—NH—$CH_2$—, $R^1$=methoxy, $R^2$=hydrogen;

Compound of Formula (III): A=D=H; B and E taken together is —$CH_2$—N(benzyl)-$CH_2$—, $R^1$=methoxy, $R^2$=hydrogen;

Compound of Formula (III): A=D=H; B and E taken together is —$CH_2$—N(phenyl-$CH_2$—$CH_2$—$CH_2$—)—$CH_2$—, $R^1$=methoxy, $R^2$=hydrogen;

Compound of Formula (III): B=E=H; A and D taken together is —$CH_2$—N(phenyl-$CH_2$—$CH_2$—$CH_2$—)—$CH_2$—, $R^1$=methoxy, $R^2$=hydrogen;

Compound of Formula (III): B=E=H; A and D taken together is —$CH_2$—N(phenyl-CH($CH_3$)—)—$CH_2$—, $R^1$=methoxy, $R^2$=hydrogen;

Compound of Formula (III): B=E=H; A and D taken together is —$CH_2$—N($CH_3$)—$CH_2$—, $R^1$=methoxy, $R^2$=hydrogen;

Compound of Formula (III): B=E=H; A and D taken together is —$CH_2$—N($CH_3CH_2$—)—$CH_2$—, $R^1$=methoxy, $R^2$=hydrogen;

Compound of Formula (III): B=E=H; A and D taken together is —$CH_2$—N(allyl)-$CH_2$—, $R^1$=methoxy, $R^2$=hydrogen;

Compound of Formula (III): B=E=H; A and D taken together is —$CH_2$—N(propargyl)-$CH_2$—, $R^1$=methoxy, $R^2$=hydrogen;

Compound of Formula (III): B=E=H; A and D taken together is —$CH_2$—N(4-$NO_2$-phenyl-$CH_2$—$CH_2$—)—$CH_2$—, $R^1$=methoxy, $R^2$=hydrogen;

Compound of Formula (III): B=E=H; A and D taken together is —CH$_2$—N(2-NO$_2$-phenyl-CH$_2$—CH$_2$—)—CH$_2$—, R$^1$=methoxy, R$^2$=hydrogen;

Compound of Formula (III): B=E=H; A and D taken together is —CH$_2$—N(3-NO$_2$-phenyl-CH$_2$—CH$_2$—)—CH$_2$—, R$^1$=methoxy, R$^2$=hydrogen;

Compound of Formula (III): B=E=H; A and D taken together is —CH$_2$—N(4-NH$_2$-phenyl-CH$_2$—CH$_2$—)—CH$_2$—, R$^1$=methoxy, R$^2$=hydrogen;

Compound of Formula (III): B=E=H; A and D taken together is —CH$_2$—N(4-NH(acetyl)-phenyl-CH$_2$—CH$_2$—)—CH$_2$—, R$^1$=methoxy, R$^2$=hydrogen;

Compound of Formula (III): B=E=H; A and D taken together is —CH$_2$—N(2-NO$_2$-benzyl-SO$_2$—)—CH$_2$—, R$^1$=methoxy, R$^2$=hydrogen;

Compound of Formula (III): B=E=H; A and D taken together is —CH$_2$—N(CHO)—CH$_2$—, R$^1$=methoxy, R$^2$=hydrogen;

Compound of Formula (III): B=E=H; A and D taken together is —CH$_2$—N(acetyl)-CH$_2$—, R$^1$=methoxy, R$^2$=hydrogen;

Compound of Formula (III): B=E=H; A and D taken together is —CH$_2$—N(2-methoxyethyl)-CH$_2$—, R$^1$-nmethoxy, R$^2$=hydrogen;

Compound of Formula (III): B=E=H; A and D taken together is —CH$_2$—N(2,2-dimethoxyethyl)-CH$_2$—, R$^1$=methoxy, R$^2$=hydrogen;

Compound of Formula (III): B=E=H; A and D taken together is —CH$_2$—N(2-phenoxyethyl)-CH$_2$—, R$^1$=methoxy, R$^2$=hydrogen;

Compound of Formula (III): B=E=H; A and D taken together is —CH$_2$—N(2-(dimethylamino)ethyl)-CH$_2$—, R$^1$=methoxy, R$^2$=hydrogen;

Compound of Formula (III): B=E=H; A and D taken together is —CH$_2$—N(2-(ethoxycarbonyl)ethyl)-CH$_2$—, R$^1$=methoxy, R$^2$=hydrogen;

Compound of Formula (III): B=D=E=H, A=N-benzylaminomethyl, R$^1$=methoxy, R$^2$=hydrogen;

Compound of Formula (III): B=D=E=H, A=N-benzyl-N-methylaminomethyl, R$^1$=methoxy, R$^2$=hydrogen;

Compound of Formula (III): D=E=H, A=N-benzyl-N-methylaminomethyl, B=phenylthiomethyl, R$^1$=methoxy, R$^2$=hydrogen;

Compound of Formula (III): D=E=H, A=N-benzyl-N-methylaminomethyl, B=methyl, R$^1$=methoxy, R$^2$=hydrogen;

Compound of Formula (III): D=E=H, A=dimethylaminomethyl, B=phenylthiomethyl, R$^1$=methoxy, R$^2$=hydrogen;

Compound of Formula (III): D=E=H, A=dimethylaminomethyl, B=methyl, R$^1$=methoxy, R$^2$=hydrogen;

Compound of Formula (III): B=D=E=H, A=(4-quinolyl)carboxymethyl, R$^1$=methoxy, R$^2$=hydrogen;

Compound of Formula (III): B=D=E=H, A=(4-pyridyl)carboxymethyl, R$^1$=methoxy, R$^2$=hydrogen;

Compound of Formula (III): B=D=E=H, A=benzoyloxymethyl, R$^1$=methoxy, R$^2$=hydrogen;

Compound of Formula (III): B=D=E=H, A=4-nitrobenzoyloxymethyl, R$^1$=methoxy, R$^2$=hydrogen;

Compound of Formula (III): B=D=E=H, A=4-chlorobenzoyloxymethyl, R$^1$=methoxy, R$^2$=hydrogen;

Compound of Formula (III): B=D=E=H, A=(2-quinolyl)carboxymethyl, R$^1$=metboxy, R$^2$=hydrogen;

Compound of Formula (III): B=D=E=H, A=(1-methyl-2-indolyl)carboxymethyl, R$^1$=methoxy, R$^2$=hydrogen;

Compound of Formula (III): B=D=E=H, A=(4-indolyl)carboxymethyl, R$^1$=methoxy, R$^2$=hydrogen;

Compound of Formula (III): B=D=E=H, A=(2-indolyl)carboxymethyl, R$^1$=methoxy, R$^2$=hydrogen;

Compound of Formula (III): B=D=H, A=E=benzyloxymethyl, R$^1$=methoxy, R$^2$=hydrogen;

Compound of Formula (III): A=E=H, B=D=(4-chloro)benzyloxymethyl, R$^1$=methoxy, R$^2$=hydrogen; and Compound of Formula (III): B=E=H, A=D=(4-chloro)benzyloxymethyl, R$^1$=methoxy, R$^2$=hydrogen.

A selected group of preferred representative compounds includes:

Compound of Formula (III): A=benzyl, B=D=E=H, R$^1$=methoxy, R$^2$=hydrogen;

Compound of Formula (III): A=4-iodobenzyl, B=D=E=H, R$^1$=methoxy, R$^2$=hydrogen;

Compound of Formula (III): A=benzyloxymethyl, B=D=E=H, R$^1$=methoxy, R$^2$=hydrogen;

Compound of Formula (III): A=benzylthioxymethyl, B=D=E=H, R$^1$=methoxy, R$^2$=hydrogen;

Compound of Formula (III): A=benzoyloxymethyl, B=D=E=H, R$^1$=methoxy, R$^2$=hydrogen;

Compound of Formula (III): A=4-fluorobenzyloxymethyl, B=D=E=H, R$^1$=methoxy, R$^2$=hydrogen;

Compound of Formula (III): A=3-fluorobenzyloxymethyl, B=D=E=H, R$^1$=methoxy, R$^2$=hydrogen;

Compound of Formula (III): A=2-fluorobenzyloxymethyl, B=D=E=H, R$^1$=methoxy, R$^2$=hydrogen;

Compound of Formula (III): A=(4-quinolyl)carboxymethyl, B=D=E=H, R$^1$=methoxy, R$^2$=hydrogen;

Compound of Formula (III): A=(4-pyridyl)carboxymethyl, B=D=E=H, R$^1$=methoxy, R$^2$=hydrogen;

Compound of Formula (III): A=(4-indolyl)carboxymethyl, B=D=E=H, R$^1$=methoxy, R$^2$=hydrogen;

Compound of Formula (III): A=4-nitrobenzoyloxymethyl, B=D=E=H, R$^1$=methoxy, R$^2$=hydrogen;

Compound of Formula (III): A=4-chlorobenzoyloxymethyl, B=D=E=H, R$^1$=methoxy, R$^2$=hydrogen;

Compound of Formula (III): A=benzoyloxymethyl, B=D=E=H, R$^1$=methoxy, R$^2$=hydrogen;

Compound of Formula (III): A=hydroxymethyl, B=D=E=H, R$^1$=methoxy, R$^2$=hydrogen;

Compound of Formula (III): A=4thiazolylmethyl, B=D=E=H, R$^1$=methoxy, R$^2$=hydrogen;

Compound of Formula (III): A=3-indolylmethyl, B=D=E=H, R$^1$=methoxy, R$^2$=hydrogen;

Compound of Formula (III): B=benzyl, A=D=E=H, R$^1$=methoxy, R$^2$=hydrogen;

Compound of Formula (III): B=benzyloxymethyl, A=D=E=H, R$^1$=methoxy, R$^2$=hydrogen;

Compound of Formula (III): D=hydroxymethyl, A=B=E=H, R$^1$=methoxy, R$^2$=hydrogen;

Compound of Formula (III): D=benzyl, A=B=E=H, $R^1$=methoxy, $R^2$=hydrogen;

Compound of Formula (III): D=benzyloxymethyl, A=B=E=H, $R^1$=methoxy, $R^2$=hydrogen;

Compound of Formula (III): D=(2-pyridyl)methoxymethyl, A=B=E=H, $R^1$=methoxy, $R^2$=hydrogen;

Compound of Formula (III): D=(3-pyridyl)methoxymethyl, A=B=E=H, $R^1$=methoxy, $R^2$=hydrogen;

Compound of Formula (III): D=(4-pyridyl)methoxymethyl, A=B=E=H, $R^1$=methoxy, $R^2$=hydrogen;

Compound of Formula (III): D=(4-cyano)benzyloxymethyl, A=B=E=H, $R^1$=methoxy, $R^2$=hydrogen;

Compound of Formula (III): D=(2-fluoro)benzyloxymethyl, A=B=E=H, $R^1$=methoxy, $R^2$=hydrogen;

Compound of Formula (III): D=(2-chloro)benzyloxymethyl, A=B=E=H, $R^1$=methoxy, $R^2$=hydrogen;

Compound of Formula (III): D=(4-chloro)benzyloxymethyl, A=B=E=H, $R^1$=methoxy, $R^2$=hydrogen;

Compound of Formula (III): D=(2-bromo)benzyloxymethyl, A=B=E=H, $R^1$=methoxy, $R^2$=hydrogen;

Compound of Formula (III): D=(4-quinolyl)methoxymethyl, A=B=E=H, $R^1$=methoxy, $R^2$=hydrogen;

Compound of Formula (III): E=benzyl, A=B=D=H, $R^1$=methoxy, $R^2$=hydrogen;

Compound of Formula (III): E=(4-pyridyl)methoxymethyl, A=B=D=H, $R^1$=methoxy, $R^2$=hydrogen;

Compound of Formula (III): E=benzyloxymethyl, A=B=D=H, $R^1$=methoxy, $R^2$=hydrogen;

Compound of Formula (III): E=dimethylaminomethyl, A=B=D=H, $R^1$=methoxy, $R^2$=hydrogen;

Compound of Formula (III): A=E=(4-chloro)benzyloxymethyl, B=D=H, $R^1$=methoxy, $R^2$=hydrogen;

Compound of Formula (III): A=E=methyl; B=D=H, $R^1$=methoxy, $R^2$=hydrogen;

Compound of Formula (III): A=D=methyl; B=E=H, $R^1$=methoxy, $R^2$=hydrogen;

Compound of Formula (III): B=E=H; A and D taken together is —$CH_2CH_2CH_2$—, $R^1$=methoxy, $R^2$=hydrogen;

Compound of Formula (III): A=D=H; B and E taken together is —$CH_2CH_2CH_2$—, $R^1$=methoxy, $R^2$=hydrogen;

Compound of Formula (III): B=E=H; A and D taken together is —$CH_2CH_2CH_2CH_2$—, $R^1$=methoxy, $R^2$=hydrogen;

Compound of Formula (III): A=D=H; B and E taken together is —$CH_2CH_2CH_2CH_2$—, $R^1$=methoxy, $R^2$=hydrogen;

Compound of Formula (III): B=E=H; A and D taken together is —$CH_2OCH_2$—, $R^1$=methoxy, $R^2$=hydrogen;

Compound of Formula (III): A=D=H; B and E taken together is —$CH_2OCH_2$—, $R^1$=methoxy, $R^2$=hydrogen;

Compound of Formula (III): B=E=H; A and D taken together is —$CH_2NHCH_2$—, $R^1$=methoxy, $R^2$=hydrogen;

Compound of Formula (III): A=D=H; B and E taken together is —$CH_2NHCH_2$—, $R^1$=methoxy, $R^2$=hydrogen;

Compound of Formula (III): B=E=H; A and D taken together is —$CH_2N(benzyl)CH_2$—, $R^1$=methoxy, $R^2$=hydrogen;

Compound of Formula (III): A=D=H; B and E taken together is —$CH_2N(benzyl)CH_2$—, $R^1$=methoxy, $R^2$=hydrogen;

Compound of Formula (III): B=E=H; A and D taken together is —$CH_2N(4$-nitro-phenyl-$CH_2CH_2)CH_2$—, $R^1$=methoxy, $R^2$=hydrogen;

Compound of Formula (III): B=E=H; A and D taken together is —$CH_2N(3$-nitro-phenyl-$CH_2CH_2)CH_2$—, $R^1$=methoxy, $R^2$=hydrogen;

Compound of Formula (III): B=E=H; A and D taken together is —$CH_2N(4$-NH(acetyl)-phenyl-$CH_2CH_2)CH_2$—, $R^1$=methoxy, $R^2$=hydrogen;

Compound of Formula (III): B=E=H; A and D taken together is —$CH_2N(phenyl$-$CH_2CH_2CH_2)CH_2$—, $R^1$=methoxy, $R^2$=hydrogen;

Compound of Formula (III): A=D=H; B and E taken together is —$CH_2N(phenyl$-$CH_2CH_2CH_2)CH_2$—, $R^1$=methoxy, $R^2$=hydrogen;

Compound of Formula (III): A=B=D=E=hydrogen; $R^1$=hydrogen, $R^2$=hydrogen; and Compound of Formula (IV): $R^1$=methoxy; $R^2$=hydrogen; A=B=D=E=hydrogen.

One object of the present invention is to provide a process for the preparation of tricyclic macrolide derivatives having the formulas:

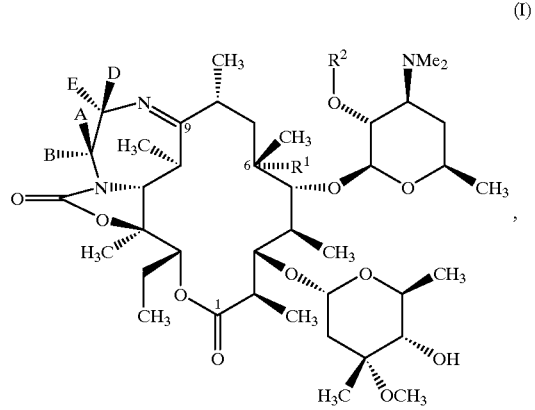
(I)

-continued

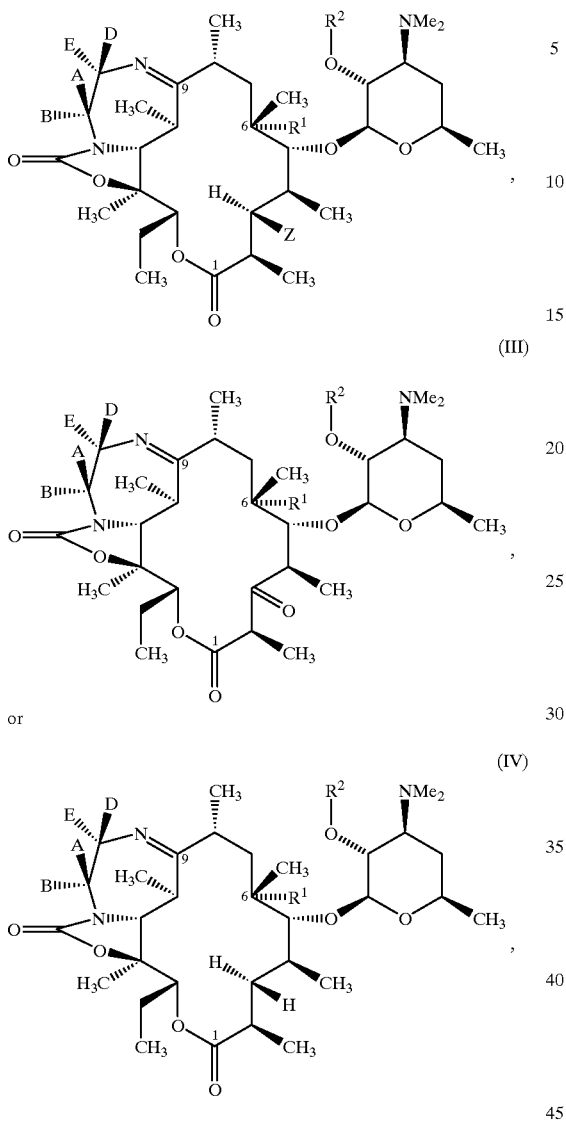

wherein:
A, B, D and E are independently selected from the group consisting of:
(a) hydrogen;
(b) $C_1$–$C_6$-alkyl, as defined below, optionally substituted with one or more substituents selected from the group consisting of:
(i) aryl, as defined below;
(ii) substituted-aryl, as defined below;
(iii) heteroaryl, as defined below;
(iv) substituted-heteroaryl, as defined below;
(v) heterocycloalkyl, as defined below;
(vi) hydroxy;
(vii) $C_1$–$C_6$-alkoxy, as defined below;
(viii) halogen consisting of Br, Cl, F or I; and
(ix) $NR^3R^4$, where $R^3$ and $R^4$ are independently selected from hydrogen and $C_1$–$C_6$-alkyl, or $R^3$ and $R^4$ are taken with the nitrogen atom to which they are connected to form a 3- to 7-membered ring optionally containing a hetero function consisting of —O—, —NH—, —N($C_1$–$C_6$-alkyl-)-, —N(aryl-$C_1$–$C_6$-alkyl-)-, —N(substituted-aryl-$C_1$–$C_6$-alkyl-)-, —N(heteroaryl-$C_1$–$C_6$-alkyl-)-, —N(substituted-heteroaryl-$C_1$–$C_6$-alkyl-)-, —S— or —S(O)$_n$—, wherein n is 1 or 2;
(c) $C_3$–$C_7$-cycloalkyl;
(d) aryl;
(e) substituted-aryl;
(f) heteroaryl;
(g) substituted-heteroaryl;
(h) heterocycloalkyl; and
(i) a group selected from option (b) above further substituted with —M—$R^5$, wherein M is selected from the group consisting of:
(aa) —C(O)—NH—;
(bb) —NH—C(O)—;
(cc) —NH—
(dd) —N(CH$_3$)—
(ee) —O—
(ff) —S(O)$_n$—, wherein n is 0, 1 or 2; and
(gg) —C(=NH)—NH—;
(hh) —C(O)—O—;
(ii) —O—C(O)—;
(jj) —O—C(O)—NH—;
(kk) —NH—C(O)—O—; and
(ll) —NH—C(O)—NH—;
and $R^5$ is selected from the group consisting of:
(aaa) $C_1$–$C_6$-alkyl, optionally substituted with a substituent selected from the group consisting of:
(i) aryl;
(ii) substituted-aryl;
(iii) heteroaryl; and
(iv) substituted-heteroaryl;
(bbb) aryl;
(ccc) substituted-aryl;
(ddd) heteroayl;
(eee) substituted-heteroaryl; and
(fff) heterocycloalkyl; or
any one pair of substituents, consisting of AB, AD, AE, BD, BE or DE, is taken together with the atom or atoms to which they are attached to form a 3- to 7-membered ring optionally containing a hetero function consisting of:
—O—,
—NH—,
—N($C_1$–$C_6$-alkyl-)-,
—N(aryl-$C_1$–$C_6$-alkyl-)-,
—N(substituted-aryl-$C_1$–$C_6$-alkyl-)-,
—N(heteroaryl-$C_1$–$C_6$-alkyl-)-,
—N(substituted-heteroaryl-$C_1$–$C_6$-alkyl-)-,
—S— or —S(O)$_n$—, wherein n is 1 or 2;
—C(O)—NH—;
—C(O)—NR$^5$—, wherein R$^5$ is as described above;
—NH—C(O)—;
—NR$^5$—C(O)—, wherein R$^5$ is as described above; and
—C(=NH)—NH—;
$R^1$ is selected from the group consisting of:
(a) hydrogen;
(b) hydroxy;
(c) —O—$C_1$–$C_3$-alkyl;
(d) —O—$C_3$–$C_5$-cycloalkyl;
(e) —O—$C_1$–$C_3$-alkyl-$C_3$–$C_5$-cycloalkyl;
(f) —O—C(O)—$C_1$–$C_3$-alkyl;
(g) —O—C(O)—O—$C_1$–$C_3$-alkyl; and
(h) —O—C(O)—NH—$C_1$–$C_3$-alkyl;
$R^2$ is hydrogen or a hydroxy-protecting group, as defined below; and
Z is hydroxy or protected-hydroxy, except when the compound is of Formulas (I) or (III) then A, B, D, and E may not all be hydrogen, D and E may not be $C_1$–$C_3$-alkyl when A and B are hydrogen, nor may one of D and E be hydrogen and the other be $C_1$–$C_3$-alkyl when A and B are hydrogen; the method comprising:

(a) treating a compound having the formula:

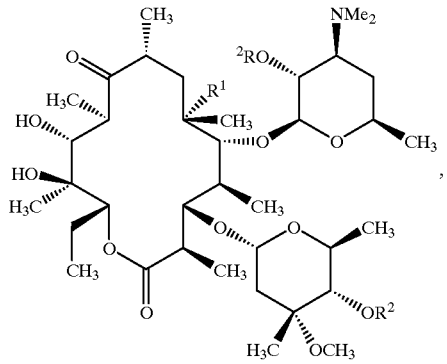

(compound (2) from Scheme 1),

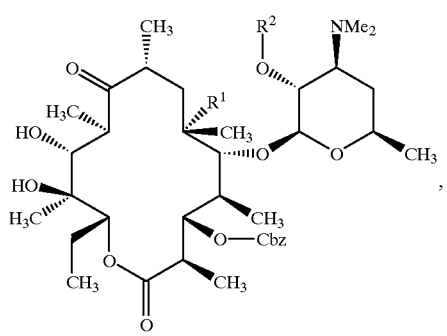

(compound (6) from Scheme 2),

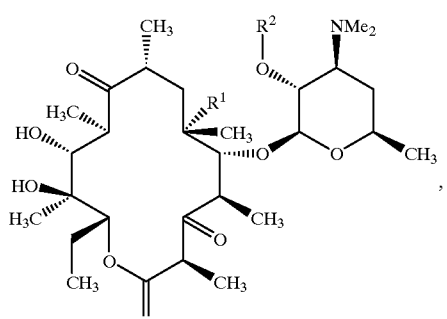

(compound (7) from Scheme 3), or

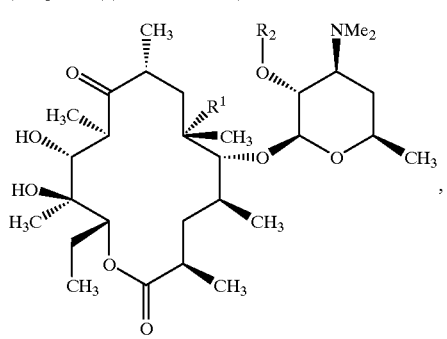

(compound (9) from Scheme 4), respectively, wherein $R^1$ is as described above and $R^2$ is a hydroxy-protecting group, with a base, and followed by reaction with carbonyldiimidazole, in an aprotic solvent, to prepare first intermediate compounds having the formulas:

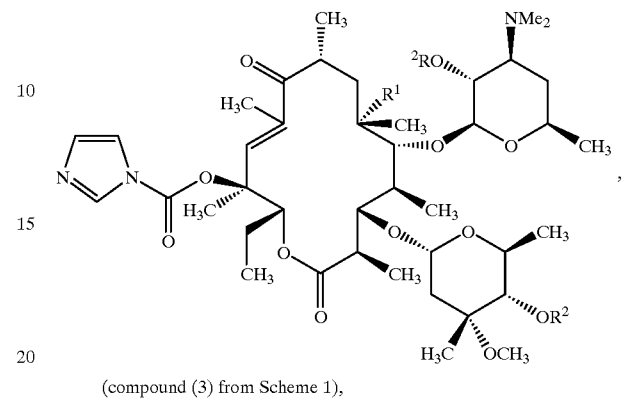

(compound (3) from Scheme 1),

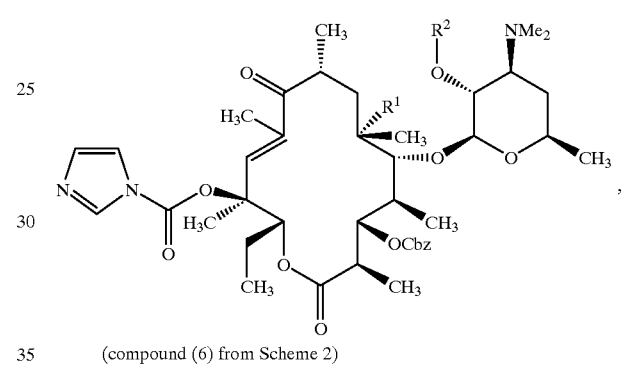

(compound (6) from Scheme 2)

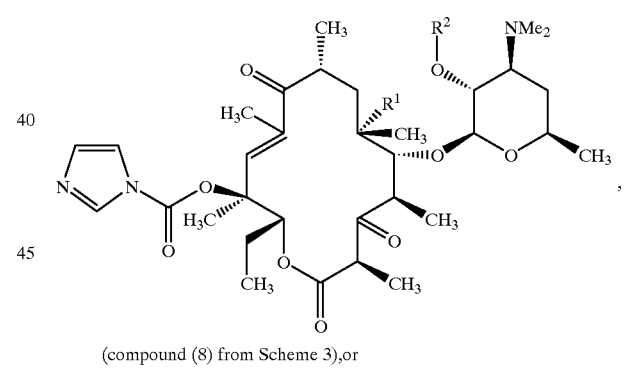

(compound (8) from Scheme 3), or

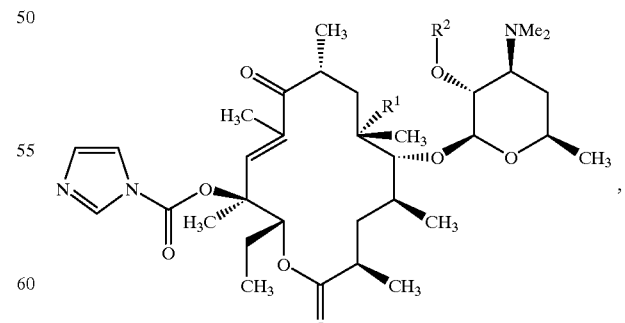

(compound (10) from Scheme 4), respectively, wherein $R^1$ and $R^2$ are as described above;

(b) reacting said first intermediate compounds (3), (6), (8), or (10) with a compound having the formula:

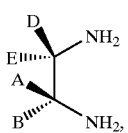

wherein A, B, D, and E are as described above, to give the bicyclic second intermediate compounds having the formulas:

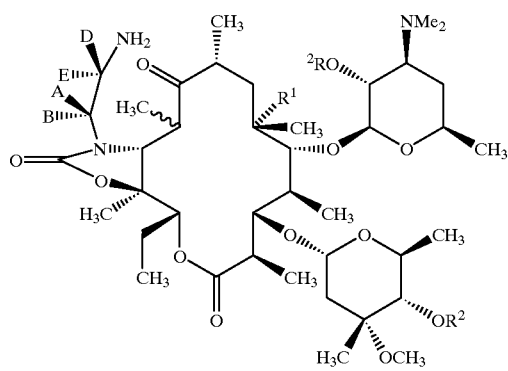

(compound (11), from Scheme 5),

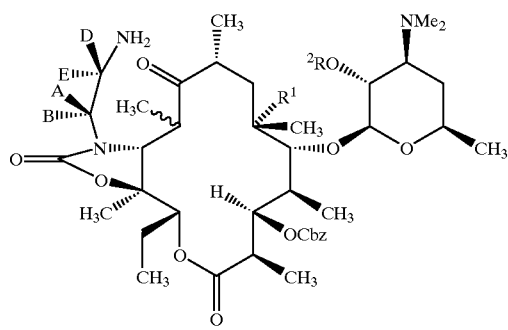

(compound (15), from Scheme 7),

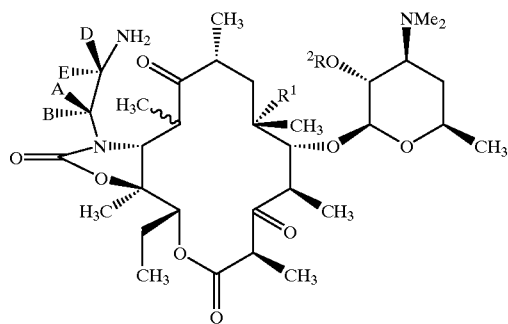

(compound (19), from Scheme 9),

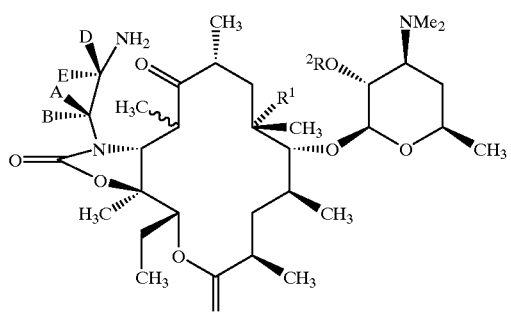

(compound (23), from Scheme 11), respectively;

wherein $R^1$ and $R^2$ are as described above;

(c) deprotecting said second intermediate compounds (11), (15), (19) or (23) by treatment with methanol or ethanol when $OR^2$ is an ester or with fluoride in THF or acetonitrile when $R^2$ is a trialkylsilyl group, for from 1 to 24 hours, to give the third intermediate compounds:

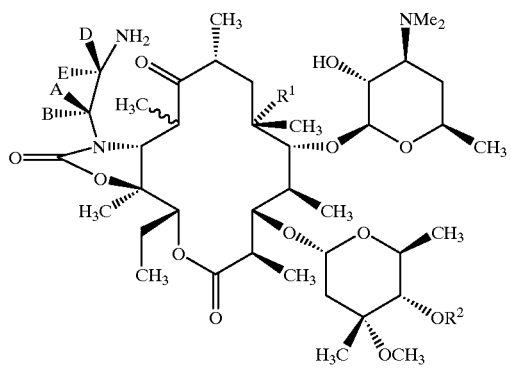

(compound (12), from Scheme 5),

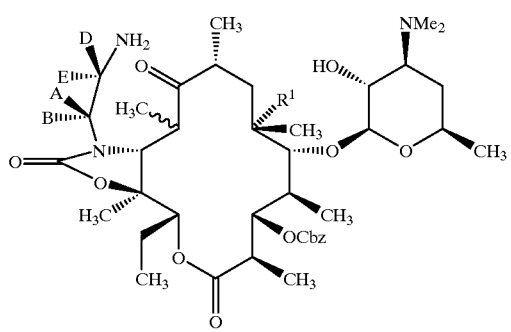

(compound (16), from Scheme 7),

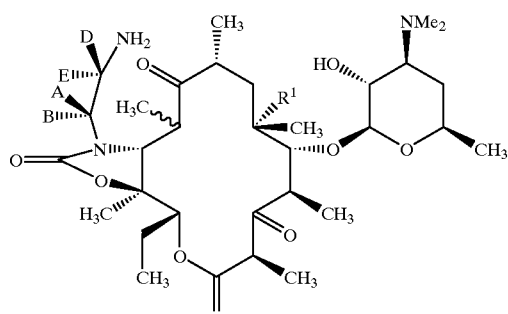

(compound (20), from Scheme 9),

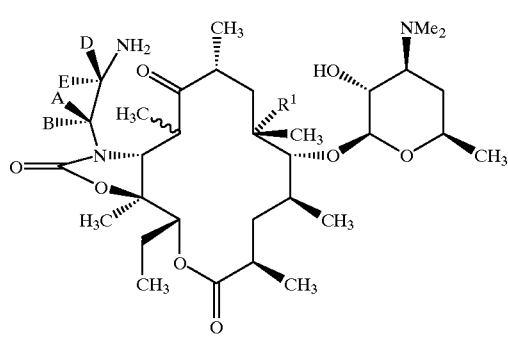

(compound (24), from Scheme 11), respectively; and (d) cyclizing said third intermediate compounds (12), (16), (20) or (24) by treatment with dilute acid, for a period of from 4 hours to 10 days to give the desired compounds (I), (II), (III) or (IV) above.

Another object of the present invention is to provide an alternate process for the preparation of tricyclic macrolide derivatives having the formulas:

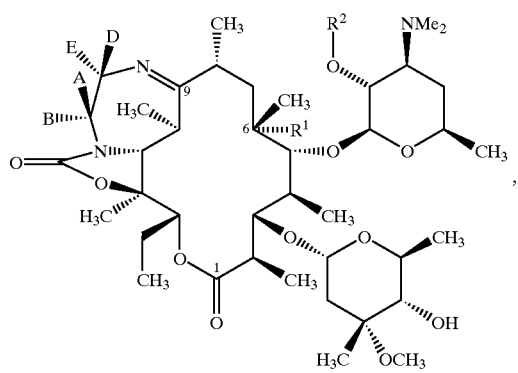

(I)

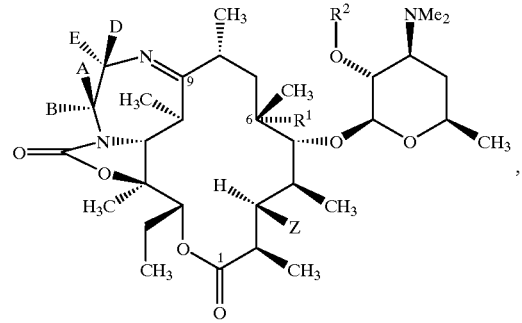

(II)

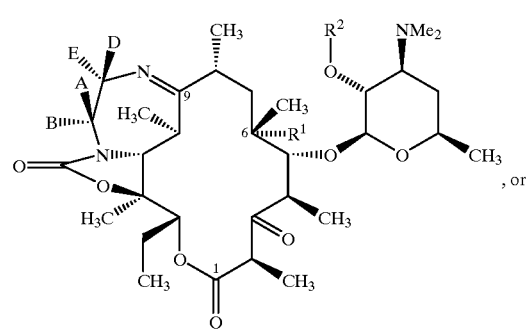

(III)

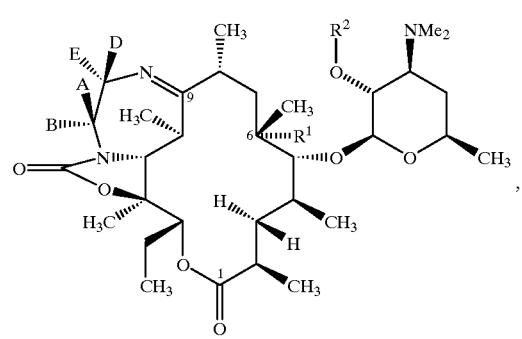

(IV)

wherein:
A, B, D and E are independently selected from the group consisting of:
(a) hydrogen;
(b) $C_1$–$C_6$-alkyl, as defined below, optionally substituted with one or more substituents selected from the group consisting of:
(i) aryl, as defined below;
(ii) substituted-aryl, as defined below;
(iii) heteroaryl, as defined below;
(iv) substituted-heteroaryl, as defined below;
(v) heterocycloalkyl, as defined below;
(vi) hydroxy;
(vii) $C_1$–$C_6$-alkoxy, as defined below;

(viii) halogen consisting of Br, Cl, F or I; and
(ix) NR$^3$R$^4$, where R$^3$ and R$^4$ are independently selected from hydrogen and C$_1$–C$_6$-alkyl, or R$^3$ and R$^4$ are taken with the nitrogen atom to which they are connected to form a 3- to 7-membered ring optionally containing a hetero function consisting of —O—, —NH—, —N(C$_1$–C$_6$-alkyl-)-, —N(aryl-C$_1$–C$_6$-alkyl-)-, —N(substituted-aryl-C$_1$–C$_6$-alkyl-)-, —N(heteroaryl-C$_1$–C$_6$-alkyl-)-, —N(substituted-heteroaryl-C$_1$–C$_6$-alkyl-)-, —S— or —S(O)$_n$—, wherein n is 1 or 2;
(c) C$_3$–C$_7$-cycloalkyl;
(d) aryl;
(e) substituted-aryl;
(f) heteroaryl;
(g) substituted-heteroaryl;
(h) heterocycloalkyl; and
(i) a group selected from option (b) above further substituted with —M—R$^5$, wherein M is selected from the group consisting of:
(aa) —C(O)—NH—;
(bb) —NH—C(O)—;
(cc) —NH—
(dd) —N(CH$_3$)—
(ee) —O—
(ff) —S(O)$_n$—, wherein n is 0, 1 or 2; and
(gg) —C(=NH)—NH—;
(hh) —C(O)—O—;
(ii) —O—C(O)—;
(jj) —C(O)—NH—;
(kk) —NH—C(O)—O—; and
(ll) —NH—C(O)—NH—;
and R$^5$ is selected from the group consisting of:
(aaa) C$_1$–C$_6$-alkyl, optionally substituted with a substituent selected from the group consisting of:
(i) aryl;
(ii) substituted-aryl;
(iii) heteroaryl; and
(iv) substituted-heteroaryl;
(bbb) aryl;
(ccc) substituted-aryl;
(ddd) heteroaryl;
(eee) substituted-heteroaryl; and
(fff) heterocycloalkyl; or
any one pair of substituents, consisting of AB, AD, AE, BD, BE or DE, is taken together with the atom or atoms to which they are attached to form a 3- to 7-membered ring optionally containing a hetero function consisting of:
—O—,
—NH—,
—N(C$_1$–C$_6$-alkyl-)-,
—N(aryl-C$_1$–C$_6$-alkyl-)-,
—N(substituted-aryl-C$_1$–C$_6$-alkyl-)-,
—N(heteroaryl-C$_1$–C$_6$-alkyl-)-,
—N(substituted-heteroaryl-C$_1$–C$_6$-alkyl-)-,
—S— or —S(O)$_n$—, wherein n is 1 or 2;
—C(O)—NH—;
—C(O)—NR$^5$—, wherein R$^5$ is as described above;
—NH—C(O)—;
—NR$^5$—C(O)—, wherein R$^5$ is as described above; and
—C(=NH)—NH—;
R$^1$ is selected from the group consisting of:
(a) hydrogen;
(b) hydroxy;
(c) —O—C$_1$–C$_3$-alkyl;

(d) —O—C$_3$–C$_5$-cycloalkyl;
(e) —O—C$_1$–C$_3$-alkyl-C$_3$–C$_5$-cycloalkyl;
(f) —O—C(O)—C$_1$–C$_3$-alkyl;
(g) —O—C(O)—O—C$_1$–C$_3$-alkyl; and
(h) —O—C(O)—NH—C$_1$–C$_3$-alkyl;

R$^2$ is hydrogen or a hydroxy-protecting group, as defined below; and

Z is hydroxy or protected-hydroxy; except when the compound is of Formulas (I) or (III) then A, B, D, and E may not all be hydrogen, D and E may not be C$_1$–C$_3$-alkyl when A and B are hydrogen, nor may one of D and E be hydrogen and the other be C$_1$–C$_3$-alkyl when A and B are hydrogen; the method comprising:

(a) treating a compound having the formula:

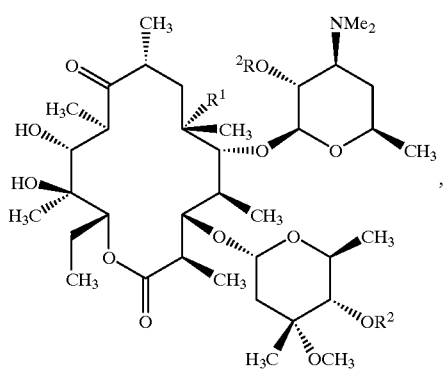

(compound (2) from Scheme 1),

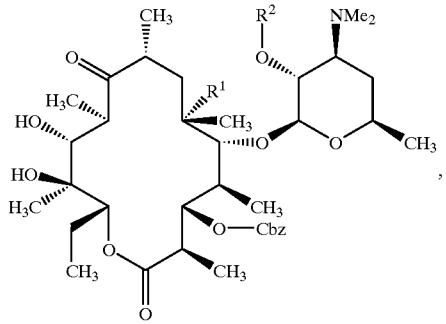

(compound (6) from Scheme 2),

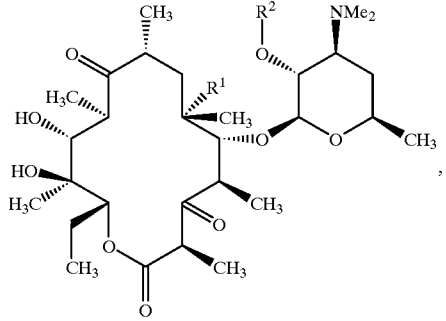

(compound (7) from Scheme 3), or

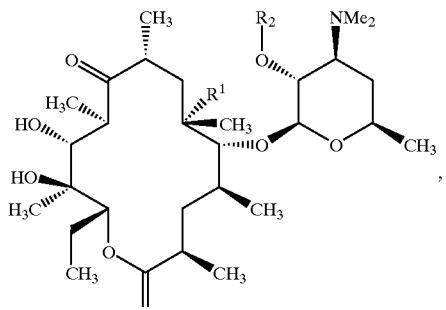

(compound (9) from Scheme 4), respectively, wherein $R^1$ is as described above and $R^2$ is a hydroxy-protecting group, with a base, to prepare first intermediate compounds having the formulas:

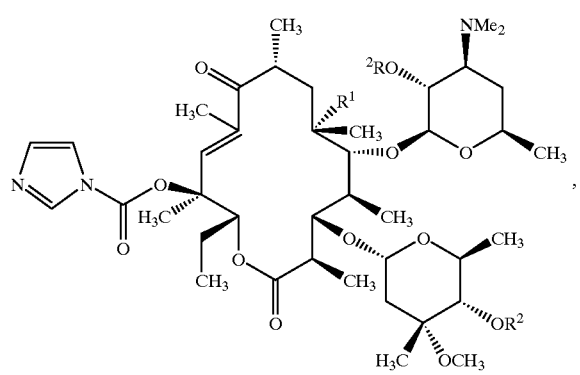

(compound (3) from Scheme 1),

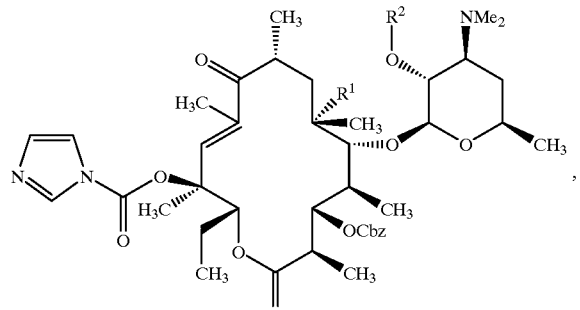

(compound (6) from Scheme 2)

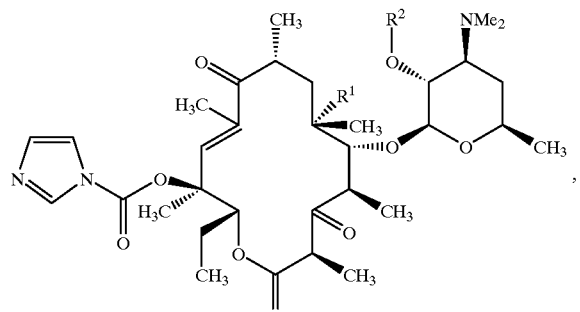

(compound (8) from Scheme 3), or

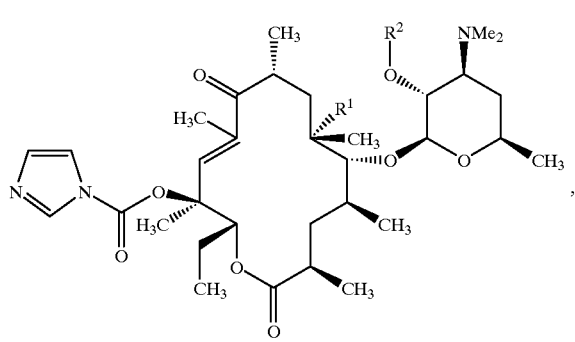

(compound (10) from Scheme 4), respectively;

wherein $R^1$ and $R^2$ are as described above;

(b) reacting said first intermediate compounds (3), (6), (8), or (10) with a compound having the having the formula:

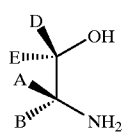

wherein A, B, D, and E are as described above, to give the bicyclic second intermediate compounds

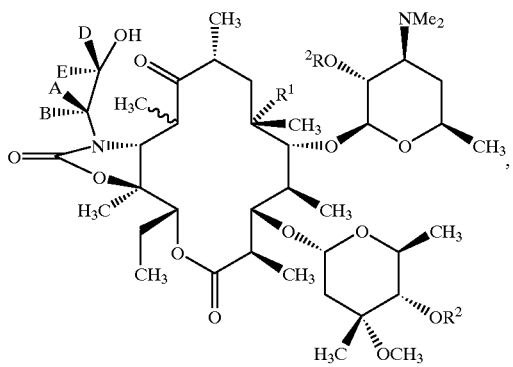

(compound (14), from Scheme 6, Y = OH),

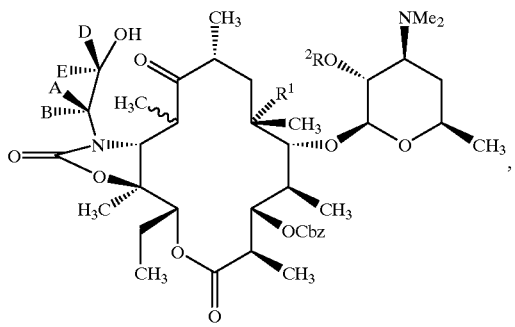

(compound (18), from Scheme 8, Y = OH),

27

-continued

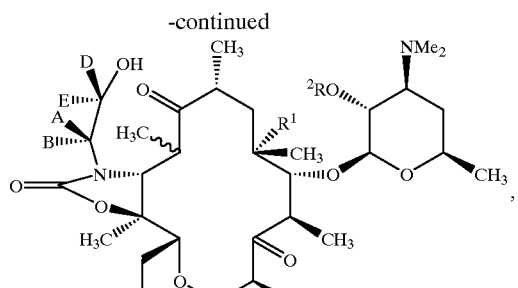

(compound (22), from Scheme 10, Y = OH), or

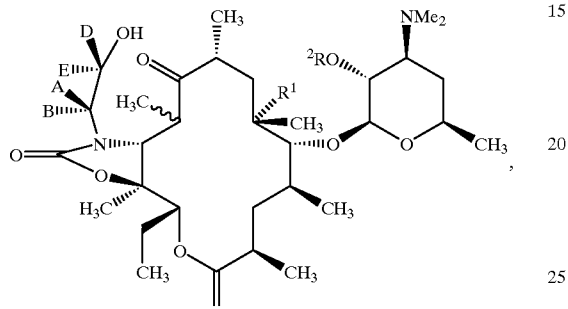

(compound (26), from Scheme 12, Y = OH), respectively, (c) reacting the hydroxy group of the said bicyclic second intermediate compounds (14), (18), (22) and (26) by treatment triphenyiphosphine and diphenylphosphoryl azide-DEAD in tetrahydrofuran, under Mitsunobu reaction conditions, to prepare the third intermediate compounds:

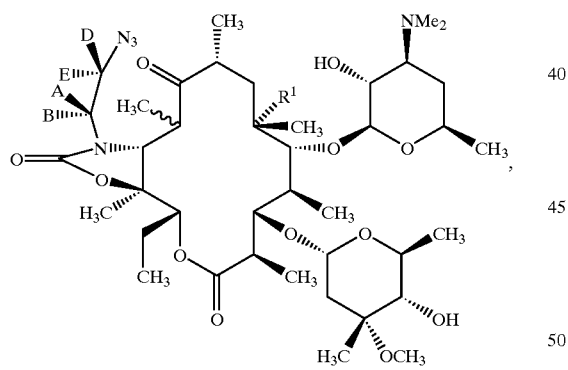

(compound (14), from Scheme 6, Y = $N_3$),

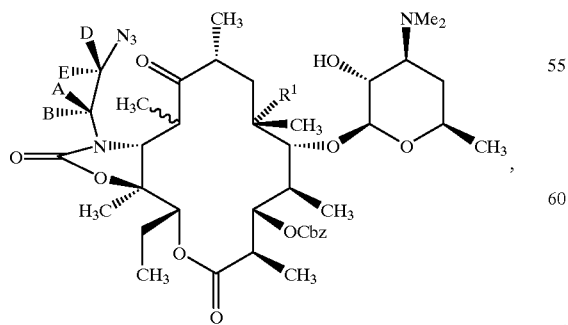

(compound (18), from Scheme 8, Y = $N_3$),

28

-continued

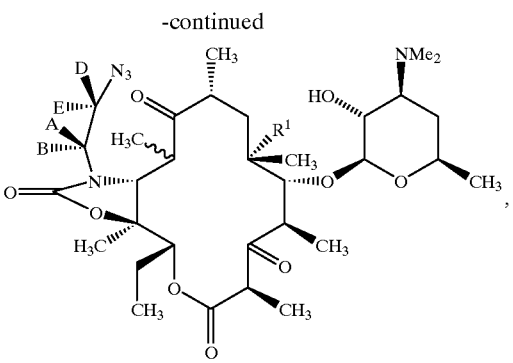

(compound (22), from Scheme 10, Y = $N_3$), or

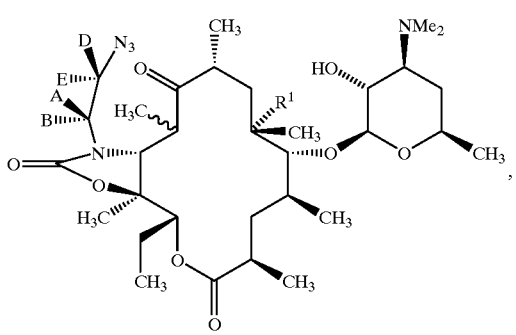

(compound (26), from Scheme 12, Y = $N_3$), respectively;

(d) reducing the third intermediate compounds having an azido group, to prepare the fourth intermediate compounds having the formulas:

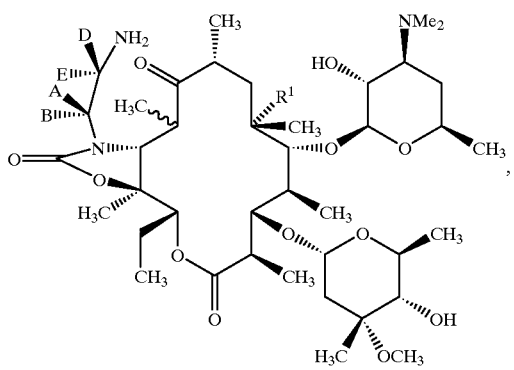

(compound (12), from Scheme 6),

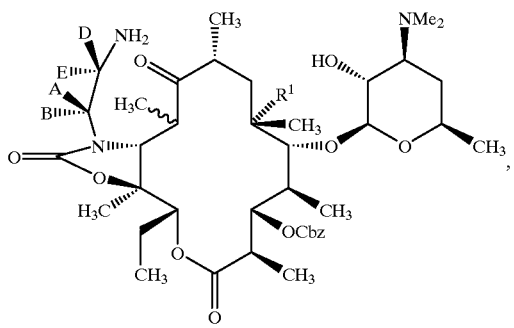

(compound (16), from Scheme 8),

-continued

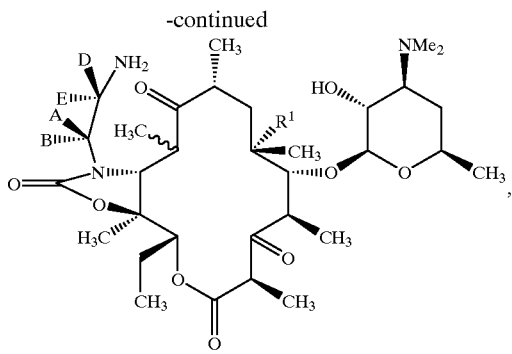

(compound (20), from Scheme 10),

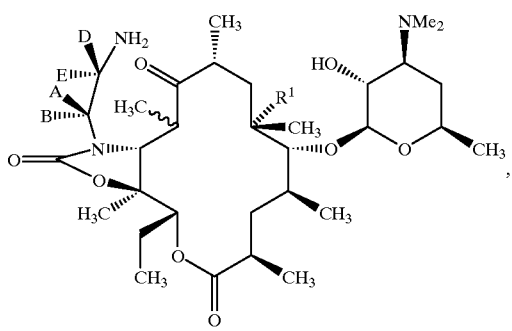

(compound (24), from Scheme 12), respectively; and
(e) cyclizing said fourth intermediate compounds (12), (16), (20) or (24), wherein Y is an amino group, by treatment with dilute acid, in an organic solvent, preferably ethanol or propanol, for a period of from 4 hours to 10 days to give the desire compounds of Formulas (I), (II), (III) or (IV).

In an alternate embodiment of the alternate process above, the third intermediate compounds may be prepared by a two-step sequence (replacing step (c) thereof) which comprises (1) reacting the hydroxy group of the bicyclic second intermediate compounds with an alkyl or aryl sulfonyl chloride, an alkyl or aryl sulfonic anhydride or trifluoromethanesulfonic anhydride in an aprotic solvent at −78° C. to room temperature to give the corresponding sulfonate, and (2) reacting the said sulfonate with lithium azide or sodium azide in an aprotic solvent at 0° C. to 100° C. to give the third intermediate compound.

Definitions:

The terms "$C_1$–$C_3$-alkyl" or "$C_1$–$C_6$-alkyl" as used herein refer to saturated, straight- or branched-chain hydrocarbon radicals containing between one and three or one and six carbon atoms, respectively. Examples of $C_1$–$C_3$ alkyl radicals include methyl, ethyl, propyl and isopropyl, and examples of $C_1$–$C_6$-alkyl radicals include, but are not limited to, methyl, ethyl, propyl, isopropyl, n-butyl, tert-butyl, neopentyl and n-hexyl.

The term "$C_1$–$C_6$-alkoxy" as used herein refers to an $C_1$–$C_6$-alkyl group, as previously defined, attached to the parent molecular moiety through an oxygen atom. Examples of $C_1$–$C_6$-alkoxy, but are not limited to, methoxy, ethoxy, propoxy, isopropoxy, n-butoxy, tert-butoxy, neopentoxy and n-hexoxy.

The term "$C_1$–$C_3$-alkyl-amino" as used herein refers to one or two $C_1$–$C_3$-alkyl groups, as previously defined, attached to the parent molecular moiety through a nitrogen atom. Examples of $C_1$–$C_3$-allyl-amino include, but are not limited to methylamino, dimethylamino, ethylamino, diethylamino, and propylamino.

The term "aprotic solvent" as used herein refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick, et al., Vol. II, in the Techniques of Chemistry Series, John Wiley & Sons, NY, 1986.

The term "aryl" as used herein refers to unsubstituted carbocyclic aromatic groups including, but not limited to, phenyl, 1- or 2-naphthyl and the like.

The term "$C_3$–$C_5$-cycloalkyl- and $C_3$–$C_7$-cycloalkyl" as used herein refers to carbocyclic groups of 3 to 5 or 3 to 7 carbons, respectively, for example, cyclopropyl, cyclobutyl, cyclopentyl, cyclohexyl, and cycloheptyl.

The term "$C_1$–$C_3$-alkyl-$C_3$–$C_5$-cycloalkyl", as used herein refers to a $C_3$–$C_5$-cycloalkyl radical, as defined above, attached to a $C_1$–$C_3$-alkyl radical by replacement of a hydrogen atom on the latter.

The terms "halo" and "halogen" as used herein refer to an atom selected from fluorine, chlorine, bromine and iodine.

The term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

The term "heterocycloalkyl" as used herein, refers to a non-aromatic 5-, 6- or 7-membered ring or a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

"Hydroxy-protecting group", as used herein, refers to an easily removable group to which are known in the art to protect a hydroxyl group against undesirable reaction during synthetic procedures and to be selectively removable. The use of hydroxy-protecting groups is well known in the art for protecting groups against undesirable reactions during a synthetic procedure and many such protecting groups are known, cf, for example, T. H. Greene and P. G. M. Wuts, *Protective Groups in Organic Synthesis*, 2nd edition, John Wiley & Sons, New York (1991). Examples of hydroxy-protecting groups include, but are not limited to, methylthiomethyl, tert-dimethylsilyl, tert-butyldiphenylsilyl, acyl substituted with an aromatic group and the like.

A the term "protected-hydroxy" refers to a hydroxy group protected with a hydroxy protecting group, as defined above, including benzoyl, acetyl, trimethylsilyl, triethylsilyl, methoxymethyl groups, for example.

The term "protogenic organic solvent" as used herein refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick, et al., Vol. 11, in the Techniques of Chemistry Series, John Wiley & Sons, NY, 1986.

The term "substituted aryl" as used herein refers to an aryl group as defined herein substituted by independent replacement of one, two or three of the hydrogen atoms thereon with F, Cl, Br, I, OH, $NO_2$, CN, C(O)—$C_1$–$C_6$-alkyl, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, OC-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$-$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_6$-cycloalkyl, $CF_3$, $CH_2CF_3$, $CHCl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkyl-amino, thio, aryl-thio, heteroarylthio, benzyl-thio, $C_1$–$C_6$-alkyl-thio, or methylthiomethyl.

The term "substituted heteroaryl" as used herein refers to a heteroaryl group as defined herein substituted by independent replacement of one, two or three of the hydrogen atoms thereon with F, Cl, Br, I, OH, $NO_2$, CN, C(O)—$C_1$–$C_6$-alkyl, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, OC-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$-$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_6$-cycloalkyl, $CF_3$, $CH_2CF_3$, $CHCl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkyl-amino, thio, aryl-thio, heteroarylthio, benzyl-thio, $C_1$–$C_6$-alkyl-thio, or methylthiomethyl.

The term "substituted heterocycloalkyl" as used herein, refers to a heterocycloalkyl group, as defined above, substituted by independent replacement of one, two or three of the hydrogen atoms thereon with F, Cl, Br, I, OH, $NO_2$, CN, C(O)—$C_1$–$C_6$-alkyl, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, OC-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, $NHCONH$—$C_1$–$C_6$-alkyl, NHCONH-aryl, NHCONH-heteroaryl, $SO_2$-$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_6$-cycloalkyl, $CF_3$, $CH_2CF_3$, $CHCl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkyl-amino, thio, aryl-thio, heteroarylthio, benzyl-thio, $C_1$–$C_6$-alkyl-thio, or methylthiomethyl.

Numerous asymmetric centers may exist in the compounds of the present invention. Except where otherwise noted, the present invention contemplates the various stereoisomers and mixtures thereof. Accordingly, whenever a bond is represented by a wavy line, it is intended that a mixture of stereo-orientations or an individual isomer of assigned or unassigned orientation may be present.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/iisk ratio. Pharmaceutically acceptable salts are well known in the art. For example, S. M. Berge, et al. describe pharmaceutically acceptable salts in detail in *J. Pharmaceutical Sciences*, 66: 1–19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuc acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters includes formates, acetates, propionates, butyates, acrylates and ethylsuccinates.

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), bucally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubjiig agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating arL They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or lower mammal by administering to the patient a therapeutically effective amount of a compound of the invention, in such amounts and for such time as is necessary to achieve the desired result. By a "therapeutically effective amount" of a compound of the invention is meant a sufficient amount of the compound to treat bacterial infections, at a reasonable benefit/risk ratio applicable to any medical treatment It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

Abbreviations

Abbreviations which have been used in the descriptions of the scheme and the examples that follow are: AIBN for azobisisobutyronitrile; Bu3SnH for tributyltin hydride; CDI for carbonyldilmidazole; DBU for 1,8-diazabicyclo[5.4.0]undec-7-ene; DEAD for diethylazodicarboxylate; DMF for dimethyl formamide; DPPA for diphenylphosphoryl azide; EtOAc for ethyl acetate; MeOH for methanol; $NaN(TMS)_2$ for sodium bis(trimethylsilyl)amide; NMMO for N-methylmorpholine N-oxide; TEA for triethylaamine; THF for tetrahydrofliran; TPP for triphenylphosphine.

Synthetic Methods

The compounds and processes of the present invention will be better understood in connection with the following synthetic schemes which illustrate the methods by which the compounds of the invention may be prepared. The groups A, B, D, E, $R^1$ and $R^2$ are as defined above unless otherwise noted below.

Scheme 1
Preparation of starting materials, 12-imidazolylcarbonyloxy macrolide (3), for compounds of Formula (I)

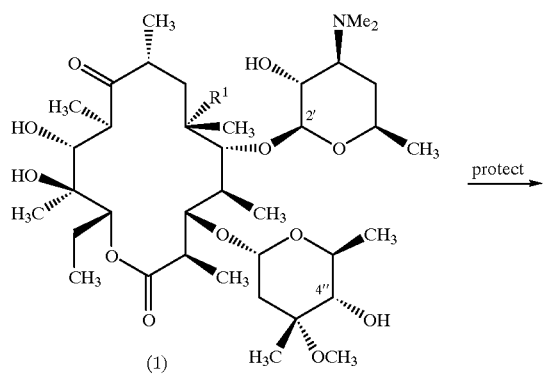

(1)
$R^1$ is as described for formula I

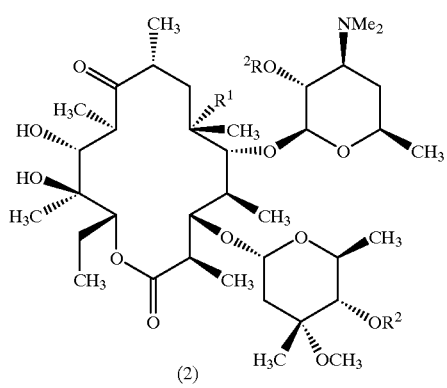

(2)
$R^2$ is a hydroxy-protecting group

NaH-CDI

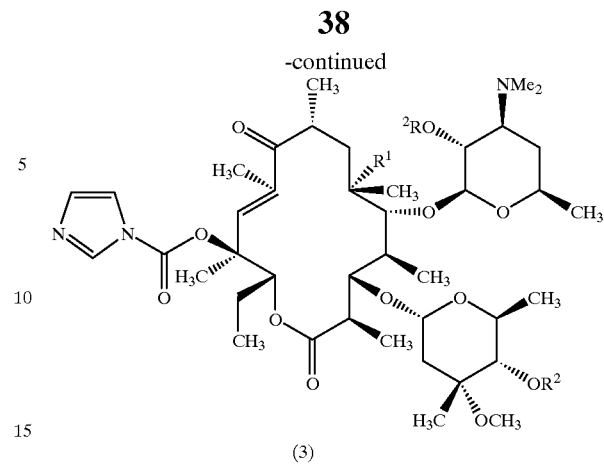

(3)
$R^1$ is as described for formula I
$R^2$ is a hydroxy-protecting group

Scheme 1 illustrates a general procedure for preparing the starting material, imidazolylcarbonyloxy macrolide (3), for compounds of Formula (I). The 2'- and 4"-hydroxyl groups of compound (1) are protected by reacting (1) with suitable hydroxy group protecting reagents (cf. T. W. Greene and P. G. M. Wuts, *Protective Groups in Organic Synthesis*, 2nd ed., John Wiley & Son, Inc., 1991) such as acetic anhydride, benzoic anhydride, benzyl chlorofonnate or a trialkylsilyl chloride in an aprotic solvent, as defined above, which does not adversely affect the reaction, preferably dichloromethane, chloroform, DMF, tetrahydrofuran (TIF), N-methyl pyrrolidinone or a mixture thereof. The protected macrolide (2) is reacted under anhydrous conditions with base such as sodium hydride, lithium hydride, potassium carbonate and followed by carbonyldjimidazole to form compound (3) in an aprotic solvent, as defined above, which does not adversely affect the reaction, preferably dichloromethane, chloroform, DMF, tetrahydrofuran (AHF), N-methyl pyrrolidinone or a mixture thereof. The reaction may require cooling or heating, depending on the conditions used. The reaction temperature may be from −20° C. to 70° C., and preferably from 0° C. to room temperature. The reaction may require 0.5 hours to 10 days, and preferably 1–5 days, to complete.

Scheme 2
Preparation of starting materials, 12-imidazolylcarbonyloxy macrolide (6), for compounds of Formula (II)

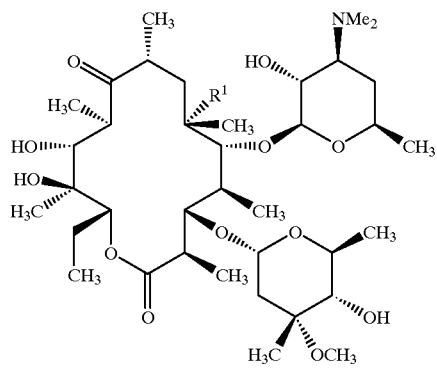

(1)
$R^1$ is as described for formula II

H⁺

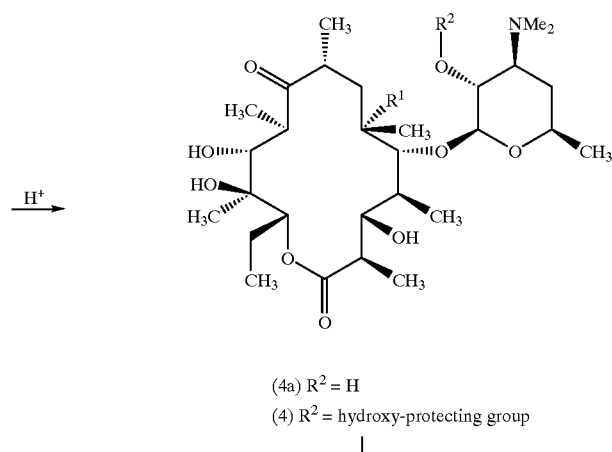

(4a) $R^2$ = H
(4) $R^2$ = hydroxy-protecting group

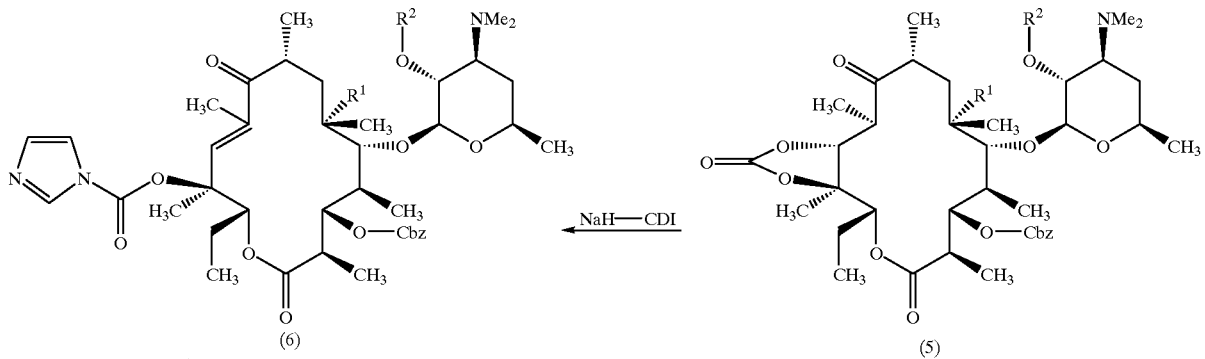

(6)
R[1] is as described for formula II
R[2] is a hydroxy-protecting group (5)
R[2] is a hydroxy-protecting group Scheme 2 illustrates a general procedure for preparing the starting materials, 12-imidazolylcarbonyloxy macrolide (6), for the preparations of compounds of Formula (II). The cladinose moiety of macrolides of formula (1) is removed either by mild aqueous acid hydrolysis or by enzymatic hydrolysis. In accordance with Scheme 2, a suspension of (1) in a solution of protogenic organic solvent (for example methanol, ethanol, isopropanol or butanol) and water is treated with dilute hydrochloric acid, chloroacetic acid, dichloroacetic acid or trifluoroacetic acid for 0.5 to 24 hours. The reaction temperature is preferably -10 to 35° C. to give the des-cladinose compounds (4a). The 2'-hydroxy group of (4a) is protected and converted to (4a) by treatment with a suitable hydroxy protecting reagent (cf. T. W. Greene and P. G. M. Wuts, *Protective Groups in Organic Synthesis*, 2nd ed., John Wiley & Son, Inc., 1991) such as acetic anhydride, benzoyl anhydride, benzyl chloroformate or trialkylsilyl chloride in an aprotic solvent, as defined above, preferably dichloromethane, chloroform, DMF, tetrahydrofuran (THF), N-nmethyl pyrrolidinone or a mixture thereof. The protected macrolide (4) is reacted under anhydrous conditions with base such as sodium hydride, lithium hydride, potassium carbonate or dimethylaminopyridine and followed by phosgene, diphosgene, triphosgene or benzyl chloroformate in an aprotic solvent, as defined above. The reactive intermediate is then trapped with benzyl alcohol to give compound (5). Compound (5) is reacted under anhydrous conditions with NaH and CDI in an aprotic solvent, preferably THF, DMF or a mixture thereof. The reaction may require cooling of heating, depending upon the conditions used. The reaction temperature may be from −20° C. to 70° C., and preferably from 0° C. to room temperature. The reaction may require 0.5 hours to 10 days, and preferably 1–5 days, to complete.

Scheme 3
Preparation of starting materials,
12-imidazolylcarbonyloxy macrolides, for compounds of Formula (III)

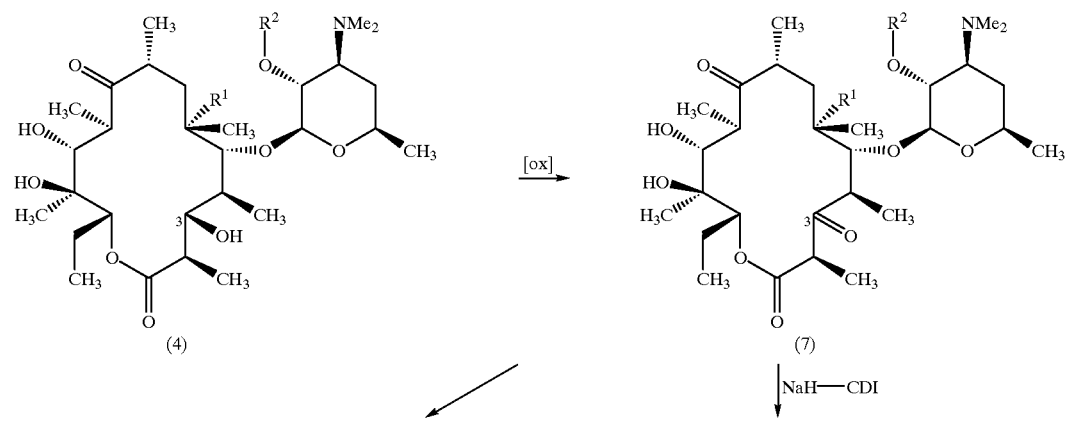

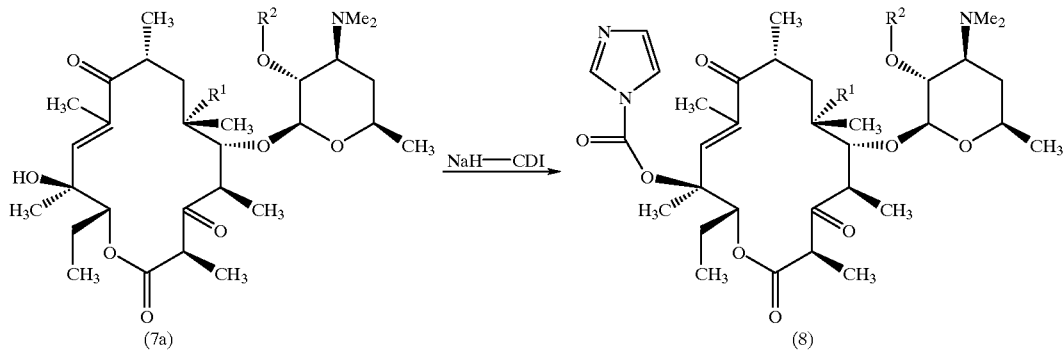

$R^1$ is as described for formula III
$R^2$ is a hydroxy-protecting group

Scheme 3 illustrates two general procedures for the synthesis of 12-imidazolylcarbonyloxy macrolide (8), starting materials for the preparation of compounds of Formula (III). In accordance with scheme 3, the 3-hydroxy group of a 2'-protected des-cladinose macrolide (4) is oxidized to the corresponding 3-oxo compound (7) using a modified Swern oxidation procedure. In scheme 3, suitable oxidizing agents are N-chlorosuccimmide-dimethyl sulfide or carbodilmide-dimethylsulfoxide. In a typical example, (4) is added into a preformed N-chlorosuccinimide and dimethyl sulfide complex in a chlorinated solvent such as methylene chloride at −10 to 25° C. After being stirred for 0.5–4 hours, a tertiary amine such as triethylamine or Hunig's base is added to produce the oxidized compound (7).

In the first approach in scheme 3, (7) is reacted with sodium hydride or lithium hydride and CDI under anhydrous conditions in an aprotic solvent, as defmed above, which does not adversely affect the reaction, preferably dichloromethane, chloroform, DMF, tetrahydrofuran (THF), N-methyl pyrrolidinone or a mixture thereof. The resulting alkoxide is then reacted with excess carbonyldiimidazole for 0.5 hours to 10 days in the same reaction mixture to produce (8). The preferred temperature is from −10° C. to room temperature.

In the second approach in Scheme 3, (7) is converted to (7a) with sodium hydride or lithium hydride and phosgene, diphosgene or triphosgene under anhydrous conditions followed by aqueous work up. Alternatively, (7) is converted to its corresponding 11-mesylate by reacting (7) with methanesulfonic anhydride in pyridine. The 1 I-mesylate is then converted to (7a) with an amino base such as DBU or dimethylarninopyridine in acetone or acetonitrile. (7a) is then reacted with sodium hydride or lithium hydride under anhydrous conditions in an aprotic solvent, as defined above, which does not adversely affect the reaction, preferably dichloromethane, chloroform, DMF, tetrahydrofuran (THF), N-methyl pyrrolidinone or a mixture thereof. The reactive alkoxide is then reacted with carbonyldiimidazole for 0.5 hours to 10 days in the same reaction mixture to produce (8). The preferred temperature is from −10° C. to room temperature.

Scheme 4
Preparation of 12-imidazolylcarbonyloxy
macrolides (10) for compounds of Formula (IV)

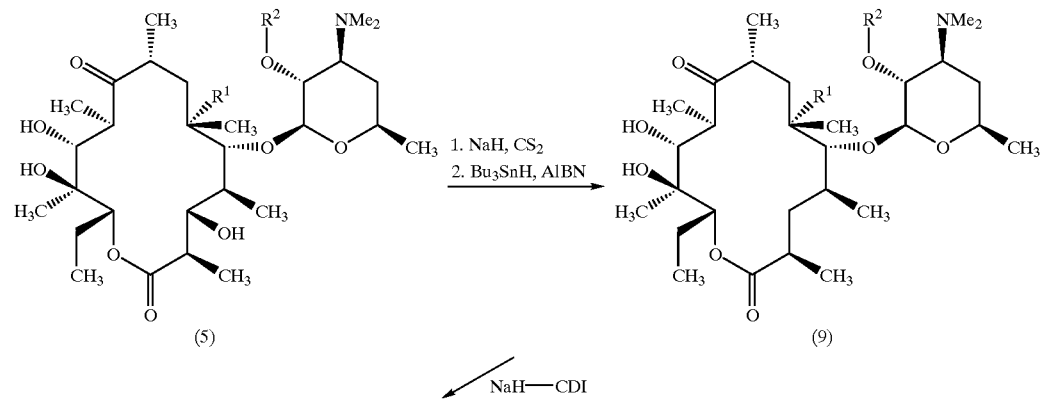

-continued

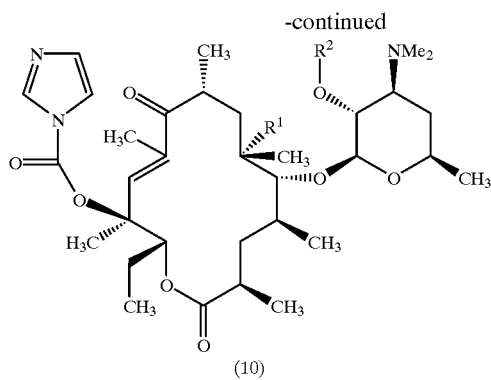

(10)

R[1] is as described for formula III
R[2] is a hydroxy-protecting group

In accordance with Scheme 4, a protected descladinose compound of formula (5) is dissolved in an aprotic solvent such as THF, then reacted with an excess of NaH at from 0° C. to −30° C. under an inert atmosphere, followed by reaction of the intermediate anion with $CS_2$, then $CH_3I$ at −5 to 10° C., to form a 3-O-xanthyl compound. This xanthate intermediate is then reacted with 1.1–1.3 equivalents of Bu3SnH under an inert atmosphere in the presence of a catalytic amount of AIBN in a solvent suitable for a free radical reaction, such as benzene or toluene, for example, at reflux conditions to afford the desired compound (9). Compounds (9) are then reacted with carbonyldiimidazole and NaH under anhydrous conditions in an aprotic solvent, as defined above, which does not adversely affect the reaction, preferably dichloromethane, chloroform, DMF, tetrahydrofuran (THF), N-methyl pyrrolidinone or a mixture thereof, at a temperature from 0° C. to room temperature for 0.5 hours to 10 days to provide the compounds of formula (10).

Scheme 5
Preparation of compounds of Formula (I)

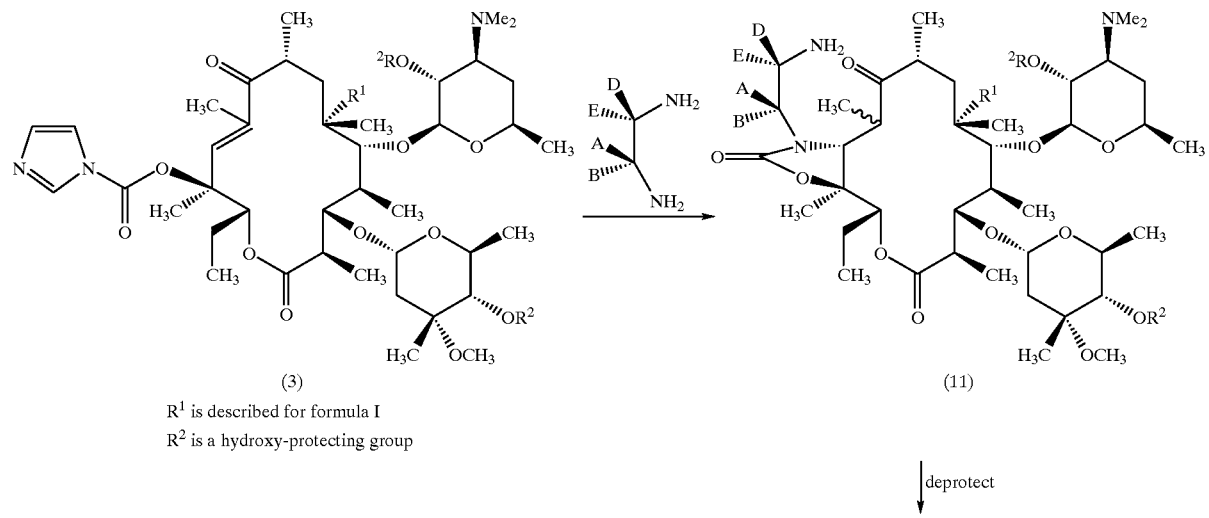

(3)
R[1] is described for formula I
R[2] is a hydroxy-protecting group (11)

↓ deprotect

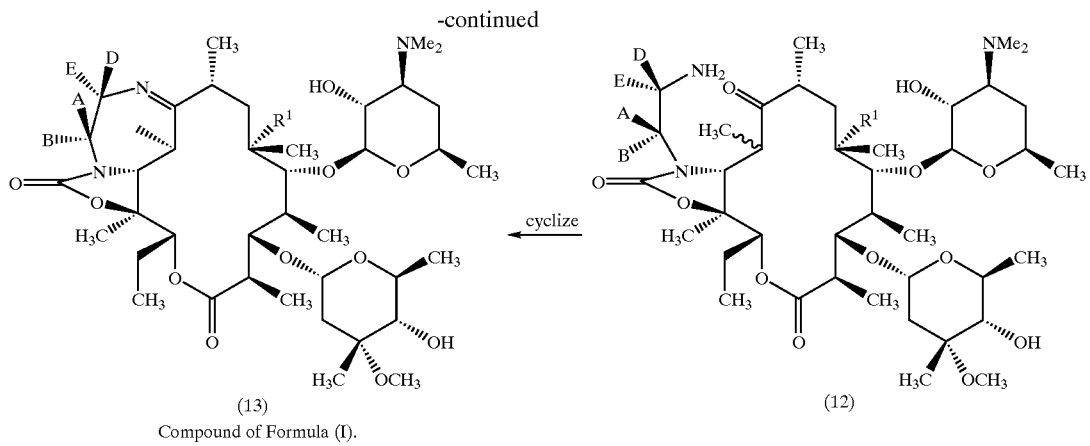

Compound of Formula (I).

In accordance with Scheme 5, a starting material compound of formula (3) is reacted with a diamiine compound having substituents A, B, D and E as defined above but with C2 or Cs symmetry or A=B=H, in a suitable solvent, such as for example, aqueous acetonitrile, DMF or aqueous DMF, to give the bicyclic compound of formula (11). The 2' and 4" hydroxy prote c ting group of compound (1) are then removed by standard methods (cf T. W. Greene and P. G. M. Wuts, *Protective Groups in Organic Synthesis*, 2nd ed., John Wiley & Son, Inc., 1991) to give (12). When $OR^2$ is an ester, for example, such as acetate or benzoate, the compound may be deprotected by treatment with methanol or ethanol. When $R^2$ is a trialkylsilyl group, the compound may be deprotected by treatment with fluoride in THF or acetonitrile, for example. Compound (12) is then cyclized by treatment with dilute acid, such as acetic acid or HCl, for example, in a suitable organic solvent, such as methanol, ethanol or propanol, for example, for a period of from 4 hours to 10 days, from room temperature to reflux, in order to prepare the compound of formula (13).

Scheme 6
Alternate Preparation of compounds of Formula (I)

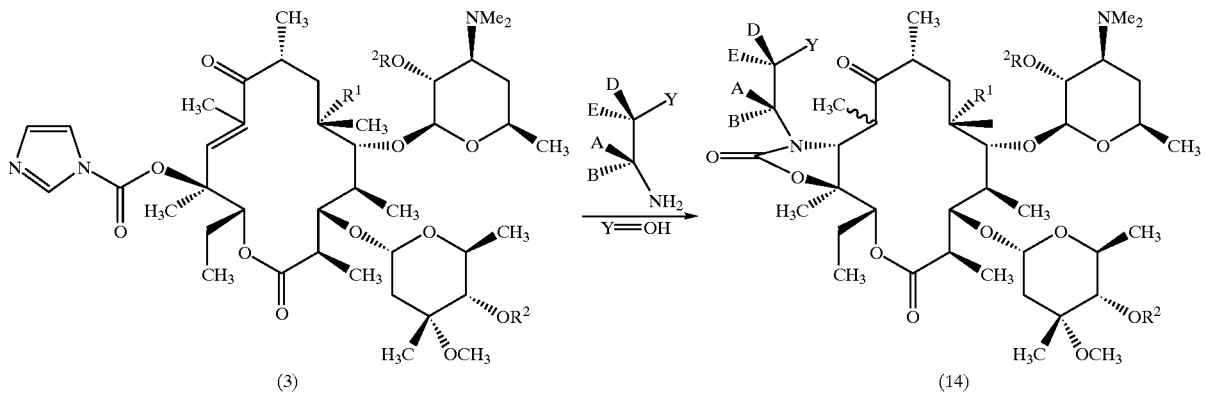

$R^1$ is as described for formula I
$R^2$ is a hydroxy-protecting group

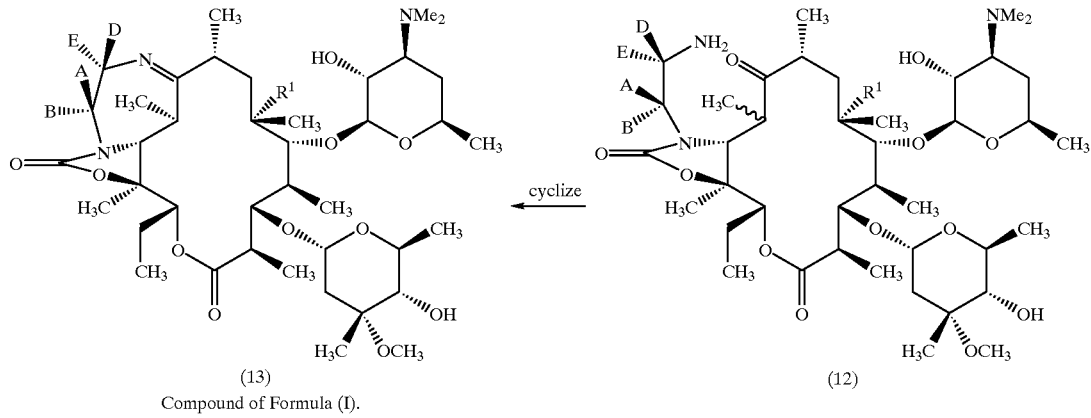

Compound of Formula (I).

Scheme 6 illustrates an alternative preparation of compounds of Formula (I). Starting material (3) is reacted with a beta-aminoalcohol (Y=OH) having substituents A, B, D and E, as defined above, in a suitable solvent system such as aqueous acetonitrile, DMF or aqueous DMF at 0–70° C. to give compound (14) where Y=OH. The azido intermediate, compound (14) Y=N$_3$, is prepared by Mitsunobu reaction by reacting compound (14) Y=OH with triphenylphosphine and diphenylphosphoryl azide-DEAD in tetrahydrofuran. Compound (14) is then deprotected by standard methods (cf. T. W. Greene and P. G. M. Wuts, *Protective Groups in Organic Synthesis*. 2nd ed., John Wiley & Son, Inc., 1991). When OR$^2$ is an ester, for example, such as acetate or benzoate, the compound may be deprotected by treatment with methanol or ethanol. When R$^2$ is a trialkylsilyl group, the compound may be deprotected by treatment with fluoride in THF or acetonitrile, for example. The azido intermediate, compound (14) Y=N$_3$, is then reduced to the amino compound (12). Suitable reducing reagents are triphenylphosphine-water, hydrogen with a catalyst, sodium borohydride, or dialkylaluminum hydride. Compound (12) is then cyclized by treatment with dilute acid, such as acetic acid or HCl, for example, in a suitable organic solvent, such as methanol, ethanol or propanol, for example, for a period of from 4 hours to 10 days, in order to prepare the compound of formula (13).

Alternatively in scheme 6, the hydroxy group (Y=OH) in (14) is activated by treatment with sulfonyl chloride, alkyl or aryl sulfonic anhydride or trifluoromethanesufonic anhydride in an aprotic solvent (e.g., diethyl ether, dichloromethane, tetrahydrofuran, chloroform, pyridine or a mixture thereof). The reaction requires cooling or heating, depending on the conditions used. The reaction temperature is preferably –100 to 10° C. The reaction may require 20 minutes to 24 hours to complete. The activated hydroxy group in (14) (e.g., Y=—OSO$_2$CF$_3$) is then converted to the corresponding azide (Y=N$_3$, 14) by reacting with lithium azide or sodium azide in the same solvent described above. The reaction temperature is preferably 0–100° C. The azido compound is then converted to (13) according to the procedures described above.

Scheme 7
Preparation of compounds of Formula (II)

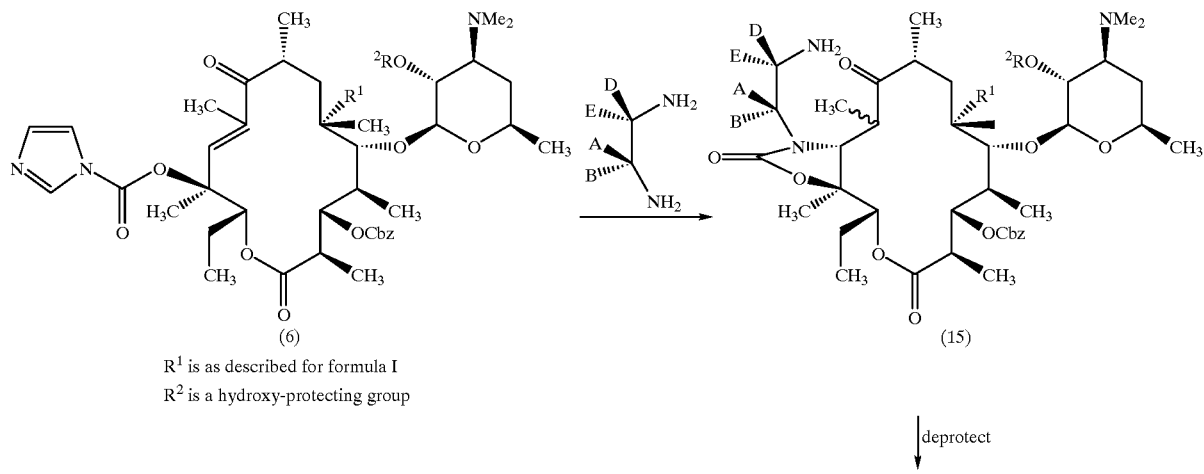

R$^1$ is as described for formula I
R$^2$ is a hydroxy-protecting group deprotect

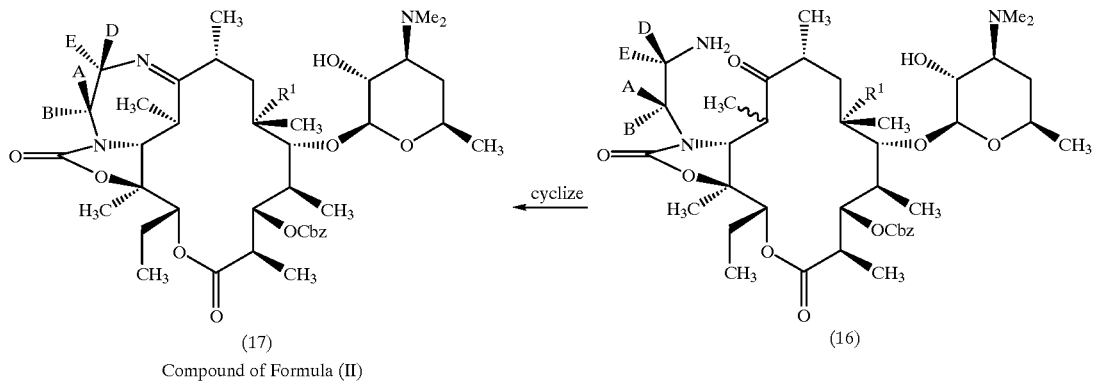

In accordance with Scheme 7, a starting material compound (6) is reacted with a diamine compound having substituents A, B, D and E as defined above but with C2 or Cs symmetry or A=B=H, in a suitable solvent, such as for example, aqueous acetonitrile, DMF or aqueous DMF, to give the bicyclic compound of formula (15). Compound (15) is then deprotected to prepare the compound of formula (16). The deprotection is accomplished by standard methods described (cf. T. W. Greene and P. G. M. Wuts, *Protective Groups in Organic Synthesis*, 2nd ed., John Wiley & Son, Inc., 1991). When $OR^2$ is an ester, for example, such as acetate or benzoate, the compound may be deprotected by treatment with methanol or ethanol. When $R^2$ is a trialkyl-silyl group, the compound may be deprotected by treatment with fluoride in THF or acetonitrile, for example. Compound (16) is then cyclized by treatment with dilute acid, such as acetic acid or HCl, for example, in a suitable organic solvent, such as ethanol or propanol, for example, for a period of from 4 hours to 10 days, from room temperature to reflux, in order to prepare the compound of formula (17).

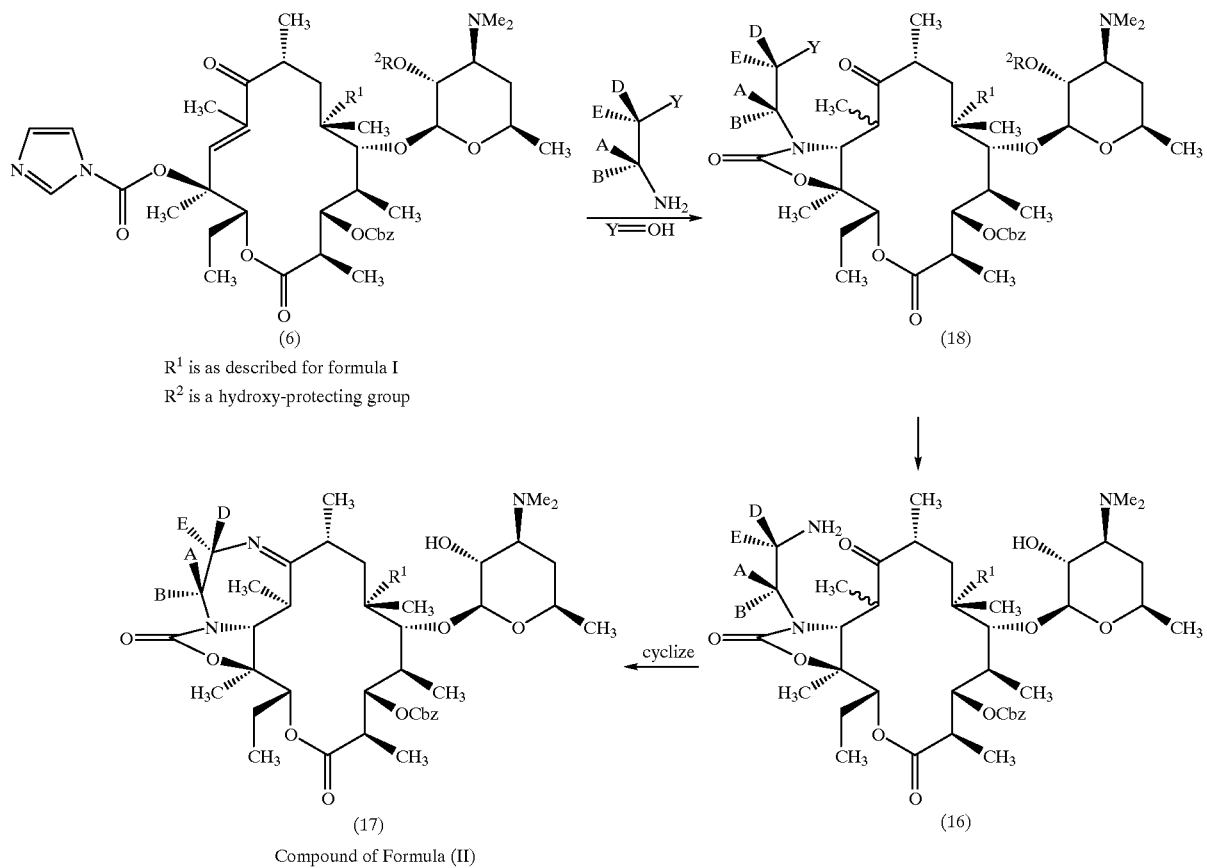

Scheme 8 illustrates an alternative preparation of compounds of Formula (II). Starting material (6) is reacted with a beta-aininoalcohol (Y=OH) having substituents A, B, D and E, as defined above, in a suitable solvent system such as aqueous acetonitrile, DMF or aqueous DMF at 0–70° C. to give compound (18) where Y=OH. The azido intermediate, compound (18) Y=N$_3$, is prepared by Mitsunobu reaction by reacting compound (18) Y=OH with triphenylphosphine and diphenylphosphoryl azide-DEAD in tetrahydrofuran. Compound (18) is then deprotected to prepare the compound of formula (16) wherein R$^2$ is H. The deprotection is accomplished by standard methods (cf. T. W. Greene and P. G. M. Wuts, *Protective Groups in Organic Synthesis*, 2nd ed., John Wiley & Son, Inc., 1991). When OR$^2$ is an ester, for example, such as acetate or benzoate, the compound may be deprotected by treatment with methanol or ethanol. When R$^2$ is a trialkylsilyl group, the compound may be deprotected by treatment with fluoride in THF or acetonitrile, for example. The azido intermediate, compound (18) Y=N$_3$, is then reduced to the amino compound (16). Suitable reducing reagents are triphenylphosphine-water, hydrogen with a catalyst, sodium borohydride, or dialkylaluminum hydride. Compound (16) is then cyclized by treatment with dilute acid, such as acetic acid or HCl, for example, in a suitable organic solvent, such as methanol, ethanol or propanol, for example, for a period of from 4 hours to 10 days, from room temperature to reflux, in order to prepare the compound of formula (17).

Alternatively in scheme 8, the hydroxy group (Y=OH) in (18) is activated by treatment with sulfonyl chloride, alkyl or aryl sulfonic anhydride or trifluoromethanesufonic anhydride in an aprotic solvent (e.g., diethyl ether, dichloromethane, tetrahydrofuran, chloroform, pyridine or a mixture thereof. The reaction requires cooling or heating, depending on the conditions used. The reaction temperature is preferably –100 to 10° C. The reaction may require 20 minutes to 24 hours to complete. The activated hydroxy group in (18) (e.g., Y=—OSO$_2$CF$_3$) is then converted to the corresponding azide (Y=N$_3$, 18) by reacting with lithium azide or sodium azide in the same solvent described above. The reaction temperature is preferably 0–100° C. The azido compound is then converted to (13) according to the procedures described above.

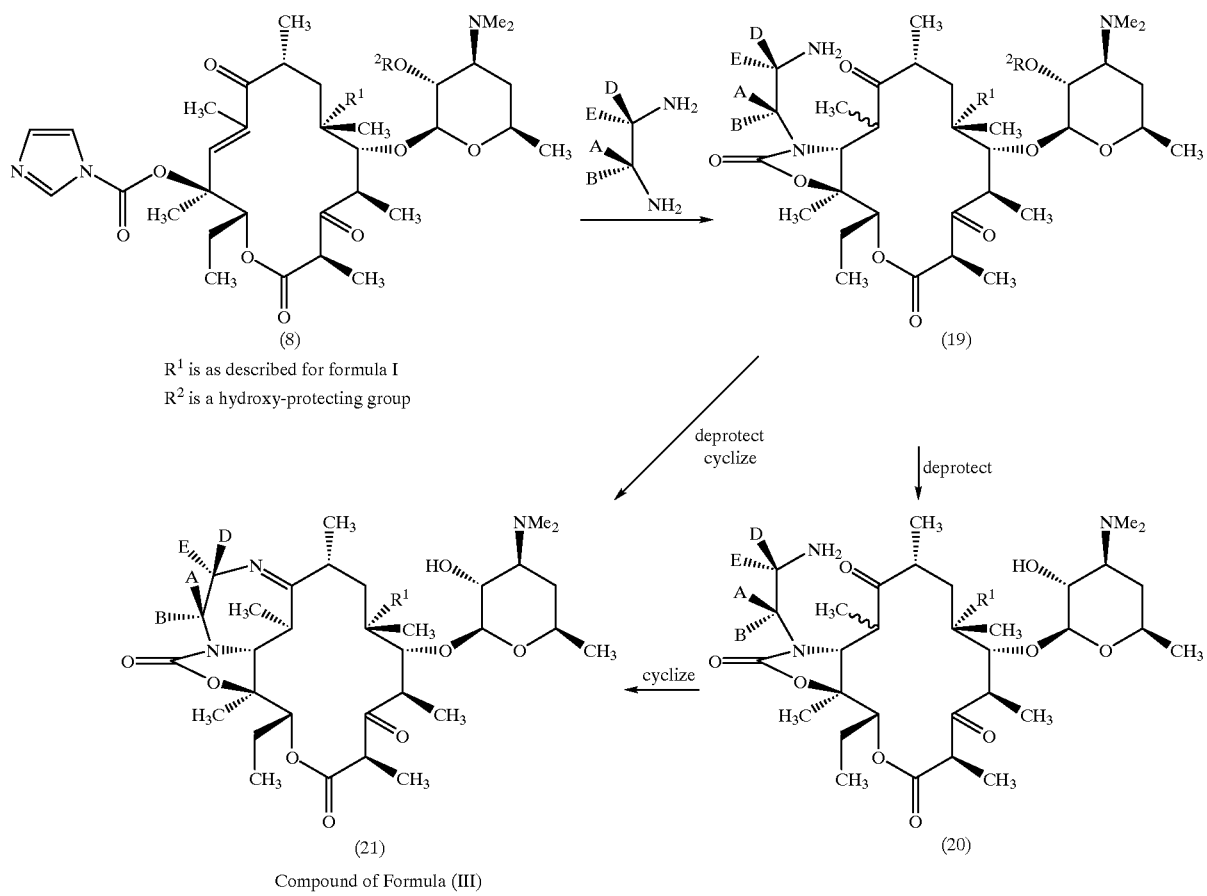

Scheme 9
Preparation of compounds of Formula (III)

In accordance with Scheme 9, a starting material compound(8) is reacted with a dia uidne compound having substituents A, B. D and E as defned above but with C2 or Cs a symmetry or A=B=H, in a suitable solvent, such as for example, aqueous acetonitrile, Dc F or aqueous Duc , to give the bicyclic compound of forrmpula (19). Compound (19) is then deprotected prepare the compound of formula (20). The deprotection is accomplished by standard methods (cf. T. W. Greene and P. G. M. Wuts, *Protective Groups in Organic Synthesis*, 2nd ed., John Wiley & Son, Inc., 1991). When OR² is an ester, for example, such as acetate or benzoate, the compound may be deprotected by treatment with methanol or ethanol. When R² is a trialkylsilyl group, the compound may be deprotected by treatment with fluoride in THF or acetonitrlle, for example. Compound (20) is then cyclized by treatment with dilute acid, such as acetic acid or HCl, for example, in a suitable organic solvent, such as ethanol Or propanol, for example, for a period of from 4 hours to 10 days, from room temperature to reflux, in order to prepare the compound of formula (21). Alternately, as is readily apparent to those skilled in the art it is possible to cyclize compound (19) first, then deprotect, to obtain the compound (21).

may be deprotected by treatment with fluoride in THF or acetonitrile, for example. The deprotected azido intermediate, compound (22) Y=N₃, is then reduced to the amino compound (20). Suitable reducing reagents are triphenylphosphine-water, hydrogen with a catalyst, sodium borohydride, or dialkylaluminum hydride. Compound (20) is then cyclized by treatment with dilute acid, such as acetic acid or HCl, for example, in a suitable organic solvent, such as methanol, ethanol or propanol, for example, for a period of from 4 hours to 10 days, from room temperature to reflux, in order to prepare the compound of formula (21).

Scheme 10
Alternate Preparation of compounds of Formula (III)

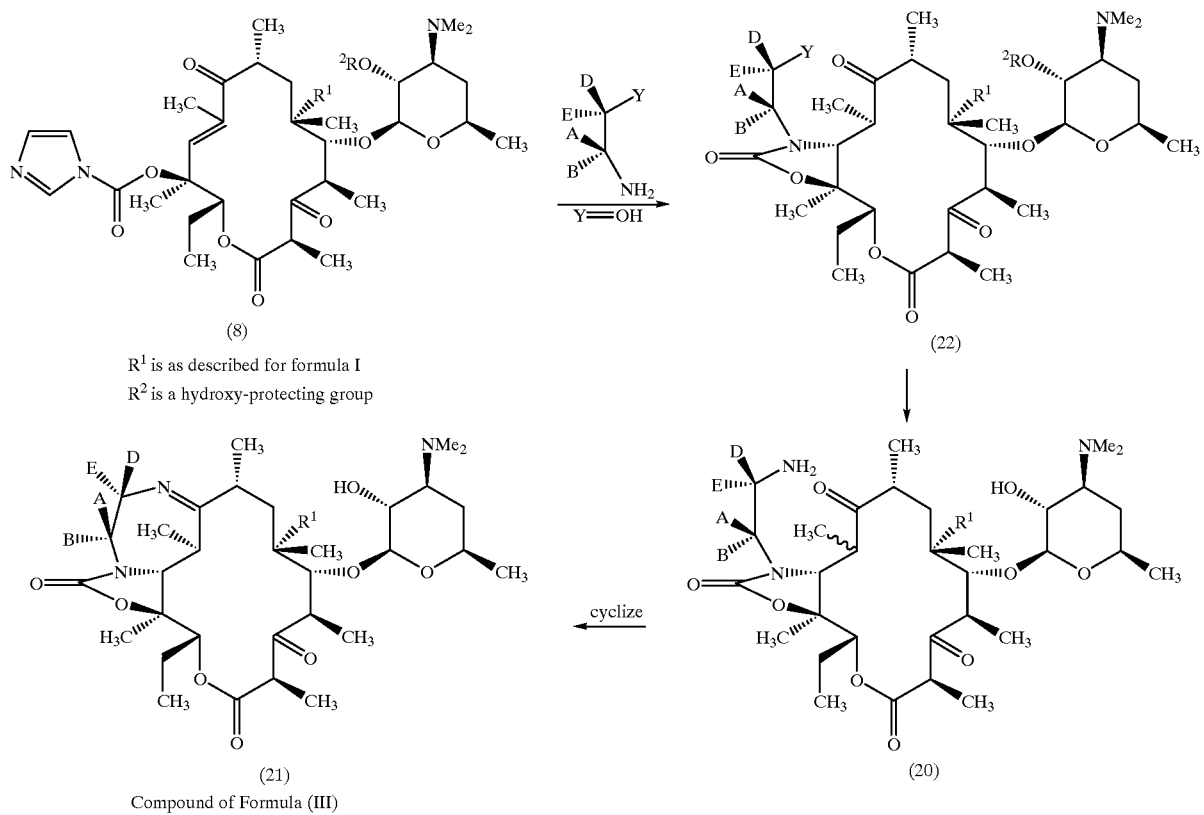

Scheme 10 illustrates an alternative preparation of compounds of Formula (III). Starting material (8) is reacted with a beta-antinoalcohol (Y=OH) having substituents A, B. D and E in a suitable solvent system such as aqueous acetonitrile, DMF or aqueous DMF at 0–70° C. to give compound (22) where Y=OH. The azido intermediate, compound (22) Y=N₃, is prepared by Mitsunobu reaction by reacting compound (22) Y=OH with triphenylphosphine and diphenylphosphoryl azide-DEAD in tetrahydrofuran. Compound (22) is then deprotected by standard methods (cf. T. W. Greene and P. G. M. Wuts, *Protective Groups in Organic Synthesis*, 2nd ed., John Wiley & Son, Inc., 1991). When OR² is an ester, for example, such as acetate or benzoate, the compound may be deprotected by treatment with methanol or ethanol. When R² is a trialkylsilyl group, the compound Alternatively in scheme 10, the hydroxy group (Y=OH) in (22) is activated by treatment with sulfonyl chloride, alkyl or aryl sulfonic anhydride or trifluoromethanesufonic anhydride in an aprotic solvent (e.g., diethyl ether, dichloromethane, tetrahydrofuran, chloroform, pyridine or a mixture thereof. The reaction requires cooling or heating, depending on the conditions used. The reaction temperature is preferably –100 to 10° C. The reaction may require 20 minutes to 24 hours to complete. The activated hydroxy group in (22) (e.g., Y=—OSO₂CF₃) is then converted to the corresponding azide (Y=N₃, 14) by reacting with lithium azide or sodium azide in the same solvent described above. The reaction temperature is preferably 0–100° C. The azido compound is then converted to (13) according to the procedures described above.

Scheme 11
Preparation of compounds of Formula (IV)

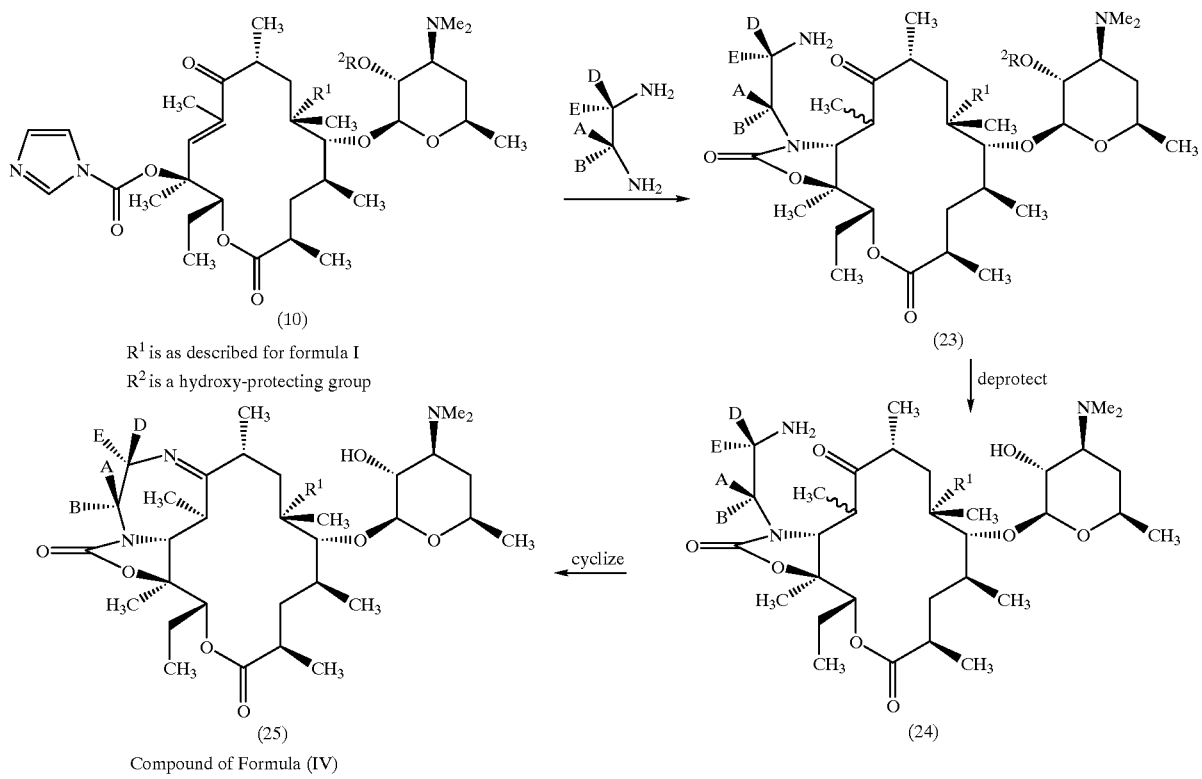

$R^1$ is as described for formula I
$R^2$ is a hydroxy-protecting group

Compound of Formula (IV)

In accordance with Scheme 11, a staring material compound (10) is reacted with a diamine compound having substituents A, B, D and E as defined above but with C2 or Cs symmetry or A=B=H, in a suitable solvent, such as for example, aqueous acetonitrile, DMF or aqueous DMF, to give the bicyclic compound of formula (23). Compound (23) is then deprotected to prepare the compound of formula (24) by standard methods (cf. T. W. Greene and P. G. M. Wuts, *Protective Groups in Organic Synthesis*, 2nd ed., John Wiley & Son, Inc., 1991). When $OR^2$ is an ester, for example, such as acetate or benzoate, the compound may be deprotected by treatment with methanol or ethanol. When $R^2$ is a trialkyl-silyl group, the compound may be deprotected by treatment with fluoride in ThF or acetonitrile, for example. Compound (24) is then cyclized by treatment with dilute acid, such as acetic acid or HCl, for example, in a suitable organic solvent, such as ethanol or propanol, for example, for a period of from 4 hours to 10 days, from room temperature to reflux, in order to prepare the compound of formula (25).

Scheme 12
Alternate Preparation of compounds of Formula (IV)

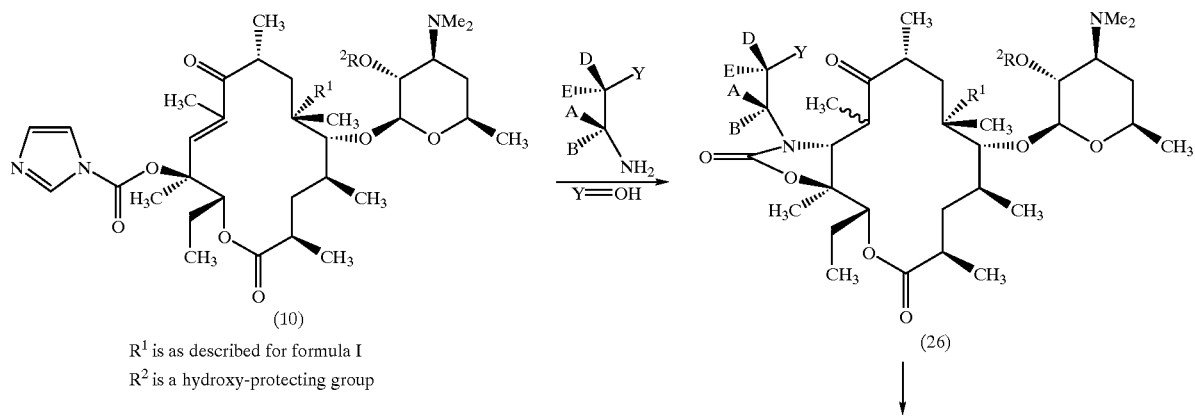

$R^1$ is as described for formula I
$R^2$ is a hydroxy-protecting group

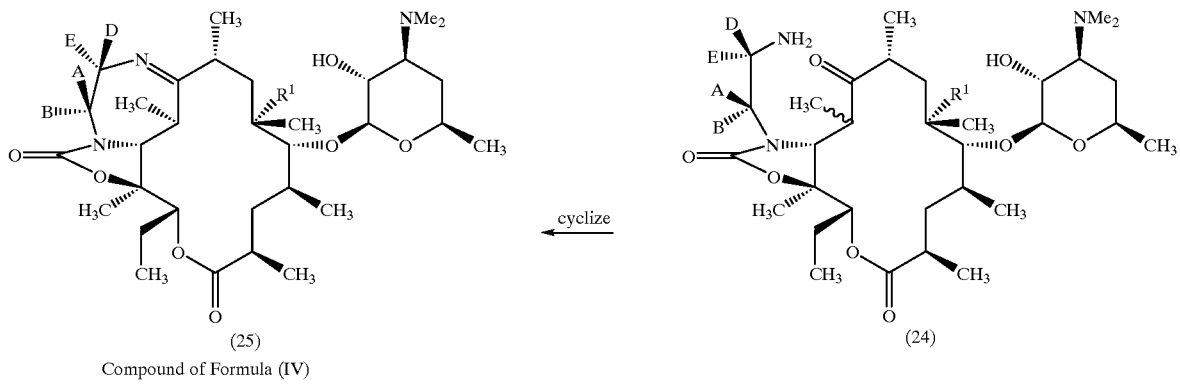

(25)  (24)
Compound of Formula (IV)   cyclize

Scheme 12 illustrates an alternative preparation of compounds of Formula (IV). Starting material (10) is reacted with an beta-aminoalcohol (Y=OH) having substituents A, B, D and E, as defined above, in a suitable solvent system such as aqueous acetonitrile, DMF or aqueous DMF at 0–70° C. to give compound (26) where Y=OH. The azido intermediate, compound (26) Y=$N_3$, is prepared by Mitsunobu reaction by reacting compound (26) Y=OH with diphenylphosphoryl azide-DEAD in tetrahydrofuran. Compound (26) is then deprotected by standard methods (cf. T. W. Greene and P. G. M. Wuts, *Protective Grous in Organic Synthesis*, 2nd ed., John Wiley & Son, Inc., 199 1). When $OR^2$ is an ester, for example, such as acetate or benzoate, the compound may be deprotected by treatment with methanol or ethanol. When $R^2$ is a trialkylsilyl group, the compound may be deprotected by treatment with fluoride in THF or acetonitrile, for example. The deprotected azido intermediate, compound (26) Y=$N_3$, is then reduced to the amino compound (24). Suitable reducing reagents are triphenylphosphine-water, hydrogen with a catalyst, sodium borohydride, or dialkylaluminum hydride. Compound (24) is then cyclized by treatment with dilute acid, such as acetic acid or HCl, for example, in a suitable organic solvent, such as methanol, ethanol or propanol, for example, for a period of from 4 hours to 10 days, in order to prepare the compound of formula (25).

Alternatively in Scheme 12, the hydroxy group (Y=OH) in (26) is activated by treatment with sulfonyl chloride, alkyl or aryl sulfonic anhydride or trifluoromethanesufonic anhydride in a solvent does not adversely affect the reaction (e.g., diethyl ether, dichioromethane, tetrahydrofliran, chloroform, pyridine or a mixture thereof. The reaction requires cooling or heating, depending on the conditions used. The reaction temperature is preferably –100 to 10° C. The reaction may require 20 minutes to 24 hours to complete. The activated hydroxy group in (26) (e.g., Y=—$OSO_2CF_3$) is then converted to the corresponding azide (Y=$N_3$, 26) by reacting with lithium azide in the same solvent described above. The reaction temp)erature is preferably 0–70° C. The azido compound may be deprotected and converted to (25) according to the procedures described above.

Scheme 13
Preparation of reagent diamine compounds

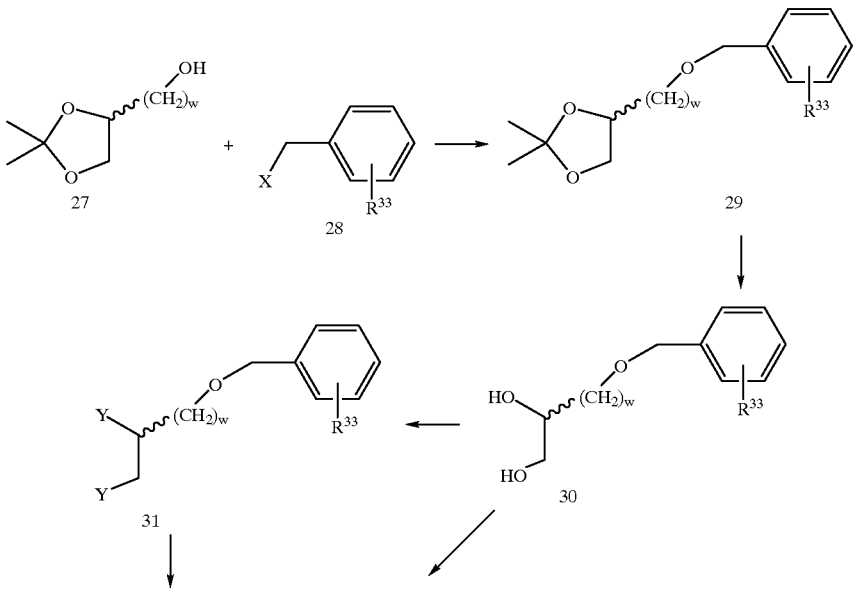

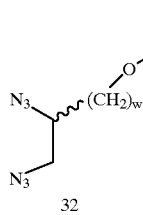
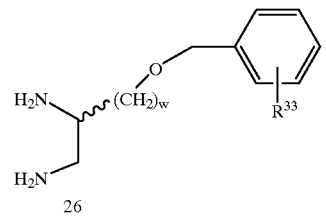

In Scheme 13 is described the preparation of diamnre compounds (26), wherein D or E is a substituted benzyloxymethyl, which may be used as reagents in Schemes, 5, 7, 9 and 11 above. These compounds may have substituents at positions D or E in accordance with the chirality of the starting material (27). Compound (27), wherein m is 1 or 2, is reacted with a compound (28), wherein X is a halogen and $R^{33}$ represents one of more substituents such as F, Cl, Br, I, OH, $NO_2$, CN, C(O)—$C_1$-$C_6$-alkyl, C(O)-aryl, C(O)-heteroaryl, $CO_2$-alkyl, $CO_2$-aryl, $CO_2$-heteroaryl, $CONH_2$, CONH—$C_1$-$C_6$-alkyl, CONH-aryl, CONH-heteroaryl, OC(O)—$C_1$-$C_6$-alkyl, OC(O)-aryl, OC(O)-heteroaryl, OC-alkyl, $OCO_2$-aryl, $OCO_2$-heteroaryl, $OCONH_2$, OCONH—$C_1$-$C_6$-alkyl, OCONH-aryl, OCONH-heteroaryl, NHC(O)—$C_1$-$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$-$C_6$-alkyl, NHCONH-aryl, NHCONH-heteroaryl, $SO_2$-$C_1$-$C_6$-alkyl, $SO_2$-aryl, $SO_2$-heteroaryl, $SO_2NH_2$, $SO_2NH$—$C_1$-$C_6$-alkyl, $SO_2NH$-aryl, $SO_2NH$-heteroaryl, $C_1$-$C_6$-alkyl, $C_3$-$C_6$-cycloalkyl, $CF_3$, $CH_2CF_3$, $CHCl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, $C_1$-$C_6$-alkoxy, methoxymethoxy, methoxyethoxy, amino, benzylamino, arylamino, heteroarylarnino, $C_1$-$C_3$-alkyl-anino, thio, arylthio, heteroarylthio, benzyl-thio, $C_1$-$C_6$-alkyl-thio, or methylthiomethyl, and the like, to give the compound (29). Compounds (27) wherein mr=l are available commercially as pure chiral compounds. Compounds (27) wherein m=2 may be prepared as pure chiral compounds by the method of Saito, et al., Tetrahedron, 48:4067 (1992). Compound (29) is hydrolyzed at room temperature in 2/1 (v/v) THF-10% HCl for about one to about 4 hours to give compound (30). Compound (30) is treated with a sulfonating agent, such as methane sulfonyl chloride or p-toluene sulfonyl chloride, or the like, to give compound (31) wherein Y is a substituted sulfonyl group. Compound (31) is then treated with sodium azide of potassium azide to give compound (32). Alternately, the azido compound (32) may prepared by Mitsunobu reaction by reacting compound (30) with triphenylphosphine and diphenylphosphoryl azide-DEAD in tetrahydrofuiran. Compound (32) is then reduced to the diamino compound (26). Suitable reducing reagents are triphenylphosphine-water, hydrogen with a catalyst, sodium borohydride, or dialkylaluminum hydride.

The compounds and processes of the present invention will be better understood in connection with the following examples, which are intended as an illustration of and not a limitation upon the scope of the invention.

EXAMPLE 1

Compound (IV): $R^1$=methoxy; $R^2$=hydrogen; A=B=D=E=hydrogen 1a. 5-O-desosamyl-6-O-methylerythronolide A A sample of clarithromycin (3-O-cladinosyl-5-O-desosaminyl-6-O-methyl-erythronolide A, Abbott Labs, 142.38 g, 190.35 mmol) was suspended in an ethanol-water solution (1700/600 mL), and 341 mL of 1N HCl was added. The reaction mixture was stirred for 24 hours, and 2 M NaOH (170 mL) and an additional 250 mL of water were added with vigorous stilxing. The precipitate was collected by filtration, washed with water, and dried to afford the title compound (95.00 g, 84%). MS m/z: 590 (M+H)+.

1b. 3-O-xanthyl-5-O-desosaminyl-6-O-methylerythronolide A

To a solution of 5-O-desosaminyl-6-O-methylerythronolide A (11.79 g, 20 mmoL, from step 1a above) in TBF (100 mL) at –20° C. under an inert atmosphere NaH (1.80 g, 60 mmoL, 60% dispersion) was added slowly over a 5 minute period. Several minutes later $CS_2$ (1.2 mL, 20 mmoL) was added. After 5 minutes of stirnng $CH_3I$ (1.24 mL, 20 mmol) was added, the reaction mixture was allowed to gradually wann to –5–0° C., and the mixture was stirred for 1 hour. The reaction mixture was diluted with EtOAc (400 mL), and the mixture was washed with saturated aqueous $NaHCO_3$ and brine, dried ($MgSO_4$), and concentrated to afford the crude product. The residue was purified by chromatography on silica gel, eluting with $CHCl_3$ and $CHCl_3$—MeOH (95:5), to afford the title compound (7.68 g; 56%). MS m/z: 680 (M+H)+. Anal. Calcd. for $C_{32}H_{57}NO_{10}S_2$: C, 56.52; H, 8.45; N, 2.06; Found: C, 56.95; H, 8.65; N, 1.92.

1c. 3-deoxy-5-O-desosaminyl-6-O-methylerythronolide A

A solution of 3-O-xanthyl-5-O-desosaminyl-6-O-methyl erythronolide A (20.00 g; 29.41 mmoL, from step 1b), $Bu_3SnH$ (9.49 mL, 35.29 mmol) and AIBN (~50 mg, catalytic) in benzene (200 mL) was heated at reflux (adding 25 mg portions of AIBN periodically) for 8 hours. The organic layer was separated and washed with 10% aqueous KF and brine, dried ($MgSO_4$), and concentrated to afford the crude product as an oil. The residue was purified by chromatography on silica gel, eluting with $CHCl_3$ and $CHCl_3$—MeOH (97.5:2.5). The material was recrystallizated from hexane to afford the title compound (5.48 g; 32%). MS m/z: 574 (M+H)+. Anal. Calcd. for $C_{30}H_{55}NO_9$: C, 62.80; H, 9.66; N, 2.44; Found: C, 63.02; H, 9.74; N, 2.30.

1d. 2'-O-acetyl-3-deoxy-5-O-desosaminyl-6-O-methylerythronolide A

Samples of 3-deoxy-5-O-desosanrinyl-6-O-methylerythronolide A (573 mg, 1.0 mmol, from Example 1c above), acetic anhydride (0.188 mL) and TEA (0.278 mL) were dissolved in 10 mL of methylene chloride, and the reaction mixture was stirred at room temperature for 20 hours. The reaction mixture was diluted with 40 mL of methylene chloride, and the organic solution was washed with saturated aqueous $NaHCO_3$ and brine, dried and concentrated to obtain the title compound (600 mg). MS m/z: 616 (M+H)+.

1e. Compound (10) from Scheme 4; $R^1$=methoxy; $R^2$=acetyl

A sample of 2'-O-acetyl-3-deoxy-5-O-desosaminyl-6-O-methylerythronolide A (0.63 g, 1.023 mmol, from Example 1d above) was dissolved in 10 mL of THF, and the solution was cooled to −60° C. To this stirred solution was added sodium bis(trimethylsilyl) amide (1.22 mL, 1.0 M in THF). After 4 hours 1,1-carbonyldiimidazole (0.66 g, 4.09 mmol) was added as a solution in 6 mL of 2:3 DMF:THF, and the reaction mixture was slowly warmed to room temperature and stirred for 16 hours. The reaction was quenched by addition of 5% aqueous $NaH_2PO_4$, and the resulting mixture was extracted with chloroform. The organic layer was washed with water, dried over $MgSO_4$ and concentrated to give the title compound. MS m/z: 692 $(M+H)^+$.

1f. Compound (23) from Scheme 11; $R^1$=methoxy; $R^2$=acetyl; A=B=D=E=hydrogen

A sample of the compound from step 1e above (0.25 g, 0.36 mmol) was dissolved in 3 mL of acetonitrile, ethylenediamine (0.24 mL, 3.6 mmol) was added, and the reaction mixture was stirred at room temperature for 3 hours. The solvent was removed under vacuum, and the residue was dissolved in ethyl acetate. This solution was washed with saturated aqueous $NaHCO_3$ solution, dried over $Na_2SO_4$ and concentrated. The residue was twice purified by flash chromatography on silica gel, eluting with 2–20% ethanol in chloroform containing 0.5–2% $NH_4OH$ to give the title compound. MS m/z: 684 $(M+H)^+$.

1g. Compound (24) from Scheme 11; $R^1$=methoxy; A=B=D=E=hydrogen

A sample of the compound from step 1f was dissolved in methanol and stirred at room temperature for 64 hours. The title compound (170 mg) was obtained after filtration and removal of the solvent 1h. Compound (IV); $R^1$=methoxy; $R^2$=hydrogen; A=B=D=E=hydrogen A sample of the compound from step 6b (170 mg, 0.265 mmol) was dissolved in 2 mL of ethanol to which was added 0.03 mL of acetic acid, and the reaction mixture was stirred at room temperature for 16 hours. The solvent was removed, and the residue was suspended in water. The solution was adjusted to approximately pH 10–11 with 2M NaOH, and the mixture was extracted with ethyl acetate. The organic extract was washed with brine, dried over $Na_2SO_4$ and concentrated. The residue was purified by flash chromatography on silica gel, eluting with 10% ethanol in chloroform containing 0.1% $NH_4OH$. The product was re-chromatographed, eluting with 0–15% ethanol in chloroform to give the title compound (55 mg). MS m/z: 624 $(M+H)^+$, 646 $(M+NH_4)^+$. Anal. Calcd. for $C_{33}H_{57}N_3O_8$: C, 63.53; H, 9.20; N, 6.73; Found: C, 64.68; H, 9.27; N, 7.01. $^{13}$CNMR: C=O (16) 156.3, $NCH_2$ (17) 42.4, $NCH_2$ (18) 49.1

EXAMPLE 2

Preparation of Intermediate Starting Material Compound (8) from Scheme 3; $R^1$=methoxy; $R^2$=benzoyl 2a. 5-O-desosaminyl-6-O-methylerythronolide A A sample of clarithromycin (3-O-cladinosyl-5-O-desosaminyl-6-O-methyl-erythronolide A, Abbott Labs, 900 g, 1.2 mole) was suspended in water (10.8 L) and ethanol (4.0 L), and the resulting slurry was stirred at room temperature until homogeneous (about 20 minutes). HCl (1.00 M, 2.16 L) was added over 15 minutes, and the reaction mixture was stirred for 20 hours. NaOH solution (2.00 M, 1.20 L) was added over 30 minutes until pH 10.5–11.0 was reached, and the reaction mixture was stirred for 2 hours. The precipitate was collected and washed with cold water, which was dried under vacuum at 50° C. to afford 601 g of the title compound. MS n/z $(M+H)^+$: 590.

2b. 2'-O-benzoyl-5-O-desosaminyl-6-O-methylerythronolide A

To a solution of 5-O-desosarninyl-6-O-methylerythronolide A, (600 g, 1.01 mol from step 2a above) in methylene chloride (2.0 L) was added 90% technical grade benzoic anhydride (380 g, 1.59 mol). Triethylamine (222 mL, 1.59 mol) was added over 10 niinutes, and the thick solution was stirred for 48 hours. Sodium bicarbonate solution (10%, 1.5 L) was added, and the mixture was stirred for 30 minutes. The layers were separated, and the organic fraction was washed with water (3×600 mL) and brine (600 mL). The organic layer was dried $(Na_2SO_4)$ and filtered, and the volatiles were removed on a rotary evaporator to leave a syrup. Trituration with a warm solution of hexane (2.0 L) and ethyl acetate (100 mL) converted the product to white crystals. The product was filtered, washed with hexane and dried in a vacuum oven overnight at ambient temperature to give the title compound (691 g). MS m/z $(M+H)^+$: 694.

2c. 2'-O-benzoyl-5-O-desosaminyl-3-deoxy-3-oxo-6-O-methylerythronolide A

A sample of N-chlorosuccinimide (57.0 g, 0.42 mol) was slurried in anhydrous methylene chloride (600 mL), and dimethyl sulfide (36.0 ML, 0.49 mol) was added dropwise over 30 minutes. A sample of the compound from step 2b (200.0 g, 0.29 mol) was dissolved in methylene chloride (1.20 L), and this solution was added to the reaction mixture over 45 minutes. After stiring for 30 minutes a solution of triethylamine (40.0 rrL) in methylene chloride (200 mL) was added dropwise over 30 minutes at 0° C. under nitrogen. The resulting solution was washed with sodium bicarbonate (10%, 3×600 mL) and brine (600 mL). The organic fraction was dried $(Na_2SO_4)$ and filtered, and the volatiles were removed on a rotary evaporator to give a thick syrup, which became a solid upon standing. The solid was crushed and dried overnight at ambient temperature in a vacuum oven to give the title compound (196 g). MS m/z $(M+H)^+$: 692.

2d. 2'-O-benzoyl-5-O-desosaminyl-3-deoxy-3-oxo-6-O-methyl-11-O-methanesulfonyl-6-O-methylerythronolide A To a solution of 2'-O-benzoyl-5-O-desosaminyl-3-deoxy-3-oxo-6-O-methylerythronolide A from step 2c above (20.00 g, 28.9 mmole) in pyridine (40 mL) cooled to 0° and held under $N_2$ was added methanesulfonic anhydride (14.6 g, 83.81 mmole), and the reaction was allowed to stir at room temperature for 17 hours. The pyridine was removed under vacuum, and the residue was dissolved in EtOAc (400 mL). This solution was washed with saturated aqueous $NaHCO_3$, $H_2O$ and brine, dried $(MgSO_4)$, decolorized with charcoal, and filtered through a diatomaceous earth filter aid. The solvent was removed under vacuum to afford the crude product (24.46 g). This material was taken directly to the next step without further purification.

2e. 10,11-anhydro-2'-O-benzoyl-5-O-desosaminyl-3-deoxy-3-oxo-6-O-methylerythronolide A The mesylate from step 2d above was dissolved in acetone (70 mL), and DBU (5.22 mL, 34.9 nmuole) added. After stirring at room temperature for 22 hours the acetone was removed under vacuum, EtOAc (250 mL) was added, and the organic layer was washed with 100-mL portions of sat. aq. $NaHCO_3$ (2×), $H_2O$ (1×), and brine (1×). The solution was dried $(MgSO_4)$, decolorized with charcoal and filtered through a diatomaceous earth filter aid. The solvent was removed under vacuum to afford the crude product (18.54 g). This material was purified by chromatography on silica gel, eluting with 40% ethyl acetate/hexanes containing 0.25% concentrated $NH_4OH$. The appropriate fractions were combined and concentrated to give the product MS m/z $(M+H)^+$: 674.

2f. Compound (8) from Scheme 3; R¹=methoxy; R-2=benzoyl

A 500 mL flask was charged with 60% NaH (1.05 g, 26.3 mmole). The NaH was rinsed with 3 portions of hexanes, and dried under a $N_2$ stream. Freshly distilled THF (90 mL) was added, and the solution was cooled to 0° C. under $N_2$. The 10,11-anhydro compound from step 2d above (8.40 g, 12.5 mmol) was then added over a one minute period. After stirring for 15 minutes, a solution of carbonyl diimidazole (5.98 g, 36.9 mole) in 60 mL of THF was added to the reaction mixture via cannula over a period of 15 minutes. After sting for 5 hours, the reaction mixture was quenched with 5% $KH_2PO_4$ solution, and the mixture was stirred at 0° C. for 20 minutes. The mixture was extracted with ethyl acetate. The combined organic extracts were washed with brine, dried over $Na_2SO_4$ and concentrated under reduced pressure. The residue was purified by chromatography on silica gel, eluting with 25%–40% acetone/hexanes. The appropriate fractions were combined and concentrated to give the product. MS m/z (M+H)⁺: 768. ¹H NMR (CDCl₃): 0.90(t, 3H), 0.95(d, 3H), 1.21(d, 3H), 1.27(d, 3H), 1.32(s, 3H), 2.25(s, 6H), 2.78(s, 3H), 2.97(m, 1H), 3.58(m, 1H), 2.63(q, 1H), 4.14(d, 1H), 4.50(d, 1H), 5.00(dd, 1H), 5.65(dd, 1H), 6.75(s, 1H), 7.05(m, 1H), 7.35(m, 1H), 7.43(dd, 2H), 7.54(t, 1H), 8.02(d, 2H), 8.07(s, 1H); ¹³C NMR (CDCl₃): 204.8, 168.8, 165.0, 145.9, 138.4, 138.1, 137.0, 132.7, 130.8, 130.5, 129.7, 128.2, 117.0, 102.1, 84.5, 81.0, 78.5, 76.9, 72.0, 69.2, 63.7, 50.9, 50.2, 47.2, 40.7, 40.3, 38.8, 31.1, 30.8, 22.5, 20.9, 20.7, 20.0, 18.8, 14.8, 14.2, 13.2, 10.4.

EXAMPLE 3

Compound of Formula (III): A, B & E=hydrogen, D=benzyl, R¹=methoxy; R²=hydrogen 3a. 2-(R)-(BOC-amino)-3-phenl-1-propanol To a 5.2 g (23.8 mmole) sample of di-t-butyl dicarbonate in 20 mL of methylene chloride held at 0° C. was added (R)-2-amino-3-phenyl-I-propanol (3.0 g, 19.8 mmole, Aldrich), and the reaction mixture was stirred 1.5 hours at room temperature. The solvent was removed, and the residue was dried under high vacuum and taken directly to the next step.

3b. 2-(R)-(BOC-amino)-1-O-methanesulfonyloxy-3-phenylpropane

The material from step 3a was dissolved in 20 mL of methylene chloride and 5 mL of THF, and the solution was cooled to 0° C. Triethylamine (4.1 mL, 29.4 mmole) was added, then methanesulfonyl chloride (1.9 mL, 24.5 mmole) was added slowly. The mixture was stirred 45 minutes at room temperature, then the solvent was removed under vacuum. The residue was dissolved in ethyl acetate, and the solution was washed with water and brine, dried ($Na_2SO_4$) and filtered. The solvent was removed under vacuum to afford 6.38 g of the title compound. MS m/z (M+H)⁺: 330, MS m/z (M+NH₄)⁺: 347.

3c. 1-azido-2-(R)-MOC-amino)-3-phenylpropane

The compound from step 3b above (6.36 g, 193 mmole) was dissolved in 25 mL of DMF, and 2.5 g (38 mmole) of $NaN_3$ was added. The reaction mixture was stirred for 24 hours at 62° C. The solution was cooled to room temperature, then extracted with ethyl acetate. The organic extract was washed with water and brine, dried ($Na_2SO_4$) and filtered. The solvent was removed under vacuum to afford 4.34 g of the title compound. MS m/z (M+H)⁺: 277, MS m/z (M+NH₄)⁺: 294.

3d. 1-azido-2-(R)-amino-3-phenylpropane

The compound from step 3c (4.3 g, 15.6 mmole) was dissolved in 30 mL of 4 N HCl in ethanol, and the reaction mixture was stirred for 1.5 hours at room temperature. The solvent was stripped and chased with ether. The residue was dissolved in water, NaCl was added, and the mixture was extracted with ethyl ether, which was discarded. The aqueous layer was adjusted to pH 12 with $K_2CO_3$, saturated with NaCl, then extracted with $CHCl_3$. The organic extract was washed with brine, dried ($Na_2SO_4$) and filtered. The solvent was removed under vacuum to afford 2.17 g of the title compound. MS m/z (M+H)⁺: 177, MS m/z (M+NH₄)⁺: 194.

3e. 1,2-(R)-diamino-3-phenylpropane

A sample of the compound from step 3d (1.2 g, 6.8 mmole) was hydrogenated (4 atm) in ethanol over 1.2 g of 10% Pd/C for 21.5 hours at room temperature. The mixture was filtered to remove the catalyst, and the solvent was removed to afford the title compound (1.055 g). MS m/z (M+H)⁺: 151, MS m/z (M+NH₄)⁺: 168.

3f. Compound (19) from Scheme 9, A=B=E=H, D=benzyl, R¹=methoxy, R²=benzoyl

Samples of the compound of formula (8) (Scheme 3; R¹=methoxy; R²=benzoyl; from Example 2, 750 mg, 0.98 mmmole) and 1,2-(R)-diamino-3-phenylpropane (from step 3e above, 1.04 g, 6.92 mmole) were dissolved in 4 mL of acetonitrile and 0.5 mL of water. The reaction mnixture was stirred for 24 hours at room temperature. The solvent was removed, and the residue was dissolved in ethyl acetate. The solution was washed with water and brine, dried $Na_2SO_4$), filtered, and the solvent was removed. The residue was purified by chromatography on silica gel, eluting with hexane to 30% acetone in hexane to give 236 mg of the title compound. MS m/z (M+H)⁺: 850.

3g. Compound (20) from Scheme 9, A=B=E=H, D=benzyl, R¹=methoxy, R²=hydrogen

A sample (217 mg, 0.26 mmole) of the compound from step 3f above in 6 mL of methanol was stirred at reflux for 4 hours. The solvent was removed, and the residue was purified by column chromatography on silica gel, eluting with 1.5% methanol in chloroform containing 1% $NH_4OH$ to afford 176 mg of the title compound. MS m/z (M+H)⁺: 746.

3h. Compound of Formula (III): A=B=E=H, D=benzyl, R¹=methoxy, R²=hydrogen

A sample of the compound from step 3g (148 mg, 0.20 mmole) was dissolved in 2.6 mL of ethanol, and of acetic acid (0.026 mL, 0.45 mmole) was added. The reaction mixture was stirred for 24 hours at reflux, then the solvent was removed. The residue was dissolved in ethyl acetate, which was washed with aqueous $K_2CO_3$, water and brine. The solution was dried $Na_2SO_4$), filtered, and the solvent was removed under vacuum to afford 150 mg of product This material was purified by column chromatography on silica gel, eluting with 0.5% to 0.6% methanol in chloroform containing 0.5% $NH_4OH$ to afford 134 mg of the title compound. MS m/z (M+H)⁺: 728. ¹H NMR (CDCl₃): 0.82(t, 3H), 1.02(d, 3H), 1.18(d, 3H), 1.32(s, 3H), 1.35(d, 3H), 1.43(s, 3H), 1.50(m, 1H), 1.87(m, 1H), 2.27(s, 6H), 2.32(s, 3H), 2.56(dd, 1H), 2.66(m, 2H), 3.03(m, 1H), 3.19(dd, 1H), 3.63(s, 1H), 3.75(q, 1H), 3.94(dd, 1H), 4.04(m, 1H), 4.13(d, 1H), 4.28(d, 1H), 4.85(dd, 1H), 7.10–7.35(m, 5H); ¹³C NMR (CDCl₃): 204.0, 177.8, 169.4, 156.0, 138.3, 130.1, 127.9, 126.1, 103.9, 81.4, 79.4, 78.5, 76.4, 70.3, 69.5, 65.9, 59.5, 57.9, 51.2, 48.7, 48.3, 46.5, 42.8, 40.2, 38.5, 36.0, 31.6, 28.2, 22.0, 21.2, 19.6, 19.0, 16.7, 14.4, 14.1, 12.7, 11.0, 10.4.

EXAMPLE 4

Compound of Formula (III): A=B=D=H, E=benzyl, R$^1$=methoxy; R$^2$=hydrogen 4a. 1-azido-2-(S)-amino-3-phenyl-propane Following the procedure of Example 3a, except substituting (S)-2-amino-3-phenyl-1-propanol (Aldrich) for the (R)-2-amino-3-phenyl-1-propanol thereof, and carrying the product forward as in Example 3, steps a–d, the title compound was prepared (1.74 g). MS m/z (M+H)$^+$: 177, MS m/z (M+NH$_4$)$^+$: 194.

4b. 1,2-(S)-diamino-3-phenylpropane

A sample of the compound from step 4a (790 mg, 4.48 mmole) was dissolved in 30 mL of THF and 6 mL of water, triphenylphosphine (5.0 g, 19.1 mmole) was added, and the reaction mixture was stfired for 24 hours at reflux. The solvent was removed, and the residue was dissolved in 2 N HCl. NaCl was added, and the solution was extracted with ethyl ether. The aqueous layer was adjusted to pH 12 with K$_2$CO$_3$, saturated with NaCl, then extracted with GlCl$_3$ and CHCl$_3$ containing 15% isopropanol. The solvent was removed under vacuum to afford 439 mg of the title compound. MS m/z (M+H)$^+$: 151, MS m/z (M+NH$_4$)$^+$: 168.

4c. Compound (19) Scheme 9, A=B=D=H, E=benzyl, R$^1$=methoxy, R$^2$=benzoyl

Samples of the compound of formula (8) (Scheme 3; R$^1$=methoxy; R$^2$=benzoyl; from Example 2,450 mg, 0.59 mmole) and 1,2-(S)-diarnino-3-phenylpropane (from step 4b above, 435 mg, 2.90 mmole) were dissolved in 2 mL of acetonitrile and 0.25 mL of water. The reaction mixture was stirred for 24 hours at room temperature. The solvent was removed, and the residue was dissolved in ethyl acetate. The solution was washed with brine, dried (Na$_2$SO$_4$), filtered, and the solvent was removed. The residue was purified by chromatography on silica gel, eluting with hexane to 25% acetone in hexane to give 405 mg of the title compound. MS m/z (M+H)$^+$: 850.

4d. Compound (20) A=B=D=H, E=benzyl, R$^1$=methoxy, R$^2$=hydrogen

A sample (386 mg, 0.45 mmole) of the compound from step 4c above in 7 mL of methanol was stirred at reflux for 4 hours. The solvent was removed, and the residue was purified by column chromatography on silica gel, eluting with 1.5% methanol in chloroform containing 1% NH$_4$OH to afford 315 mg of the title compound. MS m/z (M+H)$^+$: 746.

4e. Compound of Formula (III): A=B=D=H, E=phenyl, R$^1$=methoxy; R$^2$=hydrogen

Following the procedure of Example 3h, except substituting the (S)-compound (150 mg, 0.20 mmole) from step 4d for the (R)-isomer of 3h, the title compound (136 mg) was prepared. MS m/z (M+H)$^+$: 728. $^1$H NMR (CDCl$_3$): 0.86(t, 3H), 1.08(d, 3H), 1.19(d, 3H), 1.33(s, 3H), 1.39(d, 3H), 1.47(s, 3H), 1.54(m, 1H), 1.92(m, 1H), 2.28(s, 6H), 2.58(s, 3H), 3.19(dd, 1H), 3.52(m, 1H), 3.67(s, 1H), 3.77(q, 1H), 4.12(d, 1H), 4.27(d, 1H), 4.92(dd, 1H), 7.10–7.40(m, 5H); $^{13}$C NMR (CDCl$_3$): 203.7, 176.0, 169.4, 156.5, 139.2, 130.0, 129.7, 128.3, 127.9, 126.3, 126.1, 104.1, 80.9, 80.5, 78.6, 78.1, 70.3, 69.5, 65.9, 62.0, 61.1, 51.2, 49.5, 48.8, 48.6, 45.9, 43.3, 42.9, 41.4, 40.2, 40.0, 35.2, 28.2, 22.2, 21.1, 19.7, 19.4, 17.1, 16.8, 15.3, 14.5, 14.1, 10.4;

EXAMPLE 5

Compound of Formula (III): A=benzyl, B=D=E=H, R$^1$=methoxy, R$^2$=hydrogen

5a. Compound (22) (Scheme 10), A=benzyl; B=D=E=H, R$^1$=methoxy, R$^2$=benzoyl: Y=OH Compound (8) (Scheme 3; R$^1$=methoxy; R$^2$=benzoyl; from Example 2, 450 mg, 0.59 mmole) and (S)-2-amino-3-phenyl-1-propanol (1.97 g, 13.0 mmole, Aldrich) were dissolved in 4.5 mL of acetomitrile and 0.5 mL of water. The reaction mixture was stirred for 7 days at room temperature. The solvent was removed, and the residue was dissolved in ethyl acetate. The solution was washed with 20% aqueous KH$_2$PO$_4$, water and brine, then dried (Na$_2$SO$_4$) and filtered. The solvent was removed, and the residue dried under high vacuum to afford 1.09 g of product This material was purified by chromatography on silica gel, eluting with hexane to 20% acetone in hexane to give 644 mg of the title compound. MS m/z (M+H)$^+$: 851.

5b. Compound (22) (Scheme 10), A=benzyl; B=D=E=H, R$^1$=methoxy, R$^2$=benzoyl: Y=azido A sample of the compound from step 5a above (617 mg, 0.72 mmole) was dissolved in 12mL of THF, and triphenylphosphine (610 mg, 2.33 mmole) was added. This solution was cooled to 0° C., DEAD (0.375 mL, 2.38 mmole) was added dropwise over 3 minutes, and the mixture was stirred for 10 minutes. Next was added DPPA (0.515 mL, 2.37 mmole) dropwise over 3 minutes, and the mixture was stirred for 2 hours at 0° C. and 48 hours at room temperature. The volatiles were removed under vacuum to leave an oily residue. The residue was purified by chromatography on silica gel, eluting with hexane to 30% ethyl acetate in hexane followed by 20% acetone in hexane to afford 321 mg of the title compound. MS m/z (M+H)$^+$: 876.

5c. Compound (22) (Scheme 10), A=benzyl; B=D=E=H, R$^1$=methoxy, R$^2$=hydrogen; Y=azido A sample of the compound from step 5b above (317 mg, 0.36 mmole) was dissolved in 5 mL of methanol, and the mixture was stirred at reflux for 4.5 hours. The solvent was removed, the residue was purified by chromatography on silica gel, eluting with 1:1 acetone in hexane, and the residue was dried under high vacuum to afford 218 mg of the title compound. MS m/z (M+H)$^+$: 772.

5d. Compound (20) (Scheme 10), A=benzyl; B=D=E=H, R$^1$=methoxy, R$^2$=hydrogen

A sample of the compound from step 5c above (208 mg, 0.27 mmole) was dissolved in 3 mL of THF and 0.5 mL of water, triphenylphosphine (425 mg, 1.62 mmole) was added, and the reaction was stirred for 24 hours at reflux. The solvent was removed under vacuum, chased with toluene, and the residue dried under high vacuum. The residue was purified by chromatography on silica gel, eluting with chloroform containing 1.5% methanol and 1% NH$_4$OH to afford 196 mg of the title compound. MS m/z (M+H)$^+$: 746.

5e. Compound of Formula (III): A=benzyl, B=D=E=H, R-methoxy, R$^2$=hydrogen

A sample of the compound from step 5d above (128 mg, 0.17 mmole) was dissolved in 2.3 mL of ethanol and 0.023 mL (0.40 mmole) of acetic acid was added. The reaction mixture was stirred at reflux for 48 hours, and the solvent was removed. The residue was dissolved in ethyl acetate, and the solution was washed with aqueous K$_2$CO$_3$, water and brine. The solution was dried (Na$_2$SO$_4$), filtered, and the solvent was removed iunder vacuum to afford 100 mg of a tan compound. The residue was purified by chromatography on silica gel, eluting with chloroform containing 0.6% methanol and 0.5% NH$_4$OH progressing to chloroform containing 0.7% methanol and 0.5% NH$_4$OH to afford 52 mg of the title compound. MS m/z (M+H)⁺: 728. ¹H NMR (CDCl₃): 0.86(t, 3H), 1.08(d, 3H), 1.34(d, 3H), 1.37(d, 3H), 1.44(s, 3H), 1.52(s, 3H), 1.93(m, 1H), 2.29(s, 6H), 2.48(m, 1H), 2.67(dd, 1H), 2.86(s, 3H), 3.06(dd, 1H), 3.57(m, 1H), 3.74(q, 1H), 3.86(s, 1H), 4.33(d, 1H), 4.39(d, 1H), 4.95(dd, 1H), 7.18–7.40(m, 5H); ¹³C NMR (CDCl₃): 204.4, 169.6, 155.8, 138.0, 129.5, 129.3, 128.6, 128.5, 126.5, 103.8, 81.4, 78.8, 77.3, 70.3, 69.6, 65.9, 57.3, 53.7, 51.2, 50.8, 49.8, 47.4, 42.7, 40.3, 38.5, 35.6, 31.6, 28.2, 22.6, 22.2, 21.2, 20.6, 20.3, 15.4, 14.9, 14.1, 13.4, 11.1, 10.4.

EXAMPLE 6

Compound of Formula (III): B=benzyl, A=D=E=H, R¹=methoxy, R²=hydrogen

Following the procedures of Example 5, except replacing the (S)-2-amino-3-phenyl-1-propanol of step 55a with (R)-2-amino-3-phenyl-1-propanol (1.97 g, 13.0 mmole, Aldrich), and carrying the product forward according to the procedures of steps 5b–5e, the title compound (83 mg) was prepared. MS m/z (M+H)⁺: 728. ¹H NMR (CDCl₃): 0.73(t, 3H), 1.05(d, 3H), 1.24(d, 3H), 1.29(d, 3H), 1.33(s, 3H), 1.37(d, 3H), 1.41(s, 3H), 2.26(s, 6H), 2.44(m, 1H), 2.68(m, 1H), 2.79(s, 3H), 3.18(dd, 1H), 3.46(m, 1H), 3.60(s, 1H), 3.71(dd, 1H), 3.81(q, 1H), 3.94(dd, 1H), 4.30(dd, 1H), 4.72(dd, 1H), 7.10–7.38(m, 5H); ¹³C NMR (CDCl₃): 204.4, 180.7, 169.3, 154.5, 138.4, 128.9, 128.8, 128.6, 128.3, 126.8, 126.2, 125.1, 104.2, 103.7, 81.1, 78.5, 78.3, 78.1, 77.2, 76.2, 70.3, 69.5, 65.8, 65.7, 62.4, 58.1, 53.6, 51.2, 51.0, 49.4, 47.6, 42.9, 40.2, 38.5, 36.7, 36.0, 31.5, 28.2, 25.2, 22.6, 21.6, 21.1, 19.7, 19.3, 16.2, 15.6, 14.6, 14.3, 14.0, 12.6, 11.1, 10.4, 10.2;

EXAMPLE 7

Compound of Formula (III): A=E=phenyl, B=D=H, R¹=methoxy, R²=hydrogen

7a. Compound (19) from Scheme 9; A=E=phenyl, B=D=H, R¹=methoxy, R²=benzoyl

Compound (8) (Scheme 3; R¹=methoxy; R²=benzoyl; from Example 2, 400 mg, 0.52 mmole) and (1S,2S)-1,2-diphenyl-1,2-ethylenediamnine (500 mg, 2.36 mmole, Aldrich) were dissolved in 2 mL of acetonitrile and 0.25 mL of water. The reaction mixture was stirred for 10 days at room temperature. The mixture was diluted with methylene chloride, the solution was dried over NaCl and Na₂SO₄, filtered, and the solvent was removed. The residue (958 mg) was taken directly to the next step. MS (m/z): 666 (M+H)⁺.

7b. Compound (19) from Scheme 9; A=E=phenyl, B=D=H, R¹=methoxy, R²=hydrogen

The compound from step 7a (958 mg) was dissolved in 15 mL of methanol, and the solution was heated at reflux for 24 hours. The solvent was removed, and the residue was purified by column chromatography on silica gel, eluting with 0 to 5% methanol in methylene chloride to afford 340 mg of the title product as the C10-epi-isomer. MS (m/z): 808 (M+H)⁺. ¹H NMR (300 MHz, CDCl₃): d 6.90–7.20 (m, 10H), 5.48 (dd, 1H), 5.04 (d, 1H), 4.27 (d, 1H), 4.23 (d, 2H), 3.93 (q, 1H), 3.76 (d, 1H), 3.62 (d, 1H, H11), 3.52 (m, 2H)3.12–3.22 (m, 4H), 3.07 (s, 3H, OMe), 2.75 (dd, 1H), 2.75 (m, 1H), 2.2–2.5 (m), 2.24 (s, 6H, NMe₂), 1.94 (dq, 2H), 1.59 (s, 3H), 1.46 (d, 3H), 1.29 (d, 3H), 1.22 (d, 3H), 0.90 (t, 3H), 0.84 (d, 3H), 0.73 (d, 3H). ¹³C NMR (75 MHz, CDCl₃): d 214.2, 205.5, 171.0, 156.3, 143.5, 140.5, 128.0, 128.0, 127.9, 127.2, 126.9, 126.8, 104.1, 83.5, 78.8, 78.7, 78.2, 77.4, 77.0, 76.6, 70.2, 69.9, 69.3, 67.6, 65.6, 57.9, 51.7, 50.7, 49.0, 48.5, 41.1, 41.0, 40.1, 28.2, 21.2, 21.1, 21.0, 19.3, 18.0, 16.0, 14.4, 10.5, 9.9.

7c. Compound of Formula (III): A=E=phenyl, B=D=H, R¹=methoxy, R²=hydrogen

Following the procedure of Example 5e, except replacing the compound from 5d with the compound from 7b, the title compound was prepared. MS (m/z): 790 (M+H)⁺. ¹³C NMR (125 MHz, CDCl₃): selected signals: d 203.3, 175.7, 169.5, 156.5, 104.1.

EXAMPLE 8

Compound of Formula (III): A=methyl, B=D=E= hydrogen, R¹=methoxy, R²=hydrogen

8a. Compound (22) from Scheme 10; A=methyl, B=D=E=H, R¹=methoxy, R²=benzoyl, Y=OH Compound (8) (Scheme 3; R¹=methoxy; R²=benzoyl; from Example 2,400 mg, 0.52 mmole) and (S)-2-amino-1-propanol (0.200 mL, 2.6 mnmole, Aldrich) were dissolved in 0.9 mL of acetonitrile, 0.1 lmL of water was added, and the reaction was stirred for 40 hours at room temperature. The solvent was removed, and the residue was dissolved in ethyl acetate. The solution was washed with water and brine, dried (Na₂SO₄), filtered, and the solvent was removed. The residue was purified by chromatography on silica gel, eluting with 20% to 30% acetone in hexane to give 135 mg of the title compound. MS m/z (M+H)⁺: 775.

8b. Compound (22) from Scheme 10; A=methyl, B=D=E=H, R¹=methoxy, R²=benzoyl, Y=azido A sample of the compound from step 8a above (277 mg, 0.362 mmole) was dissolved in 6 mL of THF, and triphenylphosphine (302 mg, 1.15 mmole) was added. This solution was cooled to 0° C., DEAD (0.190 mL, 1.21 mmole) was added dropwise over 3 minutes, and the mixture was stirred for 10 minutes. Next was added DPPA (0.260 mL, 1.21 mmole) dropwise over 3 minutes, and the mixture was stirred for 3 hours at 0° C. and 24 hours at room temperature. The volatiles were removed under vacuum. The residue was purified by chromatography on silica gel, eluting with 15% to 20% acetone in hexane, then rechromatographed on silica gel, eluting with 40% ethyl acetate in hexane to 25% acetone in hexane, to afford 140 mg of the title compound. MS m/z (M+K)⁺: 838.

8c. Compound (22) from Scheme 10; A=methyl, B=D=E=H, R¹=methoxy, R²=hydrogen, Y=azido A sample of the compound from step 8b (133mg, 0.17 mmole) was dissolved in 2 mL of methanol, and the solution was stirred for 4 hours at reflux. The solvent was removed under vacuum, and the residue was dried under high vacuum to give a glassy residue. The residue was purified by chromatography on silica gel, eluting with 1:1 acetone in hexane to 100% acetone to afford the title compound (98 mg). MS m/z (M+H)⁺: 696.

8d. Compound (20) from Scheme 10; A=methyl. B=D=E=H, R¹=methoxy, R²=hydrogen

A sample of the compound from step 8c above (185 mg, 0.27 mmole) was dissolved in 4 mL of THF, and 2 mL of H₂O and triphenylphosphine (425 mg, 1.62 mmole) was added. This solution was stirred at room temperature for 40 hours and at reflux for 24 hours. The volatiles were removed under vacuum. The residue was purified by chromatography on silica gel, eluting with 3% methanol and 1% NH₄OH in chloroform to afford the title compound (128 mg). MS m/z (M+H)⁺: 670.

8e. Compound of Formula (III): A=methyl, B=D=E=H, R¹=methoxy, R²=hydrogen

A sample of the compound from step 8d above (123 mg, 0.18 mmol) was dissolved in 2.6 mL of ethanol and 0.24 mL of acetic acid, the reaction was heated at reflux for 24 hours, then stirred at room temperature for 48 hours. The solvent was removed under vacuum, and the residue was dissolved in ethyl acetate. The solution was washed with 10% aqueous $K_2CO_3$, water and brine, then dried ($Na_2SO_4$) and filtered. The solvent was removed, and residue was dried under high vacuum. The residue was purified by chromatography on silica gel, eluting with 0.5% $NH_4OH$ and 2% to 3% methanol in chloroform to afford the title compound (38 mg). MS m/z (M+H)$^+$: 652. $^1$H NMR (CDCl$_3$): 0.86 (t, 3H), 1.04 (d, 3H), 1.21 (d, 3H), 1.24 (d, 3H), 1.50 (s, 3), 1.87–1.98 (m, 2H), 2.26 (s, 6H), 2.41–2.50 (m, 1H), 2.78 (s, 3H), 3.11–3.23 (m, 3H), 3.51–3.59 (m, 1H), 3.76 (dd, 1H), 3.76 (s, 1H), 3.85 (q, 1H), 3.92 (dd, 1H), 4.31 (d, 1H), 4.37 (d, 1H), 4.90 (dd, 1H); $^{13}$C NMR (CDCl$_3$): 204.3, 181.5, 169.6, 155.6, 103.7, 81.3, 78.6, 77.9, 76.6, 70.3, 69.5, 65.8, 56.5, 53.4, 51.1, 50.6, 47.4, 47.2, 42.6, 40.2, 38.4, 35.5, 28.1, 22.0, 21.2, 20.5, 20.1, 15.8, 15.2, 14.8, 13.2, 10.6, 10.3; High resolution mass spectrum: calculated (M+H)$^+$ m/z for $C_{34}H_{58}N_3O_9$=652.4173; observed (M+H)$^+$m/z=652.4175.

EXAMPLE 9

Compound of Formula (III): B=methyl, A=D=E= hydrogen, R$^1$=methoxy, R$^2$=hydrogen Following the procedures of Example 8, except with a larger amount of the starting compound from Example 2 (1.23 g, 1.6 mmole) and replacing the (S)-2-amino-1-propanol of step 8a with an appropriately larger amount of (R)-2-amino-1-propanol (1.23 mL, 16.2 mmole, Aldrich), carrying the product forward as in steps 8b8e, the title compound was prepared (71 mg). $^1$H NMR (CDCl$_3$): 0.87 (t, 3H), 1.45 (s, 3H), 1.82–2.01 (dd, 2H), 2.26 (s, 6H), 2.37–2.51 (m, 1H), 2.72 (s, 3H), 3.07 (dd, 1H), 3.18 (dd, 1H), 3.22–3.36 (m, 1H), 3.47–3.59 (m, 1H), 3.61 (s, 1H), 3.77–3.91 (m, 2H), 4.25 (d, 1H), 4.29 (d, 1H), 5.01 (dd, 1H); $^{13}$C NMR (CDCl$_3$): 204.1, 180.7, 169.7, 154.7, 103.8, 80.6, 78.9, 78.5, 76.4, 70.3, 69.6, 65.9, 62.3, 56.6, 53.1, 51.1, 49.3, 47.8, 42.8, 40.2, 38.6, 36.5, 34.6, 31.5, 28.2, 25.3, 22.6, 21.9, 21.2, 20.7, 19.6, 19.3, 17.1, 15.8, 14.4, 14.1, 12.9, 11.0, 10.3; MS (M+H)$^+$ m/z=652. High resolution mass spectrum: calculated (M+H)$^+$m/z for $C_{34}H_{58}N_3O_9$=652.4173; observed (M+H)$^+$ m/z=652.4188.

EXAMPLE 10

Compound of Formula (III): A=D=methyl; B=E=H, R$^1$=methoxy, R$^2$=hydrogen 10a. meso-23-bis(methanesulfonyloxy)butane Samples of meso-2,3-butanediol (10 g, 111 mmole, Aldrich) and triethylamine (92.8 mL, 666 mmole) were dissolved in methylene chloride. The solution was cooled to −78° C., and methanesulfonyl chloride (25.8 nL, 333 nimole) was added dropwise. A precipitate formed. The mixture was diluted with additional methylene chloride, and the mixture was stnred for 20 minutes at −78° C. and at 0° C. for 2 hours. The reaction mixture was warmed to room temperature, diluted with additional solvent, and washed with $H_2O$, aqueous $NaHCO_3$ and aqueous NaCl. The organic solution was dried over $MgSO_4$, and the solvent was removed to afford the title compound (25.01 g). $^1$H NMR (300 MHz, CDCl$_3$): d 4.91 (q, 2H), 3.10 (s, 6H), 1.45 (d, 6H).

10b. meso-2,3-diazidobutane

A sample of the compound from step 10a (25 g) was dissolved in 250 mL of DMF, and NaN$_3$ (40 g) was added. The mixture was stirred vigorously at 85° C. for 24 hours, then cooled to room temperature. The mixture was diluted with 800 mL of ether, washed with $H_2O$, aqueous $NaHCO_3$ and aqueous NaCl, then dried over $MgSO_4$. The solution was filtered and concentrated to afford the title compound (13.00 g). $^1$H NMR (300 MHz, CDCl$_3$): d 3.50 (m, 2H), 1.30 (d, 6H).

10c. meso-2,3-butanediamine

A sample of the compound from step 10b (13.0 g, 125 mmole) was dissolved in ethanol and hydrogenated at 4 atm over 10% Pd/C for 20 hours at room temperature. The catalyst was removed by filtration, and the solvent was removed under vacuum to afford the title compound. $^1$H NMR (300 MHz, CDCl$_3$): d 2.70 (m, 2H), 1.45 (br, 4H), 1.05 (d, 6H). MS (m/z): 89 (M+H)$^+$.

10d. Compound (19) from Scheme 9; A=D=methyl; B=E= H, R$^1$=methoxy, R$^2$=benzoyl A sample of 10,11-anhydro-2'-O-benzoyl-5-O-desosaminyl-6-O-methyl-3-oxo-erythronolide A 12-O-imidazolyl carbamate (from Example 2, 500 mg, 0.651 mmole) and meso-2,3-butanediamine (500 mg, from step 10d above) were dissolved in 3 mL of acetonitrile and 0.3 mL of water, and the reaction was stirred for 72 hours at room temperature and 17 hours at reflux. The solution was diluted with methylene chloride, dried over NaCl and MgSO$_4$, and filtered. The solvent was removed, and the residue was taken directly to the next step.

10e. Compound (20) from Scheme 9; A=D=methyl; B=E=H, R$^1$=methoxy

The compound from step 10d above was dissolved in methanol, and the solution was heated at reflux for 12 hours. The solvent was removed, and the residue was taken directly to the next step. MS (m/z): 684 (M+H)$^+$.

10f. Compound of Formula (III): A=D=methyl; B=E=H, R$^1$=methoxy, R$^2$=hydrogen To the material from the previous step, dissolved in methanol, acetic acid was added, and the reaction mixture was heated at reflux for 24 hours. A solution of NH$_3$ in methanol was added, and the solution was concentrated. The residue was dissolved in ethyl acetate, and the solution was washed with 1 N NaOH, $H_2O$ and brine, then dried over $Na_2SO_4$. The solvent was removed, and the residue was purified on silica gel, eluting with 10% methanol in methylene chloride to 10% methanol (containing NH$_3$) in methylene chloride to afford the title compound. This material was rechromatographed on pH 8 silica gel, eluting with 4:1 ethyl acetate:hexane to 100% ethyl acetate to afford 116 mg of the title compound. The NMR analysis confirmed the product to be the A=D=methyl isomer. MS (m/z): 666 (M+H)$^+$. HRMS Calc. for $C_{35}H_{60}N_3O_9$: 666.4330; Observed: 666.4326. $^1$H NMR (300 MHz, CDCl$_3$): d 4.81 (dd, 1H), 4.27 (d, 1H), 4.22 (d, 2H), 4.05 (m, 1H) 3.96 (m, 1H), 3.78 (q, 1H), 3.65 (s, 1H, H11), 3.48 (m, 1H), 3.10 (dd, 1H), 3.06 (m 1H), 2.75 (q, 1H), 2.67 (s, 3H), 2.65 (m, 1H), 2.37 (m, 2H), 2.19 (s, 6H), 1.85, 1.49 (m, 2H), 1.59, 1.15 (m, 2H), 1.55 (m, 21), 1.42 (s, 3H), 1.27 (d, 3H), 1.27 (s, 3H), 1.25 (d, 2H), 1.24 (d, 3H), 1.17 (d, 3H), 1.16 (d, 3H), 1.04 (d, 311), 0.96 (d, 3H), 0.78 (t, 3H). $^{13}$C NMR (75 MHz, CDCl$_3$): d 204.2, 179.0, 169.5, 155.6, 118.8, 103.7, 81.3, 78.6, 77.7, 76.8, 70.2, 69.4, 65.8, 56.1, 55.5, 51.9, 51.0, 50.4, 47.0, 42.5, 40.1, 38.4, 35.2, 28.1, 22.3, 22.0, 21.1, 20.7, 20.1, 15.0, 14.8, 13.1, 11.5, 10.6, 12.2. IR (film): 3460 (w), 2972, 1750, 1718 (w), 1647, 1456, 1423, 1372, 1305, 1246, 1163, 1107, 1051, 989, 757 cm$^{-1}$.

EXAMPLE 11

Compound of Formula (III): A=E=methyl; B=D=H, R$^1$=methoxy, R$^2$=hydrogen 11a. 2S, 3S-butanediamine Following the procedures of Example 10 steps a–c, except substituting (R,R)-2,3-butanediol (1 g, 11.1 mmole, Aldrich)

for the meso-isomer thereof of step 10a, and carrying the product forward as in steps 10b and 10c, the title compound (494 mg) was prepared. MS (m/z): 89 (M+H)$^+$. $^1$H NMR (300 MHz, CDCl$_3$): d 2.62 (m, 2H), 1.45 (br s, 4H), 1.08 (d, 6H).

11b. Compound (19) from Scheme 9; A=E=methyl; B=D=H, R$^1$=methoxy, R$^2$=benzoyl A sample of 10,11-anhydro-2'-O-benzoyl-5-O-desosaminyl-6-O-methyl-3-oxo-erythronolide A 12-O-imidazolyl carbamate (from Example 2, 1.56 g, 2.03 mmole) and 2S, 3S-butanediamine (400 mg, 4.54 mmole, from step 11a above) were dissolved in 16 mL of 20% aqueous acetonitrile, and the reaction mixture was stirred at room temperature for 7 days. The solution was diluted with methylene chloride, dried over NaCl and MgSO$_4$, and filtered. The solvent was removed, and the residue was taken directly to the next step.

11c. Compound (20) from Scheme 9; A=E=methyl; B=D=H, R$^1$=methoxy

The compound from step 11b above was dissolved in methanol, and the solution was heated at reflux for 12 hours. The solvent was removed, and the residue was taken directly to the next step.

11d. Compound of Formula (III): A=E=methyl; B=D=H, R$^1$=methoxy, R$^2$=hydrogen The material from the previous step was dissolved in 20 mL of ethanol, acetic acid (0.80 mL) was added, and the reaction mixture was heated at reflux for 3 days. NH$_3$/methanol was added, and the solvent was removed. The residue was dissolved in ethyl acetate, and the solution was washed with 1 N NaOH, H$_2$O and brine, then dried over Na$_2$SO$_4$. The solvent was removed, and the residue was purified on neutral silica gel, eluting with 4:1 ethyl acetate-:hexane to 5% methanol in ethyl acetate to afford 682 mg of the title compound. MS (m/z): 666 (M+H)$^+$. HRMS Calc. for C$_{35}$H$_{60}$N$_3$O$_9$: 666.4330; Observed: 666.4333. $^1$H NMR (300 MHz, CDCl$_3$): d 4.85 (dd, 1H), 4.35 (d, 1H), 4.30 (d, 1H), 4.12 (q, 2H), 3.65 (s to d, 1H, J=1.2 Hz), 3.56 (m, 1H), 3.46 (br s, 1H), 3.21 (dd, 1H), 3.13 (t, 1H), 2.86 (q, 1H), 2.78 (s, 3H), 2.68 (m, 2H), 2.46 (dt, 1H), 2.28 (s, 6H), 1.95 (m, 1H), 1.68 (m, 3H), 1.52 (s, 3H), 1.38 (d, 3H), 1.36 (d, 3H0, 1.33 (s, 3H), 1.32 (d, 3H), 1.31 (d, 3H), 1.26 (d, 3H), 1.21 (d, 3H), 1.05 (d, 3H), 0.87 (t, 3H). $^{13}$C NMR (75 MHz, CDCl$_3$): d 203.9, 177.9, 169.5, 156.4, 103.8, 81.1, 78.5, 78.4, 77.6, 70.3, 69.5, 65.8, 60.4, 56.9, 52.3, 50.9, 50.6, 47.6, 43.9, 40.2, 39.5, 35.0, 28.1, 21.7, 21.1, 20.8, 20.2, 19.9, 18.3, 16.3, 15.6, 14.7, 14.1, 13.6, 10.1. IR (KBr): 3441, 2972, 2938, 1755, 1117 (w), 1653, 1457, 1425, 1376, 1306, 1248, 1167, 1109, 1053 cm$^{-1}$.

EXAMPLE 12

Compound of Formula (III): B=D=H; A and E taken together is —CH$_2$CCH$_2$)H—. R$^1$=methoxy, R$^2$=hydrogen 12a. racemic-trans-1,2-cyclopentanediamine Following the procedures of Example 10 steps a–c, except substituting (DL)-1,2-cyclopentanediol (5.0 g, 49.0 mmole, Aldrich) for the diol of step 10a, and carrying the product forward as in steps 10b and 10c, the title compound (2.76 g) was prepared. MS (m/z): 101 (M+H)$^+$. $^1$H NMR (300 MHz, CDCl$_3$): d 2.75 (m, 2H), 2.00 (m, 2H), 1.65 (m, 2H), 1.50 (s, 4H), 1.30 (m, 2H).

12b. Compound (19) from Scheme 9; B=D=H; A and E taken together is —CH$_2$CH$_2$CH$_2$—, R$^1$=methoxy, R$^2$=benzoyl Samples of 10,11-anhydro-2'-O-benzoyl-5-O-desosaminyl-6-O-methyl-3-oxo-erythronolide A 12-O-imidazolyl carbamate (from Example 2, 200 mg, 0.26 mmole) and racemic-trans-1,2-cyclopentanediamine (104 mg, 1.04 mmole, from step 12a) were 3 dissolved in 20% aqueous acetonitrile, and the reaction mixture was stirred at room temperature for 4 days and at reflux for 8 hours. The solution was diluted with 100 mL of ethyl acetate, dried over NaCl and MgSO$_4$, and filtered. The solvent was removed, and the residue was purified by chromatography on silica gel, eluting with 5% to 10% methanol in methylene chloride to afford the title compound (88 mg). MS (m/z): 800 (M+H)$^+$.

12c. Compound (20) from Scheme 9; B=D=H; A and E taken together is —CH$_2$CH$_2$CH—, R$^1$=methoxy The compound from step 12b above (88 mg) was dissolved in methanol, and the solution was heated at reflux for 10 hours. The solvent was removed, and the residue was purified by chromatography on silica gel, eluting with 5% methanol in methylene chloride to afford the titde compound. MS (m/z): 696 (M+H)$^+$.

12d. Compound of Formula (III): B=D=H; A and E taken together is —CH$_2$CHWCH—, R$^1$=methoxy, R$^2$=hydrogen Following the procedure of Example ld the title compound was prepared. MS (m/z): 678 (M+H)$^+$.

EXAMPLE 13

Compound of Formula (III): B=E=H; A and D taken together is —CH$_2$CH$_2$CH$_2$CH$_2$—, R$^1$=methoxy, R$^2$=hydrogen 13a. Compound (19) from Scheme 9; B=E=H; A and D taken together is —CH$_2$CH$_2$CH$_2$CH$_2$—, R$^1$=methoxy, R$^2$=benzoyl Following the procedure of Example 11, step 11b, except substituting cis-1,2-cyclohexanediamine (800 mg, 1.04 mmole, Aldrich) for the diamine thereof, the title compound was prepared.

13b. Compound of Formula (III): B=E=H; A and D taken together is —CH$_2$CH$_2$CH$_2$CH$_2$—, R$^1$=methoxy, R$^2$=hydrogen Following the procedures of Example 11 steps c and d, substituting the compound of step 13a for the compound of 11b thereof, the title compound was prepared. The product was a mixture of compounds (B=E=H and A=D=H), and the title compound was obtained by chromatography on silica gel, eluting with 2–5% methanol/methylene chloride. $^1$H NMR (300 MHz, CDCl$_3$): d 4.87 (dd, 1H), 4.34 (d, 1H), 4.31 (d, 1H), 4.10 (br s, 1H), 4.07 (br m, 1H), 3.84 (q, 1H), 3.70 (s, 1H, H11), 3.56 (m, 1H), 3.22 (dd, 1H), 3.14 (pent, 1H), 2.78 (s, 3H, OMe), 2.49 (m, 1H), 2.30 (s, 6H), 1.30–2.00 (m), 1.49 (s, 1H), 1.39 (s, 3H), 1.37 (d, 3H), 1.32 (d, 3H), 1.26 (d, 3H), 1.22 (d, 3H), 1.06 (d, 3H), 0.85 (t, 3H). $^{13}$C NMR (75 MHz, CDCl$_3$): d 203.8, 178.1, 169.3, 155.6, 103.7, 81.1, 78.6, 78.1, 76.64, 70.2, 69.3, 65.7, 56.3, 55.9, 55.8, 51.0, 50.4, 47.4, 42.6, 40.1, 38.2, 35.4, 34.4, 28.1, 25.2, 25.1, 25.0, 21.9, 21.0, 20.2, 20.1, 19.2, 15.6, 14.7, 12.9, 10.6, 10.2. MS (m/z): 692 (M+H)$^+$.

EXAMPLE 14

Compound of Formula (III): A=B=D=E=H, R$^1$=hydrogen, R$^2$=hydrogen 14a. 2'-O-acetyl-6-deoxy-erythromycin A A sample of 6-deoxyerythromycin A (4.34 g, 6.04 mmole, Abbott Labs) was dissolved in 250 mL of methylene chloride, and acetic anhydride (1.54 g, 15 mmole) and triethylamnine (1.22 g, 12 mmole) were added. The reaction mixture was stirred at room temperature for 16 hours, then poured into 5% aqueous NaHCO$_3$. The mixture was extracted with methylene chloride, and the organic layer was dried, filtered and concentrated. The residue was chased with toluene, ethylene dichloride, chloroform and methylene chloride. The residue then dried under high vacuum to afford 4.46 g of the title product, which was taken to the next step without firther purification. MS m/z (M+H)$^+$: 760.

14b. 2'-O-acetyl-6-deoxy-4"-triethylsilyl-erythrofycin A

A sample of the compound from step 14a (4.44 g, 5.84 mmole) was dissolved in 100 mL of dry methylene chloride, and imidazole (1.59 g, 23.3 mmole) was added. The mixture was cooled to 0° C., and a solution of triethylsilyl chloride (1.76 g, 117 mmole) in 25 mL of methylene chloride dropwise. The reaction mixture was stirred for 1 hour at 0° C. and at room temperature for 16 hours. The reaction mixture was poured into 5% aqueous NaHCO$_3$, and the mixture was extracted with CHCl$_3$. The organic extract was washed with saturated brine, dried over MgSO$_4$, filtered and concentrated. The residue was dried under high vacuum for 48 hours to afford 5.38 g of the title product, which was taken to the next step without further purification. MS m/z (M+H)$^+$: 874.

14c. 2'-O-acetyl-10,11-anhydro-6-deoxy-4"-triethylsilyl-erythromycin A 12-O-imidazolyl carbamate (Compound (3) from Scheme 5, R$^1$=hydrogen, 2'-R$^2$=acetyl; 4"-R$^2$=trietylsilyl)

A sample of the compound from step 14b (5.36 g, 6.13 mmole) was dissolved in 45 mL of dry DMF, and carbonyld$^{idazole}$ (4.98 g, 30 mmole) was added. After the reagent had dissolved, the solution was diluted with 15 mL of THF, and the solution was cooled to 0° C. To this solution was added NaH (807 mg, 60% dispersion, 20.2 mmole) in portions. The reaction mixture was stirred for 30 minutes, and 10 mL of H$_2$O was added. The reaction mixture was poured into saturated brine, and the resulting mixture was extracted with ethyl acetate. The ethyl acetate solution was washed with brine, dried over MgSO$_4$, filtered and concentrated. The residue was co-distilled with ethylene dichloride, chloroform and methylene chloride. The residue was dried under high vacuum for 16 hours to afford 6.95 g of the title product, which was taken to the next step without further purification. MS m/z (M+H)$^+$: 986.

14d. Compound (11) from Scheme 5; A=B=D=E=H; R$^2$=hydrogen, 2'-R$^2$=acetyl; 4"-R$^2$=triethylsilyl A sample of the compound from step 14c (6.93 g, 6.13 mmole) was dissolved in 50 mL of acetonitrile, ethylene diamine was added (4.31 g, 7.19 mmole), and the solution was stiffed for 17 hours at room temperature. The reaction mixture was poured into saturated brine containing NH$_4$OH. This mixture was extracted with chloroform, and the organic extracts were combined, filtered and concentrated. The residue was co-disfilled with ethylene dichloride, chloroform and methylene chloride. The residue was dried under high vacuum for 72 hours to afford 5.77 g of the title product which was taken to the next step without further purification. MS m/z (M+H)$^+$: 924.

14e. Compound (12) from Scheme 5; A=B=D=E=H; R$^1$=hydrogen, 2'-R$^2$=4"-R$^2$=hydrogen A sample of the compound from step 14d (5.75 g) was dissolved in THF (120 mL) and 14.3 mL of tetrabutylammonium fluoride (1 M in Th) was added in one portion. The reaction mixture was stirred at room temperature for 4 hours, diluted with 400 mL of methanol, and stirred at room temperature for 64 hours. The solution was concentrated and then poured into 5% aqueous NaHCO$_3$ containing 0.5% NH$_4$OH. The mixture was extracted with CHCl$_3$, the extract was washed with brine, and dried over MgSO$_4$. The solvent was removed, and the residue was co-distilled with ethylene chloride and methylene chloride. The residue was further dried under vacuum for 16 hours to afford the title compound (5.59 g).

14f. Compound of Formula (I): A=B=D=E=H; R$^1$=hydrogen, R$^2$=hydrogen

A sample of the compound from step 14e (5.56 g, 7.07 mmole) was dissolved in 60 mL of ethanol, and acetic acid (637 mg, 106 mmole) was added. The solution was heated at reflux for 3.5 hours, cooled to room temperature, then poured into 5% aqueous NaHCO$_3$. This mixture was extracted with CHCl$_3$, and the organic extracts were combined, dried over MgSO$_4$, filtered and concentrated. The residue was co-disfilled with ethylene dichloride, chloroform and methylene chloride, then dried under high vacuum for 72 hours to afford 4.12 g of the product. This material was purified by chromatography on silica gel, eluting with 1:6 TEA:ethyl acetate, to afford the title compound (1.29 g). MS n'z (M+H)$^+$: 768. $^1$H NMR (CDCl$_3$) d: 0.88 (m), 2.28 (s), 3.28 (s), 4.23 (m), 4.85 (m), 4.92 (m). $^{13}$C NMR (CDCl$_3$) d: 40.3 (N(CH$_3$)$_2$), 42.8 (NCH2), 49.4 (OCH$_3$), 49.9 (NCH$_2$), 155.8 (O—CO—N). IR (CDCl$_3$): 1755 cm$^{-1}$.

EXAMPLE 15

Compound of Formula (III): R$^1$=OCH$_3$, R$^2$=H; A=B=D=H; E=—CH$_2$NH$_2$ 15a. 1,2-diazido-3-(BOC-amino)propane A sample of 3-(BOC-amino)propene (Aldrich, 15.72 g, 0.1 mole), manganese triacetate (80.43 g, 0.3 mole) and NaN$_3$ (65.01 g, 1.0 nmmole) were suspended in 400 mL of acetic acid, and the mixture was heated at 100° C. for 10 minutes. The mixture was cooled in an ice bath and diluted with 400 mL of 1N NaOH. The mixture was extracted with ethyl acetate, which was washed with 1 N cold NaOH, H$_2$O, NaHCO$_3$, brine and dried over Na$_2$SO$_4$. The solvent was removed, and the residue was chromatographed on silica gel, eluting with 4:1 hexane:ether to give 7.18 g of the title compound. MS m/z (M+NH$_4$)$^+$: 259.

15b. 1,2-diamino-3-(BOC-amino)propane

The compound of the previous step was dissolved in ethanol and hydrogenated (4 atm H$_2$) over Pd/C for 22 hours at room temperature. The solvent was removed, and the product was taken to the next step. MS m/z (M+H)$^+$: 190.

15c. Compound of Formula (III): R$^1$=OCH$_3$, R$^2$=H; A=B=D=H; E=—CH$_2$NH$_2$ Following the procedures of Example 3 steps f–h, samples of the compound of formula (8) (Scheme 3; R$^1$=methoxy; R$^2$=benzoyl, from Example 2,400 mg, 0.52 mmole) and the compound from step 15b (1.478 g, 7.81 mmol) were reacted and the title product was obtained. Chromatographic separation of the isomers of the N-BOC compound, followed by deprotection with HCl in ethanol at room temperature gives the title compound. MS m/z (M+H)$^+$: 889.

EXAMPLE 16

Compound of Formula (III): R$^1$=OCH$_3$, R$^2$=H; A=B=D=H; D=—CH$_2$NH$_2$

The compound was obtained by chromatography of the mixture obtained in Example 15c. MS (m/z): 889 (i+H)$^+$.

EXAMPLE 17

Compound of Formula (III): $R^1$=$OCH_3$, $R^2$=H; B= E=H; A and D taken together is —$CH_2CH_2CH_2$—

17a. Cyclopentane cis-1,2-diamine

Following the procedures of Example 10 steps a–c, except substituting cis-1,2-cyclopentanediol for the diol of step 10a, and carrying the product forward as in steps 10b and 10c, the title compound was prepared.

17b. Compound of Formula ($R^1$); $R^1$=$OCH_3$, $R^2$H; B=E=H; A and D taken together is —$CH_2CH_2CH_2$—

Following the procedures of Example 10 steps d–f, except substituting cis-1,2-cyclopentanediamine, from the previous step, for the meso-2,3-butanediamine thereof, the title compound was prepared. The product was a mixture of compounds (B=E=H and A=D=H), and the title compound was obtained by chromatography on silica gel, eluting with 2–5% methanol/methylene chloride. MS (m/z): 678 $(M+H)^+$.

EXAMPLE 18

Compound of Formula (III): $R^1$=$OCH_3$, $R^2$=H; B= E=H; A and D taken together is —$CH_2OCH_2$—

18a. Tetrahydrofuran cis-3,4-diamine

Following the procedures of Example 10 steps a–c, except substituting 1,4-anhydroerythritol for the diol of step 10a, and carrying the product forward as in steps 10b and 10c, the title compound was prepared.

18b. Compound of Formula (III): $R^1$=$OCH_3$, $R^2$=H; B=E=H; A and D taken together is —$CH_2OCH_2$—

Following the procedures of Example 10 steps d–f, except substituting tetrahydrofliran cis-3,4diamine, from the previous step, for the meso-2,3-butanediamine of step 10d, the title compound was prepared. The product was a mixture of compounds (B=E=H and A=D=H), and the tidle compound was obtained by chromatography on silica gel, eluting with 2–5% methanol/methylene chloride. MS (m/z): 680 $(M+H)^+$.

EXAMPLE 19

Compound of Formula (III): $R^1$=$OCH_3$, $R^2$=H; B= E=H; A and D taken together is —$CH_2$—NH—$CH_2$—

19a. Cis-3,4-diamino-1-BOC-pyrrolidine

Pyrolline (Aldrich) was N-protected by treatment with di-tert-butyl dicarbonate and $Et_3N$ in $CH_2Cl_2$ at room temperature. The N-BOC-pyrroline was oxidized with catalytic $OsO_4$ and excess N-methylmorpholine N-oxide (NNMO) in THF and t-butanol according to the procedure of *Tetrahedron Lett.*, 1976: 1973 to give the N-BOC-pyrroline-3,4-diol. Following the procedures of Example 10 steps a–c, except substituting N-BOC-pyrroline-3,4-diol for the diol of step 10a, and carrying the product forward as in steps 10b and 10c, the title compound was prepared.

19b. Compound of Formula (III): $R^1$=$OCH_3$, $R^2$H; B=E=H; A and D taken together is —$CH_2$—N—(BOC)—$CH_2$—

Following the procedures of Example 10 steps d–f, except substituting cis-3,4-diamino-(1-BOC-pyrrolidine), from the previous step, for the meso-2,3-butanediamine of step 10d, the title compound was prepared.

19c. Compound of Formula (III): $R^1$=$OCH_3$, $R^2$=H; B=E=H; A and D taken together is —$CH_2$—NH—$CH_2$—

Compound of 19b was treated with 4N HCl/dioxane in $CH_2Cl_2$ at room temperature gave the title compound. The product was a mixture of compounds (B=E=H and A=D=H), and the title compound was obtained by chromatography on silica gel, eluting with 2–5% methanol/methylene chloride. MS (m/z): 679 $(M+H)^+$.

EXAMPLE 20

Compound of Formula (III): $R^1$=$OCH_3$, $R^2$=H; B= E=H; A and D taken together is —$CH_2$—N(Cbz)-$CH_2$—

Starting with the Compound of Formula (III): $R^1$=$OCH_3$, $R^2$=H; B=E=H; A and D taken together is —$CH_2$—NH—$CH_2$—, from Example 19 above, adding the Cbz group by treatment with benzyloxycarbonyloxysuccinimide in ethyl acetate at room temperature, the title compound was prepared. MS (m/z): 813 $(M+H)^+$.

EXAMPLE 21

Compound of Formula (III): $R^1$=$OCH_3$, $R^2$=H; B= E=H; A and D taken together is —$CH_2$—N(benzyl)-$CH_2$—

Starting with the Compound of Formula (III): $R^1$=OCH3, $R^2$=H; B=E=H; A and D taken together is —$CH_2$—NH—$CH_2$—, from Example 19 above, reacting the amine of the —$CH_2$—NH—$CH_2$— group with benzyl bromide in the presence of triethylamine in methylene chloride at room temperature, the title compound was prepared. MS (m/z): 769 $(M+H)^+$.

EXAMPLE 22

Compound of Formula (III): $R^1$=$OCH_3$, $R^2$=H; B= E=H; A and D taken together is —$CH_2$—N(benzoyl)-$CH_2$—

Starting with the Compound of Formula (III): $R^1$=OCH3, $R^2$=H; B=E=H; A and D taken together is —$CH_2$—NH—$CH_2$—, from Example 19 above, reacting the amine of the —$CH_2$—NH—$CH_2$— group with benzoyl chloride in the presence of triethylamine, the title compound is prepared.

EXAMPLE 23

Compound of Formula (III): $R^1$=$OCH_3$, $R^2$=H; B= E=H; A and D taken together is —$CH_2$—N(ghenyl-$CH_2$—$CH_2$—)—$CH_2$—

Staring with the Compound of Formula (III): $R^1$=OCH3, $R^2$=H; B=E=H; A and D taken together is —$CH_2$—NH—$CH_2$—, from Example 19 above, reacting the amine of the —$CH_2$—H—$CH_2$— group with 2-phenylethyl bromide in the presence of triethylamine, the title compound was prepared. MS (m/z): 783 $(M+H)^+$.

EXAMPLE 24

Compound of Formula (III): $R^1$=$OCH_3$, $R^2$=H; B= E=H; A and D taken together is —$CH_2$—N(4Cl-phenyl-$CH_2$—)—$CH_2$—

Starting with the Compound of Formula (III): $R^1$=OCH3, $R^2$=H; B=E=H; A and D taken together is —$CH_2$—NH—$CH_2$—, from Example 19 above, reacting the amine of the —$CH_2$—NH—$CH_2$— group with 4-chlorobenzyl chloride in the presence of diisopropylethylamine in methylene chloride at room temperature, the title compound was prepared. MS (m/z): 803 $(M+H)^+$.

EXAMPLE 25

Compound of Formula (III): $R^1$=$OCH_3$, $R^2$=1H; B=E=H; A and D taken together is —$CH_2$—N(4-pyridyl-$CH_2$—)$CH_2$—

Starting with the Compound of Formula (E); $R^1$=OCH3, $R^2$=H; B=E=H; A and D taken together is —$CH_2$—NH—$CH_2$—, from Example 19 above, reacting the amine of the —$CH_2$—NH—$CH_2$— group with 4-picolyl chloride hydrochloride in the presence of diisopropylethylamine in THE at room temperature, the title compound was prepared. MS (m/z): 770 (M+H)$^+$.

EXAMPLE 26

Compound of Formula (III): $R^1$=$OCH_3$, $R^2$=H; B=E=H; A and D taken together is —$CH_2$—N(2-pyridyl-$CH_2$—)—$CH_2$—

Starting with the Compound of Formula (III): $R^1$=OCH3, $R^2$=H; B=E=H; A and D taken together is —$CH_2$—NH—$CH_2$—, from Example 19 above, reacting the amine of the —$CH_2$—NH—$CH_2$— group with 2-picolyl chloride in the presence of triethylamine, the title compound is prepared.

EXAMPLE 27

Compound of Formula (III): $R^1$=$OCH_3$, $R^2$=H; B=E=H; A and D taken together is —$CH_2$—NH(3-pyridyl-$CH_2$—)—$CH_2$—

Starting with the Compound of Formula (III): $R^1$=OCH3, $R^2$=H; B=E=H; A and D taken together is —$CH_2$—NH—$CH_2$—, from Example 19 above, reacting the amine of the —$CH_2$—NH—$CH_2$— group with 3-picolyl chloride in the presence of triethylamine, the title compound is prepared.

EXAMPLE 28

Compound of Formula (III): $R^1$=$OCH_3$, $R^2$=H; B=E=H; A and D taken together is —$CH_2$—N(4-quinolyl-$CH_2$—)—$CH_2$—

Starting with the Compound of Formula (III): $R^1$=OCH3, $R^2$=H; B=E=H; A and D taken together is —$CH_2$—NH—$CH_2$—, from Example 19 above, reacting the amnine of the —$CH_2$— NH—$CH_2$— group with 4-chloromethylquinoline in the presence of triethylamine, the title compound is prepared.

EXAMPLE 29

Compound of Formula (III): $R^1$=$OCH_3$, $R^2$=H; B=E=H; A=D=—$CH_2$—O—$CH_2$-phenyl 29a. $PhCH_2OCH_2CH(NH_2)CH(NH_2)CH_2OCH_2Ph$ Meso-erythritol (Aldrich) is 1,4dibenzylated by reaction with NaH and benzyl bromide in DMF according to the procedure of El Amin, et al., *J. Org. Chem.* 44:3442, (1979). Following the procedures of Example 10 steps a–c, except substituting 1,4-dibenzyl-meso-eyythritol for the diol of step 10a, and carrying the product forward as in steps 10b and 10c, the title compound is prepared.

29b. Compound of Formula (III): $R^1$=$OCH_3$, $R^2$=H; B=E=H; A=D=—$CH_2$—O—$CH_2$-phenyl Following the procedures of Example 10 steps d–f, except substituting $PhCH_2OCH_2CH(NH_2)CH(NH_2)CH_2OCH_2Ph$, from the previous step, for the meso-2,3-butanediamine of step 10d, the title compound is prepared.

EXAMPLE 30

Compound of Formula (III): $R^1$=$OCH_3$, $R^2$=H; B=E=H; A=D=—$CH_2$—OH

Starting with the Compound of Formula (III): $R^1$=OCH3, $R^2$=H; B=E=H; A=D=—$CH_2$—O—$CH_2$-phenyl, from Example 29 above, removing the benzyl groups by hydrogenation over Pd/C, the title compound is prepared.

EXAMPLE 31

Compound of Formula (III): $R^1$=$OCH_3$, $R^2$=H; B=E=H; A=D—$CH_2$—O-phenyl

Starting with the Compound of Formula (III): $R^1$=OCH3, $R^2$=H; B=E=H; A=D=—$CH_2$—OH, from Example 30 above, reacting the —$CH_2$—OH groups (of substituents A and D) with phenol, triphenylphosphine and DEAD under Mitsunobu conditions the title compound is prepared.

EXAMPLE 32

Compound of Formula (III): $R^1$=$OCH_3$, $R^2$=H; A=B=H; D and E taken together is —$CH_2$—$CH_2$—$CH_2$—$CH_2$—

Following the procedures of Example 3 except substituting 1-amino-1-cyclopentane-methanol (Aldrich) for the 2-(R)-arnino-3-phenyl-1-propanol thereof, the title compound is obtained.

EXAMPLE 33

Compound of Formula (III): $R^1$=$OCH_3$, $R^2$=H; A and B taken together is —$CH_2$—$CH_2$—$CH_2$—$CH_2$—; D=E=H Following the procedures of Example 5, except replacing the (S)-2-amino-3-phenyl-1-propanol of step 5a with 1-amino-1-cyclopentanemethanol (Aldrich), the title compound is obtained.

EXAMPLE 34

Compound of Formula (III): $R^1$=$OCH_3$, $R^2$=H; A=B=H; D and E taken together is —$CH_2$—O—$CH_2$—

34a. 3-amino-3-aminomethyloxetane

A sample of tris(hydroxymethyl)methylainine (Aldrich) is reacted with di-t-butyldicarbonate and triethylainine to give N-BOC-tris(hydroxymethyl)methylamine. This compound is reacted with 1 equivalent of methanesulfonyl chloride and triethylainine to give 3-(BOC-amrno)-3-hydroxymethyloxetane. This compound is converted to the title compound according to the procedures of Example 3 steps b–e.

34b. Compound of Formula (I); $R^1$=$OCH_3$, $R^2$=H; A=B=H; D and E taken together is —$CH_2$—O—$CH_2$—

Following the procedures of Example 3 steps f–h except substituting the compound from step 34a for the (R)-3-phenyl-1,2-propanediamine thereof, the title compound is obtained.

EXAMPLE 35

Compound of Formula (III): $R^1$=$OCH_3$, $R^2$=H; A=D=E=H; B=—$CH_2$—$CH_2$-phenyl Following the procedures of Example 5, except replacing the (S)-2-amino-3-phenyl-1-propanol of step 5a with (S)-homophenylalaninol (prepared by $LiAlH_4$ reduction of the (S)-homophenylalanine available from Aldrich), the title compound was obtained. MS (m/z): 742 (M+H)$^+$.

EXAMPLE 36

Compound of Formula (III): $R^1$=$OCH_3$, $R^2$=H; A=
D=E=H; B=—$CH_2$—$CH_2$—$CH_2$-phenyl 36a. 2-(R)-amino-5-phenylpentanoic acid (±)-2-Amino-5-phenylpentanoic acid (35 g, from Example 40a) was suspended in water (3 L) and solubilized by adjust the pH to 12 with 7 N NaOH solution. The pH was readjusted to pH 8 with 1 M phosphoric acid while stiirng at 45° C. The solution was cooled to 40° C., and L-amino acid oxidase (Sigma, 0.7 unit/mg) was added. The reaction was stirred with good aeration for 2 weeks. The reaction mixture was concentrated to 500 mL under vacuum, the pH was adjusted to 5, and the precipitate was collected. The material was recrystallized from ethanol-water to afford 17.32 g of the title compound).

36b. 2-()-amino-5-phenylpentanol

The compound from step 36a was reduced with LiA 1$H_4$ under standard conditions to give the title compound.

36c. Compound of Formula (III): $R^1$=$OCH_3$, $R^2$C A=D=E=H; B=—$CH_2$—$CH_2$—$CH_2$-phenyl Following the procedures of Example 5, except replacing the (S)-2-amino-3-phenyl-1-propanol of step 5a with the 2-(R)-arnino-5-phenylpentanol from step 36b, the title compound was obtained. MS (m/z): 756 $(M+H)^+$.

EXAMPLE 37

Compound of Formula (III): $R^1$=$OCH_3$, $R^2$=H; A=
D=E=H; B=—$CH_2$—O—$CH_2$-phenyl 37a 1-N-(CBZ)-2-(S)-diamino-3-O-benzylpropane N-BOC-O-benzyl-D-serine (Bachem) is reduced under the reaction conditions described by Kotokos, Synthesis, 299–301 (1990) to give the N-BOC-O-benzyl-D-serinol. This compound is treated according to the procedures of Example 10a–c to give the corresponding amine. The amine is converted to the benzyloxycarbonyl (CBZ) derivative, and the BOC group was removed to give the title compound.

37b. Compound of Formula $R^1$=$OCH_3$, $R^2$=H; A=D=E=H; B=—$CH_2$—O—$CH_2$-phenyl Following the procedures of Example 10 steps d–f, except substituting the material from the previous step, for the meso-2,3-butanedianmine of step 10d, the title compound was prepared. MS (mjz): 758 $(M+H)^+$.

EXAMPLE 38

Compound of Formula (E); $R^1$=$OCH_3$, $R^2$=H; A=
D=E=H; B—$CH_2$—$CH_2$-(4-$OCH_3$-phenyl)-

38a. (S)-homo-O-methyltyrosinol

D-Homo-O-methyltyrosine (prepared according to the procedure of Melillo, et al., J. Org. Chem., 5:5149–5150 (1987)) is reduced with $LiAlH_4$ under standard conditions to give the title compound.

38b. Compound of Formula $R^1$=$OCH_3$, $R^2$=H; A=D=E=H; B=—$CH_2$—$CH_2$-(4$OCH_3$phenyl)

Following the procedures of Example 5, except replacing the (S)-2-amino-3-phenyl-1-propanol of step 5a with the compound of step 38a, the title compound is obtained.

EXAMPLE 39

Compound of Formula $R^1$=$OCH_3$, $R^2$=H; A=—
$CH_2$—$CH_2$-phenyl; B=D=E=H

Following the procedures of Example 5, except substituting (R)-homophenyl-alaninol (prepared by $LiAlH_4$ reduction of the (R)-homophenylalanine (Aldrich) compound) for the (S)-2-amnino-3-phenyl-1-propanol of step 5a, the title compound was obtained. MS (m/z): 742 $(M+H)^+$.

EXAMPLE 40

Compound of Formula $R^1$=$OCH_3$, $R^2$=H; A=—
$CH_2$—$CH_2$—$CH_2$-phenyl; B=D=E=H 40a. (±)-2-Amino-5-phenylpentanoic acid Diethyl acetamidomalonate (220 g) in 1 L of absolute ethanol was added to a stirred solution of sodium ethoxide in ethanol, prepared by dissolving sodium (24 g) in absolute ethanol (500 mL), under nitrogen. The reaction mixture was refluxed under nitrogen for 30 minutes, then 1-bromo-3-phenylpropane (200g) was added. The reaction mixture was refluxed overnight, cooled to ambient temperature, filtered, and the solvent was removed under vacuum. Concentrated HCl (800 mL) was added to the residue, and the reaction mixture was refluxed for 14 hours. The cooled aqueous solution was washed with ether, and the residual ether in the aqueous phase was removed by bubbling nitrogen through the solution. The pH of the aqueous phase was adjusted to pH 7–8 by the addition of ammonium hydroxide. The title compound was collected by filtration, air dried and recrystallized from ethanol-water (150 g) m.p. 255–257° C. MS m/z: 194 $(M+H)^+$.

40b. (±)-2-amino-5-phenylpentanol

The compound from step 40a was reduced with $LiAlH_4$ under standard conditions to give the title compound.

40c. Compound of Formula (III): $R^1$=$OCH_3$, $R^2$=H; A=—$CH_2$—$CH_2$—$CH_2$-phenyl; B=D=E=H Following the procedures of Example 5, except replacing the (S)-2-anino-3-phenyl-1-propanol of step 5a with the (+)-2-amino-5-phenylpentanol from step 40b, and separating the isomers by chromatography the title compound was obtained. MS (m/z): 756 $(M+H)^+$.

EXAMPLE 41

Compound of Formula (III): $R^1$=$OCH_3$, $R^2$=H;
A=—$CH_2$—O—$CH_2$-phenyl: B=D=E=H Following the procedures of Example 37, except substituting the N-BOC-O-benzyl-L-serine (Sigma) for the N-BOC-O-benzyl-D-serine thereof the title compound was prepared. MS (m/z): 758 $(M+H)^+$.

EXAMPLE 42

Compound of Formula (III): $R^1$=$OCH_3$, $R^2$=H; B=
D=E=H; A=—$CH_2$—$CH_2$-(4-$OCH_3$-phenyl)

42a. (R)-homo-O-methyltyrosinol (R)-Homo-O-methyltyrosine (prepared according to the procedure of Melillo, et al., J. Org. Chem., 52:5149–5150 (1987)) is reduced with $LiAlH_4$ under standard conditions to give the title compound.

42b. Compound of Formula (III): $R^1$=$OCH_3$, $R^2$=H; B=D=E=H; A=—$CH_2$—$CH_2$-(4-$OCH_3$-phenyl)

Following the procedures of Example 5, except replacing the (S)-2-amino-3-phenyl-1-propanol of step 5a with the compound of step 42a, the title compound is obtained.

EXAMPLE 43

Compound of Formula (III): $R^1$=$OCH_3$, $R^2$=H; A=
B=D=H; E=—$CH_2CH_2$Ph

Following the procedures of Example 3 except replacing the 2-(R)-amino-3-phenyl-1-propanol of step 3a thereof with (R)-homo-phenylalaninol prepared by $LiAlH_4$ reduction under standard conditions of the (R)-homo-phenylalanine compound available from Aldrich) the title compound is prepared.

EXAMPLE 44

Compound of Formula (III): $R^1$=OCH$_3$, $R^2$=H; A=B=E=H; D=—CH$_2$CH$_2$Ph

Following the proc edures of Example 3 except replacing the 2-R)-amino-3-phenyl-1-propanol of step 3a the reof with (S)-homo-phenylalaninol (prepared by LiAlH$_4$ reduction under standard conditions of the (S)-homo-phenylalanine compound available from Aldrich) the title compound is prepared.

EXAMPLE 45

Compound of Formula (III): $R^1$=OCH$_3$, $R^2$=H; A=B=D=H; E=—CH$_2$CH$_2$CH$_2$Ph Following the procedures of Example 3 except replacing the 2-(R)-amino-3-phenyl-1-propanol of step 3a thereof with (±)-2-amino-5-phenylpentanol (prepared in Example 40b) and separating the desired isomer by chromatography the title compound is prepared.

EXAMPLE 46

Compound of Formula (III): $R^1$=OCH$_3$, $R^2$=H; A=B=E=H; D=—CH$_2$CH$_2$CH$_2$Ph Following the procedures of Example 3 except replacing the 2-(R)-amino-3-phenyl-1-propanol of step 3a thereof with 2-(R)-amino-5-phenylpentanol (prepared in Example 36b) the title compound is prepared.

EXAMPLE 47

Compound of Formula (III): R1=OCH$_3$, R2=H; A=—CH$_2$CH$_2$OPh; B=D=E=H

47a. N-a-Boc-L-homoserine benzyl ester

The title compound is prepared from N-a-Boc-L-aspartic acid a-benzyl ester, ethyl chloroformate, N-methylmofpholine and sodium borohydride in tetrahydrofuran and methanol according to the procedures described by Kokotos, *Synthesis*, (1990): 299–301.

47b. 4-Phenoxy-2-(S)-Boc-aminobutyric acid benzyl ester

A solution of N-a-Boc-L-homo-serine benzyl ester, phenol and triphenylphosphine in THF is treated with diethylazodicarboxylate (DEAD) at 0° C. After being stirred at room temperature for 2 hours, the reaction is worked up and product purified by silica gel chromatography. (cf. Organic Reactions, Vol. 42, John Wiley & Son, Inc, 1992).

47c. 4-phenoxy-2-(S)-Boc-aminobutane-1-ol

Lithium aluminum hydride is added into a stirred solution of 4-phenoxy-2-(S)-Boc-aminobutyric acid benzyl ester, from step 47b, in TUF at 0° C. The reaction mixture is heated to reflux for 0.5 hour and cooled to ice-cold temperature. Water, equal weight to the lithium aluminum hydride used, is added and stirred at room temperature overnight. The reaction is diluted with ethyl acetate and dried over sodium sulfate. After filtration and removal of solvent in vacuo, the product is purified by silica gel chromatography.

47d. 4-phenoxy-2-(S)-aminobutane-1-ol

The amino protecting group of 4-phenoxy-2-(S)-Boc-aminobutane-1-ol from step 47c is removed by treatment of the protected compound with hydrogen chloride in dioxane. (cf. T. W. Greene and P. G. M. Wuts: Protective Groups in Organic Synthesis. 2nd ed., John Wiley and Son, 1991, pp 309–315.)

47e. Compound (22) Scheme 10: (III): $R^1$=OCH$_3$, $R^2$=Bz; A=—CH2CH2—OPh; B=D=E=H; Y=OH The title compound is prepared from 4-phenoxy-2-(S)-aminobutane-1-ol and compound (8) in aqueous acetonitrile according to the procedures described in Example 5.

47f. Compound (20) Scheme 10: $R^1$=OCH$_3$, A=—CH2CH2-OPh; B=D=E=H

The title compound is prepared from the compound of step 47d according to the procedures described in Example 5.

47g. Compound of Formula (III): R1=OCH$_3$, R2=H; A=—CH2CH2OPh; B=D=E=H

The title compound of Example 47 is prepared from the compound of 47f according to the procedures described in Example 5.

EXAMPLE 48

Compound of Formula (III): R1=OCH$_3$, R2=H; A=—CH2CH2NHCbz; B=D=E=H

48a. N-a-(S)-Boc-N-g-Cbz-2,4-diaminobutyric acid benzyl ester

Diphenylphosphoryl azide is added into a solution of N-a-(S)-Boc-L-glutamic acid a a-benzyl ester in TFF and the resulting solution is refluxed for 2 hours. Benzyl alcohol is added and the reaction mixture is refluxed for an additional hour. The product is purified by silica gel chromatography.

48b. N-a-(S)-Boc-N-g-Cbz-2,4-diamino-butane-1-ol

Lithium aluminum hydride is added into a stirred solution of N-a-(S)-Boc-N-g-Cbz-diaminobutyric acid benzyl ester, from step 48a, in THF at 0° C. The reaction mixture is heated to reflux for 0.5 hour and cooled to ice-cold temperature. Water, equal weight to the lithium aluminum hydride used, is added and stirred at room temperature overnight The reaction is diluted with ethyl acetate and dried over sodium sulfate. After filtration and removal of solvent in vacuo, the product is purified by silica gel chromatography.

48c. 2-(S)-4-N-Cbz-diamino-1-butanol

The amino protecting group of N-a-(S)-Boc-N-g-Cbz-2, 4-diamino-butane-1-ol from step 48b is removed by treatment of the protected compound with hydrogen chloride in dioxane according to literature method. (cf. T. W. Greene and P. G. M. Wuts: Protective Groups in Organic Synthesis. 2nd ed., John Wiley and Son, 1991, pp 309–315.).

48d. Compound (22) Scheme 10: $R^1$=OCH$_3$, R2=bz; A=—CH2CH2—NHCbz; B=D=E=H; Y=OH The title compound is prepared from 2-(S)-amino-4-N-g-Cbz-diamino-butane-1-ol, from step 48c, and compound (8) from Scheme 3 in aqueous acetonitrile according to the procedures described in Example 5.

48e. Compound (20) Scheme 10: $R^1$=OCH$_3$; A=—CH2CH2—NHCbz; B=D=E=H

The title compound is prepared from the compound of step 48d according to the procedures described in Example 5.

48f. Compound of Formula (III): R1=OCH$_3$, R2=H; A=—CH2CH2NHCbz; B=D=E=H

The title compound is prepared from the compound of step 48e according to the procedures described in Example 5.

EXAMPLE 48-A

Compound of Formula (III): R1=OCH$_3$, R2=H; A—CH2CH2NH2; B=D=E=H

The title compound is prepared from the compound of Example 48 and hydrogen in the presence of Pd-C in ethanol.

EXAMPLE 49

Compound of Formula (III): R1=OCH$_3$, R2=H;
A=—CH2CO2Bzl; B=D=E=H 49a 4-hydroxy-3-N-(S)-Boc-aminobutyric acid benzyl ester The title compound is prepared from N-a-Boc-L-aspartic acid g-benzyl ester, ethyl chloroformate, N-methylmorpholine and sodium borohydride in tetrahydrofuran and methanol according to the procedures described by Kokotos, *Synthesis*, (1990): 299–301.

49b. 4-hydroxy-3-(S)-aminobutyric acid benzyl ester

The amino protecting group of 4-hydroxy-3-N-(S)-Boc-aminobutyric acid benzyl ester, from step 49a, is removed by treatment of the protected compound with hydrogen chloride in dioxane according to literature method.(cf. T. W. Greene and P. G. M. Wuts: Protective Groups in Organic Synthesis. 2nd ed., John Wiley and Son, 1991, pp309–315.)

49c. Compound (22) Scheme 10: R$^1$=OCH$_3$; R$^2$=bz; A=—CH2CO2Bzl; B=D=E=H; Y=OH The title compound is prepared from 4-hydroxy-3-(S)-aminobutyric acid benzyl ester, from step 49b and compound (8) of Scheme 3 in aqueous acetonitrile according to the procedures described in Example 5.

49d. Compound (20) Scheme 10: R$^1$=OCH$_3$; A=—CH2CO2Bzl; B=D=E=H

The title compound is prepared from the compound of step 49c according to the procedures described in Example 5.

49e. Compound of Formula (III): R1=OCH$_3$, R2=H; A=—CH2CO2Bzl; B=D=E=H

The title compound is prepared from compound from the compound of step 49d according to the procedures described in Example 5.

EXAMPLE 49-A

Compound of Formula (III): R1=OCH$_3$, R2=H;
A=—CH2COOH; B=D=E=H

The title compound is prepared from the compound of Example 49 and hydrogen in the presence of Pd-C in ethanol.

EXAMPLE 49-B

Formula (III): R1=OCH$_3$, R2=H; A=—CH2CH2OH; B=D=E=H

The title compound is prepared from the title compound of Example 49-A, ethyl chloroformate, N-methylmorpholine and sodium borohydride in tetrahydrofuran and methanol according to the procedures described by Kokotos, *Synthesis*, (1990): 299–301.

EXAMPLE 50

Compound of Formula (III): R1=OCH$_3$, R2=H;
A—CH2CH2NH(4'-Pyridyl); B=D=E=H

The title compound is prepared from the compound of Example 48-A, 4-chloropyridine, and CuO or CuBr-K2CO$_3$ heated at 70–90° C. overnight The reaction mixture is partitioned between ethyl acetate and water. The organic phase is washed once with dilute hydrochloric acid followed by saturated sodium bicarbonate. The product is purified by silica gel chromatography.

EXAMPLE 51

Compound of Formula (III): R$^1$=OCH$_3$, R$^2$=H; A=B=D=H; E=—CH$_2$OH 51a. 1,2-diamino-3-propanol Allyl acetate (Aldrich) is reacted with manganese triacetate, sodium azide and acetic acid. The resulting compound is treated with NaHCO$_3$ and methanol followed by hydrogenation to give the title compound.

51b. Compound of Formula (III): R$^1$=OCH$_3$, R$^2$=H; A=B=D=H; E=—CH$_2$OH

Following the procedures of Example 3 steps f–h, except substituting 1,2-diamino-3-propanol from the previous step, for the 1,2-(R)-diamino-3-phenylpropane thereof, the title compound is prepared, and the diastereomers are separated by chromatography.

EXAMPLE 52

Compound of Formula (III): R$^1$=OCH$_3$, R$^2$=H; A=B=E=H; D=—CH$_2$OH

The compound was separated from the diastereomeric mixture of Example 51b by chromatography. MS (m/z): xxx (M+H)$^+$.

EXAMPLE 53

Compound of Formula (III): R$^1$=OCH$_3$, R$^2$=H; A=B=E=H; D=—CH$_2$NHBenzoyl

The compound is prepared from the compound of Example 16 by treatment with benzoyl chloride and TEA.

EXAMPLE 54

Compound of Formula (III): R$^1$=OCH$_3$, R$^2$=H; A=B=E=H; D=—CH$_2$NHBenzal

The compound is prepared from the compound of Example 16 by treatment with benzaldehyde, NaCNBH$_3$ and acetic acid in methanol at room temperature.

EXAMPLE 55

Compound of Formula (III): R$^1$=OCH$_3$, R$^2$=H; A=B=D=H; E=—CH$_2$NHBenzoyl

The compound is prepared from the compound of Example 15 by treatment with benzoyl chloride and TEA.

EXAMPLE 56

Compound of Formula (III): R$^1$=OCH$_3$, R$^2$=H; A=B=D=H; E=—CH$_2$NHBenzyl

The compound is prepared from the compound of Example 15 by treatment with benzaldehyde, NaCNBH$_3$ and acetic acid in methanol at room temperature.

EXAMPLE 57

Compound of Formula (III): (III): R$^1$=OCH$_3$, R$^2$=H; B=D=H; A=E=(4-chloro)benzyloxymethyl 57a. (R,R)-(+)-1,4-bis-O-(4-chlorobenzyl)-2,3-butanediamine Following the procedure of Example 10 steps a–c, replacing the meso-2,3-butanediol thereof with (R,R)-(+)-1,4-bis-O-(4-chlorobenzyl)-D-threitol (Aldrich) the title compound was obtained.

57b. Compound of Formula (III): $R^1$=$OCH_3$, $R^2$=H; B=D=H; A=E=(4-chloro)benzyloxymethyl Following the procedures of Example 10 steps d–f, replacing the meso-2,3-butanediamine of step d thereof with the diamine from step 57a, the title compound was prepared. MS (m/z): 946 (M+H)$^+$.

EXAMPLE 58

Compound of Formula (III): $R^1$=$OCH_3$, $R^2$=H; A=B=E=H; D=—$CH_2$—N($CH_3$)-benzyl The title compound was prepared by treating the compound of Example 54 with HCHO, $NaCNBH_3$ and acetic acid in methanol at room temperature. MS (m/z): 771 (M+H)$^+$.

EXAMPLE 59

Compound of Formula (III): $R^1 OCH3$, $R^7$=H; A=B=D=H; E=—$CH_2$—N($CH_3$)-benzul The title compound is prepared by treating the compound of Example 56 with HCHO, $NaCNBH_3$ and acetic acid in methanol at room temperature.

EXAMPLE 60

Compound of Formula (III): $R^1$=$OCH_3$, $R^2$=H; A=B=D=H; E=—$CH_2$—NH-phenyl

The title compound is prepared by treating the compound of Example 51 with triphenyl phosphine, DEAD and aniline under Mitsunobu conditions.

EXAMPLE 61

Compound of Formula (III): $R^1$=$OCH_3$, $R^2$=H; A=B=E=H; D=—$CH_2$—NH-phenyl

The title compound is prepared by treating the compound of Example 52 with triphenyl phosphine, DEAD and aniline under Mitsunobu conditions.

EXAMPLE 62

Compound of Formula (III): A=4-methoxybenzyloxymethyl, B=D=E=H, $R^1$=methoxy, $R^2$=hydrogen Following the procedures of Example 5, except replacing the (S)-2-amino-3-phenyl-1-propanol of step 5a with (R)-2-amino-3-(4-methoxybenzyloxy)-1-propanol, and carrying the product forward according to the procedures of steps 5b–5e, the title compound was prepared. MS m/z (M+H)$^+$: 788.

The (R)-2-amino-3-(nmethoxybenzyloxy)-1-propanol was prepared as follows:

Step 62a. 4-(4-methoxybenzyloxy)methyl-2,2-dimethyl[1,3]dioxolane

Commercially available (R)-(−)-1,2-O-isopropylideneglycerol (also known as (R)-4-hydroxymethyl-2,2-dimethyl[1,3]dioxolane, 4.0 mL, 31 mmole, Lancaster) was added via syringe over 10 minutes to a suspension of sodium hydride (as a 60% mineral oil dispersion, 1.3 g, 32.05 mmole) in DMF (30 mL) at ice bath temperature under nitrogen. The mixture was stirred for fifteen minutes, then warmed to room temperature and diluted with ThF (50 mL). The mixture was cooled to 0° C. again, and 4methoxybenzyl bromide (31 mmole) was added. The mixture was stirred at room temperature for 16 hours, then the reaction was quenched by addition of water. The reaction mixture was extracted with EtOAc and the combined organic layers were washed with water and brine, dried ($Na_2SO_4$) and concentrated in vacuo to give the title compound (5.8 g). MS m/z (M+$NH_4$)$^+$: 270.

Step 62b. 3-(4-methoxybenzyloxypropane-1,2-diol

To the product from step 62a (5.72 g, 22.7 mmole) in methanol (100 mL) was added (p-toluenesulfonic acid (500 mg, 2.63 mmole), and the mixture was stirred at room temperature for 22 hours. After addition of water (5 mnL), the mixture was stirred another 24 hours. The solvents were removed, and the residue was partitioned between 1:1 saturated $NaHCO_3$:brine and $CHCl_3$. The organic phase was dried ($Na_2SO_4$) and concentrated in vacuo to give the product ((4.82 g) MS m/z (M+$NH_4$)$^+$: 230) as an oil, which was taken directly to the next step.

Step 62c. 1-t-butyldimethylsilyloxy-3-(4-methoxybenzyloxy)-2-propanol

To the product from step 62b (4.63 g, 21.8 mmole) and imidazole (1.65 g, 24.2 mmole) in DMF at 0° C. was added t-butyldimethylsilyl chloride, and the mixture was stirred for 20 minutes. The mixture was stirred at room temperature for 24 hours, then extracted with ethyl acetate. The combined organic layers were washed with water and brine, dried ($Na_2SO_4$) and concentrated in vacuo to give the crude title compound (7.03 g), which was taken directly to the next step. MS m/z (M+$NH_4$)$^+$: 344.

Step 62d. 1-t-butyldimethylsilyloxy-2-methanesulfonyloxy-3-(4methoxybenzyloxy)propane To the product from step 62c (7.0 g, 21 inmole) and triethylamine (52 mmole) in methylene chloride at −10° C. was added methanesulfonyl chloride ((43 mmole), the cooled mixture was stirred for one hour, then stirred at room temperature for 10 minutes. The solvent was removed under vacuum, and the residue was partitioned between ethyl acetate and water. The organic extract was washed with water and brine, dried ($Na_2SO_4$) and concentrated in vacui to give the title compound (8.0 g). MS m/z (M+$NH_4$)$^+$: 422.

Step 62e. (R)-2-azido-3-(4methoxybenzyloxy)-1-propanol

The compound from step 62d (7.98 g) was stirred with sodium azide in DMF (60 mL) for 64 hours at 50° C. The temperature was then raised to 85° C., and the mixture was stirred for 24 hours. The reaction was quenched with water, and the mixture was extracted with ethyl acetate. The combined organic layers were washed with water and brine, dried ($Na_2SO_4$) and concentrated in vacua. The residue was treated with tetrabutylamrnmonium fluoride (20 mmole) in THF (20 mL) at room temperature for 16 hours. The solvent was removed under vacuum, and the residue was partitioned between ethyl acetate and water. The organic extract was washed with water and brine, dried ($Na_2SO_4$) and concentrated in vacua. Chromatography of the residue on silica gel, eluting with hexane containing increasing amounts of ethyl acetate gave the pure title compound (3.03 g). MS m/z (M+$NH_4$)$^+$: 255.

Step 62f. (R)-2-amino-3-(4-methoxybenzyloxy)-1-propanol

The compound from step 62e (2.98 g, 12.6 mmole) was dissolved in $H_2O$/THF 1:9 and stirred with triphenylphosphine (19.8 g, 75.5 mmole) for 24 hours at reflux. The solvent was removed, and the residue was taken up in 10% aqueous $KH_2PO_4$. The solution was washed with ether, then carefully basified to pH 10 with $K_2CO_3$. NaCl was added to the solution, which was then extracted with chloroform. The organic phase was washed with water and brine, dried ($Na_2SO_4$) and concentrated in vacuo to give the title compound (2.295 g). MS m/z (M+H)$^+$: 212. Anal. Calcd. for $C_{11}H_{17}NO_3$: C, 62.54; H, 8.11; N, 6.63; Found: C, 62.66; H, 7.95; N, 6.47.

EXAMPLE 63

Compound of Formula (III): A=4-hydroxymethyl, B=D=E=H, $R^1$=methoxy, $R^2$=hydrogen Treating the compound of Example 62 with tiifluoroacetic acid in methylene chloride at room temperature for 20 minutes, followed by chromatography on silica gel, the title compound was prepared. MS m/z $(M+H)^+$: 688.

EXAMPLE 64

Compound of Formula (III): A=4-benzyloxybenzyl, B=D=E=H, $R^1$=methoxy, $R^2$=hydrogen Following the procedures of Example 5, except replacing the (S)-2-amnino-3-phenyl-1-propanol of step 5a with (S)-2-amino-3-(4-benzyloxyphenyl)-1-propanol and the $CH_3CN/H_2O$ solvent system with 19:5:4:5 $CH_3CN:H_2O:DMF:THF$, then carrying the product forward according to the procedures of steps 5b–5e, the title compound was prepared. MS m/z $(M+H)^+$: 834.

Step 64a. (S)-2-amino-3-(4-benzyloxyphenyl)-1-propanol

BOC-O-benzyl-L-tyrosine (5.0 g, 13.46 mmole, Bachem) was treated with ethoxycarbonyl chloride (13.60 mmole) and N-methylmorpholine (13.64 mmole) in THF (50 mL) at −10° C. for 10 minutes. The mixture was filtered, and the filtrate was added to an aqueous solution (50 mL) of $NaBH_4$ (2.1 g, 55.5 mmole) at 0° C. The mixture was stirred at 0° C. for 0.5 hours and 15 minutes at room temperature, then carefully acidified to about pH 2 with concentrated HCl. The mixture was extracted with ethyl acetate, which was washed with water and concentrated. The residue was dissolved in methanol, HCl/morpholine (4 M, 30 mL) was added, and the mixture was stirred for 45 minutes. The mixture was diluted with water, then basified with $Na_2CO_3$. The solvents were removed under vacuum, and the aqueous solution was extracted with chloroform. The organic phase was washed with brine, dried ($Na_2SO_4$), concentrated, filtered, and the solvent removed under vacuum to give the desired compound. Anal. Calcd. for $C_{16}H_{19}NO_2$: C, 74.16; H, 7.47; N, 5.41; Found: C, 74.13; H, 7.74; N, 5.25. MS m/z $(M+H)^+$: 258.

EXAMPLE 65

Compound of Formula (III): A=4-hydroxybenzyl, B=D=E=H, $R^1$=methoxy, $R^2$=hydrogen Treating the compound of Example 62 with hydrogen at atmospheric pressure over
10% Pd/C catalyst for 48 hours in ethanol, followed by chromatography on silica gel, the title compound was prepared. MS m/z $(M+H)^+$: 744.

EXAMPLE 66

Compound of Formula (III): A=S-benzylthioxymethyl, B=D=E=H, $R^1$=methoxy, $R^2$=hydrogen Following the procedures of Example 5, except replacing the (S)-2-amino-3-phenyl-1-propanol of step 5a with (S)-benzyl-L-cysteinolol (Aldrich), and carrying the product forward according to the procedures of steps 5b–5e, the title compound was prepared. MS m/z $(M+H)^+$: 774.

EXAMPLE 67

Compound of Formula (III): A=3-indolylmethyl, B=D=E=H, $R^1$=methoxy, $R^2$=hydrogen Following the procedures of Example 5, except replacing the (S)-2-arnino-3-phenyl-1-propanol of step 5a with (R)-tryptophanol (TCI), and carrying the product forward according to the procedures of steps 5b–5e, the title compound was prepared. MS m/z $(M+H)^+$: 767.

EXAMPLE 68

Compound of Formula (III): A=4-(benzyloxycarbonylamino)benzyl, B=D=E=H, $R^1$=methoxy, $R^2$=hydrogen Following the procedures of Example 5, except replacing the (S)-2-amino-3-phenyl-1-propanol of step 5a with (S)-2-amino-3-(4-(benzyloxycarbonylamino)phenyl)-1-propanol and the $CH_3CN/H_2O$ solvent system with 9:3:3:5 $CH_3CN:H_2O:DMF:THF$, then carrying the product forward according to the procedures of steps 5b–S5e, the title compound was prepared. MS m/z $(M+H)^+$: 877. The (S)-2-amino-3-(4-(benzyloxycarbonylamino)phenyl)-1-propanol starting material was prepared by the method described in Example 64, except substituting N-BOC-p-CBZ-amino-L-phenylalanine (Bachem) for the BOC-O-benzyl-L-tyrosine thereof. Anal. Calcd. for $C_{17}H_{20}N_2O_3$: C, 67.18; H, 6.76; N, 9.22; Found: C, 67.37; H, 6.80; N, 9.05. MS m/z $(M+H)^+$: 301.

EXAMPLE 69

Compound of Formula (III): A=4-thiazolylmethyl, B=D=E=H, $R^1$=methoxy, $R^2$=hydrogen Following the procedures of Example 5, except replacing the (S)-2-amino-3-phenyl-1-propanol of step 5a with (S)-2-amino-3-(4-thiazolyl)-1-propanol (prepared by reduction of BOC-(4-thiazolyl)-L-alanine, which was prepared according to the procedure of Hsiao, et al., *Synthetic Commun.*, 20: 3507 (1990) followed by removal of the BOC group by standard methods) and carrying the product forward according to the procedures of steps 5b–5e, the title compound was prepared. MS m/z $(M+H)^+$: 735.

EXAMPLE 70

Compound of Formula (III): A=4-iodobenzyl, B=D=E=H, $R^1$=methoxy, $R^2$=hydrogen Following the procedures of Example 5, except replacing the (S)-2-amino-3-phenyl-1-propanol of step 5a with (R)-2-amino-3-(4-iodophenyl)-1-propanol (prepared by reduction of BOC-4-iodo-L-phenylalanine (Bachem) followed by removal of the BOC group by standard methods) and the $CH_3CN/H_2O$ solvent system with 4.5:1:5 $CH_3CN:H_2O:DMF$, then carrying the product forward according to the procedures of steps 5b–5e, the title compound was prepared. MS m/z $(M+H)^+$: 854.

EXAMPLE 71

Compound of Formula (III): A=4-fluorobenzyloxy, B=D=E=H, $R^1$=methoxy, $R^2$=hydrogen Following the procedures of Example 5, except replacing the (S)-2-amino-3-phenyl-1-propanol of step 5a with (R)-2-amino-3-(4-fluorophenyl)-1-propanol, and carrying the product forward according to the procedures of steps 5b–5e, the title compound was prepared. MS m/z $(M+H)^+$: 776.

Step 71a. (R)-2-amino-3-(4-fluorophenyl)-1-propanol

To N-BOC-L-serine (10.25 g, 50 mmole) dissolved in DMF (50 mL) at 0° C. was added NaH (4.1 g, 110 mmole). After gas evolution ceased, 4-fluorobenzyl bromide (55 mmole) was added, and the reaction mixture was stirred for 5 hours at 0° C. The reaction was quenched with water (10 mL), and the solvents were removed under vacuum at 50° C. The residue was dissolved in water (200 mL), which was washed with ether. The aqueous phase was acidified with HCl to pH 2, and the solution was extracted with ethyl acetate. The combined organic solution was washed with water and brine, dried over $Na_2SO_4$, and the solvent removed. The residue was treated according to the procedure of Example 64a to afford the title compound. MS m/z $(M+H)^+$: 200.

EXAMPLE 72

Compound of Formula (III): A=3-fluorobenzyloxy, B=D=E=H, $R^1$=methoxy, $R^2$=hydrogen Following the procedures of Example 5, except replacing the (S)-2-armino-3-phenyl-1-propanol of step 5a with (R)-2-amino-3-(3-fluorophenyl)-1-propanol, and carrying the product forward according to the procedures of steps 5b–5e, the title compound was prepared. MS m/z $(M+H)^+$: 776. The (R)-2-amino-3-(3-fluorophenyl)-1-propanol was prepared according to Example 71, except substituting 3-fluorobenzyl bromide for the 4-fluorobenzyl bromide. MS m/z $(M+H)^+$: 200.

EXAMPLE 73

Compound of Formula (III): A=2-fluorobenzyloxy, B=D=E=H, $R^1$=methoxy, $R^2$=hydrogen Following the procedures of Example 5, except replacing the (S)-2-amino-3-phenyl-1-propanol of step 5a with (R)-2-amino-3-(2-fluorophenyl)-1-propanol, and carrying the product forward according to the procedures of steps 5b–5e, the title compound was prepared. MS m/z $(M+H)^+$: 776. The (R)-2-amino-3-(2-fluorophenyl)-1-propanol was prepared according to Example 71, except substituting 2-fluorobenzyl bromide for the 4-fluorobenzyl bromide. MS m/z $(M+H)^+$: 200.

EXAMPLE 74

Compound of Formula (III): A=B=E=H, D=(4-cyanobenzyloxy)methyl, $R^1$=methoxy, $R^2$=hydrogen Following the procedures of Example 3f–3h, except replacing the 1,2-(R)-diamino-3-phenylpropane of step 3f with (S)-3-(4-cyanobenzyloxy)propane-1,2-diamine, the title compound was prepared. MS m/z $(M+H)^+$: 783.

The (S)-3-(4-cyanobenzyloxy)propane-1,2-diamine was prepared as follows:
Step 74a. (S)-4-(4-cyanobenzyloxy)methyl-2,2-dmethyl [1.3]dioxolane Commercially available (S)-alpha,beta-isopropylideneglycerol (2 mL, 16.12 mmole, Fluka) (another name for which is 4-hydroxymethyl-2,2-dimethyl [1,3]dioxolane) was added via syringe over several minutes to a suspension of sodium hydride (as a 60% mineral oil dispersion 0.73 g, 18.29 mmole) in DMF (30 mL) at ice bath temperature under nitrogen. The mixture was stirred for fifteen minutes during which time additional DMF (5 mL) was added. To this mixture was added a solution of commercially available 4-cyanobenzyl bromide (2.98 g, 15.2 mmole) in DMF (10 mL) dropwise over five minutes followed by warming of the reaction mixture to room temperature. After two hours the reaction mixture was partitioned between ammonium chloride solution and EtOAc. The aqueous phase was extracted 3x with EtOAc and the combined organics dried ($MgSO_4$) and concentrated in vacuo to give a yellow oil. Pure title compound was isolated by flash chromatography on silica gel (EtOAc-hexane) as a clear oil (3.27 g, 87%) MS DCl, $(M+H)^+/(M+NH_4)^+$ m/z 248, 265.

Step 74b. (S)-3-(4-cyanobenzyloxy)propane-1,2-diol
The product from step 74a (3.27 gm, 13.22mmole) was stirred at room temperature in 2/1 (v/v) THF-10% HCl (30 mL) for about two hours. The reaction mixture was partitioned between brine and EtOAc. The organic phase was dried ($MgSO_4$) and concentrated in vacuo to give the crude product as a clear oil, which was taken directly to the next step. MS DCI, $(M+NH_4)^+$ m/z 225.

Step 74c. (S)-3-(4-cyanobenzyloxy)-1,2-bis(methanesulfonyloxy)propane

The product from step 74b (13.2 mmole) was dissolved in pyridine (16 mnL) and the solution was chilled in an ice bath. To the cold solution was added methanesulfonyl chloride (2.4 mL, 29 mmole) dropwise via syringe. After one hour the mixture was partitioned between 10% HCl and EtOAc. The aqueous phase was extracted with EtOAc (2×) and the combined organics were dried ($Na_2SO_4$) and concentrated in vacuo to give the product as an oil (4.58 g, 95%), which was taken directly to the next step. MS DCI $(M+NH_4)^+$ m/z 381.

Step 74d. (S)-3-(4-cyanobenzyloxy)-1,2-bis(azido)propane
The product from step 3 (4.58 g, 12.6 mmole) was dissolved in DMF (50 mL) and sodium azide (3.6 g, 55 mmole) was added. The resulting suspension was heated in an oil bath (70–85° C.) under nitrogen with stirring, overnight. The reaction mixture was subsequently partitioned between 5% $NaHCO_3$ and ether. After the addition of NaCl the aqueous phase was extracted with ether(3×) and the combined organics dried ($Na_2SO_4$) and concentrated to a small volume. Dilution with ethanol (75 mL) was followed by further concentration to remove the ether. The solution was taken directly to the next step.

Step 74e. (S)-3-(4-cyanobenzyloxy)propane-1,2-diamine
To the solution from step 74d was added 5% Pd/C (0.373 g) and the mixture vacuum degassed (3×) followed by a hydrogen balloon at room temperature. After two hours 0.211 g catalyst was added and the balloon refilled with hydrogen. After a total of three and one half hours the catalyst was removed by filtration and the ifiltrate concentrated in vacuo to give the title compound (2.3 g, 89%). MS DCI $(M+H)^+$ m/z 232.

EXAMPLE 75

Compound of Formula (III): A=B=E=H, D=(4(t-butyloxycarbonyl)-aminobenzyloxy)methyl, $R^1$= methoxy, $R^2$=hydrogen Following the procedure of Example 74, except substituting (S)-3-(4-(t-butyloxycarbonyl)aminobenzyloxy) propane-1,2-diamnine for the (S)-3-(4cyanobenzyloxy) propane-1,2-diamine thereof, the title compound was prepared. MS m/z $(M+H)^+$: 887.

The (S)-3-(4-(t-butyloxycarbonyl)aminobenzyloxy) propane-1,2-diamine was prepared as follows:
Step 75a. (S)-4-(4-aminobenzyloxy)methyl-2,2-dimethyl[1,3]dioxolane D-4-(4-cyanobenzyloxy)methyl-2,2-dimethyl[1,3] dioxolane (15.2 mmole, from step 74a above) was reduced with Raney nickel in methanolic ammonia. The product was purified by flash chromatography on silica gel (chloroform-methanol-ammonium hydroxide) to give the title compound. MS DCI m/z: 252/269 $(M+H)^+/(M+NH_4)^+$.

Step 75b. (S)-4-(4-(t-butyloxycarbonylamino)benzyloxy)methyl-2,2-dimethyl[1.3]dioxolane Treatment of the compound from step 75a (1.49 g, 5.9 mmole) in dioxane (25 ml) at room temperature with di-t-butyl dicarbonate (1.42 g, 6.52 mmole) gave the title compound after 45 minutes. The product was purified by flash chromatography on silica gel (EtOAc-hexane)to give the title compound as a clear oil (0.94 g, 45%). MS DCI m/z: 369 $(M+NH_4)^+$.

Step 75c. (S)-3-(4(t-butyloxycarbonyl)aminobenzyloxy)propane-1,2-diamine

Following the procedure of Example 74b, except substituting the compound of step 75b for the compound of step 74a, and carrying the product forward as in steps 74c–74e, the title compound was prepared.

EXAMPLE 76

Compound of Formula (III): A=B=E=H. D=(4-(dimethylamino)benzyloxy)methyl, $R^1$=methoxy, $R^2$=hydrogen The compound of Example 74 (0.46 g, 0.58 mmole) was reduced with Raney nickel in methanolic ammonia to convert the cyano group into a free amino group. The product was purified by flash chromatography on silica gel (chloroform-methanol-ammonium hydroxide). MS ESI m/z: 787 $(M+H)^+$. The amine was treated with formic acid (16 mL) and 37% formalin solution (8 mL) followed by heating on a steam bath. Over the course of six hours an additional 6 mL of formalin solution was added. The reaction mixture was subsequently diluted with water (50 mL), chilled in an ice bath and made basic by dropwise addition of sodium hydroxide (15.5 g, 0.39 mole) in water (100 ml). The mixture was then allowed to warm to room temperature and stir overnight. The crude product was isolated by extraction with chloroform. The combined extracts were dried $(Na_2SO_4)$ and concentrated in vacuo. The crude product was a mixture of 2'-OH and 2'-$OCH_2OH$. Dissolution in methanol followed by heating to reflux for several hours converted all material to the 2'-OH form. Purification by flash chromatography on silica gel (as above) gave the title compound (0.0753 g, 16%). MS APCI m/z: 815 $(M+H)^+$.

EXAMPLE 77

Compound of Formula (III): A=B=E=H. D=(4-pyridyl)methoxymethyl, $R^1$=methoxy, $R^2$=hydrogen Following the procedure of Example 74, except substituting (S)-3-(4-pyridylmethyloxy)propane-1,2-diamine for the (S)-3-(4-cyanobenzyloxy)propane-1,2-diamine thereof, the title compound was prepared. The (S)-3-(4-pyridylmethyloxy)propane-1,2-diamine was prepared according to the procedures of Steps 74a–74e, except substituting 4-pyridylmethyl chloride for the 4-cyanobenzyl bromide of Step 74a. MS APCI m/z: 759 $(M+H)^+$.

EXAMPLE 78

Compound of Formula (III): A=B=E=H D=(2-chloro)benzyloxymethyl, $R^1$=methoxy, $R^2$=hydrogen Following the procedure of Example 74, except substituting (S)-3-(2-chloro-benzyloxy)propane-1,2-diamine for the (S)-3-(4-cyanobenzyloxy)propane-1,2-diamine thereof, the title compound was prepared. The (S)-3-(2-chlorobenzyloxy)propane-1,2-diamine was prepared according to the procedures of Steps 74a–74e, except substituting 2-chlorobenzyl chloride for the 4-cyanobenzyl bromide of Step 74a. MS APCI m/z: 792 $(M+H)^+$.

EXAMPLE 79

Compound of Formula (III): A=B=E=H, D=(4-chloro)benzyloxymethyl, $R^1$=methoxy, $R^2$=hydrogen Following the procedure of Example 74, except substituting (S)-3-(4-chloro-benzyloxy)propane-1,2-diamine for the (S)-3-(4-cyanobenzyloxy)propane-1,2-diamine thereof, the title compound was prepared. The (S)-3-(4-chlorobenzyloxy)propane-1,2-diamine was prepared according to the procedures of Steps 74a–74e, except substituting 4-chlorobenzyl chloride for the 4-cyanobenzyl bromide of Step 74a. MS APCI m/z: 792 $(M+H)^+$.

EXAMPLE 80

Compound of Formula (III): A=B=E=H, D=(3-chloro)benzyloxyrethyl, $R^1$=methoxy, $R^2$=hydrogen Following the procedure of Example 74, except substituting (S)-3-(3-chlorobenzyloxy)propane-1,2-diamine for the (S)-3-(4-cyanobenzyloxy)propane-1,2-diamine thereof, the title compound was prepared. The (S)-3-(43-chlorobenzyloxy)propane-1,2-diamine was prepared according to the procedures of Steps 74a–74e, except substituting 3-chlorobenzyl chloride for the 4-cyanobenzyl bromide of Step 74a. mp. 78–79° C. MS APCI m/z: 792 $(M+H)^+$.

EXAMPLE 81

Compound of Formula (III): A=B=E=H, D=(2-pyridyl)methoxymethyl, $R^1$=methoxy, $R^2$=hydrogen Following the procedure of Example 74, except substituting (S)-3-(2-pyridylmethoxy)propane-1,2-diamine for the (S)-3-(4-cyanobenzyloxy)propane-1,2-diamine thereof, the title compound was prepared. The (S)-3-(2-pyridylmethoxy)propane-1,2-diamine was prepared according to the procedures of Steps 74a–74e, except substituting 2-pyridylmethyl chloride for the 4-cyanobenzyl bromide of Step 74a. MS APCI m/z: 759 $(M+H)^+$.

EXAMPLE 82

Compound of Formula (III): A=B=E=H, D=(3-pyridyl)methoxymethyl, $R^1$=methoxy, $R^2$=hydrogen Following the procedure of Example 74, except substituting (S)-3-(3-pyridylmethoxy)propane-1,2-diamine for the (S)-3-(4-cyanobenzyloxy)propane-1,2-diamine thereof, the title compound was prepared. The (S)-3-(3-pyridylmethoxy)propane-1,2-diamine was prepared according to the procedures of Steps 74a–74e, except substituting 3-pyridylmethyl chloride for the 4-cyanobenzyl bromide of Step 74a. MS APCI mi/z: 759 $(M+H)^+$.

EXAMPLE 83

Compound of Formula (III): A=B=E=H, D=(4-methyl-2-quinolyl)methoxymethyl, $R^1$=methoxy, $R^2$=hydrogen Following the procedure of Example 74, except substituting (S)-3-((4-methyl-2-quinolyl)methoxy)propane-1,2- diamine for the (S)-3-(4-cyanobenzyloxy)propane-1,2-diamine thereof, the title compound was prepared. The (S)-3-((4-methyl-2-quinolyl)methoxy)propane-1,2-diamine was prepared according to the procedures of Steps 74a–74e, except substituting 4-methyl-2-quinolylmethyl chloride for the 4-cyanobenzyl bromide of Step 74a. MS APCI m/z: 823 (M+H)$^+$.

EXAMPLE 84

Compound of Formula (III): A=B=E=H, D=(4-(methoxycarbonyl)benzyl)oxymethyl, R$^1$=methoxy, R$^2$=hydrogen Following the procedure of Example 74, except substituting (S)-3-(4-(methoxycarbonyl)benzyloxy)propane-1,2-diamine for the (S)-3-(4cyanobenzyloxy)propane-1,2-diamine thereof, the title compound was prepared. The (S)-3-(4-(methoxycarbonyl)benzyloxy)propane-1,2-diamine was prepared according to the procedures of Steps 74a–74e, except substituting 4-(methoxycarbonyl)benzyl bromide for the 4-cyanobenzyl chloride of Step 74a. MS APCI m/z: 816 (M+H)$^+$.

EXAMPLE 85

Compound of Formula (III): A=B=E=H, D=(4-quinolyl)methoxymethyl, R$^1$=methoxy, R$^2$=hydrogen Following the procedure of Exanple 74, except substituting (S)-3-(4-quinolyl)-methoxy)propane-1,2-diamine for the (S)-3-(4-cyanobenzyloxy)propane-1,2-diamine thereof, the title compound was prepared. The (S)-3-(4-quinolyl)methoxy)propane-1,2-diamine was prepared according to the procedures of Steps 74a–74e, except substituting 4-quinolylmethyl chloride for the 4cyanobenzyl bromide of Step 74a. MS APCI m/z: 809 (M+H)$^+$.

EXAMPLE 86

Compound of Formula (III): A=B=D=H, E=(4-pyridyl)methoxymethyl, R$^1$=methoxy, R$^2$=hydrogen Following the procedure of Example 74, except substituting (R)-3-(4-pyridyl-methyloxy)propane-1,2-diamine for the (S)-3-(4-cyanobenzyloxy)propane-1,2-diamine thereof, the title compound was prepared. The (R)-3-(4-pyridylmethyloxy)propane-1,2-diamine was prepared according to the procedures of Steps 74a–74e, except substituting 4-pyridylmethyl chloride for the 4-cyanobenzyl bromide of Step 74a and (R)-alpha,beta-isopropylideneglycerol for the (S)-alpha,beta-isopropylideneglycerol. MS APCI m/z: 759 (M+H)$^+$.

EXAMPLE 87

Compound of Formula (III): A=B=E=H, D=(2-(N-morpholinyl)ethoxy)methyl, R$^2$=hydrogen Following the procedure of Example 74, except substituting (S)-3-(2-(N-morpholinyl)ethoxy)methoxy)propane-1,2-diamine for the (S)-3-(4-cyanobenzyloxy)propane-1,2-diarnine thereof, the title compound was prepared. The (S)-3-(2-(N-morpholinyl)ethoxy)methoxy)propane-1,2-diamine was prepared according to the procedures of Steps 74a–74e, except substituting 4-(2-chloroethyl)morpholine hydrochloride for the 4-cyanobenzyl bromide of Step 74a. MS APCI m/z: 781 (M+H)$^+$.

EXAMPLE 88

Compound of Formula (III): A=B=E=H, D= benzyloxymethyl, R$^1$=methoxy, R$^2$=hydrogen Following the procedure of Example 74, except substituting (S)-3-benzyloxypropane-1,2-diamine for the (S)-3-(4-cyanobenzyloxy)propane-1,2-diamine thereof, the title compound was prepared. The (S)-3-benzyloxypropane-1,2-diamine was prepared according to a modification of the procedure of Step 37a. The boc group was removed by treatment with 1.5 N HCl in glacial acetic acid at room temperature for thirty minutes. The crude product was precipitated with diethyl ether, then partitioned between aqueous sodium hydroxide and methylene chloride. The organic phase was dried (MgSO$_4$) and concentrated in vacuo to give the title compound as an oil. MS APCI m/z: 758 (M+H)$^+$.

EXAMPLE 89

Compound of Formula (III): A=B=D=H, E= benzyloxymethyl, R$^1$=methoxy, R$^2$=hydrogen Following the procedure of Example 74, except substituting (R)-3-benzyloxypropane-1,2-diamine for the (S3-(4-cyanobenzyloxy)propane-1,2-diamine thereof, the title compound was prepared. The (R)-3-benzyloxypropane-1,2-diamine was prepared according to a modification of the procedure of Step 37a, except substituting N-Boc-0 benzyl-L-serine. MS APCI m/z: 758 (M+H)$^+$.

EXAMPLE 90

Compound of Formula (III): A=B=E=H, D=(4methoxy)benzyloxymethyl, R$^1$=methoxy, R$^2$=hydrogen Following the procedure of Example 74, except substituting (S)-3-(4-methoxy)-benzyloxy)propane-1,2-diamine for the (S)-3-(4-cyanobenzyloxy)propane-1,2-diamine thereof, the title compound was prepared. The (S)-3-(4methoxy)benzyloxy)-propane-1,2-diamine was prepared according to the procedures of Steps 74a–74e, except substituting 4-methoxybenzyl chloride for the 4cyanobenzyl bromide of Step 74a. MS APCI m/z: 788 (M+H)$^+$.

EXAMPLE 91

Compound of Formula (III): A=B=E=H, D=2-phenoxyethyl, R$^2$=hydrogen

Following the procedure of Example 74, except substituting (S)-3-phenoxybutane-1,2-diamine for the (S)-3-(4-cyanobenzyloxy)propane-1,2-diamine thereof, the title compound was prepared. The (S)-3-phenoxyoxybutane-1,2-diamine was prepared according to the procedures of Steps 74b–74e, except substituting 4-phenoxyethyl-2,2-dimethyl [1,3]dioxolane for the 4-hydroxymethyl-2,2dimethyl[1,3]dioxolane of step 74b. MS APCI m/z: 758 (M+H)$^+$.

Step 91 a. 4-phenoxyethyl-2,2-dimethyl[1.3]dioxolane

To a sample of 4-hydroxyethyl-2,2-dimethyl[1,3]dioxolane (2.88 g, 19.75 mmole, prepared according to Saito, et al., *Tetrahedron*, 48:4067 (1992)) in methylene chloride (25 mL) was added triethylamine (3.2 ml, 22.7 mmole). The mixture was cooled in an ice bath and a solution of tosyl chloride (4.14 g, 21.7 nmmole) in methylene chloride (25 mL) was added dropwise. On completion the reaction mixture was allowed to slowly warm to room temperature under a nitrogen atmosphere. After five days the reaction mixture was partitioned between chloroformn and 5% NaBCO$_3$. The aqueous phase was extracted with chloroform, and the combined organic layers were dried Na$_2$SO$_4$) and concentrated in vacuo. The crude tosylate was purified by flash chromatography on silica gel (EtOAc-hexane) to give a clear oil (1.52 g, 26%) MS DCI m/z:

301/318 (M+H)⁺/(M+NH₄)⁺. The tosylate in DMF (6 mL) was subsequently added dropwise to an ice cold solution of sodium phenoxide (prepared by adding phenol (0.59 g, 6.3 mmole) in DMF (3 mL) to a suspension of sodium hydride (60% mineral oil dispersion, 0.28 gm, 7.06 mmole) in DMF (10 ml)). After several hours the reaction mixture was partitioned between 5% NaHCO₃ and EtOAc. The aqueous phase was extracted with EtOAc (2×) and the combined organic layers were dried (MgSO₄) and concentrated in vacuo. MS DCI m/z: 223/240 (M+H)⁺/(M+NH₄)⁺.

EXAMPLE 92

Compound of Formula (III): A=B=E=H, D=2-(benzyloxy)ethyl, R²=hydrogen

Following the procedure of Example 3f–3h, except substituting the 1,2-(R)-diamino-3-phenylpropane of step 3f with (S)-3-benzyloxybutane-1,2-diamine, the title compound was prepared. MS APCI m/z: 772 (M+H)⁺.

(R)-4-benzyloxybutane-1,2-diamine was prepared according to the procedure of Example 74a, except substituting (S)-4-hydroxyethyl-2,2-dimethyl[1,3]dioxolane for the (S)-alpha,beta-isopropylideneglycerol, and benzyl bromide for 4-cyanobenzyl bromide and carrying the product forward according to steps 74b–74e.

EXAMPLE 93

Compound of Formula (III): A=B=E=H, D=(4-methyl-1-piperazinyl)methyl, R¹=methoxy, R²=hydrogen Step 93a. Compound of Formula (III): A=B=E=H, D=hydroxymethyl, R¹=methoxy, R²=hydrogen To a solution of the compound of Example 90 (1.88 g, 2.39 mmole) in methylene chloride (75 mL) at room temperature under nitrogen was added a solution of trifluoroacetic acid (2.21 mL, 28.7 mmole) in methylene chloride (10 mL) dropwise over 11 minutes. After four hours the reaction was quenched by the dropwise addition of 5% NaHCO₃ (250 mL). The phases were separated and the organic layer was dried (Na₂SO₄) and concentrated in vacuo to give the crude product which was purified by flash chromatography on silica gel (chloroform-methanol-ammonium hydroxide) to give the title compound (1.04 g, 65%). MS DCI (M+H)⁺ m/z 668.

Step 93b. Compound of Formula (III): A=B=E=H, D=methanesulfonyloxymethyl, R¹=methoxy, R²=hydrogen To a solution of the compound from step 93 a (0.93 g, 1.40 mmole) in pyridine (6 nL) in an ice bath under nitrogen was added methane sulfonylchloride (0.39 nlL, 5.04 mmole) dropwise via syringe. After 45 minutes the reaction mixture was partitioned between chloroform and 5% NaHCO₃. The aqueous phase was extracted with chloroform (4×) and the combined organic layers were washed with water (2×), dried (Na₂SO₄) and concentrated in vacuo. The residue was dissolved in toluene and concentrated in vacuo (3×) to give the title compound, which was taken directly to the next step. MS APCI (M+H)⁺ m/z 746.

Step 93c. Compound of Formula (III): A=B=E=H, D=(4-methyl-1-piperazinyl)methyl, R¹=methoxy, R²=hydrogen To a solution of the compound from step 93b (0.075 g, 0.10 mmole) in acetonitrile (3 mnL) was added N-methyl piperazine (0.110 mL, 1.0 mmole, Aldrich) and the mixture heated to reflux under nitrogen overnight. Subsequent concentration in vacuo followed by flash chromatography on silica gel (eluting with chloroform-methanol-ammonium hydroxide) gave the title compound (0.0197 g, 26%). MS APCI (M+H)⁺ m/z 750.

EXAMPLE 94

Compound of Formula (III): A=B=E=H, D=N-methyl-N-benzylaminomethyl, R¹=methoxy, R²=hydrogen Following the procedure of Example 93c, except replacing the N-methyl piperazine with N-benzylmethylamine, the title compound was prepared. MS APCI (M+H)⁺ m/z 771.

EXAMPLE 95

Compound of Formula (III): A=B=E=H, D=N-morpholinylmethyl, R¹=methoxy, R²=hydrogen Following the procedure of Example 93c, except replacing the N-methyl piperazine with morpholine, the title compound was prepared. MS APCI (M+H)⁺ m/z 737.

EXAMPLE 96

Compound of Formula (III): A=B=E=H, D=(1-pipeidinyl)methyl, R¹=methoxy, R²=hydrogen Following the procedure of Example 93c, except replacing the N-methyl piperazine with piperidine, the title compound was prepared. MS APCI (M+H)⁺ m/z 737.

EXAMPLE 97

Compound of Formula (III): A=B=E=H, D=(N,N-dimethyl)aminomethyl, R¹=methoxy, R²=hydrogen Following the procedure of Example 93c, except replacing the N-methyl piperazine with dimethylamine, the title compound was prepared. MS APCI (M+H)⁺ m/z 723.

EXAMPLE 98

Compound of Formula (III): A=B=E=H, D=hydroxymethyl, R¹=methoxy, R²=hydrogen

To a solution of the compound of Example 90 (1.88 g, 2.39 mmole) in methylene chloride (75 mL) at room temperature under nitrogen was added a solution of trifluoroacetic acid (2.21 mL, 28.7 mmole) in methylene chloride (10 mL) dropwise over 11 minutes. After four hours the reaction was quenched by the dropwise addition of 5% NaHCO₃ (250 mL). The phases were separated and the organic layers were dried (Na₂SO₄) and concentrated in vacuo to give the crude product which was purified by flash chromatography on silica gel (chloroform-methanol-armmonium hydroxide) to give the title compound (1.04 g, 65%). MS DCI (M+H)⁺ m/z 668.

EXAMPLE 99

Compound of Formula (III): A=B=E=H, D=(methylthioxy)methoxymethyl, R¹=methoxy, R²=hydrogen Following the procedure of Example 74, except substituting (S)-3-((methylthioxy)-methoxy)propane-1,2-diamine for the (S)-3-(4-cyanobenzyloxy)propane-1,2-diamine thereof, the title compound was prepared. The (S)-3-((methylthioxy)methoxy)propane-1,2-diamine was prepared according to the procedures of Steps 74a–74e, except substituting chloromethyl methylsulfide for the 4-cyanobenzyl bromide of Step 74a MS m/z (4+H)⁺: 758.

EXAMPLE 100

Compound of Formula (III): A=B=E=H, D-(3,5-dimethoxyhenzyloxymethyl, R¹=methoxy, R²=hydrogen Following the procedure of Example 74, except substituting (S)-3-(3,5-dimethoxy-benzyloxy)propane-1,2- diamine for the (S)-3-(4-cyanobenzyloxy)propane-1,2-diamine thereof, the title compound was prepared. The (S)-3-(3,5-dimethoxybenzyloxy)propane-1,2-diamine was prepared according to the procedures of Steps 74a–74e, except substituting 3,5-dimethoxybenzyl bromide for the 4-cyanobenzyl bromide of Step 74a. mp. 64–65° C. MS m/z (M+H)$^+$: 758.

EXAMPLE 101

Compound of Formula (III): A=B=E=H, D=(4-fluorobenzyloxymethyl, R$^1$=methoxy, R$^2$=hydrogen Following the procedure of Example 74, except substituting (S)-3-(4fluoro-benzyloxy)propane-1,2-diamine for the (S)-3-(4-cyanobenzyloxy)propane-1,2-diamine thereof, the title compound was prepared. The (S)-3-(4-fluorobenzyloxy)propane-1,2-diamine was prepared according to the procedures of Steps 74a–74e, except substituting 4-fluorobenzyl bromide for the 4-cyanobenzyl bromide of Step 74a. mp 107.2–108.5° C. $^1$H NMR (CDCl$_3$, 500 MHz) d 0.88 (t, 3H), 1.06 (d, 3H), 1.21 (d, 3H), 1.26 (d, 3H), 1.29 (d, 3H), 1.35 (s, 3H), 1.41 (d, 3H), 1.49 (s, 3H), 1.55 (m, 1H), 1.71 (m, 2H), 1.93 (m, 1H), 2.30 (s, 6H), 2.50 (m, 1H), 2.67 (s, 3H), 2.73 (m, 2H), 3.10 (m, 1H), 3.48 (m, 1H), 3.57 (m, 1H), 4.19 (d, 1H), 4.23 (d, 1H), 4.32 (d, 1H), 4.55 (s, 2H), 4.95 (d, 1H), 7.02 (m, 2H), 7.34 (m, 2H).

EXAMPLE 102

Compound of Formula (III): A=B=E=H, D=(2-fluorobenzylox)methyl, R$^1$=methoxy, R$^2$=hydrogen Following the procedure of Example 74, except substituting (S)-3-(2-fluoro-benzyloxy)propane-1,2-diamine for the (S)-3-(4-cyanobenzyloxy)propane-1,2-diaminethereof, the title compound was prepared. The (S)-3-(2-fluorobenzyloxy)propane-1,2-diamine was prepared according to the procedures of Steps 74a–74e, except substituting 2-fluorobenzyl bromide for the 4-cyanobenzyl bromide of Step 74a. mp 106.9–108.8° C.

EXAMPLE 103

Compound of Formula (III): A=B=E=H, D=(4-bromobenzyloxy)methyl, R$^1$=methoxy, R$^2$=hydrogen Following the procedure of Example 74, except substituting (S)-3-(4-bromo-benzyloxy)propane-1,2-diamine for the (S)-3-(4-cyanobenzyloxy)propane-1,2-diamine thereof, the title compound was prepared. The (S)-3-(4bromobenzyloxy)propane-1,2-diamine was prepared according to the procedures of Steps 74a–74e, except substituting 4-bromobenzyl bromide for the 4-cyanobenzyl bromide of Step 74a. mp 111.5–112.3° C.

EXAMPLE 104

Compound of Formula (III): A=B=E=H, D=(2-bromobenzyloxy)methyl, R$^1$=methoxy, R$^2$=hydrogen Following the procedure of Example 74, except substituting (S)-3-(2-bromo-benzyloxy)propane-1,2-diamine for the (S)-3-(4-cyanobenzyloxy)propane-1,2-diamine thereof, the title compound was prepared. The (S)-3-(2-bromobenzyloxy)propane-1,2-diamine was prepared according to the procedures of Steps 74a–74e, except substituting 2-bromobenzyl bromide for the 4-cyanobenzyl bromide of Step 74a. mp 87.0–88.0° C.

EXAMPLE 105

Compound of Formula (III): A=B=E=H, D=(3-bromobenzyloxy)methyl, R$^1$=methoxy, R$^2$=hydrogen Following the procedure of Example 74, except substituting (S)-3-(3-bromo-benzyloxy)propane-1,2-diamine for the (S)-3-(4-cyanobenzyloxy)propane-1,2-diamine thereof, the title compound was prepared. The (S)-3-(3-bromobenzyloxy)propane-1,2-diamine was prepared according to the procedures of Steps 74a–74e, except substituting 3-bromobenzyl bromide for the 4-cyanobenzyl bromide of Step 74a. mp 104.0–105.0° C.

EXAMPLE 106

Compound of Formula (III): A=D=H; B and E taken together is —CH$_2$CH$_2$CH$_2$CH$_2$—, R$^1$=methoxy, R$^2$=hydrogen The title compound was obtained from Example 13. The product of that example was a mixture of compounds (B=E=H and A=D=H), and the title compound of the present example was obtained by chromatography on silica gel, eluting with 2–5% methanol/methylene chloride. MS m/z (M+H)$^+$: 692.

EXAMPLE 107

Compound of Formula (III): A=D=H; B and E taken together is —CH$_2$CH$_2$CH$_2$-. R$^1$=methoxy. R$^2$=hyogen The title compound was obtained from Example 17. The product of that example was a mixture of compounds (B=E=H and A=D=H), and the title compound of the present example was obtained by chromatography on silica gel, eluting with 2–5% methanol/methylene chloride. MS m/z (M+H)$^+$: 678.

EXAMPLE 108

Compound of Formula (III): A=D=H; B and E taken together is —CH$_2$OCH$_2$—, R$^1$=methoxy, R$^2$=hydrogen The title compound was obtained from Example 18. The product of that example was a mixture of compounds (B=E=H and A=D=H), and the title compound of the present example was obtained by chromatography on silica gel, eluting with 2–5% methanol/methylene chloride. MS nIz (M+H)$^+$: 680.

EXAMPLE 109

Compound of Formula (III): A=D=H; B and E taken together is —CH$_2$—NH—CH$_2$—, R$^1$=methoxy, R$^2$=hydrogen The title compound was obtained from Example 19. The product of that example was a mixture of compounds (B=E=H and A=D-=H), and the title compound of the present example was obtained by chromatography on silica gel, eluting with 2–5% methanol/methylene chloride. MS m/z (M+H)$^+$: 679.

EXAMPLE 110

Compound of Formula (III): A=D=H; B and E taken together is —CH$_2$—N(benzyl)-CH$_2$—, R$^1$=methoxy, R$^2$=hydrogen The title compound was obtained from the compound of Example 109 by treatment with benzyl bromide according to the procedure of Example 21. MS m/z (M+H)$^+$: 769.

EXAMPLE 111

Compound of Formula (III): A=D=H; B and E taken together is —$CH_2$—N(phenyl-$CH_2$—$CH_2$—$CH_2$—)—$CH_2$—, $R^1$=methoxy, $R^2$=hydrogen The title compound was obtained from the compound of Example 109 by treatment with 3-phenylpropyl bromide in the presence of diisopropylethylaamine in TBF at room temperature. MS m/z $(M+H)^+$: 797.

EXAMPLE 112

Compound of Formula (III): B=E=H; A and D taken together is —$CH_2$—N(phenyl-$CH_2$—$CH_2$—$CH_2$—)—$C_2$—, $R^1$=methoxy, $R^2$=hydrogen The title compound was obtained from the compound of Example 19 by treatment with 3-phenylpropyl bromide in ThF at room temperature. MS m/z $(M+H)^+$: 797.

EXAMPLE 113

Compound of Formula (III): B=E=H; A and D taken together is —$CH_2$—N(phenyl-CH($CH_3$)—)—$CH_2$—, $R^1$=methoxy, $R^2$=hydrogen The title compound was obtained from the compound of Example 19 by treatment with 1-phenylethyl bromide in TBF at room temperature. MS m/z $(M+H)^+$: 783.

EXAMPLE 114

Compound of Formula (III): B=E=H; A and D taken together is —$CH_2$—N($CH_3$)—$CH_2$—, $R^1$=methoxy, $R^2$=hydrogen The title compound was obtained from the compound of Example 19 by treatment with methyl bromide in TBF at room temperature. The resulting mixtures of quaternary salts were treated with thiophenol and sodium carbonate in refluxing acetone to give the title compound. MS m/z $(M+H)^+$: 693.

EXAMPLE 115

Compound of Formula (III): B=E=H; A and D taken together is —$CH_2$—N($CH_3CH_2$—)—$CH_2$—, $R^1$=methoxy, $R^2$=hydrogen The title compound was obtained from the compound of Example 19 by treatment with acetaldehyde and acetic acid in the presence of 4 atm of hydrogen and 10% Pd/C in ethanol. MS m/z $(M+H)^+$: 707.

EXAMPLE 116

Compound of Formula (III): B=E=H; A and D taken together is —$CH_2$—N(allyl)-$CH_2$—, $R^1$=methoxy, $R^2$=hydrogen The title compound was obtained from the compound of Example 19 by treatment with allyl bromide according to the procedure of Example 112. MS m/z $(M+H)^+$: 719.

EXAMPLE 117

Compound of Formula (III): B=E=H; A and D taken together is —$CH_2$—N(propargyl)-$CH_2$—, $R^1$=methoxy, $R^2$=hydrogen The title compound was obtained from the compound of Example 19 by treatment with propargyl bromide according to the procedure of Example 112. MS m/z $(M+H)^+$: 717.

EXAMPLE 118

Compound of Formula (III): B=E=H; A and D taken together is —$CH_2$—N(4-$NO_2$-phenyl-$CH_2$—$CH_2$—)—$CH_2$, $R^1$=methoxy, $R^2$=hydrogen The title compound was obtained from the compound of Example 19 by treatment with 2-(4-nitrophenyl)ethyl bromide in the presence of diisopropylethylamine in methylene chloride at room temperature. MS m/z $(M+H)^+$: 828.

EXAMPLE 119

Compound of Formula (III): B=E=H; A and D taken together is —$CH_2$—N(2-$NO_2$-phenyl-$CH_2$—$CH_2$—)—$CH_2$—, $R^1$=methoxy, $R^2$=hydrogen The title compound was obtained from the compound of Example 19 by treatment with 2-(2-nitrophenyl)ethyl bromide according to the procedure of Example 118. MS m/z $(M+H)^+$: 828.

EXAMPLE 120

Compound of Formula (III): B=E=H; A and D taken together is —$CH_2$—N(3-$NO_2$-phenyl-$CH_2$—$CH_2$—)—$CH_2$—, $R^1$=methoxy, $R^2$=hydrogen The title compound was obtained from the compound of Example 19 by treatment with 2-(3-nitrophenyl)ethyl bromide according to the procedure of Example 118. MS m/z $(M+H)^+$: 828.

EXAMPLE 121

Compound of Formula (III): B=E=H; A and D taken together is —$CH_2$—N(4-$NH_2$-phenyl-$CH_2$—$CH_2$—)—$CH_2$—, $R^1$=methoxy, $R^2$=hydrogen The title compound was obtained from the compound of Example 118 by reduction with 1 atm $H_2$ over 10% Pd/C in methanol. MS m/z $(M+H)^+$: 798.

EXAMPLE 122

Compound of Formula (III): B=E=H; A and D taken together is —$CH_2$—N(4-NH(acetyl)-phenyl-$CH_2$—$CH_2$—)—$CH_2$—, $R^1$=methoxy, $R^2$=hydrogen The title compound was obtained from the compound of Example 121 by treatment with acetic anhydride in methylene chloride, followed by refluxing in methanol. MS m/z $(M+H)^+$: 840.

EXAMPLE 123

Compound of Formula (III): B=E=H; A and D taken together is —$CH_2$—N(2-$NO_2$-benzyl-$SO_2$—)—$CH_2$—, $R^1$=methoxy, $R^2$=hydrogen The title compound was obtained from the compound of Example 19 by treatment with 2-nitrobenzylsulfonyl chloride according to the procedure of Example 118. MS m/z $(M+H)^+$: 878.

EXAMPLE 124

Compound of Formula (III): B=E=H; A and D taken together is —$CH_2$—N(CHO)—$CH_2$—, $R^1$=methoxy, $R^2$=hydrogen The title compound was obtained from the compound of Example 21 by treatment with 5% formic acid in methanol over 10% Pd/C at room temperature. MS m/z $(M+H)^+$: 707.

EXAMPLE 125

Compound of Formula (III): B=E=H; A and D taken toptether is —CH$_2$—N(acetyl)-CH$_2$—, R$^1$=methoxy, R$^2$=hydrogen The title compound was obtained from the compound of Example 19 by treatment with ethyl acetate at room temperature. MS m/z (M+H)$^+$: 721.

EXAMPLE 126

Compound of Formula (III): B=E=H; A and D taken together is —CH$_2$—N(2-methoxyethyl)-CH$_2$—, R$^1$=methoxy, R$^2$=hydrogen The title compound was obtained from the compound of Example 19 by treatment with 2-methoxyethyl bromide according to the procedure of Example 111. MS m/z (M+H)$^+$: 737.

EXAMPLE 127

Compound of Formula (III): B=E=H; A and D taken together is —CH$_2$—N(2,2-dimethoxyethyl)-CH$_2$—, R$^1$=methoxy, R$^2$=hydrogen The title compound was obtained from the compound of Example 19 by treatment with 2,2-diethoxyethyl bromide according to the procedure of Example 111. MS m/z (M+H)$^+$: 767.

EXAMPLE 128

Compound of Formula (III): B=E=H; A and D taken together is —CH$_2$—N(2-phenoxyethyl)-CH$_2$—, R$^1$=methoxy, R$^2$=hydrogen The title compound was obtained from the compound of Example 19 by treatment with 2-phenoxyethyl bromide according to the procedure of Example 118. MS m/z (M+H)$^+$: 799.

EXAMPLE 129

Compound of Formula (III): B=E=H; A and D taken together is —CH$_2$—N(2-(dimethylamino)ethyl)-CH$_2$—. R$^1$=methoxy, R$^2$=hydrogen The title compound was obtained from the compound of Example 19 by treatment with 1,2-dibromoethane according to the procedure of Example 111, followed by treatment with dimethylamine at room temperature. MS m/z (M+H)$^+$: 750.

EXAMPLE 130

Compound of Formula (III): B=E=H; A and D taken together is —CH$_2$—N(2-(ethoxycarbonyl)ethyl)-CH$_2$—, R$^1$=methoxy, R$^2$=hydrogen The title compound was obtained from the compound of Example 19 by treatment with methyl acrylate in TBF at room temperature. MS m/z (M+H)$^+$: 799.

EXAMPLE 131

Compound of Formula (III) B=D=E=H, A=N-benzylaminomethyl, R$^1$=methoxy, R$^2$=hydrogen The title compound was prepared by treatment of the compound of Example 63 with methanesulfonyl chloride (2 equivalents) and tiiethylamine in methylene chloride at 0° C. for 2 hours. The resulting compound was then treated with benzylamine in acetonitrile at 140° C. MS m/z (M+H)$^+$: 757.

EXAMPLE 132

Compound of Formula (III): B=D=E=H, A=N-benzyl-N-methylaminomethyl, R$^1$=methoxy, R$^2$=hydrogen The title compound was prepared from the intermediate methanesulfonyl compound of Example 131 by treatment with N-benzyl-N-methylamine in acetonitrile at 140° C. MS m/z (M+H)$^+$: 771.

EXAMPLE 133

Compound of Formula (III): D=E=H, A=N-benzyl-N-methylaminomethyl, B=phenylthiomethyl, R$^1$=methoxy, R$^2$=hydrogen The title compound was prepared from the compound of Example 21 by treatment with methyl bromide (3 equivalents) in ThF at room temperature followed by treatment with phenylthiol and sodium carbonate in refluxing acetone. The mixture of products was separated by chromatography on silica gel. MS m/z (M+H)$^+$: 893.

EXAMPLE 134

Compound of Formula (III): D=E=H, A=N-benzyl-N-methylaminomethyl, B=methyl, R$^1$=methoxy, R$^2$=hydrogen The title compound was prepared from the compound of Example 133 by treatment with excess Raney nickel in ethanol at room temperature for 24 hours. MS m/z (N+H)$^+$: 785.

EXAMPLE 135

Compound of Formula (III): D=E=H, A=dimethylaminomethyl, B=phenylthiomethyl, R$^1$=methoxy, R$^2$=hydrogen The title compound was prepared from the compound of Example 19 by treatment with methyl bromide (2 equivalents), followed by treatment with phenylthiol and sodium carbonate in refluxing acetone. The mixture of products was separated by chromatography on silica gel. MS m/z (M+H)$^+$: 817.

EXAMPLE 136

Compound of Formula (III): D=E=H, A=dimethylaminomethyl, B=methyl, R$^1$=methoxy, R$^2$=hydrogen The title compound was prepared from the compound of Example 135 by treatment with excess Raney nickel in ethanol at room temperature for 30 minutes. MS m/z (M+H)$^+$: 709.

EXAMPLE 137

Compound of Formula (III): B=D=E=H, A=(4-quinolyl)carboxymethyl, R$^1$=methoxy, R$^2$=hydrogen The title compound was prepared from the compound of Example 63 (Compound of Formula (III): A=hydroxymethyl, B=D=E=H, R$^1$=methoxy, R$^2$=hydrogen) by esterification at room temperature in methylene chloride

EXAMPLE 138

Compound of Formula (III): B=D=E=H, A=(4-pyridylicarboxymethyl, $R^1$=methoxy, $R^2$=hydrogen The title compound was prepared from the compound of Example 63 (Compound of Formula (III): A=hydroxymethyl, B=D=E=H, $R^1$=methoxy, $R^2$=hydrogen) by esterification at room temperature in methylene chloride with picolylic acid in the presence of dicyclohexylcarbodiimide and dimethylaminopyridine, followed isolation and treatment of the intermediate with refluxing methanol for 24 hours. MS m/z $(M+H)^+$: 773.

EXAMPLE 139

Compound of Formula (III): B=D=E=H, A=benzoyloxymethyl, $R^1$=methoxy, $R^2$=hydrogen The title compound was prepared from the compound of Example 63 (Compound of Formula (III): A=hydroxymethyl, B=D=E=H, $R^1$=methoxy, $R^2$=hydrogen) by esterification at room temperature in methylene chloride with benzoic acid in the presence of dicyclohexylcarbodiimide and dimethylaminopyridine, followed isolation and treatment of the intermediate with refluxing methanol for 24 hours. MS m/z $(M+H)^+$: 772.

EXAMPLE 140

Compound of Formula (III): B=D=E=H, 4-nitrobenzoyloxymethyl, $R^1$=methoxy, $R^2$=hydrogen The title compound was prepared from the compound of Example 63 (Compound of Formula (III): A=hydroxymethyl, B=D=E=H, $R^1$=methoxy, $R^2$=hydrogen) by esterification at room temperature in methylene chloride with 4-nitrobenzoic acid in the presence of dicyclohexylcarbodiimide and dimethylaminopyridine, followed isolation and treatment of the intermediate with refluxing methanol for 24 hours. MS m/z $(M+H)^+$: 817.

EXAMPLE 141

Compound of Formula (III): B=D=E=H, 4-chlorobenzoyloxymethyl, $R^1$=methoxy, $R^2$=hydrogen The title compound was prepared from the compound of Example 63 (Compound of Formula (III): A=hydroxymethyl, B=D=E=H, $R^1$=methoxy, $R^2$=hydrogen) by esterification at room temperature in methylene chloride with 4-chlorobenzoic acid in the presence of dicyclohexylcarbodiimide and dimethylaminopyridine, followed isolation and treatment of the intermediate with refluxing methanol for 24 hours. MS m/z $(M+H)^+$: 806.

EXAMPLE 142

Compound of Formula (III): B=D=E=H, A=(2-quinolyl)carboxymethyl, $R^1$=methoxy, $R^2$=hydrogen The title compound was prepared from the compound of Example 63 (Compound of Formula (III): A=hydroxymethyl, B=D=E=H, $R^1$=methoxy, $R^2$=hydrogen) by esterification at room temperature in methylene chloride with quinoline-2-carboxylic acid in the presence of dicyclohexylcarbodiimide and dimethylaminopyfidine, followed isolation and treatment of the intermediate with refluxing methanol for 24 hours. MS m/z $(M+H)^+$: 823.

EXAMPLE 143

Compound of Formula (III): B=D=E=H, A=(1-methyl-2-indolyl)carboxymethyl, $R^1$=methoxy, $R^2$=hydrogen The title compound was prepared from the compound of Example 63 (Compound of Formula (III): A=hydroxymethyl, B=D=E=H, $R^1$=methoxy, $R^2$=hydrogen) by esterification at room temperature in methylene chloride with 1-methyl-2-indolecarboxylic acid in the presence of dicyclohexylcarbodiimide and dimethylarinopyridine, followed isolation and treatment of the intermdiate with refluxing methanol for 24 hours. MS m/z $(M+H)^+$: 825.

EXAMPLE 144

Compound of Formula (III): B=D=E=H, (4-indolyl)carboxymethyl, $R^1$=methoxy, $R^2$=hydrogen The title compound was prepared from the compound of Example 63 (Compound of Formula (III): A=hydroxymethyl, B=D=E=H, $R^1$=methoxy, $R^2$=hydrogen) by esterification at room temperature in methylene chloride with 4-indolecarboxylic acid in the presence of dicyclohexylcarbodiimide and dimethylaminopyridine, followed isolation and treatment of the intermediate with refluxing methanol for 24 hours. MS m/z $(M+H)^+$: 811.

EXAMPLE 145

Compound of Formula (III): B=D=E=H, (2-indolyl)carboxymethyl, $R^1$=methoxy, $R^2$=hydrogen The title compound is prepared from the compound of Example 63 (Compound of Formula (E): A=hydroxymethyl, B=D=E=H, $R^1$=methoxy, $R^2$=hydrogen) by esterification at room temperature in methylene chloride with 2-indolecarboxylic acid in the presence of dicyclohexylcarbodiimide and dimethylaminopyridine, followed by isolation and treatment of the intermediate with refluxing methanol for 24 hours.

EXAMPLE 146

Compound of Formula (III): B=D=H, A=E=benzyloxymethyl, $R^1$=methoxy, $R^2$=hydrogen The title compound was prepared from the compound of Example 57 by treatment with hydrogen over 10% Pd/C in the presence of sodium bicarbonate in ethanol at room temperature. MS m/z $(M+H)^+$: 878.

EXAMPLE 147

Compound of Formula (III): A=E=H, B=D=(4-chloro)benzyloxymethyl, $R^1$=methoxy, $R^2$=hydrogen 147a. (S,S)-(+)-1,4-bis-O-(4-chlorobenzyl)-2,3-butanediamine Following the procedure of Example 10 steps a–c, replacing the meso-2,3-butanediol thereof with (S,S)-(+)-1,4-bis-O-(4-chlorobenzyl)-threitol (Aldrich) the title compound was obtained.

147b. Compound of Formula (III): A=E=H, B=D=(4-chloro)benzyloxymethyl, R$^1$=methoxy, R$^2$=hydrogen Following the procedures of Example 10 steps d–f, replacing the meso-2,3-butanediamine of step 10d with the dianiine from step 147a, the title compound was prepared. MS m/z (M+H)$^+$: 946.

EXAMPLE 148

Compound of Formula (III): B=E=H, A=D=(4-chloro)benzyloxymethyl, R$^1$=methoxy, R$^2$=hydrogen 148a. (S,R)-(+)-1,4-bis-O-(4-chlorobenzyl-2,3-butanediamine Following the procedure of Example 10 steps a–c, replacing the meso-2,3-butanediol thereof with meso-1,4-bis-O-(4-chlorobenzyl)-threitol (Aldrich) the title compound was obtained.

148b. Compound of Formula (E): B=E=H, A=D=(4-chloro)benzyloxymethyl, R$^1$=methoxy, R$^2$=hydrogen Following the procedures of Example 10 steps d–f, replacing the meso-2,3-butanediamine of step 10d with the diamine from step 148a, the title compound was prepared. MS m/z (M+H)$^+$: 946.

EXAMPLE 149

In Vitro Assay of Antibacterial Activity

Representative compounds of the present invention were assayed in vitro for antibacterial activity as follows: Twelve petri dishes containing successive aqueous dilutions of the test compound mixed with 10 mL of sterilized Brain Heart Infusion (BHI) agar (Difco 0418-01-5) were prepared. Each plate was inoculated with 1:100 (or 1:10 for slow-growing strains, such as Micrococcus and Streptococcus) dilutions of up to 32 different microorganisms, using a Steers replicator block. The inoculated plates were incubated at 35–37° C. for 20 to 24 hours. In addition, a control plate, using BHI agar containing no test compound, was prepared and incubated at the beginning and end of each test.

An additional plate containing a compound having known susceptibility patterns for the organisms being tested and belonging to the same antibiotic class as the test compound was also prepared and incubated as a further control, as well as to provide test-to-test comparability. Erythromycin A was used for this purpose.

After incubation, each plate was visually inspected. The minimum inhibitory concentration (MIC) was defmed as the lowest concentration of drug yielding no growth, a slight haze, or sparsely isolated colonies on the inoculum spot as compared to the growth control. The results of this assay, shown below in Table 1 demonstrate the antibacterial activity of the compounds of the invention.

In a separate assay representative compounds of the invention were assayed in vitro for antibacterial activity against the *H. Influenza* Dill AMP R strain, according to the protocol described above. The results of this assay, shown below in Table 2 demonstrate the antibacterial activity of the compounds of the invention against the *H. Influenza* Dill AMP R organism.

TABLE 1

Antibacterial Activity (MIC's) of Selected Compounds

| MICROORGANISM | Ery A (Ref. std) | Cmpd of Ex 1 | Cmpd of Ex 3 | Cmpd of Ex 4 | Cmpd of Ex 5 | Cmpd of Ex 6 | Cmpd of Ex 7 |
|---|---|---|---|---|---|---|---|
| *STAPHYLOCOCCUS AUREUS* ATCC 6538P | 0.2 | 6.2 | 0.39 | 0.2 | 0.2 | 0.1 | 3.1 |
| *STAPHYLOCOCCUS AUREUS* A5177 | 6.2 | 6.2 | 0.39 | 0.2 | na | 0.05 | na |
| *STAPHYLOCOCCUS AUREUS* A-5278 | >100 | >100 | >100 | >100 | >100 | >100 | 100 |
| *STAPHYLOCOCCUS AUREUS* CMX 642A | 0.39 | 6.2 | 0.39 | 0.78 | 0.2 | 0.1 | 3.1 |
| *STAPHYLOCOCCUS AUREUS* NCTC10649M | 0.2 | 6.2 | 0.39 | 0.78 | 0.2 | 0.1 | 3.1 |
| *STAPHYLOCOCCUS AUREUS* CMX 553 | 0.2 | 6.2 | 0.39 | 0.78 | 0.2 | 0.2 | 3.1 |
| *STAPHYLOCOCCUS AUREUS* 1775 | >100 | >100 | >100 | >100 | >100 | >100 | 100 |
| *STAPHYLOCOCCUS EPIDERMIDIS* 3519 | 0.39 | 12.5 | 0.39 | 0.78 | 0.2 | 0.1 | 1.56 |
| *ENTEROCOCCUS FAECIUM* ATCC 8043 | 0.05 | 0.78 | 0.05 | 0.1 | 0.05 | 0.1 | 0.39 |
| *STREPTOCOCCUS BOVIS* A-5169 | 0.05 | 0.39 | 0.02 | 0.02 | 0.01 | 0.01 | 0.2 |
| *STREPTOCOCCUS AGALACTIAE* CMX 508 | 0.05 | 0.39 | 0.01 | 0.005 | 0.02 | 0.02 | 0.2 |
| *STREPTOCOCCUS PYOGENES* EES61 | 0.05 | 0.39 | 0.01 | 0.05 | 0.02 | 0.02 | 0.2 |
| *STREPTOCOCCUS PYOGENES* 930 | >100 | >100 | 100 | >100 | >100 | >100 | 50 |
| *STREPTOCOCCUS PYOGENES* PIU 2548 | 6.2 | 0.78 | na | na | 0.39 | 0.39 | 1.56 |
| *MICROCOCCUS LUTEUS* ATCC 9341 | 0.02 | 0.39 | 0.1 | 0.1 | 0.05 | 0.02 | 0.39 |
| *MICROCOCCUS LUTEUS* ATCC 4698 | 0.2 | 0.39 | 0.39 | 0.39 | 0.2 | 0.1 | 1.56 |
| *ESCHERICHIA COLI* JUHL | 100 | na | >100 | >100 | 12.5 | 12.5 | >100 |
| *ESCHERICHIA COLI* SS | 0.2 | na | na | na | 0.39 | 0.02 | 3.1 |
| *ESCHERICHIA COLI* DC-2 | >100 | 0.78 | >100 | 100 | 12.5 | 12.5 | >100 |
| *ESCHERICHIA COLI* H560 | 25 | 50 | >100 | 25 | 3.1 | 3.1 | >100 |
| *ESCHERICHIA COLI* KNK 437 | 50 | 25 | >100 | >100 | 6.2 | 6.2 | >100 |
| *ENTEROBACTER AEROGENES* ATCC 13048 | 100 | >100 | >100 | 100 | 50 | 12.5 | >100 |
| *KLEBSIELLA PNEUMONIAE* ATCC 8045 | 100 | >100 | >100 | >100 | 50 | 12.5 | >100 |
| *PROVIDENCIA STUARTII* CMX 640 | >100 | 100 | >100 | >100 | >100 | 100 | >100 |
| *PSEUDOMONAS AERUGINOSA* BMH10 | >100 | >100 | >100 | >100 | 50 | 50 | >100 |
| *PSEUDOMONAS AERUGINOSA* 5007 | >100 | >100 | >100 | >100 | >100 | 100 | >100 |
| *PSEUDOMONAS AERUGINOSA* K799/WT | 50 | >100 | >100 | >100 | 50 | 25 | >100 |
| *PSEUDOMONAS AERUGINOSA* K799/61 | 0.78 | >100 | 3.1 | 1.56 | 0.78 | 0.39 | 6.2 |
| *PSEUDOMONAS CEPACIA* 296I | >100 | 12.5 | >100 | >100 | 25 | 50 | >100 |
| *ACINETOBACTER CALCOACETICUS* CMX 669 | 6.2 | >100 | >100 | 25 | 12.5 | 12.5 | 50 |
| *PSEUDOMONAS AERUGINOSA* DPHD-5263 | >100 | 50 | >100 | >100 | >100 | 12.5 | >100 |
| *PSEUDOMONAS AERUGINOSA* DPHD-2862 | >100 | >100 | >100 | >100 | >100 | 100 | >100 |
| *CANDIDA ALBICANS* CCH 442 | >100 | >100 | >100 | 100 | >100 | >100 | >100 |
| *MYCOBACTERIUM SMEGMATIS* ATCC 114 | 0.02 | 3.1 | >100 | na | 0.2 | na | 1.56 |

TABLE 1-continued

Antibacterial Activity (MIC's) of Selected Compounds

| MICROORGANISM | Cmpd of Ex 8 | Cmpd of Ex 9 | Cmpd of Ex 10 | Cmpd of Ex 11 | Cmpd of Ex 13 | Cmpd of Ex 14 | Cmpd of Ex 16 |
|---|---|---|---|---|---|---|---|
| STAPHYLOCOCCUS AUREUS ATCC 6538P | 0.78 | 0.39 | 0.39 | 0.39 | 0.78 | 0.1 | 0.2 |
| STAPHYLOCOCCUS AUREUS A5177 | 0.78 | 0.39 | na | 0.39 | 0.78 | 6.2 | 0.39 |
| STAPHYLOCOCCUS AUREUS A-5278 | >100 | >100 | >100 | >100 | >100 | >100 | >100 |
| STAPHYLOCOCCUS AUREUS CMX 642A | 0.78 | 0.39 | 0.39 | 0.39 | 0.78 | 0.2 | 0.2 |
| STAPHYLOCOCCUS AUREUS NCTC10649M | 0.78 | 0.2 | 0.39 | 0.39 | 0.78 | 0.2 | 0.2 |
| STAPHYLOCOCCUS AUREUS CMX 553 | 0.78 | 0.39 | 0.39 | 0.39 | 0.78 | 0.1 | 0.39 |
| STAPHYLOCOCCUS AUREUS 1775 | >100 | >100 | >100 | >100 | >100 | >100 | >100 |
| STAPHYLOCOCCUS EPIDERMIDIS 3519 | 0.78 | 0.39 | 0.39 | 0.39 | 0.78 | 0.2 | 0.2 |
| ENTEROCOCCUS FAECIUM ATCC 8043 | 0.78 | 0.05 | na | 0.1 | 0.1 | 0.05 | 0.2 |
| STREPTOCOCCUS BOVIS A-5169 | 0.1 | na | 0.05 | 0.01 | — | <=0.005 | 0.02 |
| STREPTOCOCCUS AGALACTIAE CMX 508 | 0.1 | 0.01 | na | 0.05 | 0.02 | 0.01 | 0.05 |
| STREPTOCOCCUS PYOGENES EES61 | 0.1 | 0.01 | na | 0.005 | 0.02 | <=0.005 | 0.01 |
| STREPTOCOCCUS PYOGENES 930 | >100 | >100 | >100 | >100 | >100 | — | >100 |
| STREPTOCOCCUS PYOGENES PIU 2548 | 0.78 | 0.39 | 0.39 | 0.39 | 0.2 | 1.56 | — |
| MICROCOCCUS LUTEUS ATCC 9341 | 1.56 | 0.1 | 0.1 | 0.2 | 0.2 | 0.78 | 0.02 |
| MICROCOCCUS LUTEUS ATCC 4698 | 1.56 | 0.39 | 0.2 | 0.39 | 0.78 | 0.78 | 0.2 |
| ESCHERICHIA COLI JUHL | 100 | na | 25 | 25 | 50 | 50 | 12.5 |
| ESCHERICHIA COLI SS | 0.78 | na | 0.2 | 0.39 | 0.39 | 0.39 | 0.1 |
| ESCHERICHIA COLI DC-2 | 50 | 25 | 25 | 25 | 100 | 50 | 12.5 |
| ESCHERICHIA COLI H560 | 25 | 25 | 25 | 6.2 | 50 | 50 | 6.2 |
| ESCHERICHIA COLI KNK 437 | 100 | 100 | na | 25 | 100 | 100 | 12.5 |
| ENTEROBACTER AEROGENES ATCC 13048 | 100 | 25 | 50 | 25 | 100 | 100 | 12.5 |
| KLEBSIELLA PNEUMONIAE ATCC 8045 | 100 | 25 | na | 12.5 | 100 | 25 | 12.5 |
| PROVIDENCIA STUARTII CMX 640 | >100 | >100 | >100 | >100 | >100 | >100 | >100 |
| PSEUDOMONAS AERUGINOSA BMH10 | 100 | 100 | >100 | >100 | >100 | 100 | 50 |
| PSEUDOMONAS AERUGINOSA 5007 | >100 | >100 | >100 | >100 | >100 | >100 | >100 |
| PSEUDOMONAS AERUGINOSA K799/WT | 100 | 100 | na | >100 | >100 | 100 | 100 |
| PSEUDOMONAS AERUGINOSA K799/61 | na | 6.2 | na | na | 3.1 | 3.1 | 0.39 |
| PSEUDOMONAS CEPACIA 296I | >100 | >100 | 100 | >100 | >100 | — | >100 |
| ACINETOBACTER CALCOACETICUS CMX 669 | 25 | 12.5 | 25 | 6.2 | >100 | 12.5 | 12.5 |
| PSEUDOMONAS AERUGINOSA DPHD-5263 | >100 | >100 | >100 | >100 | >100 | >100 | >100 |
| PSEUDOMONAS AERUGINOSA DPHD-2862 | >100 | >100 | >100 | >100 | >100 | >100 | >100 |
| CANDIDA ALBICANS CCH 442 | >100 | >100 | >100 | >100 | 3.1 | >100 | >100 |
| MYCOBACTERIUM SMEGMATIS ATCC 114 | 6.2 | 3.1 | 6.2 | 6.2 | 0.39 | 3.1 | 1.56 |

| MICROORGANISM | Cmpd of Ex 17 | Cmpd of Ex 18 | Cmpd of Ex 19 | Cmpd of Ex 20 | Cmpd of Ex 21 | Cmpd of Ex 23 | Cmpd of Ex 24 |
|---|---|---|---|---|---|---|---|
| STAPHYLOCOCCUS AUREUS ATCC 6538P | 0.78 | 0.39 | 0.39 | 1.56 | 0.78 | 0.2 | 0.78 |
| STAPHYLOCOCCUS AUREUS A5177 | 0.78 | 0.78 | 0.39 | 0.78 | 0.78 | 0.2 | 0.78 |
| STAPHYLOCOCCUS AUREUS A-5278 | >100 | >100 | >100 | >100 | >100 | >100 | >100 |
| STAPHYLOCOCCUS AUREUS CMX 642A | 0.78 | 0.78 | 0.39 | 1.56 | 6.2 | 0.2 | 0.78 |
| STAPHYLOCOCCUS AUREUS NCTC10649M | 0.78 | 0.78 | 0.39 | 1.56 | 0.78 | 0.2 | 0.78 |
| STAPHYLOCOCCUS AUREUS CMX 553 | 0.78 | 0.78 | 0.39 | 1.56 | 0.78 | 0.2 | 0.78 |
| STAPHYLOCOCCUS AUREUS 1775 | >100 | >100 | >100 | >100 | >100 | >100 | >100 |
| STAPHYLOCOCCUS EPIDERMIDIS 3519 | 0.78 | 0.78 | 0.39 | 0.78 | 0.78 | 0.78 | 0.78 |
| ENTEROCOCCUS FAECIUM ATCC 8043 | 0.2 | 0.1 | 0.05 | 0.39 | 0.2 | 0.05 | 0.2 |
| STREPTOCOCCUS BOVIS A-5169 | 0.02 | 0.05 | 0.005 | 0.1 | 0.05 | <=0.005 | 0.05 |
| STREPTOCOCCUS AGALACTIAE CMX 508 | 0.05 | 0.05 | 0.05 | 0.1 | 0.05 | <=0.005 | 0.2 |
| STREPTOCOCCUS PYOGENES EES61 | 0.05 | 0.05 | 0.05 | 0.005 | 0.01 | <=0.005 | 0.05 |
| STREPTOCOCCUS PYOGENES 930 | >100 | >100 | >100 | >100 | 100 | >100 | 100 |
| STREPTOCOCCUS PYOGENES PIU 2548 | 0.39 | 0.39 | 0.78 | 0.78 | 0.39 | 0.78 | 0.78 |
| MICROCOCCUS LUTEUS ATCC 9341 | 0.1 | 0.05 | 0.1 | 0.39 | 0.78 | 0.05 | 0.2 |
| MICROCOCCUS LUTEUS ATCC 4698 | 0.78 | 0.78 | 0.2 | 0.78 | 3.1 | 0.2 | 0.78 |
| ESCHERICHIA COLI JUHL | >100 | — | 12.5 | >100 | >100 | 50 | >100 |
| ESCHERICHIA COLI SS | 0.78 | 0.78 | 0.2 | 3.1 | 1.56 | 0.05 | 6.2 |
| ESCHERICHIA COLI DC-2 | >100 | >100 | 6.2 | >100 | 100 | 12.5 | >100 |
| ESCHERICHIA COLI H560 | 100 | >100 | 3.1 | 100 | 50 | 6.2 | >100 |
| ESCHERICHIA COLI KNK 437 | >100 | >100 | 6.2 | >100 | >100 | 25 | >100 |
| ENTEROBACTER AEROGENES ATCC 13048 | >100 | >100 | 12.5 | >100 | >100 | 100 | >100 |
| KLEBSIELLA PNEUMONIAE ATCC 8045 | >100 | >100 | 12.5 | >100 | >100 | 100 | >100 |
| PROVIDENCIA STUARTII CMX 640 | >100 | >100 | >100 | >100 | >100 | >100 | >100 |
| PSEUDOMONAS AERUGINOSA BMH10 | >100 | >100 | 50 | >100 | 100 | >100 | >100 |
| PSEUDOMONAS AERUGINOSA 5007 | >100 | >100 | >100 | >100 | >100 | >100 | >100 |
| PSEUDOMONAS AERUGINOSA K799/WT | >100 | >100 | >100 | >100 | >100 | 100 | >100 |
| PSEUDOMONAS AERUGINOSA K799/61 | 12.5 | 6.2 | 0.39 | 6.2 | 3.1 | 0.2 | 6.2 |
| PSEUDOMONAS CEPACIA 296I | >100 | >100 | >100 | >100 | >100 | 100 | >100 |
| ACINETOBACTER CALCOACETICUS CMX 669 | 100 | >100 | 6.2 | 100 | 50 | 6.2 | >100 |
| PSEUDOMONAS AERUGINOSA DPHD-5263 | >100 | >100 | >100 | >100 | >100 | >100 | >100 |
| PSEUDOMONAS AERUGINOSA DPHD-2862 | >100 | >100 | >100 | >100 | >100 | >100 | >100 |
| CANDIDA ALBICANS CCH 442 | >100 | >100 | >100 | >100 | >100 | >100 | >100 |
| MYCOBACTERIUM SMEGMATIS ATCC 114 | 12.5 | 3.1 | 3.1 | 3.1 | — | 0.39 | 1.56 |

TABLE 1-continued

Antibacterial Activity (MIC's) of Selected Compounds

| MICROORGANISM | Cmpd of Ex 25 | Cmpd of Ex 35 | Cmpd of Ex 36 | Cmpd of Ex 37 | Cmpd of Ex 39 | Cmpd of Ex 40 | Cmpd of Ex 41 |
|---|---|---|---|---|---|---|---|
| STAPHYLOCOCCUS AUREUS ATCC 6538P | 0.78 | 0.39 | 0.2 | 0.1 | 0.78 | 0.78 | 0.05 |
| STAPHYLOCOCCUS AUREUS A5177 | 0.78 | — | — | 0.1 | 0.39 | 0.78 | 0.05 |
| STAPHYLOCOCCUS AUREUS A-5278 | >100 | >100 | >100 | >100 | >100 | >100 | >100 |
| STAPHYLOCOCCUS AUREUS CMX 642A | 0.78 | 0.78 | 0.2 | 0.1 | 0.78 | 0.78 | 0.05 |
| STAPHYLOCOCCUS AUREUS NCTC10649M | 0.39 | 0.78 | 0.2 | 0.1 | 0.39 | 0.78 | 0.05 |
| STAPHYLOCOCCUS AUREUS CMX 553 | 0.78 | — | — | 0.1 | 0.39 | 0.78 | 0.05 |
| STAPHYLOCOCCUS AUREUS 1775 | >100 | >100 | >100 | >100 | >100 | >100 | >100 |
| STAPHYLOCOCCUS EPIDERMIDIS 3519 | 0.78 | 0.39 | 0.2 | 0.1 | 0.78 | 0.39 | — |
| ENTEROCOCCUS FAECIUM ATCC 8043 | 0.1 | 0.2 | 0.2 | 0.05 | 0.1 | 0.05 | 0.02 |
| STREPTOCOCCUS BOVIS A-5169 | 0.1 | 0.01 | 0.01 | <=0.005 | 0.01 | 0.02 | <=0.005 |
| STREPTOCOCCUS AGALACTIAE CMX 508 | 0.1 | 0.02 | 0.05 | 0.02 | 0.05 | 0.05 | 0.02 |
| STREPTOCOCCUS PYOGENES EES61 | 0.05 | — | — | <=0.005 | 0.01 | 0.02 | 0.01 |
| STREPTOCOCCUS PYOGENES 930 | >100 | 50 | 50 | 100 | 100 | 100 | >100 |
| STREPTOCOCCUS PYOGENES PIU 2548 | 0.78 | 0.39 | 0.39 | 0.39 | 0.2 | 0.2 | 0.2 |
| MICROCOCCUS LUTEUS ATCC 9341 | 0.1 | 0.2 | 0.05 | 0.01 | 0.1 | 0.05 | 0.01 |
| MICROCOCCUS LUTEUS ATCC 4698 | 0.39 | — | — | 0.2 | 0.2 | 0.39 | 0.1 |
| ESCHERICHIA COLI JUHL | >100 | >100 | 50 | 50 | 100 | >100 | 6.2 |
| ESCHERICHIA COLI SS | 0.78 | — | — | 0.39 | 0.39 | 0.78 | 0.2 |
| ESCHERICHIA COLI DC-2 | >100 | — | — | 25 | 100 | 100 | 3.1 |
| ESCHERICHIA COLI H560 | 100 | 50 | 25 | 25 | 25 | 25 | 1.56 |
| ESCHERICHIA COLI KNK 437 | >100 | 100 | 12.5 | 25 | 100 | >100 | 6.2 |
| ENTEROBACTER AEROGENES ATCC 13048 | >100 | 100 | 25 | 50 | >100 | >100 | 12.5 |
| KLEBSIELLA PNEUMONIAE ATCC 8045 | >100 | >100 | 50 | 50 | >100 | >100 | 25 |
| PROVIDENCIA STUARTII CMX 640 | >100 | >100 | 100 | >100 | >100 | >100 | 50 |
| PSEUDOMONAS AERUGINOSA BMH10 | >100 | >100 | 50 | 50 | 50 | >100 | 50 |
| PSEUDOMONAS AERUGINOSA 5007 | >100 | >100 | 100 | >100 | >100 | >100 | 50 |
| PSEUDOMONAS AERUGINOSA K799/WT | 100 | >100 | 50 | >100 | 100 | >100 | 12.5 |
| PSEUDOMONAS AERUGINOSA K799/61 | 0.78 | 3.1 | 1.56 | 0.78 | 1.56 | 0.78 | 0.2 |
| PSEUDOMONAS CEPACIA 296I | >100 | 100 | 50 | 100 | 100 | >100 | 12.5 |
| ACINETOBACTER CALCOACETICUS CMX 669 | 100 | 50 | 50 | 25 | 50 | 50 | 6.2 |
| PSEUDOMONAS AERUGINOSA DPHD-5263 | >100 | >100 | 50 | >100 | >100 | >100 | 12.5 |
| PSEUDOMONAS AERUGINOSA DPHD-2862 | >100 | >100 | 50 | >100 | >100 | >100 | 50 |
| CANDIDA ALBICANS CCH 442 | >100 | >100 | 100 | >100 | >100 | >100 | >100 |
| MYCOBACTERIUM SMEGMATIS ATCC 114 | 3.1 | 0.39 | 0.39 | 0.39 | 0.39 | 0.39 | 0.2 |

| MICROORGANISM | Cmpd of Ex 52 | Cmpd of Ex 58 | Cmpd of Ex 62 | Cmpd of Ex 63 | Cmpd of Ex 64 | Cmpd of Ex 65 | Cmpd of Ex 66 |
|---|---|---|---|---|---|---|---|
| STAPHYLOCOCCUS AUREUS ATCC 6538P | 0.78 | 0.78 | 0.2 | 0.78 | 0.39 | 0.39 | 0.1 |
| STAPHYLOCOCCUS AUREUS A5177 | 0.78 | 0.78 | 0.2 | 0.78 | 0.2 | 0.39 | 0.1 |
| STAPHYLOCOCCUS AUREUS A-5278 | >100 | >100 | >100 | >100 | 50 | >100 | >100 |
| STAPHYLOCOCCUS AUREUS CMX 642A | 0.78 | 0.78 | 0.2 | 1.56 | 0.39 | 0.39 | 0.2 |
| STAPHYLOCOCCUS AUREUS NCTC10649M | 0.78 | 0.78 | 0.2 | 0.78 | 0.2 | 0.39 | 0.1 |
| STAPHYLOCOCCUS AUREUS CMX 553 | 0.78 | 0.78 | 0.2 | 1.56 | 0.2 | 0.39 | 0.2 |
| STAPHYLOCOCCUS AUREUS 1775 | >100 | >100 | >100 | >100 | 50 | >100 | >100 |
| STAPHYLOCOCCUS EPIDERMIDIS 3519 | 0.78 | 0.78 | 0.2 | 0.78 | 0.39 | 0.39 | 0.2 |
| ENTEROCOCCUS FAECIUM ATCC 8043 | 0.2 | 0.2 | 0.1 | 0.2 | 0.2 | 0.1 | 0.02 |
| STREPTOCOCCUS BOVIS A-5169 | 0.05 | 0.01 | 0.1 | 0.05 | 0.1 | 0.01 | 0.01 |
| STREPTOCOCCUS AGALACTIAE CMX 508 | 0.05 | 0.02 | 0.1 | 0.2 | 0.1 | 0.02 | 0.01 |
| STREPTOCOCCUS PYOGENES EES61 | 0.05 | 0.01 | 0.1 | 0.1 | 0.05 | 0.02 | 0.01 |
| STREPTOCOCCUS PYOGENES 930 | >100 | >100 | >100 | >100 | 25 | >100 | >100 |
| STREPTOCOCCUS PYOGENES PIU 2548 | 1.56 | 0.39 | 0.2 | — | 0.78 | 1.56 | 0.39 |
| MICROCOCCUS LUTEUS ATCC 9341 | 0.1 | 0.1 | 0.01 | 0.2 | 0.1 | 0.05 | 0.02 |
| MICROCOCCUS LUTEUS ATCC 4698 | 0.39 | 0.39 | 0.02 | 0.78 | 0.78 | 0.39 | 0.2 |
| ESCHERICHIA COLI JUHL | 100 | >100 | 12.5 | — | — | 50 | 25 |
| ESCHERICHIA COLI SS | 0.39 | 0.39 | 0.2 | 0.78 | 6.2 | 0.39 | 0.39 |
| ESCHERICHIA COLI DC-2 | 100 | >100 | 50 | >100 | >100 | 50 | 12.5 |
| ESCHERICHIA COLI H560 | 50 | 50 | 100 | 50 | >100 | 50 | 12.5 |
| ESCHERICHIA COLI KNK 437 | 100 | >100 | 100 | >100 | >100 | 100 | 25 |
| ENTEROBACTER AEROGENES ATCC 13048 | >100 | >100 | 25 | >100 | >100 | >100 | >100 |
| KLEBSIELLA PNEUMONIAE ATCC 8045 | >100 | >100 | 25 | >100 | >100 | >100 | >100 |
| PROVIDENCIA STUARTII CMX 640 | >100 | >100 | >100 | >100 | >100 | >100 | >100 |
| PSEUDOMONAS AERUGINOSA BMH10 | >100 | >100 | 100 | >100 | >100 | >100 | 100 |
| PSEUDOMONAS AERUGINOSA 5007 | >100 | >100 | 100 | >100 | >100 | >100 | >100 |
| PSEUDOMONAS AERUGINOSA K799/WT | >100 | >100 | 25 | >100 | >100 | >100 | 100 |
| PSEUDOMONAS AERUGINOSA K799/61 | 1.56 | 3.1 | 0.2 | 1.56 | 12.5 | 0.78 | 0.39 |
| PSEUDOMONAS CEPACIA 296I | >100 | >100 | 12.5 | >100 | >100 | 100 | 100 |
| ACINETOBACTER CALCOACETICUS CMX 669 | 50 | >100 | 12.5 | 100 | >100 | 100 | 25 |
| PSEUDOMONAS AERUGINOSA DPHD-5263 | >100 | >100 | 50 | >100 | >100 | >100 | 100 |
| PSEUDOMONAS AERUGINOSA DPHD-2862 | >100 | >100 | 100 | >100 | >100 | >100 | >100 |
| CANDIDA ALBICANS CCH 442 | >100 | >100 | >100 | >100 | 50 | >100 | >100 |
| MYCOBACTERIUM SMEGMATIS ATCC 114 | 12.5 | 3.1 | 0.1 | 6.2 | 1.56 | 6.2 | 0.39 |

TABLE 1-continued

Antibacterial Activity (MIC's) of Selected Compounds

| MICROORGANISM | Cmpd of Ex 68 | Cmpd of Ex 69 | Cmpd of Ex 70 | Cmpd of Ex 71 | Cmpd of Ex 72 | Cmpd of Ex 73 |
|---|---|---|---|---|---|---|
| STAPHYLOCOCCUS AUREUS ATCC 6538P | 0.2 | 0.2 | 0.1 | 0.1 | 0.1 | 0.1 |
| STAPHYLOCOCCUS AUREUS A5177 | 0.2 | 0.2 | 0.1 | 0.1 | 0.1 | 0.1 |
| STAPHYLOCOCCUS AUREUS A-5278 | >100 | >100 | 100 | >100 | >100 | >100 |
| STAPHYLOCOCCUS AUREUS CMX 642A | 0.2 | 0.39 | 0.2 | 0.1 | 0.1 | 0.1 |
| STAPHYLOCOCCUS AUREUS NCTC10649M | 0.2 | 0.2 | 0.2 | 0.1 | 0.1 | 0.1 |
| STAPHYLOCOCCUS AUREUS CMX 553 | 0.2 | 0.2 | 0.2 | 0.1 | 0.1 | 0.1 |
| STAPHYLOCOCCUS AUREUS 1775 | >100 | >100 | 100 | >100 | >100 | >100 |
| STAPHYLOCOCCUS EPIDERMIDIS 3519 | 0.39 | 0.2 | 0.2 | 0.1 | 0.2 | 0.1 |
| ENTEROCOCCUS FAECIUM ATCC 8043 | 0.2 | 0.1 | 0.1 | 0.05 | 0.05 | 0.05 |
| STREPTOCOCCUS BOVIS A-5169 | 0.05 | 0.01 | 0.01 | 0.02 | <=0.005 | 0.01 |
| STREPTOCOCCUS AGALACTIAE CMX 508 | 0.05 | 0.02 | 0.05 | 0.01 | 0.01 | <=0.005 |
| STREPTOCOCCUS PYOGENES EES61 | 0.1 | 0.02 | 0.02 | 0.01 | 0.01 | <=0.005 |
| STREPTOCOCCUS PYOGENES 930 | 50 | >100 | 50 | 25 | 50 | 100 |
| STREPTOCOCCUS PYOGENES PIU 2548 | 0.78 | 0.39 | 0.39 | 0.39 | 0.39 | 0.39 |
| MICROCOCCUS LUTEUS ATCC 9341 | 0.1 | 0.05 | 0.1 | 0.01 | <=0.005 | 0.01 |
| MICROCOCCUS LUTEUS ATCC 4698 | 0.39 | 0.2 | 0.2 | 0.1 | 0.2 | 0.1 |
| ESCHERICHIA COLI JUHL | — | 100 | 100 | 25 | 50 | 50 |
| ESCHERICHIA COLI SS | 1.56 | 0.39 | 1.56 | 0.39 | 0.39 | 0.2 |
| ESCHERICHIA COLI DC-2 | 100 | 50 | 50 | 12.5 | 25 | 25 |
| ESCHERICHIA COLI H560 | 50 | 50 | 50 | 12.5 | 12.5 | 12.5 |
| ESCHERICHIA COLI KNK 437 | >100 | >100 | >100 | 25 | 50 | 50 |
| ENTEROBACTER AEROGENES ATCC 13048 | >100 | >100 | 100 | 50 | 50 | 100 |
| KLEBSIELLA PNEUMONIAE ATCC 8045 | >100 | >100 | 100 | 50 | 50 | 100 |
| PROVIDENCIA STUARTII CMX 640 | >100 | >100 | >100 | 100 | >100 | >100 |
| PSEUDOMONAS AERUGINOSA BMH10 | >100 | >100 | 100 | 50 | 50 | 100 |
| PSEUDOMONAS AERUGINOSA 5007 | >100 | >100 | 100 | 100 | 100 | >100 |
| PSEUDOMONAS AERUGINOSA K799/WT | >100 | >100 | >100 | 100 | 50 | >100 |
| PSEUDOMONAS AERUGINOSA K799/61 | 3.1 | 0.78 | 0.78 | 0.78 | 0.39 | 0.39 |
| PSEUDOMONAS CEPACIA 296I | >100 | >100 | 50 | 25 | 50 | 25 |
| ACINETOBACTER CALCOACETICUS CMX 669 | 100 | 25 | 50 | 12.5 | 25 | 50 |
| PSEUDOMONAS AERUGINOSA DPHD-5263 | >100 | >100 | 100 | >100 | >100 | 100 |
| PSEUDOMONAS AERUGINOSA DPHD-2862 | >100 | >100 | 100 | 100 | >100 | 100 |
| CANDIDA ALBICANS CCH 442 | >100 | >100 | 100 | >100 | >100 | >100 |
| MYCOBACTERIUM SMEGMATIS ATCC 114 | 3.1 | 3.1 | 0.2 | 0.2 | 0.39 | 0.39 |

| MICROORGANISM | Cmpd of Ex 74 | Cmpd of Ex 75 | Cmpd of Ex 76 | Cmpd of Ex 77 | Cmpd of Ex 78 | Cmpd of Ex 79 | Cmpd of Ex 80 |
|---|---|---|---|---|---|---|---|
| STAPHYLOCOCCUS AUREUS ATCC 6538P | 0.2 | 0.78 | 0.39 | 0.39 | 0.39 | 0.39 | 0.39 |
| STAPHYLOCOCCUS AUREUS A5177 | 0.1 | 0.78 | 0.39 | 0.2 | — | — | — |
| STAPHYLOCOCCUS AUREUS A-5278 | >100 | >100 | >100 | >100 | 100 | 100 | 100 |
| STAPHYLOCOCCUS AUREUS CMX 642A | 0.2 | 0.78 | 0.39 | 0.39 | 0.78 | 0.39 | 0.39 |
| STAPHYLOCOCCUS AUREUS NCTC10649M | 0.1 | 0.78 | 0.2 | 0.39 | 0.39 | 0.39 | |
| STAPHYLOCOCCUS AUREUS CMX 553 | 0.1 | 0.78 | 0.39 | 0.39 | 0.78 | 0.39 | 0.39 |
| STAPHYLOCOCCUS AUREUS 1775 | >100 | >100 | >100 | >100 | 100 | 100 | 100 |
| STAPHYLOCOCCUS EPIDERMIDIS 3519 | 0.2 | 0.78 | 0.39 | 0.39 | 0.39 | 0.39 | 0.39 |
| ENTEROCOCCUS FAECIUM ATCC 8043 | 0.02 | 0.39 | 0.1 | 0.05 | 0.05 | 0.1 | 0.05 |
| STREPTOCOCCUS BOVIS A-5169 | <=0.005 | 0.05 | 0.01 | <=0.005 | <=0.005 | 0.01 | <=0.005 |
| STREPTOCOCCUS AGALACTIAE CMX 508 | 0.02 | 0.39 | 0.1 | 0.01 | <=0.005 | <=0.005 | <=0.005 |
| STREPTOCOCCUS PYOGENES EES61 | <=0.005 | 0.1 | 0.1 | <0.005 | <=0.005 | 0.01 | 0.01 |
| STREPTOCOCCUS PYOGENES 930 | >100 | >100 | >100 | >100 | 25 | 50 | 50 |
| STREPTOCOCCUS PYOGENES PIU 2548 | — | 1.56 | 0.39 | — | 0.2 | 0.39 | 0.2 |
| MICROCOCCUS LUTEUS ATCC 9341 | 0.02 | 0.39 | 0.2 | 0.05 | 0.02 | 0.05 | 0.05 |
| MICROCOCCUS LUTEUS ATCC 4698 | 0.39 | 3.1 | 0.39 | 0.39 | 0.39 | 0.39 | 0.2 |
| ESCHERICHIA COLI JUHL | >100 | >100 | >100 | >100 | >100 | >100 | >100 |
| ESCHERICHIA COLI SS | 0.39 | 12.5 | 0.39 | 0.39 | 1.56 | 1.56 | 1.56 |
| ESCHERICHIA COLI DC-2 | 100 | >100 | >100 | 100 | >100 | >100 | >100 |
| ESCHERICHIA COLI H560 | 100 | >100 | 50 | 50 | >100 | >100 | >100 |
| ESCHERICHIA COLI KNK 437 | >100 | >100 | >100 | >100 | >100 | >100 | >100 |
| ENTEROBACTER AEROGENES ATCC 13048 | >100 | >100 | >100 | >100 | >100 | >100 | >100 |
| KLEBSIELLA PNEUMONIAE ATCC 8045 | >100 | >100 | >100 | >100 | >100 | >100 | >100 |
| PROVIDENCIA STUARTII CMX 640 | >100 | >100 | >100 | >100 | >100 | >100 | >100 |
| PSEUDOMONAS AERUGINOSA BMH10 | >100 | >100 | >100 | >100 | >100 | >100 | >100 |
| PSEUDOMONAS AERUGINOSA 5007 | >100 | >100 | >100 | >100 | >100 | >100 | >100 |
| PSEUDOMONAS AERUGINOSA K799/WT | 100 | >100 | >100 | 100 | >100 | >100 | >100 |
| PSEUDOMONAS AERUGINOSA K799/61 | 3.1 | 6.2 | 1.56 | 1.56 | 3.1 | 3.1 | 3.1 |
| PSEUDOMONAS CEPACIA 296I | 50 | >100 | >100 | >100 | >100 | 100 | 100 |
| ACINETOBACTER CALCOACETICUS CMX 669 | 50 | >100 | 25 | 25 | 100 | 100 | 100 |
| PSEUDOMONAS AERUGINOSA DPHD-5263 | >100 | >100 | >100 | >100 | >100 | >100 | >100 |
| PSEUDOMONAS AERUGINOSA DPHD-2862 | >100 | >100 | >100 | >100 | >100 | >100 | >100 |
| CANDIDA ALBICANS CCH 442 | >100 | >100 | >100 | >100 | 100 | 100 | 100 |
| MYCOBACTERIUM SMEGMATIS ATCC 114 | 0.39 | 3.1 | 6.2 | 0.78 | 0.78 | 0.78 | 1.56 |

TABLE 1-continued

Antibacterial Activity (MIC's) of Selected Compounds

| MICROORGANISM | Cmpd of Ex 81 | Cmpd of Ex 82 | Cmpd of Ex 83 | Cmpd of Ex 84 | Cmpd of Ex 85 | Cmpd of Ex 86 | Cmpd of Ex 87 |
|---|---|---|---|---|---|---|---|
| STAPHYLOCOCCUS AUREUS ATCC 6538P | 0.39 | 0.39 | 0.2 | 0.2 | 0.2 | 0.39 | 1.56 |
| STAPHYLOCOCCUS AUREUS A5177 | 0.39 | 0.39 | 0.2 | 0.2 | 0.2 | 0.2 | 1.56 |
| STAPHYLOCOCCUS AUREUS A-5278 | >100 | >100 | >100 | >100 | >100 | >100 | >100 |
| STAPHYLOCOCCUS AUREUS CMX 642A | 0.39 | 0.39 | 0.2 | 0.2 | 0.2 | 0.39 | 1.56 |
| STAPHYLOCOCCUS AUREUS NCTC10649M | 0.39 | 0.39 | 0.2 | 0.2 | 0.39 | 0.39 | 1.56 |
| STAPHYLOCOCCUS AUREUS CMX 553 | 0.39 | 0.39 | 0.2 | 0.2 | 0.2 | 0.39 | 1.56 |
| STAPHYLOCOCCUS AUREUS 1775 | >100 | >100 | >100 | >100 | >100 | >100 | >100 |
| STAPHYLOCOCCUS EPIDERMIDIS 3519 | 0.39 | 0.39 | 0.39 | 0.39 | 0.2 | 0.39 | 1.56 |
| ENTEROCOCCUS FAECIUM ATCC 8043 | 0.05 | 0.05 | 0.05 | 0.05 | 0.02 | 0.05 | 0.39 |
| STREPTOCOCCUS BOVIS A-5169 | 0.05 | 0.05 | 0.02 | <=0.005 | 0.01 | <=0.005 | 0.05 |
| STREPTOCOCCUS AGALACTIAE CMX 508 | 0.05 | 0.05 | 0.01 | 0.02 | 0.02 | 0.01 | 0.2 |
| STREPTOCOCCUS PYOGENES EES61 | 0.05 | 0.05 | 0.01 | 0.02 | <=0.005 | <0.005 | 0.2 |
| STREPTOCOCCUS PYOGENES 930 | >100 | >100 | 100 | 100 | 100 | >100 | >100 |
| STREPTOCOCCUS PYOGENES PIU 2548 | 0.39 | 0.39 | 0.39 | 0.2 | 0.1 | — | 3.1 |
| MICROCOCCUS LUTEUS ATCC 9341 | 0.05 | 0.05 | 0.05 | 0.1 | 0.02 | 0.05 | 0.1 |
| MICROCOCCUS LUTEUS ATCC 4698 | 0.39 | 0.39 | 0.39 | 0.39 | 0.78 | 0.39 | 1.56 |
| ESCHERICHIA COLI JUHL | >100 | >100 | >100 | >100 | >100 | >100 | >100 |
| ESCHERICHIA COLI SS | 1.56 | 0.78 | 1.56 | 1.56 | 0.78 | 0.39 | 1.56 |
| ESCHERICHIA COLI DC-2 | >100 | >100 | >100 | >100 | >100 | 100 | >100 |
| ESCHERICHIA COLI H560 | 50 | >100 | >100 | >100 | >100 | 50 | >100 |
| ESCHERICHIA COLI KNK 437 | >100 | >100 | >100 | >100 | >100 | >100 | >100 |
| ENTEROBACTER AEROGENES ATCC 13048 | >100 | >100 | >100 | >100 | >100 | >100 | >100 |
| KLEBSIELLA PNEUMONIAE ATCC 8045 | — | — | >100 | >100 | >100 | >100 | >100 |
| PROVIDENCIA STUARTII CMX 640 | >100 | >100 | >100 | >100 | >100 | >100 | >100 |
| PSEUDOMONAS AERUGINOSA BMH10 | >100 | >100 | >100 | >100 | >100 | >100 | >100 |
| PSEUDOMONAS AERUGINOSA 5007 | >100 | >100 | >100 | >100 | >100 | >100 | >100 |
| PSEUDOMONAS AERUGINOSA K799/WT | >100 | >100 | >100 | >100 | >100 | 100 | >100 |
| PSEUDOMONAS AERUGINOSA K799/61 | 3.1 | 3.1 | 6.2 | 3.1 | 3.1 | 1.56 | 3.1 |
| PSEUDOMONAS CEPACIA 296I | >100 | >100 | 50 | >100 | 100 | >100 | >100 |
| ACINETOBACTER CALCOACETICUS CMX 669 | 100 | >100 | 100 | >100 | 100 | 25 | >100 |
| PSEUDOMONAS AERUGINOSA DPHD-5263 | >100 | >100 | >100 | >100 | >100 | >100 | >100 |
| PSEUDOMONAS AERUGINOSA DPHD-2862 | >100 | >100 | >100 | >100 | >100 | >100 | >100 |
| CANDIDA ALBICANS CCH 442 | >100 | >100 | >100 | >100 | >100 | >100 | >100 |
| MYCOBACTERIUM SMEGMATIS ATCC 114 | 3.1 | 3.1 | 0.39 | 0.78 | 3.1 | 0.78 | 12.5 |

| MICROORGANISM | Cmpd of Ex 88 | Cmpd of Ex 89 | Cmpd of Ex 90 | Cmpd of Ex 91 | Cmpd of Ex 92 | Cmpd of Ex 93 | Cmpd of Ex 94 |
|---|---|---|---|---|---|---|---|
| STAPHYLOCOCCUS AUREUS ATCC 6538P | 0.39 | 0.39 | 0.39 | 0.78 | 0.39 | 0.78 | 0.78 |
| STAPHYLOCOCCUS AUREUS A5177 | 0.2 | 0.39 | 0.39 | 0.78 | 0.2 | 0.78 | 0.78 |
| STAPHYLOCOCCUS AUREUS A-5278 | >100 | >100 | >100 | >100 | >100 | >100 | >100 |
| STAPHYLOCOCCUS AUREUS CMX 642A | 0.39 | 0.39 | 0.39 | 0.78 | 0.39 | 0.78 | 0.78 |
| STAPHYLOCOCCUS AUREUS NCTC10649M | 0.2 | 0.39 | 0.78 | 0.78 | 0.39 | 0.78 | 0.78 |
| STAPHYLOCOCCUS AUREUS CMX 553 | 0.2 | 0.39 | 0.39 | 0.78 | 0.39 | 0.78 | 0.78 |
| STAPHYLOCOCCUS AUREUS 1775 | >100 | >100 | >100 | >100 | >100 | >100 | >100 |
| STAPHYLOCOCCUS EPIDERMIDIS 3519 | 0.39 | 0.39 | 0.39 | 0.78 | 0.39 | 0.78 | 0.78 |
| ENTEROCOCCUS FAECIUM ATCC 8043 | 0.2 | 0.1 | 0.02 | 0.1 | 0.1 | 0.39 | 0.2 |
| STREPTOCOCCUS BOVIS A-5169 | 0.02 | 0.01 | — | 0.01 | 0.05 | 0.02 | 0.01 |
| STREPTOCOCCUS AGALACTIAE CMX 508 | 0.05 | 0.01 | 0.02 | 0.05 | 0.05 | 0.1 | 0.02 |
| STREPTOCOCCUS PYOGENES EES61 | <=.005 | 0.02 | <=0.005 | 0.05 | 0.05 | 0.02 | 0.01 |
| STREPTOCOCCUS PYOGENES 930 | — | 100 | — | 100 | 100 | >100 | >100 |
| STREPTOCOCCUS PYOGENES PIU 2548 | — | 0.2 | 0.78 | 0.39 | 0.39 | 3.1 | 0.39 |
| MICROCOCCUS LUTEUS ATCC 9341 | 0.1 | 0.05 | 0.1 | 0.1 | 0.05 | 0.1 | 0.1 |
| MICROCOCCUS LUTEUS ATCC 4698 | 0.2 | 0.39 | 0.78 | 0.39 | 0.39 | 0.78 | 0.39 |
| ESCHERICHIA COLI JUHL | >100 | 100 | >100 | >100 | >100 | >100 | >100 |
| ESCHERICHIA COLI SS | 1.56 | 0.39 | 0.78 | 3.1 | 1.56 | 0.78 | 0.39 |
| ESCHERICHIA COLI DC-2 | >100 | 100 | >100 | >100 | >100 | >100 | >100 |
| ESCHERICHIA COLI H560 | 100 | 25 | 50 | >100 | >100 | 100 | 50 |
| ESCHERICHIA COLI KNK 437 | >100 | 100 | >100 | >100 | >100 | >100 | >100 |
| ENTEROBACTER AEROGENES ATCC 13048 | >100 | >100 | >100 | >100 | >100 | >100 | >100 |
| KLEBSIELLA PNEUMONIAE ATCC 8045 | >100 | >100 | >100 | >100 | >100 | >100 | >100 |
| PROVIDENCIA STUARTII CMX 640 | >100 | >100 | >100 | >100 | >100 | >100 | >100 |
| PSEUDOMONAS AERUGINOSA BMH10 | >100 | >100 | >100 | >100 | >100 | >100 | >100 |
| PSEUDOMONAS AERUGINOSA 5007 | >100 | >100 | >100 | >100 | >100 | >100 | >100 |
| PSEUDOMONAS AERUGINOSA K799/WT | >100 | >100 | >100 | >100 | >100 | >100 | >100 |
| PSEUDOMONAS AERUGINOSA K799/61 | 6.2 | 1.56 | 6.2 | 12.5 | 6.2 | 3.1 | 3.1 |
| PSEUDOMONAS CEPACIA 296I | 100 | 25 | >100 | >100 | >100 | >100 | >100 |
| ACINETOBACTER CALCOACETICUS CMX 669 | 100 | 25 | 100 | >100 | >100 | 50 | >100 |
| PSEUDOMONAS AERUGINOSA DPHD-5263 | >100 | 100 | >100 | >100 | >100 | >100 | >100 |
| PSEUDOMONAS AERUGINOSA DPHD-2862 | >100 | >100 | >100 | >100 | >100 | >100 | >100 |
| CANDIDA ALBICANS CCH 442 | >100 | >100 | >100 | >100 | >100 | >100 | >100 |
| MYCOBACTERIUM SMEGMATIS ATCC 114 | 0.39 | 0.78 | 0.78 | 1.56 | 1.56 | 12.5 | 3.1 |

TABLE 1-continued

| | Antibacterial Activity (MIC's) of Selected Compounds | | | | | | |
|---|---|---|---|---|---|---|---|
| MICROORGANISM | Cmpd of Ex 95 | Cmpd of Ex 96 | Cmpd of Ex 97 | Cmpd of Ex 98 | Cmpd of Ex 99 | Cmpd of Ex 100 | Cmpd of Ex 101 |
| STAPHYLOCOCCUS AUREUS ATCC 6538P | 0.39 | 0.2 | 0.2 | 0.78 | 0.39 | 0.1 | 0.05 |
| STAPHYLOCOCCUS AUREUS A5177 | 0.39 | 0.2 | 0.2 | 0.78 | 0.39 | 0.1 | 0.05 |
| STAPHYLOCOCCUS AUREUS A-5278 | >100 | >100 | >100 | >100 | >100 | >100 | >100 |
| STAPHYLOCOCCUS AUREUS CMX 642A | 0.39 | 0.39 | 0.2 | 0.78 | 0.39 | 0.2 | 0.1 |
| STAPHYLOCOCCUS AUREUS NCTC10649M | 0.39 | 0.39 | 0.78 | 0.78 | 0.39 | 0.05 | 0.05 |
| STAPHYLOCOCCUS AUREUS CMX 553 | 0.39 | 0.39 | 0.39 | 0.78 | 0.39 | 0.1 | 0.05 |
| STAPHYLOCOCCUS AUREUS 1775 | >100 | >100 | >100 | >100 | >100 | >100 | >100 |
| STAPHYLOCOCCUS EPIDERMIDIS 3519 | 0.39 | 0.39 | 0.39 | 0.78 | 0.39 | 0.2 | 0.1 |
| ENTEROCOCCUS FAECIUM ATCC 8043 | 0.2 | 0.1 | 0.1 | 0.2 | 0.1 | 0.01 | <=0.005 |
| STREPTOCOCCUS BOVIS A-5169 | 0.02 | 0.01 | 0.01 | 0.05 | 0.05 | 0.01 | <=0.005 |
| STREPTOCOCCUS AGALACTIAE CMX 508 | 0.1 | 0.05 | 0.02 | 0.05 | 0.05 | 0.01 | <=0.005 |
| STREPTOCOCCUS PYOGENES EES61 | 0.05 | 0.02 | 0.02 | 0.05 | 0.05 | 0.01 | <=0.005 |
| STREPTOCOCCUS PYOGENES 930 | >100 | >100 | >100 | >100 | >100 | 100 | >100 |
| STREPTOCOCCUS PYOGENES PIU 2548 | 0.39 | 0.39 | 0.2 | 1.56 | 0.39 | 0.2 | 0.05 |
| MICROCOCCUS LUTEUS ATCC 9341 | 0.1 | 0.02 | 0.05 | 0.1 | 0.1 | <0.005 | <=0.005 |
| MICROCOCCUS LUTEUS ATCC 4698 | 0.39 | 0.39 | 0.78 | 0.39 | 0.39 | 0.1 | 0.02 |
| ESCHERICHIA COLI JUHL | 100 | 25 | 50 | 100 | >100 | >100 | >100 |
| ESCHERICHIA COLI SS | 0.39 | 0.39 | 0.39 | 0.39 | 0.78 | 1.56 | 0.2 |
| ESCHERICHIA COLI DC-2 | >100 | 25 | 50 | 100 | >100 | >100 | >100 |
| ESCHERICHIA COLI H560 | 50 | 12.5 | 25 | 50 | >100 | 50 | 100 |
| ESCHERICHIA COLI KNK 437 | >100 | 50 | 50 | 100 | >100 | >100 | >100 |
| ENTEROBACTER AEROGENES ATCC 13048 | >100 | 100 | 100 | >100 | >100 | >100 | >100 |
| KLEBSIELLA PNEUMONIAE ATCC 8045 | >100 | 100 | 100 | >100 | >100 | >100 | >100 |
| PROVIDENCIA STUARTII CMX 640 | >100 | >100 | >100 | >100 | >100 | >100 | >100 |
| PSEUDOMONAS AERUGINOSA BMH10 | >100 | 100 | >100 | >100 | >100 | >100 | >100 |
| PSEUDOMONAS AERUGINOSA 5007 | >100 | >100 | >100 | >100 | >100 | >100 | >100 |
| PSEUDOMONAS AERUGINOSA K799/WT | >100 | >100 | >100 | >100 | >100 | >100 | >100 |
| PSEUDOMONAS AERUGINOSA K799/61 | 1.56 | 0.78 | 0.78 | 1.56 | 6.2 | 1.56 | 1.56 |
| PSEUDOMONAS CEPACIA 296I | >100 | >100 | >100 | >100 | >100 | 100 | 100 |
| ACINETOBACTER CALCOACETICUS CMX 669 | 25 | 12.5 | 25 | 50 | 100 | 100 | 100 |
| PSEUDOMONAS AERUGINOSA DPHD-5263 | >100 | >100 | >100 | >100 | >100 | >100 | >100 |
| PSEUDOMONAS AERUGINOSA DPHD-2862 | >100 | >100 | >100 | >100 | >100 | >100 | >100 |
| CANDIDA ALBICANS CCH 442 | >100 | >100 | >100 | >100 | >100 | >100 | >100 |
| MYCOBACTERIUM SMEGMATIS ATCC 114 | 3.1 | 3.1 | 12.5 | 12.5 | 3.1 | 0.78 | 0.39 |

| MICROORGANISM | Cmpd of Ex 102 | Cmpd of Ex 103 | Cmpd of Ex 104 | Cmpd of Ex 105 |
|---|---|---|---|---|
| STAPHYLOCOCCUS AUREUS ATCC 6538P | 0.2 | 0.05 | 0.05 | 0.05 |
| STAPHYLOCOCCUS AUREUS A5177 | 0.1 | 0.05 | 0.05 | 0.05 |
| STAPHYLOCOCCUS AUREUS A-5278 | >100 | 100 | 100 | 100 |
| STAPHYLOCOCCUS AUREUS CMX 642A | 0.2 | 0.05 | 0.05 | 0.05 |
| STAPHYLOCOCCUS AUREUS NCTC10649M | 0.1 | 0.05 | 0.05 | 0.02 |
| STAPHYLOCOCCUS AUREUS CMX 553 | 0.1 | 0.05 | 0.05 | 0.05 |
| STAPHYLOCOCCUS AUREUS 1775 | >100 | 100 | 100 | 100 |
| STAPHYLOCOCCUS EPIDERMIDIS 3519 | 0.2 | 0.05 | 0.05 | 0.05 |
| ENTEROCOCCUS FAECIUM ATCC 8043 | 0.01 | <=0.005 | 0.01 | <=0.005 |
| STREPTOCOCCUS BOVIS A-5169 | 0.01 | <=0.005 | 0.01 | <=0.005 |
| STREPTOCOCCUS AGALACTIAE CMX 508 | 0.01 | <=0.005 | 0.01 | <=0.005 |
| STREPTOCOCCUS PYOGENES EES61 | 0.01 | <=0.005 | 0.01 | <=0.005 |
| STREPTOCOCCUS PYOGENES 930 | >100 | 25 | 25 | 25 |
| STREPTOCOCCUS PYOGENES PIU 2548 | 0.2 | 0.05 | 0.05 | 0.05 |
| MICROCOCCUS LUTEUS ATCC 9341 | <=0.005 | <=0.005 | 0.02 | <=0.005 |
| MICROCOCCUS LUTEUS ATCC 4698 | 0.02 | <=0.005 | 0.1 | 0.01 |
| ESCHERICHIA COLI JUHL | 100 | 100 | 100 | 100 |
| ESCHERICHIA COLI SS | 0.39 | 0.39 | 0.78 | 0.39 |
| ESCHERICHIA COLI DC-2 | >100 | 100 | 100 | 100 |
| ESCHERICHIA COLI H560 | 50 | 100 | 50 | 50 |
| ESCHERICHIA COLI KNK 437 | >100 | >100 | >100 | >100 |
| ENTEROBACTER AEROGENES ATCC 13048 | >100 | >100 | >100 | >100 |
| KLEBSIELLA PNEUMONIAE ATCC 8045 | >100 | >100 | >100 | >100 |
| PROVIDENCIA STUARTII CMX 640 | >100 | >100 | >100 | >100 |
| PSEUDOMONAS AERUGINOSA BMH10 | >100 | >100 | >100 | >100 |
| PSEUDOMONAS AERUGINOSA 5007 | >100 | >100 | >100 | >100 |
| PSEUDOMONAS AERUGINOSA K799/WT | >100 | >100 | >100 | >100 |
| PSEUDOMONAS AERUGINOSA K799/61 | 3.1 | 0.78 | 3.1 | 1.56 |
| PSEUDOMONAS CEPACIA 296I | 50 | 50 | 100 | 100 |
| ACINETOBACTER CALCOACETICUS CMX 669 | 50 | 50 | 100 | 100 |
| PSEUDOMONAS AERUGINOSA DPHD-5263 | >100 | >100 | >100 | >100 |
| PSEUDOMONAS AERUGINOSA DPHD-2862 | >100 | >100 | >100 | >100 |
| CANDIDA ALBICANS CCH 442 | >100 | 50 | 100 | 100 |
| MYCOBACTERIUM SMEGMATIS ATCC 114 | 0.01 | 0.2 | 0.39 | 0.78 |

TABLE 1-continued

Antibacterial Activity (MIC's) of Selected Compounds

| MICROORGANISM | Cmpd of Ex 106 | Cmpd of Ex 107 | Cmpd of Ex 108 | Cmpd of Ex 109 | Cmpd of Ex 110 | Cmpd of Ex 111 | Cmpd of Ex 112 |
|---|---|---|---|---|---|---|---|
| STAPHYLOCOCCUS AUREUS ATCC 6538P | 0.2 | 0.78 | 0.39 | 0.39 | | 0.2 | 0.39 |
| STAPHYLOCOCCUS AUREUS A5177 | 0.2 | 0.78 | 0.39 | 0.39 | 0.2 | 0.2 | 0.39 |
| STAPHYLOCOCCUS AUREUS A-5278 | >100 | >100 | >100 | >100 | >100 | >100 | >100 |
| STAPHYLOCOCCUS AUREUS CMX 642A | 0.39 | 0.78 | 0.78 | 0.39 | 0.39 | 0.39 | 0.78 |
| STAPHYLOCOCCUS AUREUS NCTC10649M | 0.2 | 0.78 | 0.78 | 0.39 | | 0.2 | 0.78 |
| STAPHYLOCOCCUS AUREUS CMX 553 | 0.2 | 0.78 | 0.78 | 0.78 | 0.2 | 0.2 | 0.78 |
| STAPHYLOCOCCUS AUREUS 1775 | >100 | >100 | >100 | >100 | >100 | >100 | >100 |
| STAPHYLOCOCCUS EPIDERMIDIS 3519 | 0.2 | 0.78 | 1.56 | 0.39 | 0.2 | — | 0.78 |
| ENTEROCOCCUS FAECIUM ATCC 8043 | 0.05 | 0.1 | 0.2 | 0.1 | 0.05 | 0.1 | 0.1 |
| STREPTOCOCCUS BOVIS A-5169 | <=.005 | 0.01 | 0.02 | 0.05 | 0.02 | 0.01 | <=.005 |
| STREPTOCOCCUS AGALACTIAE CMX 508 | 0.02 | 0.02 | 0.1 | 0.1 | 0.02 | 0.05 | 0.02 |
| STREPTOCOCCUS PYOGENES EES61 | <=.005 | 0.02 | 0.1 | 0.05 | 0.005 | 0.02 | 0.02 |
| STREPTOCOCCUS PYOGENES 930 | >100 | >100 | >100 | >100 | 50 | 50 | >100 |
| STREPTOCOCCUS PYOGENES PIU 2548 | — | 0.39 | 0.39 | 0.78 | 0.2 | 0.39 | 0.2 |
| MICROCOCCUS LUTEUS ATCC 9341 | 0.05 | 0.05 | 0.1 | 0.05 | 0.05 | 0.05 | 0.1 |
| MICROCOCCUS LUTEUS ATCC 4698 | 0.39 | 0.39 | 0.78 | 0.2 | 0.78 | 0.39 | 0.2 |
| ESCHERICHIA COLI JUHL | 25 | >100 | — | 25 | 50 | 100 | 100 |
| ESCHERICHIA COLI SS | 0.39 | 0.39 | 0.78 | 0.2 | 0.2 | 0.39 | 0.39 |
| ESCHERICHIA COLI DC-2 | 25 | >100 | >100 | 12.5 | 25 | 100 | >100 |
| ESCHERICHIA COLI H560 | 12.5 | 50 | >100 | 6.2 | 12.5 | 50 | 50 |
| ESCHERICHIA COLI KNK 437 | 25 | >100 | >100 | 25 | 50 | >100 | 100 |
| ENTEROBACTER AEROGENES ATCC 13048 | 50 | >100 | >100 | 25 | | >100 | 100 |
| KLEBSIELLA PNEUMONIAE ATCC 8045 | 100 | >100 | >100 | 25 | >100 | >100 | 100 |
| PROVIDENCIA STUARTII CMX 640 | >100 | >100 | >100 | >100 | >100 | >100 | >100 |
| PSEUDOMONAS AERUGINOSA BMH10 | 100 | >100 | >100 | 50 | 50 | >100 | 100 |
| PSEUDOMONAS AERUGINOSA 5007 | >100 | >100 | >100 | >100 | >100 | 100 | >100 |
| PSEUDOMONAS AERUGINOSA K799/WT | 100 | >100 | >100 | >100 | >100 | 1.56 | >100 |
| PSEUDOMONAS AERUGINOSA K799/61 | 0.78 | 6.2 | 6.2 | 0.39 | 1.56 | 50 | 0.78 |
| PSEUDOMONAS CEPACIA 296I | 100 | >100 | >100 | >100 | 50 | 25 | 100 |
| ACINETOBACTER CALCOACETICUS CMX 669 | 12.5 | 50 | 100 | 25 | 25 | >100 | 50 |
| PSEUDOMONAS AERUGINOSA DPHD-5263 | 100 | >100 | >100 | >100 | >100 | >100 | >100 |
| PSEUDOMONAS AERUGINOSA DPHD-2862 | >100 | >100 | >100 | >100 | >100 | >100 | >100 |
| CANDIDA ALBICANS CCH 442 | >100 | >100 | >100 | >100 | >100 | 0.39 | 100 |
| MYCOBACTERIUM SMEGMATIS ATCC 114 | 3.1 | 1.56 | 12.5 | 3.1 | — | | 0.39 |

| MICROORGANISM | Cmpd of Ex 113 | Cmpd of Ex 114 | Cmpd of Ex 115 | Cmpd of Ex 116 | Cmpd of Ex 117 | Cmpd of Ex 118 | Cmpd of Ex 119 |
|---|---|---|---|---|---|---|---|
| STAPHYLOCOCCUS AUREUS ATCC 6538P | 0.78 | 1.56 | 1.56 | 0.78 | 0.78 | 0.39 | 0.39 |
| STAPHYLOCOCCUS AUREUS A5177 | 0.39 | 0.78 | — | 0.78 | 0.78 | 0.2 | 0.39 |
| STAPHYLOCOCCUS AUREUS A-5278 | >100 | >100 | >100 | >100 | >100 | >100 | >100 |
| STAPHYLOCOCCUS AUREUS CMX 642A | 0.78 | 1.56 | 1.56 | 0.78 | 0.78 | 0.39 | 0.39 |
| STAPHYLOCOCCUS AUREUS NCTC10649M | 0.78 | 1.56 | 0.78 | 0.39 | 0.78 | 0.39 | 0.2 |
| STAPHYLOCOCCUS AUREUS CMX 553 | 0.78 | 1.56 | 1.56 | 0.78 | 0.78 | 0.39 | 0.2 |
| STAPHYLOCOCCUS AUREUS 1775 | >100 | >100 | >100 | >100 | >100 | >100 | >100 |
| STAPHYLOCOCCUS EPIDERMIDIS 3519 | 1.56 | 1.56 | 1.56 | 0.78 | 1.56 | 0.39 | 0.39 |
| ENTEROCOCCUS FAECIUM ATCC 8043 | 0.2 | 0.2 | 0.1 | 0.2 | 0.2 | 0.2 | 0.1 |
| STREPTOCOCCUS BOVIS A-5169 | 0.01 | 0.02 | <=.005 | <=.005 | 0.05 | <=.005 | 0.02 |
| STREPTOCOCCUS AGALACTIAE CMX 508 | 0.2 | 0.1 | 0.05 | 0.05 | 0.05 | 0.02 | 0.02 |
| STREPTOCOCCUS PYOGENES EES61 | 0.05 | 0.05 | 0.05 | — | — | 0.05 | 0.02 |
| STREPTOCOCCUS PYOGENES 930 | >100 | >100 | >100 | >100 | >100 | >100 | >100 |
| STREPTOCOCCUS PYOGENES PIU 2548 | 0.39 | 1.56 | 0.78 | 0.78 | 0.78 | 0.78 | 0.78 |
| MICROCOCCUS LUTEUS ATCC 9341 | 0.1 | 0.1 | 0.1 | 0.2 | 0.2 | 0.05 | 0.05 |
| MICROCOCCUS LUTEUS ATCC 4698 | 0.78 | 1.56 | 0.39 | 0.39 | 0.39 | 0.2 | 0.39 |
| ESCHERICHIA COLI JUHL | >100 | 100 | >100 | 50 | >100 | 100 | 100 |
| ESCHERICHIA COLI SS | 1.56 | 0.78 | 0.39 | 0.39 | 1.56 | 0.78 | 0.78 |
| ESCHERICHIA COLI DC-2 | >100 | 100 | 50 | 100 | >100 | >100 | >100 |
| ESCHERICHIA COLI H560 | 50 | 50 | 12.5 | 50 | 50 | 100 | >100 |
| ESCHERICHIA COLI KNK 437 | >100 | 100 | 25 | >100 | >100 | >100 | >100 |
| ENTEROBACTER AEROGENES ATCC 13048 | >100 | 100 | 50 | >100 | >100 | >100 | >100 |
| KLEBSIELLA PNEUMONIAE ATCC 8045 | >100 | >100 | 50 | >100 | >100 | >100 | >100 |
| PROVIDENCIA STUARTII CMX 640 | >100 | >100 | >100 | >100 | >100 | >100 | >100 |
| PSEUDOMONAS AERUGINOSA BMH10 | >100 | >100 | >100 | 100 | >100 | >100 | >100 |
| PSEUDOMONAS AERUGINOSA 5007 | >100 | >100 | >100 | >100 | >100 | >100 | >100 |
| PSEUDOMONAS AERUGINOSA K799/WT | >100 | >100 | >100 | >100 | >100 | >100 | >100 |
| PSEUDOMONAS AERUGINOSA K799/61 | 3.1 | 6.2 | 0.78 | 3.1 | 3.1 | 0.78 | 0.78 |
| PSEUDOMONAS CEPACIA 296I | >100 | >100 | >100 | >100 | >100 | >100 | >100 |
| ACINETOBACTER CALCOACETICUS CMX 669 | 50 | 25 | 25 | 50 | >100 | 50 | 100 |
| PSEUDOMONAS AERUGINOSA DPHD-5263 | >100 | >100 | >100 | >100 | >100 | >100 | >100 |
| PSEUDOMONAS AERUGINOSA DPHD-2862 | >100 | >100 | >100 | >100 | >100 | >100 | >100 |
| CANDIDA ALBICANS CCH 442 | >100 | >100 | >100 | >100 | >100 | >100 | >100 |
| MYCOBACTERIUM SMEGMATIS ATCC 114 | 1.56 | 6.2 | 12.5 | 1.56 | 3.1 | 0.78 | 0.78 |

TABLE 1-continued

Antibacterial Activity (MIC's) of Selected Compounds

| MICROORGANISM | Cmpd of Ex 120 | Cmpd of Ex 121 | Cmpd of Ex 122 | Cmpd of Ex 123 | Cmpd of Ex 124 | Cmpd of Ex 125 | Cmpd of Ex 126 |
|---|---|---|---|---|---|---|---|
| STAPHYLOCOCCUS AUREUS ATCC 6538P | 0.2 | 0.78 | 0.39 | 1.56 | 0.78 | 12.5 | 1.56 |
| STAPHYLOCOCCUS AUREUS A5177 | 0.2 | 0.78 | 0.39 | 1.56 | 1.56 | 6.2 | 1.56 |
| STAPHYLOCOCCUS AUREUS A-5278 | >100 | >100 | >100 | >100 | >100 | >100 | >100 |
| STAPHYLOCOCCUS AUREUS CMX 642A | 0.2 | 0.78 | 0.78 | 3.1 | 0.78 | 12.5 | 1.56 |
| STAPHYLOCOCCUS AUREUS NCTC10649M | 0.2 | 0.78 | 0.78 | 3.1 | 0.78 | 6.2 | 1.56 |
| STAPHYLOCOCCUS AUREUS CMX 553 | 0.2 | 0.78 | 0.78 | 3.1 | 0.78 | 6.2 | 1.56 |
| STAPHYLOCOCCUS AUREUS 1775 | >100 | >100 | >100 | >100 | >100 | >100 | >100 |
| STAPHYLOCOCCUS EPIDERMIDIS 3519 | 0.39 | 0.78 | 0.78 | 3.1 | 3.1 | 6.2 | 1.56 |
| ENTEROCOCCUS FAECIUM ATCC 8043 | 0.05 | 0.05 | 0.78 | 0.39 | 0.2 | 1.56 | 0.2 |
| STREPTOCOCCUS BOVIS A-5169 | 0.01 | 0.01 | 0.02 | 0.1 | 0.05 | 0.2 | 0.02 |
| STREPTOCOCCUS AGALACTIAE CMX 508 | 0.01 | 0.02 | 0.1 | 0.1 | 0.1 | 0.39 | 0.05 |
| STREPTOCOCCUS PYOGENES EES61 | 0.01 | 0.02 | 0.02 | 0.1 | 0.02 | 0.1 | 0.05 |
| STREPTOCOCCUS PYOGENES 930 | >100 | >100 | 100 | >100 | >100 | >100 | >100 |
| STREPTOCOCCUS PYOGENES PIU 2548 | 0.39 | 0.78 | 6.2 | 3.1 | 3.1 | — | 1.56 |
| MICROCOCCUS LUTEUS ATCC 9341 | 0.02 | 0.05 | 0.05 | 0.39 | 0.1 | 0.78 | 0.2 |
| MICROCOCCUS LUTEUS ATCC 4698 | 0.2 | 0.2 | 1.56 | 1.56 | 0.39 | 6.2 | 0.78 |
| ESCHERICHIA COLI JUHL | 50 | 50 | 100 | >100 | 100 | >100 | >100 |
| ESCHERICHIA COLI SS | 0.39 | 0.2 | 0.78 | 6.2 | 0.78 | 0.78 | 0.78 |
| ESCHERICHIA COLI DC-2 | 50 | 50 | 100 | >100 | 100 | >100 | >100 |
| ESCHERICHIA COLI H560 | 50 | 25 | 50 | >100 | 50 | >100 | >100 |
| ESCHERICHIA COLI KNK 437 | >100 | 50 | 50 | >100 | 100 | >100 | >100 |
| ENTEROBACTER AEROGENES ATCC 13048 | >100 | 100 | 100 | >100 | >100 | >100 | >100 |
| KLEBSIELLA PNEUMONIAE ATCC 8045 | >100 | 100 | >100 | >100 | >100 | >100 | >100 |
| PROVIDENCIA STUARTII CMX 640 | >100 | >100 | >100 | >100 | >100 | >100 | >100 |
| PSEUDOMONAS AERUGINOSA BMH10 | >100 | 100 | >100 | >100 | >100 | >100 | >100 |
| PSEUDOMONAS AERUGINOSA 5007 | >100 | >100 | >100 | >100 | >100 | >100 | >100 |
| PSEUDOMONAS AERUGINOSA K799/WT | >100 | >100 | >100 | >100 | 100 | >100 | >100 |
| PSEUDOMONAS AERUGINOSA K799/61 | 0.78 | 0.39 | 0.78 | 25 | 0.78 | 6.2 | 3.1 |
| PSEUDOMONAS CEPACIA 296I | 100 | 100 | >100 | >100 | >100 | >100 | >100 |
| ACINETOBACTER CALCOACETICUS CMX 669 | 50 | 12.5 | 25 | >100 | 12.5 | 100 | 100 |
| PSEUDOMONAS AERUGINOSA DPHD-5263 | >100 | >100 | >100 | >100 | >100 | >100 | >100 |
| PSEUDOMONAS AERUGINOSA DPHD-2862 | >100 | >100 | >100 | >100 | >100 | >100 | >100 |
| CANDIDA ALBICANS CCH 442 | >100 | >100 | >100 | >100 | >100 | >100 | >100 |
| MYCOBACTERIUM SMEGMATIS ATCC 114 | 0.78 | 6.2 | 25 | 12.5 | 25 | 50 | 12.5 |

| MICROORGANISM | Cmpd of Ex 127 | Cmpd of Ex 128 | Cmpd of Ex 129 | Cmpd of Ex 130 | Cmpd of Ex 131 | Cmpd of Ex 132 | Cmpd of Ex 133 |
|---|---|---|---|---|---|---|---|
| STAPHYLOCOCCUS AUREUS ATCC 6538P | 3.1 | 0.39 | 1.56 | 1.56 | 0.39 | 0.39 | 0.78 |
| STAPHYLOCOCCUS AUREUS A5177 | 1.56 | 0.39 | 1.56 | 0.78 | 0.39 | 0.39 | 0.78 |
| STAPHYLOCOCCUS AUREUS A-5278 | >100 | >100 | >100 | >100 | >100 | 100 | 25 |
| STAPHYLOCOCCUS AUREUS CMX 642A | 3.1 | 0.39 | 1.56 | 1.56 | 0.39 | 0.39 | 1.56 |
| STAPHYLOCOCCUS AUREUS NCTC10649M | 1.56 | 0.39 | 1.56 | 1.56 | 0.39 | 0.39 | 1.56 |
| STAPHYLOCOCCUS AUREUS CMX 553 | 1.56 | 0.39 | 1.56 | 1.56 | 0.39 | 0.39 | 1.56 |
| STAPHYLOCOCCUS AUREUS 1775 | >100 | >100 | >100 | >100 | >100 | 100 | 25 |
| STAPHYLOCOCCUS EPIDERMIDIS 3519 | 1.56 | 0.39 | 1.56 | 3.1 | 0.39 | 0.39 | 1.56 |
| ENTEROCOCCUS FAECIUM ATCC 8043 | 0.39 | 0.1 | 0.39 | 0.2 | 0.1 | 0.1 | 0.1 |
| STREPTOCOCCUS BOVIS A-5169 | 0.1 | <=0.005 | 0.05 | 0.1 | — | 0.01 | — |
| STREPTOCOCCUS AGALACTIAE CMX 508 | 0.2 | — | 0.05 | 0.1 | 0.05 | 0.02 | — |
| STREPTOCOCCUS PYOGENES EES61 | 0.1 | <=0.005 | 0.02 | 0.1 | 0.02 | 0.02 | 0.02 |
| STREPTOCOCCUS PYOGENES 930 | >100 | >100 | >100 | >100 | >100 | 50 | 6.2 |
| STREPTOCOCCUS PYOGENES PIU 2548 | 1.56 | 0.78 | 3.1 | 6.2 | 0.78 | 0.78 | 1.56 |
| MICROCOCCUS LUTEUS ATCC 9341 | 0.39 | 0.05 | 0.2 | 0.2 | 0.02 | 0.05 | 0.2 |
| MICROCOCCUS LUTEUS ATCC 4698 | 1.56 | 0.39 | 1.56 | 0.78 | 0.2 | 0.2 | 1.56 |
| ESCHERICHIA COLI JUHL | >100 | 100 | 100 | >100 | 50 | 100 | >100 |
| ESCHERICHIA COLI SS | 1.56 | 1.56 | 0.78 | 0.78 | 0.2 | 0.78 | 12.5 |
| ESCHERICHIA COLI DC-2 | >100 | >100 | 50 | >100 | 25 | 100 | >100 |
| ESCHERICHIA COLI H560 | >100 | >100 | 50 | >100 | 12.5 | 50 | >100 |
| ESCHERICHIA COLI KNK 437 | >100 | >100 | >100 | >100 | 25 | >100 | >100 |
| ENTEROBACTER AEROGENES ATCC 13048 | >100 | >100 | 100 | >100 | 50 | >100 | >100 |
| KLEBSIELLA PNEUMONIAE ATCC 8045 | >100 | >100 | 100 | >100 | 50 | >100 | >100 |
| PROVIDENCIA STUARTII CMX 640 | >100 | >100 | >100 | >100 | >100 | >100 | >100 |
| PSEUDOMONAS AERUGINOSA BMH10 | >100 | >100 | >100 | >100 | >100 | >100 | >100 |
| PSEUDOMONAS AERUGINOSA 5007 | >100 | >100 | >100 | >100 | >100 | >100 | >100 |
| PSEUDOMONAS AERUGINOSA K799/WT | >100 | >100 | >100 | >100 | 50 | 100 | >100 |
| PSEUDOMONAS AERUGINOSA K799/61 | 3.1 | 6.2 | 1.56 | 3.1 | 0.78 | 1.56 | 12.5 |
| PSEUDOMONAS CEPACIA 296I | >100 | >100 | >100 | >100 | 25 | >100 | >100 |
| ACINETOBACTER CALCOACETICUS CMX 669 | 50 | 100 | 12.5 | 50 | 25 | 50 | >100 |
| PSEUDOMONAS AERUGINOSA DPHD-5263 | >100 | >100 | >100 | >100 | >100 | >100 | >100 |
| PSEUDOMONAS AERUGINOSA DPHD-2862 | >100 | >100 | >100 | >100 | >100 | >100 | >100 |
| CANDIDA ALBICANS CCH 442 | >100 | >100 | >100 | >100 | >100 | >100 | 50 |
| MYCOBACTERIUM SMEGMATIS ATCC 114 | 25 | 1.56 | 50 | 25 | 1.56 | 0.78 | 0.78 |

TABLE 1-continued

Antibacterial Activity (MIC's) of Selected Compounds

| MICROORGANISM | Cmpd of Ex 134 | Cmpd of Ex 135 | Cmpd of Ex 136 | Cmpd of Ex 137 | Cmpd of Ex 138 | Cmpd of Ex 139 | Cmpd of Ex 140 |
|---|---|---|---|---|---|---|---|
| STAPHYLOCOCCUS AUREUS ATCC 6538P | 0.78 | 1.56 | 1.56 | 0.02 | 0.39 | 0.1 | 0.1 |
| STAPHYLOCOCCUS AUREUS A5177 | 0.78 | 1.56 | 1.56 | 0.02 | 0.39 | 0.1 | 0.1 |
| STAPHYLOCOCCUS AUREUS A-5278 | >100 | >100 | >100 | >100 | >100 | >100 | >100 |
| STAPHYLOCOCCUS AUREUS CMX 642A | 0.78 | 3.1 | 1.56 | 0.05 | 0.39 | 0.1 | 0.1 |
| STAPHYLOCOCCUS AUREUS NCTC10649M | 0.78 | 3.1 | 1.56 | 0.05 | 0.39 | 0.1 | 0.1 |
| STAPHYLOCOCCUS AUREUS CMX 553 | 0.78 | 3.1 | 1.56 | 0.05 | 0.39 | 0.1 | 0.1 |
| STAPHYLOCOCCUS AUREUS 1775 | >100 | >100 | >100 | >100 | >100 | >100 | >100 |
| STAPHYLOCOCCUS EPIDERMIDIS 3519 | 0.78 | 3.1 | 1.56 | 0.05 | 0.39 | 0.1 | 0.1 |
| ENTEROCOCCUS FAECIUM ATCC 8043 | 0.1 | 0.39 | 0.2 | 0.01 | 0.1 | 0.02 | 0.05 |
| STREPTOCOCCUS BOVIS A-5169 | 0.01 | 0.1 | 0.02 | — | 0.01 | <=0.005 | <=0.005 |
| STREPTOCOCCUS AGALACTIAE CMX 508 | 0.02 | 0.2 | 0.1 | — | 0.1 | 0.02 | 0.02 |
| STREPTOCOCCUS PYOGENES EES61 | 0.02 | 0.2 | 0.1 | 0.01 | 0.02 | 0.01 | <=0.005 |
| STREPTOCOCCUS PYOGENES 930 | >100 | >100 | >100 | 6.2 | >100 | 25 | 50 |
| STREPTOCOCCUS PYOGENES PIU 2548 | 0.78 | 1.56 | 1.56 | 0.2 | 1.56 | 0.39 | 0.2 |
| MICROCOCCUS LUTEUS ATCC 9341 | 0.05 | 0.2 | 0.1 | 0.01 | 0.02 | 0.05 | 0.01 |
| MICROCOCCUS LUTEUS ATCC 4698 | 0.78 | 1.56 | 0.78 | 0.2 | 0.39 | 0.2 | 0.1 |
| ESCHERICHIA COLI JUHL | 100 | >100 | 100 | 25 | 50 | 25 | 50 |
| ESCHERICHIA COLI SS | 1.56 | 1.56 | 0.78 | 0.02 | 0.78 | 0.39 | 0.78 |
| ESCHERICHIA COLI DC-2 | 100 | >100 | >100 | 12.5 | 50 | 25 | 50 |
| ESCHERICHIA COLI H560 | 50 | >100 | 100 | 12.5 | 50 | 25 | 25 |
| ESCHERICHIA COLI KNK 437 | >100 | >100 | >100 | 25 | 50 | 50 | 50 |
| ENTEROBACTER AEROGENES ATCC 13048 | >100 | >100 | >100 | 100 | >100 | 100 | >100 |
| KLEBSIELLA PNEUMONIAE ATCC 8045 | >100 | >100 | >100 | 100 | >100 | 100 | >100 |
| PROVIDENCIA STUARTII CMX 640 | >100 | >100 | >100 | 100 | >100 | >100 | >100 |
| PSEUDOMONAS AERUGINOSA BMH10 | >100 | >100 | >100 | 100 | >100 | >100 | >100 |
| PSEUDOMONAS AERUGINOSA 5007 | >100 | >100 | >100 | 100 | >100 | >100 | >100 |
| PSEUDOMONAS AERUGINOSA K799/WT | >100 | >100 | >100 | 50 | >100 | 100 | >100 |
| PSEUDOMONAS AERUGINOSA K799/61 | 1.56 | 6.2 | 1.56 | 0.2 | 0.78 | 0.39 | 0.39 |
| PSEUDOMONAS CEPACIA 296I | >100 | >100 | >100 | 50 | 100 | 25 | 25 |
| ACINETOBACTER CALCOACETICUS CMX 669 | 50 | >100 | 25 | 50 | 50 | 25 | 25 |
| PSEUDOMONAS AERUGINOSA DPHD-5263 | >100 | >100 | >100 | 100 | >100 | >100 | >100 |
| PSEUDOMONAS AERUGINOSA DPHD-2862 | >100 | >100 | >100 | 50 | >100 | 100 | >100 |
| CANDIDA ALBICANS CCH 442 | >100 | >100 | >100 | >100 | >100 | >100 | >100 |
| MYCOBACTERIUM SMEGMATIS ATCC 114 | 0.78 | 1.56 | 6.2 | 0.2 | 3.1 | 0.78 | 0.39 |

| MICROORGANISM | Cmpd of Ex 141 | Cmpd of Ex 142 | Cmpd of Ex 143 | Cmpd of Ex 144 | Cmpd of Ex 146 | Cmpd of Ex 147 | Cmpd of Ex 148 |
|---|---|---|---|---|---|---|---|
| STAPHYLOCOCCUS AUREUS ATCC 6538P | 0.1 | 0.2 | 0.1 | 0.1 | 0.39 | 1.56 | 1.56 |
| STAPHYLOCOCCUS AUREUS A5177 | 0.1 | 0.2 | 0.2 | 0.1 | — | 1.56 | 1.56 |
| STAPHYLOCOCCUS AUREUS A-5278 | 50 | >100 | 50 | >100 | 50 | 6.2 | 12.5 |
| STAPHYLOCOCCUS AUREUS CMX 642A | 0.1 | 0.2 | 0.2 | 0.1 | 0.39 | 1.56 | 1.56 |
| STAPHYLOCOCCUS AUREUS NCTC10649M | 0.1 | 0.2 | 0.2 | 0.1 | 0.39 | 1.56 | 1.56 |
| STAPHYLOCOCCUS AUREUS CMX 553 | 0.1 | 0.2 | 0.2 | 0.1 | 0.39 | 1.56 | 1.56 |
| STAPHYLOCOCCUS AUREUS 1775 | 50 | >100 | 50 | >100 | 50 | 12.5 | 12.5 |
| STAPHYLOCOCCUS EPIDERMIDIS 3519 | 0.1 | 0.2 | 0.2 | 0.1 | 0.39 | 1.56 | 1.56 |
| ENTEROCOCCUS FAECIUM ATCC 8043 | 0.02 | 0.1 | 0.02 | 0.1 | 0.05 | 0.78 | 0.78 |
| STREPTOCOCCUS BOVIS A-5169 | <=0.005 | 0.01 | 0.01 | <=0.005 | 0.05 | 0.39 | 0.2 |
| STREPTOCOCCUS AGALACTIAE CMX 508 | 0.02 | 0.01 | 0.02 | <=0.005 | 0.05 | 0.78 | 0.39 |
| STREPTOCOCCUS PYOGENES EES61 | <=0.005 | 0.01 | 0.02 | <=0.005 | 0.05 | 0.78 | 0.2 |
| STREPTOCOCCUS PYOGENES 930 | 50 | >100 | 50 | 100 | 12.5 | 3.1 | 6.2 |
| STREPTOCOCCUS PYOGENES PIU 2548 | 0.2 | 0.39 | 0.39 | 0.39 | 0.78 | 3.1 | 3.1 |
| MICROCOCCUS LUTEUS ATCC 9341 | 0.01 | 0.02 | 0.01 | 0.01 | 0.05 | 0.39 | 0.39 |
| MICROCOCCUS LUTEUS ATCC 4698 | 0.1 | 0.1 | 0.2 | 0.1 | 0.2 | 3.1 | 1.56 |
| ESCHERICHIA COLI JUHL | 50 | 50 | 50 | 50 | 50 | >100 | >100 |
| ESCHERICHIA COLI SS | 0.78 | 1.56 | 0.78 | 0.78 | 0.78 | >100 | 25 |
| ESCHERICHIA COLI DC-2 | 50 | 25 | 50 | 50 | 100 | >100 | >100 |
| ESCHERICHIA COLI H560 | 12.5 | 25 | 25 | 50 | 25 | >100 | >100 |
| ESCHERICHIA COLI KNK 437 | 50 | 100 | 50 | 50 | 25 | >100 | >100 |
| ENTEROBACTER AEROGENES ATCC 13048 | >100 | >100 | >100 | 100 | >100 | >100 | >100 |
| KLEBSIELLA PNEUMONIAE ATCC 8045 | 100 | >100 | >100 | 100 | 100 | >100 | >100 |
| PROVIDENCIA STUARTII CMX 640 | >100 | >100 | >100 | >100 | 100 | >100 | >100 |
| PSEUDOMONAS AERUGINOSA BMH10 | 100 | >100 | >100 | >100 | 100 | >100 | >100 |
| PSEUDOMONAS AERUGINOSA 5007 | >100 | >100 | >100 | >100 | 100 | >100 | >100 |
| PSEUDOMONAS AERUGINOSA K799/WT | >100 | >100 | >100 | >100 | 100 | >100 | >100 |
| PSEUDOMONAS AERUGINOSA K799/61 | 1.56 | 1.56 | 1.56 | 0.78 | 0.78 | 12.5 | 25 |
| PSEUDOMONAS CEPACIA 296I | 25 | >100 | 50 | 50 | 25 | >100 | >100 |
| ACINETOBACTER CALCOACETICUS CMX 669 | 25 | 25 | 50 | 50 | 50 | >100 | >100 |
| PSEUDOMONAS AERUGINOSA DPHD-5263 | >100 | >100 | >100 | >100 | 100 | >100 | >100 |
| PSEUDOMONAS AERUGINOSA DPHD-2862 | >100 | >100 | >100 | >100 | 100 | >100 | >100 |
| CANDIDA ALBICANS CCH 442 | >100 | >100 | 100 | >100 | 50 | 50 | >100 |
| MYCOBACTERIUM SMEGMATIS ATCC 114 | 0.2 | 1.56 | 0.2 | 1.56 | 0.39 | 1.56 | 1.56 |

TABLE 2

Antibacterial Activity (MIC's) of Selected Compounds against *H. Influenza* Dill AMP R

| Example No. | MIC |
|---|---|
| Ery A Standard | 4 |
| 7 | 64 |
| 18 | 8 |
| 19 | 16 |
| 40 | 4 |
| 41 | 2 |
| 72 | 2 |
| 83 | 16 |
| 92 | 32 |
| 99 | 32 |
| 120 | 4 |
| 123 | 128 |
| 125 | 128 |
| 129 | 64 |
| 131 | 4 |
| 135 | 64 |
| 139 | 2 |

What is claimed is:

1. A compound having the formula:

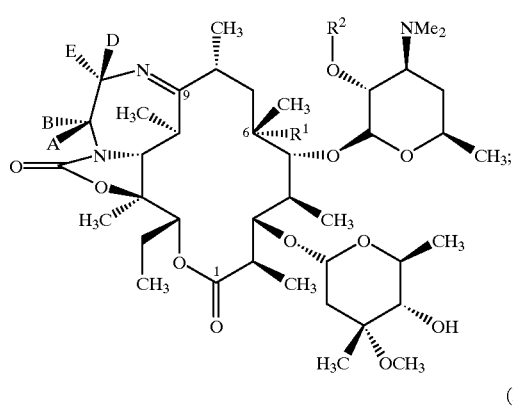
(I)

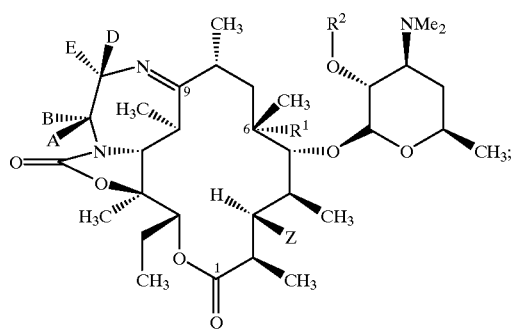
(II)

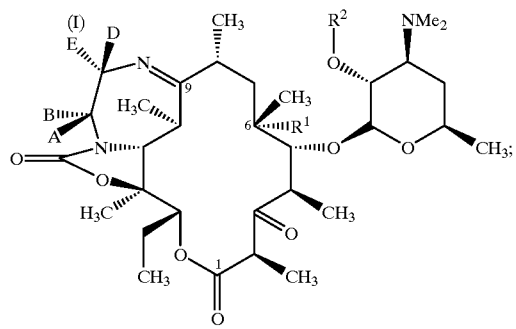
(III)

or

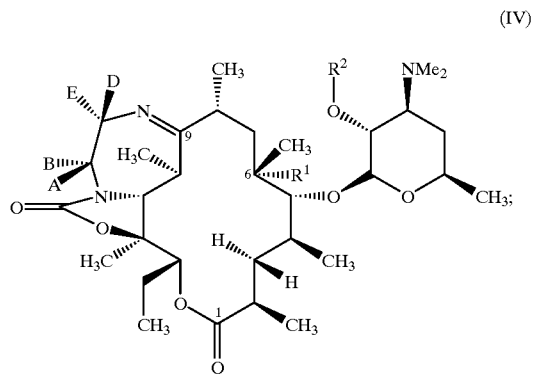
(IV)

or pharmaceutically acceptable salts and esters thereof, wherein a first substituent, optionally a second substituent, and optionally a third substituent selected from A, B, D and E are independently selected from the group consisting of:

(a) $C_1-C_6$ alkyl, substituted with one or more substituents selected from the group consisting of:
  (i) aryl;
  (ii) substituted-aryl;
  (iii) heteroaryl;
  (iv) substituted-heteroaryl;
  (v) heterocycloalkyl;
  (vi) hydroxy;
  (vii) $C_1-C_6$ alkoxy;
  (viii) halogen consisting of Br, Cl, F or I; and
  (ix) $NR^3R^4$, wherein $R^3$ and $R^4$ are independently selected from hydrogen and $C_1-C_6$-alkyl, or $R^3$ and $R^4$ taken together with a first hetero function, wherein said first hetero function is the nitrogen atom to which $R^3$ and $R^4$ are connected, form a non-aromatic 3- to 7-membered ring;
  said ring optionally containing a second hetero function selected from the group consisting of —O—, —NH—, —N($C_1-C_6$-alkyl-)-, —N(aryl-$C_1-C_6$-alkyl-)-, —N(substituted-aryl-$C_1-C_6$-alkyl-)-, —N(heteroaryl-$C_1-C_6$-alkyl-)-, —N(substituted-heteroaryl-$C_1-C_6$-alkyl-)-, —S— and —S(O)$_n$—, wherein n is 1 or 2;

(b) $C_3-C_7$-cycloalkyl;
(c) aryl;
(d) substituted-aryl;
(e) heteroaryl;
(f) substituted-heteroaryl;
(g) heterocycloalkyl; and
(h) $C_1-C_6$-alkyl-M—$R^5$, wherein the $C_1-C_6$-alkyl group is optionally substituted with a substituent in group (a)(i)–(a)(ix), and wherein M is selected from the group consisting of:
(aa) —C(O)—NH—;
(bb) —NH—C(O)—;
(cc) —NH—;
(dd) —N(CH₃)—;
(ee) —O—;
(ff) —S(O)$_n$—, wherein n is 0, 1 or 2;
(gg) —C(=NH)—NH—;
(hh) —C(O)—O—;
(ii) —O—C(O)—;
(jj) —O—C(O)—NH—;
(kk) —NH—C(O)—O—; and
(ll) —NH—C(O)—NH—;
R⁵ is selected from the group consisting of:
(aaa) C₁–C₆-alkyl, optionally substituted with a substituent selected from the group consisting of:
(i) aryl;
(ii) substituted-aryl;
(iii) heteroaryl; and
(iv) substituted-heteroaryl;
(bbb) aryl;
(ccc) substituted-aryl;
(ddd) heteroaryl;
(eee) substituted-heteroaryl; and
(fff) heterocycloalkyl;
said optional second and optional third substituents selected from a group (a)–(h) above and further selected from a group consisting of:
(i) hydrogen; and
(j) C₁–C₆-alkyl;
a fourth substituent selected from A, B, D and E is hydrogen or C₁–C₆-alkyl; R¹ is selected from the group consisting of:
(a) hydrogen;
(b) —O—C₁–C₃-alkyl;
(c) —O—C₃–C₅-cycloalkyl;
(d) —O—C₁–C₃-alkyl-C₃–C₅-cycloalkyl;
(e) —O—C(O)—C₁–C₃-alkyl;
(f) —O—C(O)—O—C₁–C₃-alkyl; and
(g) —O—C(O)—NH—C, C₃-alkyl;
R² is hydrogen or a hydroxy-protecting group; and Z is hydroxy or protected-hydroxy.
2. A compound having the formula (I)

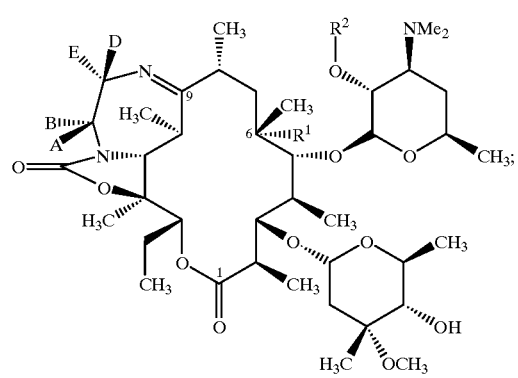

(II)

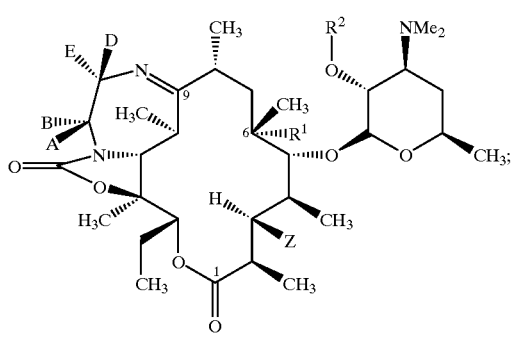

(III)

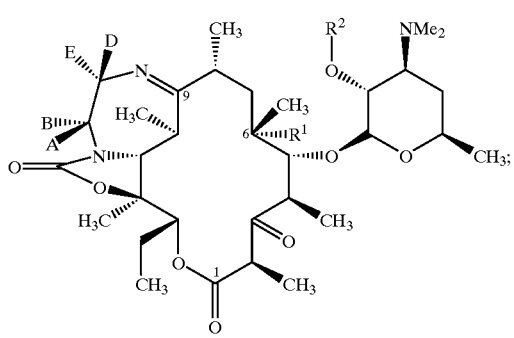

or (IV)

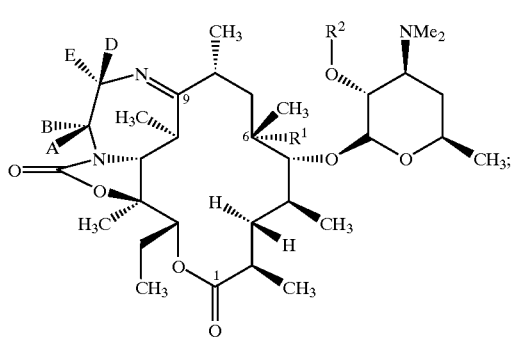

or pharmaceutically acceptable salts or esters thereof,
wherein any one pair of substituents selected from a substituent A, B, D or E taken together with the atom or atoms to which they are attached form a pair AB, AD, AE, BD, BE or DE;
wherein each pair is taken together with the atom or atoms to which they are attached to form a 3- to 7-membered ring optionally containing a hetero function consisting of:
—O—;
—NH—;
—N(C₁–C₆-alkyl-)-;
—N(aryl)-;
—N(aryl-C₁–C₆-alkyl-)-;
—N(substituted-aryl-C₁–C₆-alkyl-)-;
—N(heteroaryl-C₁–C₆-alkyl-)-;
—N(substituted-heteroaryl-C₁–C₆-alkyl-)-;
—S(O)$_n$—, wherein n is 0, 1 or 2;
—C(O)—NH—;
—C(O)—NR⁵—, wherein
R⁵ is selected from the group consisting of:

(aaa) $C_1$–$C_6$ akyl, optionally substituted with a substituent selected from the group consisting of:
  (i) aryl;
  (ii) substituted-aryl;
  (iii) heteroaryl; and
  (iv) substituted-heteroaryl;
(bbb) aryl;
(ccc) substituted-aryl;
(ddd) heteroaryl;
(eee) substituted-heteroaryl; and
(fff) heterocycloalkyl;
—NH—C(O)—;
—NR$^5$—C(O)—, wherein R$^5$ is as described above; and
—C(=NH)—NH;
and wherein the remaining two, non-ring forming, substituents are each hydrogen;

R$^1$ is selected from the group consisting of:
  (a) hydrogen;
  (b) —O—$C_1$–$C_3$-alkyl;
  (c) —O—$C_3$–$C_5$-cycloalkyl;
  (d) —O—$C_1$–$C_3$-alkyl-$C_3$–$C_5$-cycloalkyl;
  (e) —O—C(O)—$C_1$–$C_3$-alkyl;
  (f) —O—C(O)—O—$C_1$–$C_3$-alkyl; and
  (g) —O—C(O)—NH—$C_1$–$C_3$-alkyl;

R$^2$ is hydrogen or a hydroxy-protecting group; and
Z is hydroxy or protected-hydroxy.

3. A compound according to claim 1 or 2 having the formula:

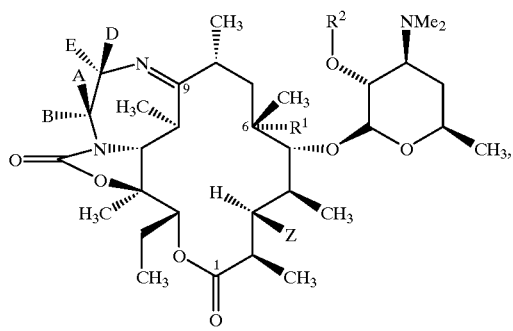

wherein A, B, D, E, R$^1$–R$^5$ and Z are as described therein.

4. A compound according to claim 1 or 2 having the formula:

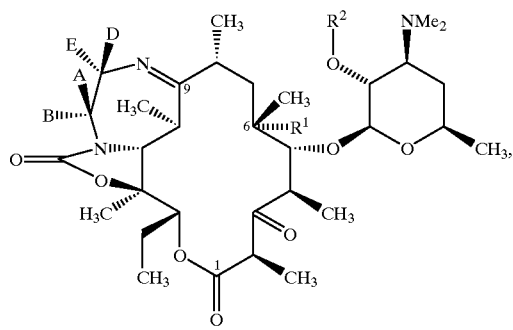

wherein A, B, D, E, and R$^1$–R$^5$ are as described therein.

5. A compound according to claim 1 or 2 having the formula:

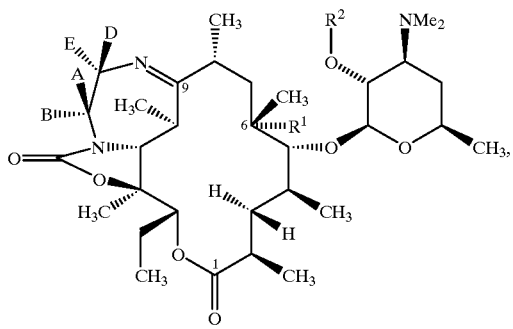

wherein A, B, D, E, and R$^1$–R$^5$ are as described therein.

6. A compound according to claim 4 wherein R$^1$ is hydrogen, or methoxy, R$^2$ is hydrogen, and A, B, D, E and R$^2$–R$^5$ are as described therein.

7. A compound according to claim 1 or 2 having the formula:

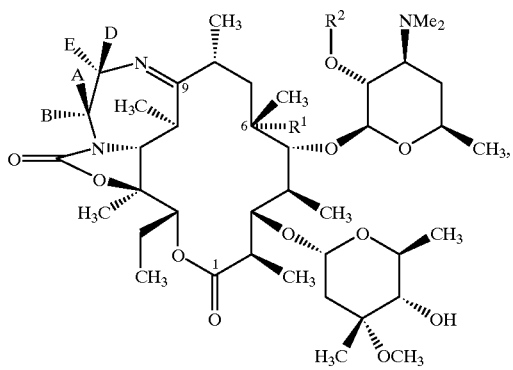

wherein A, B, D, E, and R$^1$–R$^5$ are as described therein.

8. A process for preparing a compound having the formula:

(I)

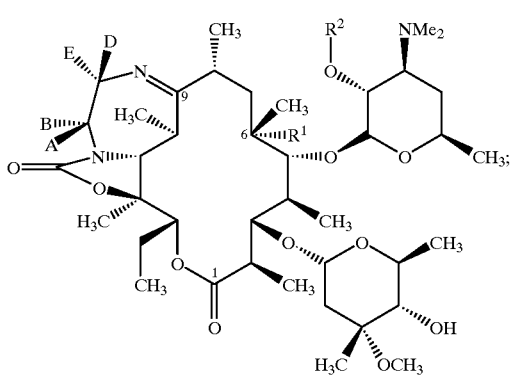

-continued

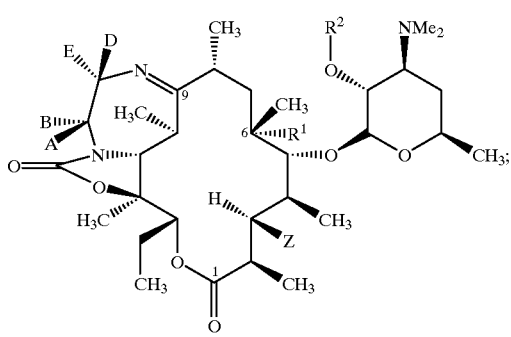
(II)

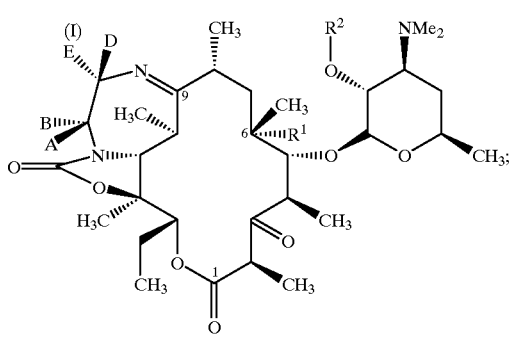
(III)

or

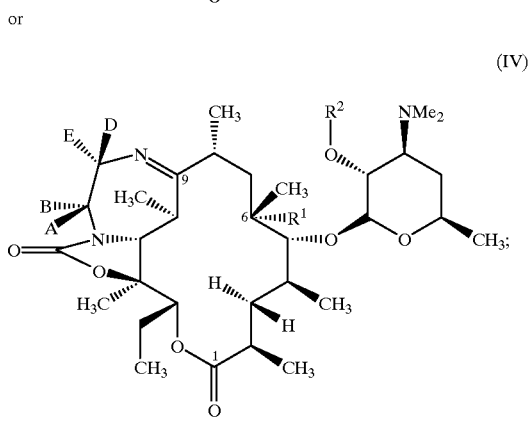
(IV)

or pharmaceutically acceptable salts and esters thereof, wherein a first substituent, optionally a second substituent, and optionally a third substituent selected from A, B, D and E are independently selected from the group consisting of:
(a) $C_1$–$C_6$ alkyl, substituted with one or more substituents selected from the group consisting of:
  (i) aryl;
  (ii) substituted-aryl;
  (iii) heteroaryl;
  (iv) substituted-heteroaryl;
  (v) heterocycloalkyl;
  (vi) hydroxy;
  (vii) $C_1$–$C_6$ alkoxy;
  (viii) halogen consisting of Br, Cl, F or I; and
  (ix) $NR^3R^4$, wherein $R^3$ and $R^4$ are independently selected from hydrogen and $C_1$–$C_6$-alkyl, or $R^3$ and $R^4$ taken together with a first hetero function, wherein said first hetero function is the nitrogen atom to which $R^3$ and $R^4$ are connected, form a non-aromatic 3- to 7-membered ring;

said ring optionally containing a second hetero function selected from the group consisting of —O—, —NH—, —N($C_1$–$C_6$-alkyl-)-, —N(aryl-$C_1$–$C_6$-alkyl-)-, —N(substituted-aryl-$C_1$–$C_6$-alkyl-)-, —N(heteroaryl-$C_1$–$C_6$-alkyl-)-, —N(substituted-heteroaryl-$C_1$–$C_6$-alkyl-)-, —S— and —S(O)$_n$—, wherein n is 1 or 2;
(b) $C_3$–$C_7$-cycloalkyl;
(c) aryl;
(d) substituted-aryl;
(e) heteroaryl;
(f) substituted-heteroaryl;
(g) heterocycloalkyl; and
(h) $C_1$–$C_6$-alkyl-M—$R^5$, wherein the $C_1$–$C_6$-alkyl group is optionally substituted with a substituent in group (a)(i)–(a)(ix), and wherein M is selected from the group consisting of:
  (aa) —C(O)—NH—;
  (bb) —NH—C(O)—;
  (cc) —NH—;
  (dd) —N($CH_3$)—;
  (ee) —O—;
  (ff) —S(O)$_n$—, wherein n is 0, 1 or 2;
  (gg) —C(=NH)—NH—;
  (hh) —C(O)—O—;
  (ii) —O—C(O)—;
  (jj) —O—C(O)—NH—;
  (kk) —NH—C(O)—O—; and
  (ll) —NH—C(O)—NH—;
$R^5$ is selected from the group consisting of:
  (aaa) $C_1$–$C_6$-alkyl, optionally substituted with a substituent selected from the group consisting of:
    (i) aryl;
    (ii) substituted-aryl;
    (iii) heteroaryl; and
    (iv) substituted-heteroaryl;
  (bbb) aryl;
  (ccc) substituted-aryl;
  (ddd) heteroaryl;
  (eee) substituted-heteroaryl; and
  (fff) heterocycloalkyl;
said optional second and optional third substituents selected from a group (a)–(h) above and further selected from a group consisting of:
  (i) hydrogen; and
  (j) $C_1$–$C_6$-alkyl;
a fourth substituent selected from A, B, D and E is hydrogen or $C_1$–$C_6$-alkyl; $R^1$ is selected from the group consisting of:
(a) hydrogen;
(b) —O—$C_1$–$C_3$-alkyl;
(c) —O—$C_3$–$C_5$-cycloalkyl;
(d) —O—$C_1$–$C_3$-alkyl-$C_3$–$C_5$-cycloalkyl;
(e) —O—C(O)—$C_1$–$C_3$-alkyl;
(f) —O—C(O)—O—$C_1$–$C_3$-alkyl; and
(g) —O—C(O)—NH—C, $C_3$-alkyl;
$R^2$ is hydrogen or a hydroxy-protecting group; and Z is hydroxy or protected-hydroxy; the method comprising:

(a) treating a compound having the formula:

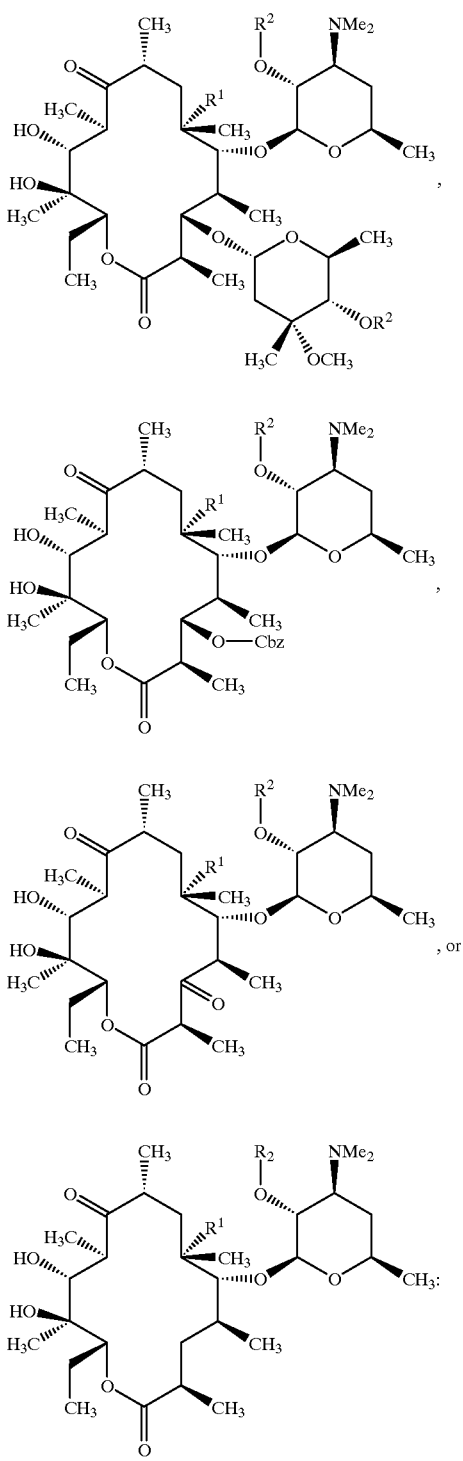

respectively,
wherein $R^1$ is as defined above and $R^2$ is a hydroxy-protecting group; with a base, followed by reaction with carbonyldiimidazole, in an aprotic solvent, to prepare first intermediate compounds having the formula:

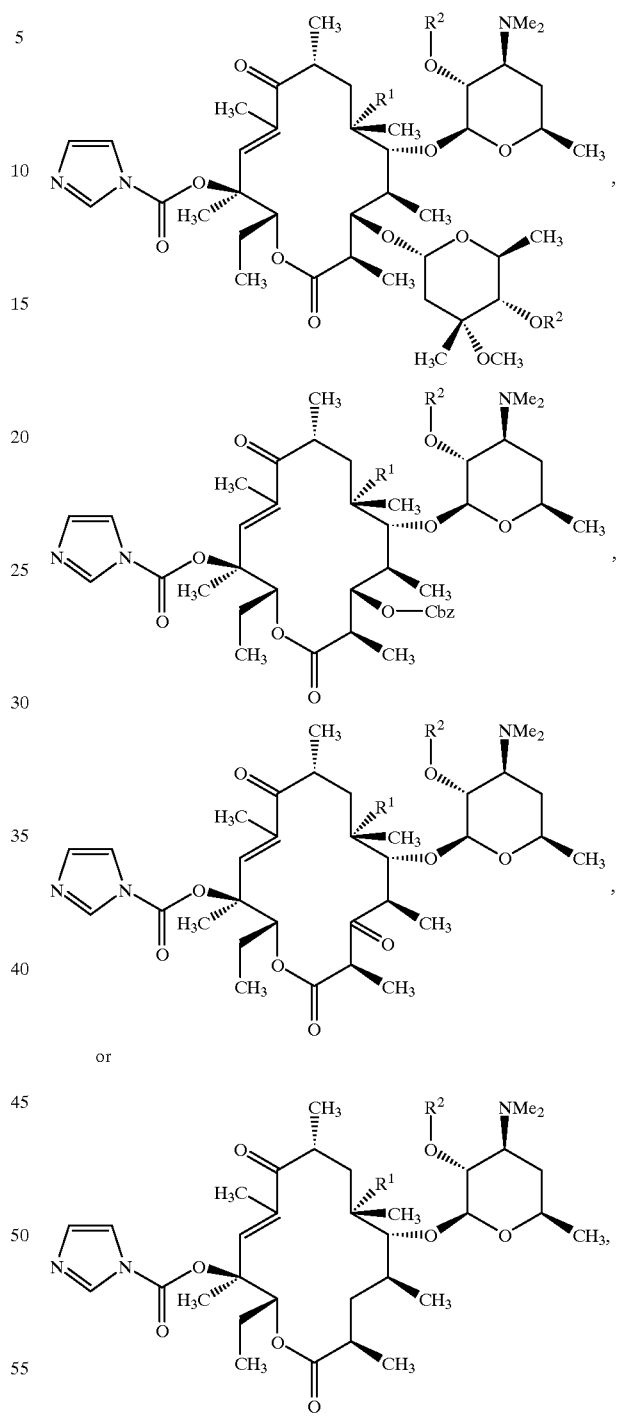

respectively;
wherein $R^1$ and $R^2$ are as defined above;

(b) reacting said first intermediate compounds with a compound having the formula:

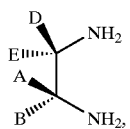

wherein A, B, D and E are as defined above, to give a bicyclic second intermediate compound having the formula:

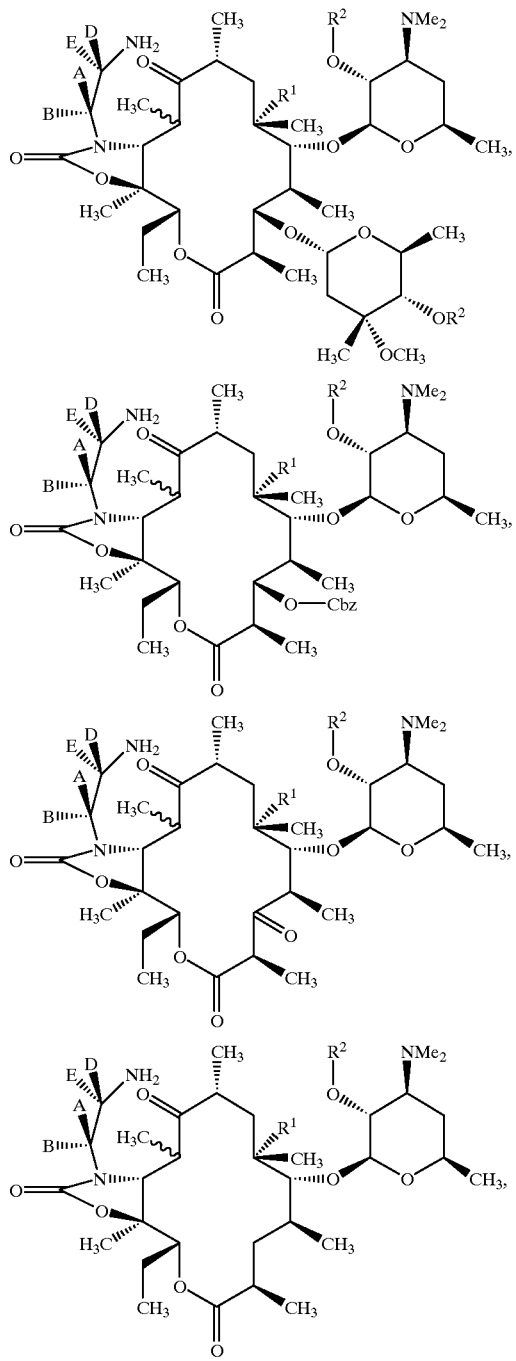

respectively, wherein $R^1$ and $R^2$ are as defined above;

(c) deprotecting said second intermediate compounds by treatment with methanol or ethanol when $OR^2$ is an ester or with fluoride in THFP or acetonitrile when $R^2$ is a triaLkylsilyl group, for from 1 to 24 hours, to give the third intermediate compounds:

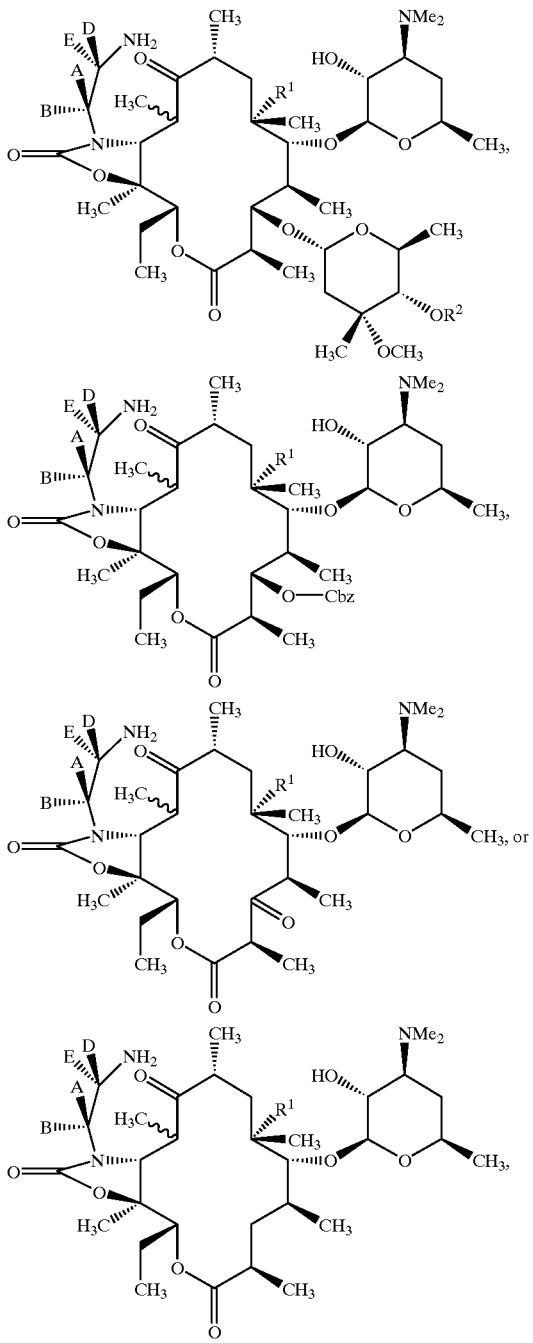

respectively;

(d) cyclizing said third intermediate compounds by treatment with dilute acid for a period of from 4 hours to 10 days to give the desired compounds (I), (II), (III) or (IV) above.

9. A process for preparing a compound having the formula:

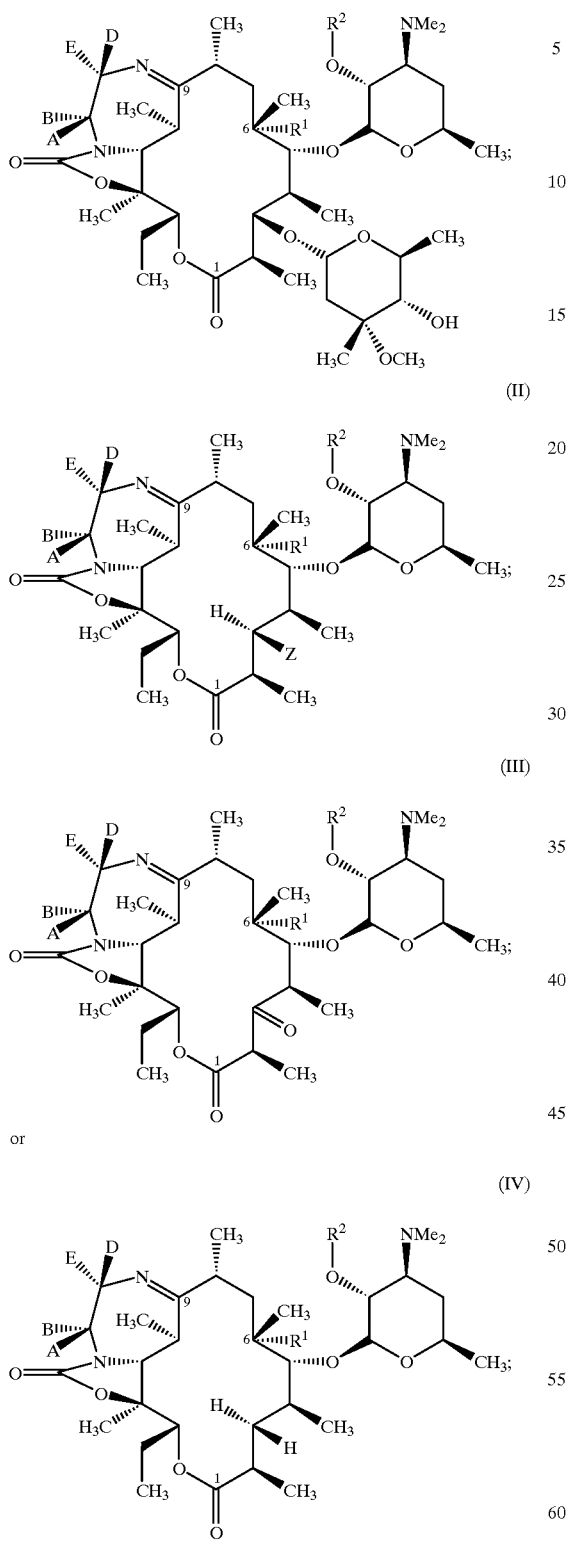

(I)

(II)

(III)

or (IV)

or pharmaceutically acceptable salts or esters thereof, wherein any one pair of substituents selected from a substituent A, B, D or E taken together with the atom or atoms to which they are attached form a pair AB, AD, AE, BD, BE or DE;

wherein each pair is taken together with the atom or atoms to which they are attached to form a 3- to 7-membered ring optionally containing a hetero function consisting of:
—O—;
—NH—;
—N($C_1$-$C_6$-alkyl-)-;
—N(aryl)-;
—N(aryl-$C_1$-$C_6$-alkyl-)-;
—N(substituted-aryl-$C_1$-$C_6$-alkyl-)-;
—N(heteroaryl-$C_1$-$C_6$-alkyl-)-;
—N(substituted-heteroaryl-$C_1$-$C_6$-alkyl-)-;
—S(O)$_n$—, wherein n is 0, 1 or 2;
—C(O)—NH—;
—C(O)—NR$^5$—, wherein
  R$^5$ is selected from the group consisting of:
    (aaa) $C_1$-$C_6$ akyl, optionally substituted with a substituent selected from the group consisting of:
      (i) aryl;
      (ii) substituted-aryl;
      (iii) heteroaryl; and
      (iv) substituted-heteroaryl;
    (bbb) aryl;
    (ccc) substituted-aryl;
    (ddd) heteroaryl;
    (eee) substituted-heteroaryl; and
    (fff) heterocycloalkyl;
—NH—C(O)—;
—NR$^5$—C(O)—, wherein R$^5$ is as described above; and
—C(=NH)—NH;
and wherein the remaining two, non-ring forming, substituents are each hydrogen;
R$^1$ is selected from the group consisting of:
  (a) hydrogen;
  (b) —O—$C_1$-$C_3$-alkyl;
  (c) —O—$C_3$-$C_5$-cycloalkyl;
  (d) —O—$C_1$-$C_3$-alkyl-$C_3$-$C_5$-cycloalkyl;
  (e) —O—C(O)—$C_1$-$C_3$-alkyl;
  (f) —O—C(O)—O—$C_1$-$C_3$-alkyl; and
  (g) —O—C(O)—NH—$C_1$-$C_3$-alkyl;
R$^2$ is hydrogen or a hydroxy-protecting group; and
Z is hydroxy or protected-hydroxy; the method comprising:
  (a) treating a compound having the formula:

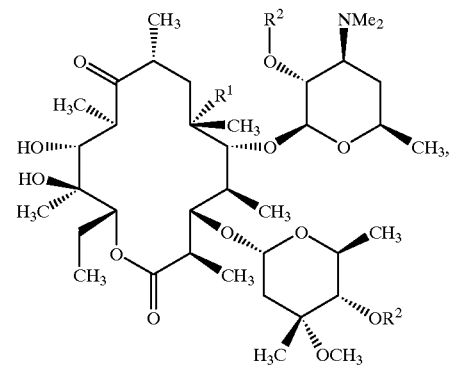

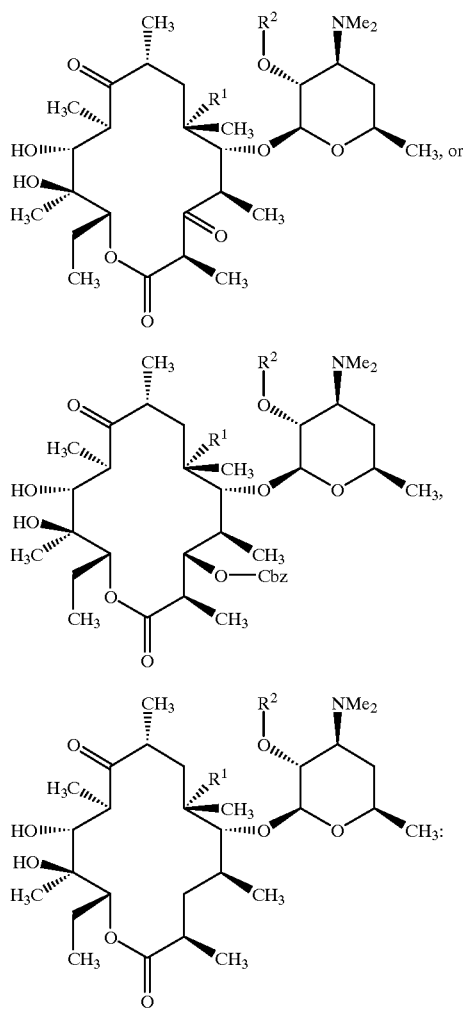

respectively, wherein $R^1$ is as defined above and $R^2$ is a hydroxy-protecting group; with a base, followed by reaction with carbonyldiimidazole, in an aprotic solvent, to prepare a first intermediate compound having the formula:

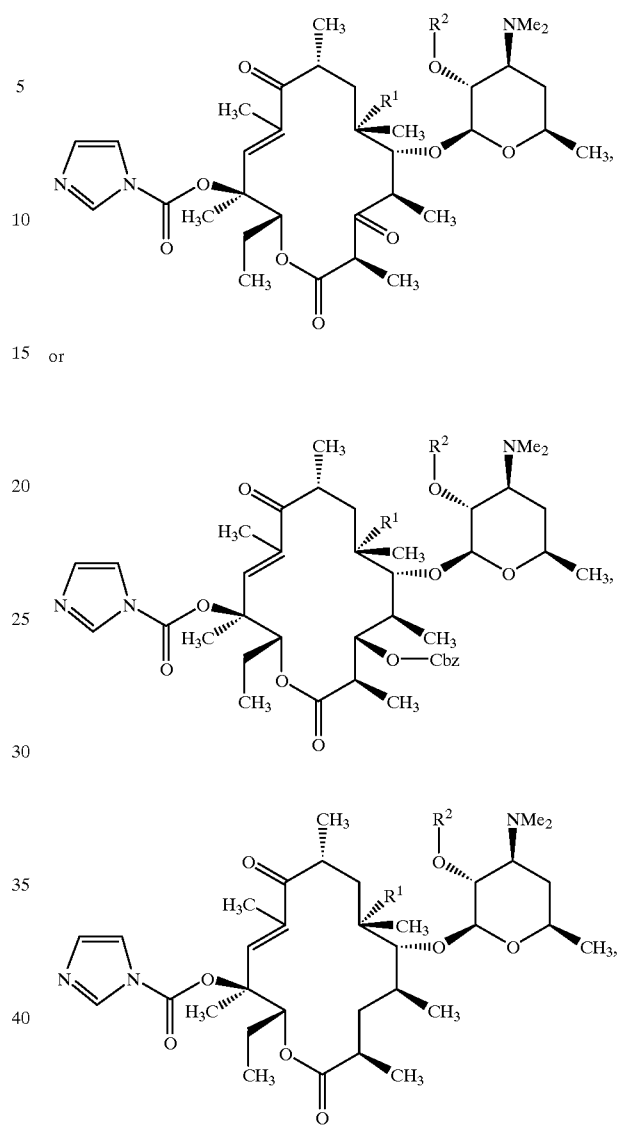

respectively;

wherein $R^1$ and $R^2$ are as defined above;

(b) reacting said first intermediate compounds with a compound having the formula:

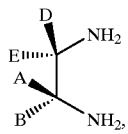

wherein A, B, D and E are as defined above, to give a bicyclic second intermediate compound having the formula:

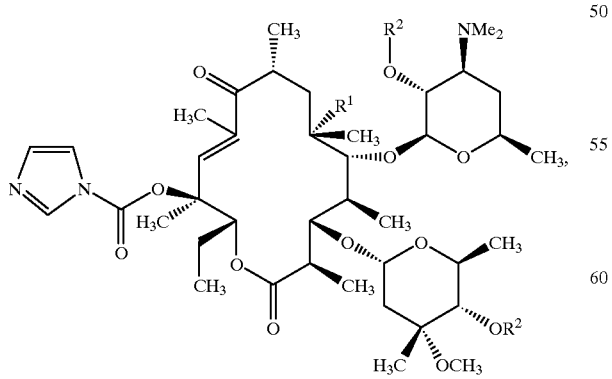

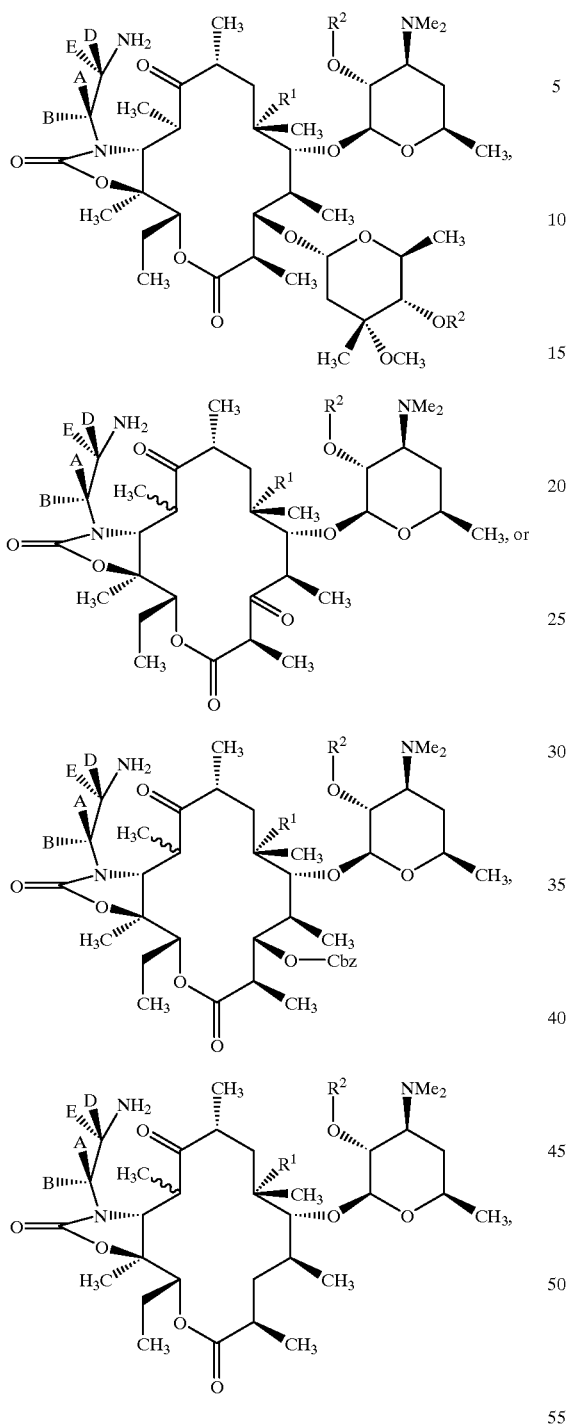

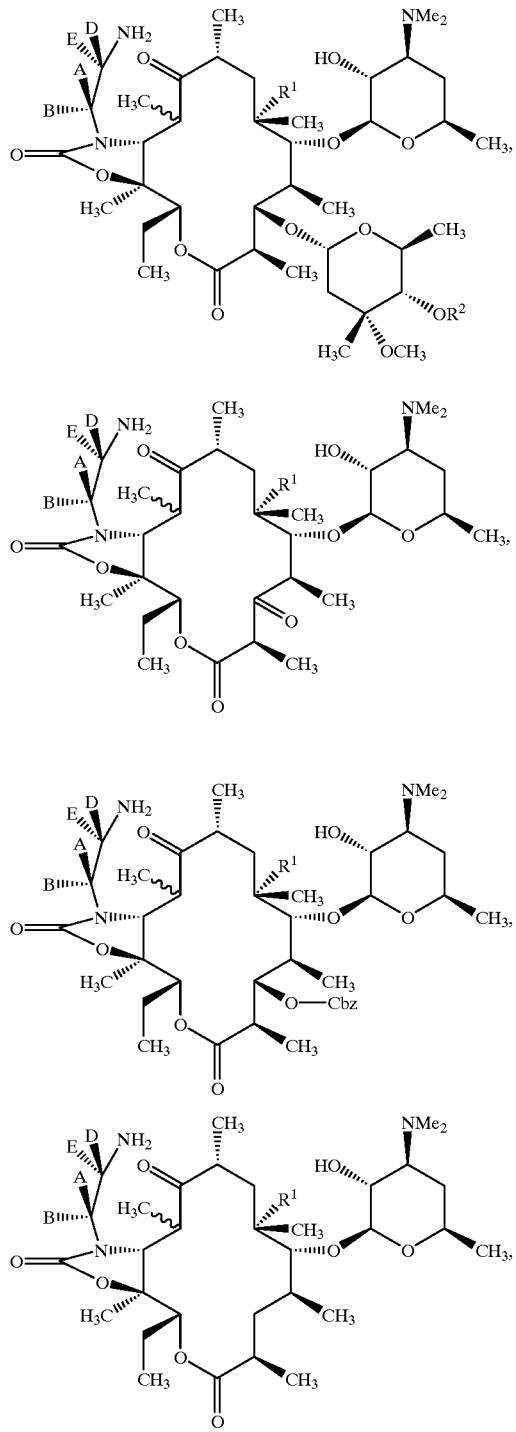

respectively, wherein $R^1$ and $R^2$ are as defined above;

(c) deprotecting said second intermediate compounds by treatment with methanol or ethanol when $OR^2$ is an ester or with fluoride in nIF or acetonitrile when $R^2$ is a trialkylsilyl group, for from 1 to 24 hours, to give the third intermediate compounds:

respectively;

(d) cychzing said third intermediate compounds by treatment with dilute acid for a period of from 4 hours to 10 days to give the desired compounds (I), (II), (III) or (IV) above.

10. A compound of Formula III

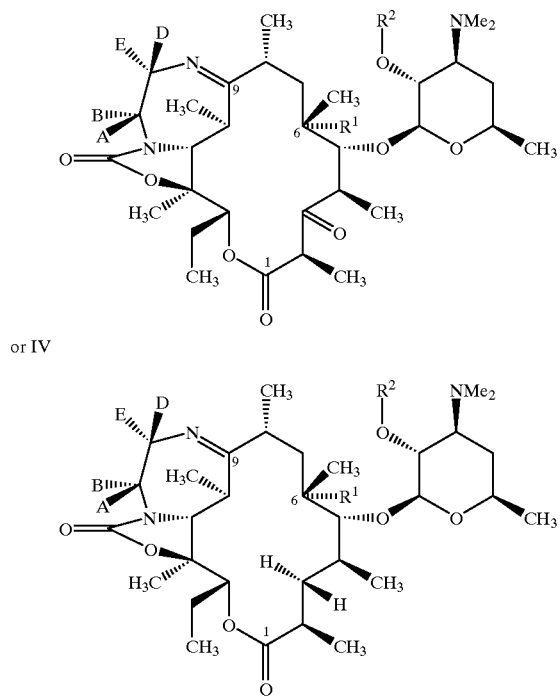

or IV selecting from the group consisting of:
Compound of Formula (IV): $R^1$=methoxy; $R^2$=hydrogen; A=B=D=E=hydrogen;
Compound of Formula (III): A=B=E=H, D=benzyl, $R^1$=methoxy, $R^2$=hydrogen;
Compound of Formula (III): A=B=D=H, E=benzyl, $R^1$=methoxy, $R^2$=hydrogen;
Compound of Formula (III): A=benzyl, B=D=E=H, $R^1$=methoxy, $R^2$=hydrogen;
Compound of Formula (III): B=benzyl, A=D=E=H, $R^1$=methoxy, $R^2$=hydrogen;
Compound of Formula (III): A=E=phenyl, B=D=H, $R^1$=methoxy, $R^2$=hydrogen;
Compound of Formula (III): B=D=H; A and E taken together is —$CH_2CH_2CH_2$—, $R^1$=methoxy, $R^2$=hydrogen;
Compound of Formula (III): B=E=H; A and D taken together is —$CH_2CH_2CH_2CH_2$—, $R^1$=methoxy, $R^2$=hydrogen;
Compound of Formula (III): $R^1$=OCH3, $R^2$=H; A=B=D=H; E=—CH2NH2;
Compound of Formula (III): $R^1$=OCH3, $R^2$=H; A=B=E=H; D=—CH2NH2;
Compound of Formula (III): $R^1$=OCH3, $R^2$=H; B=E=H; A and D taken together is —CH2CH2CH2—;
Compound of Formula (III): $R^1$=OCH3, $R^2$=H; B=E=H; A and D taken together is —CH2OCH2—;
Compound of Formula (III): $R^1$=OCH3, $R^2$=H; B=E=H; A and D taken together is —CH2—NH—CH2—;
Compound of Formula (III): $R^1$=OCH3, $R^2$=H; B=E=H; A and D taken together is —CH2—N(benzyl)-CH2—;
Compound of Formula (III): $R^1$=OCH3, $R^2$=H; B=E=H; A and D taken together is —CH2—N(phenyl-CH2—CH2—)—CH2—;
Compound of Formula (III): $R^1$=OCH3, $R^2$=H; B=E=H; A and D taken together is —CH2—N(4-Cl-phenyl-CH2—)—CH2—;
Compound of Formula (III): $R^1$=OCH3, $R^2$=H; B=E=H; A and D taken together is —CH2—N(4-pyridyl-CH2—)—CH2—;
Compound of Formula (III): $R^1$=OCH3, $R^2$=H; B=E=H; A and D taken together is —CH2—N(2-pyridyl-CH2—)—CH2—;
Compound of Formula (III): $R^1$=OCH3, $R^2$=H; B=E=H; A and D taken together is —CH2—NH(3-pyridyl-CH2—)—CH2—;
Compound of Formula (III): $R^1$=OCH3, $R^2$=H; B=E=H; A and D taken together is —CH2—N(4-quinolyl-CH2—)—CH2—;
Compound of Formula (III): $R^1$=OCH3, $R^2$=H; B=E=H; A=D=—CH2—O—CH2-phenyl;
Compound of Formula (III): $R^1$=OCH3, $R^2$=H; B=E=H; A=D=—CH2—OH;
Compound of Formula (III): $R^1$=OCH3, $R^2$=H; B=E=H; A=D=—CH2—O-phenyl;
Compound of Formula (III): $R^1$=OCH3, $R^2$=H; A=B=H; D and E taken together is —CH2—CH2—CH2—CH2—;
Compound of Formula (III): $R^1$=OCH3, $R^2$=H; A and B taken together is —CH2—CH2—CH2—CH2—; D=E=H;
Compound of Formula (III): $R^1$=OCH3, $R^2$=H; A=B=H; D and E taken together is —CH2—O—CH2—;
Compound of Formula (III): $R^1$=OCH3, $R^2$=H; A=D=E=H; B=—CH2—CH2-phenyl;
Compound of Formula (III): $R^1$=OCH3, $R^2$=H; A=D=E=H; B=—CH2—CH2—CH2-phenyl;
Compound of Formula (III): $R^1$=OCH3, $R^2$=H; A=D=E=H; B=—CH2—O—CH2-phenyl;
Compound of Formula (III): $R^1$=OCH3, $R^2$=H; A=D=E=H; B=—CH2—CH2-(4-$OCH_3$-phenyl);
Compound of Formula (III): $R^1$=OCH3, $R^2$=H; A=—CH2—CH2-phenyl; B=D=E=H;
Compound of Formula (III): $R^1$=OCH3, $R^2$=H; A=—CH2—CH2—CH2-phenyl; B=D=E=H;
Compound of Formula (III): $R^1$=OCH3, $R^2$=H; A=—CH2—O—CH2-phenyl; B=D=E=H;
Compound of Formula (III): $R^1$=OCH3, $R^2$=H; A=D=E=H; B=—CH2—CH2-(4-$OCH_3$-phenyl);
Compound of Formula (III): $R^1$=OCH3, $R^2$=H; A=B=D=H; E=—CH2CH2Ph;
Compound of Formula (III): $R^1$=OCH3, $R^2$=H; A=B=E=H; D=—CH2CH2Ph;
Compound of Formula (III): $R^1$=OCH3, $R^2$=H; A=B=D=H; E=—CH2CH2CH2Ph;
Compound of Formula (III): $R^1$=OCH3, $R^2$=H; A=B=E=H; D=—CH2CH2CH2Ph;
Compound of Formula (III): $R^1$=OCH3, $R^2$=H; A=—CH2CH2OPh; B=D=E=H;
Compound of Formula (III): $R^1$=$OCH_3$, $R^2$=H; A=—CH2CH2NH2; B=D=E=H;
Compound of Formula (III): R1=OCH3, R2=H; A=—CH2CH2NH2; B=D=E=H;
Compound of Formula (III): $R^1$=OCH3, $R^2$=H; A=—CH2CH2OH; B=D=E=H;
Compound of Formula (III): R1=OCH3, R2=H; A=—CH2COOH; B=D=E=H;
Formula (III): R1=OCH3, R2=H; A=—CH2CH2OH; B=D=E=H;

Compound of Formula (III): $R^1$=OCH3, $R^2$=H; A=—CH2CH2NH(4'-Pyridyl-); B=D-E=H;

Compound of Formula (III): $R^1$=OCH3, $R^2$=H; A=B=D=H; E=—CH2OH;

Compound of Formula (III): $R^1$=OCH$_3$, $R^2$=H; A=B=E=H; D=—CH2OH;

Compound of Formula (III): $R^1$=OCH3, $R^2$=H; A=B=E=H; D=—CH2NHBenzoyl;

Compound of Formula (III): $R^1$=OCH3, $R^2$=H; A=B=E=H; D=—CH2NHBenzyl;

Compound of Formula (III): $R^1$=OCH3, $R^2$=H; A=B=D=H; E=—CH2NHBenzoyl;

Compound of Formula (III): $R^1$=OCH3, $R^2$=H; A=B=D=H; E=—CH2NHBenzyl;

Compound of Formula (III): $R^1$=OCH3, $R^2$=H; B=D=H; A=E=—CH2OCH2(4-Cl-phenyl-);

Compound of Formula (III): $R^1$=OCH3, $R^2$=H; A=B=E=H; D=—CH2—N(CH$_3$)-Benzyl;

Compound of Formula (III): $R^1$=OCH3, $R^2$=H; A=B-D=H; E=—CH2—N(CH$_3$)-Benzyl;

Compound of Formula (III): $R^1$=OCH3, $R^2$=H; A=B=D=H; E=—CH2—NH-phenyl;

Compound of Formula (III): $R^1$=OCH3, $R^2$=H; A=B=E=H; D=—CH2—NH-phenyl;

Compound of Formula (III): A=4-ethoxybenzyloxymethyl, B=D=E=H, $R^1$=methoxy, $R^2$=hydrogen;

Compound of Formula (III): A=hydroxymethyl, B=D=E=H, $R^1$=methoxy, $R^2$=hydrogen;

Compound of Formula (III): A=4-benzyloxybenzyl, B=D=E=H, $R^1$=methoxy, $R^2$=hydrogen;

Compound of Formula (III): A=4-hydroxybenzyl, B=D=E=H, $R^1$=methoxy, $R^2$=hydrogen;

Compound of Formula (III): A=S-benzylthioxymethyl, B=D=E=H, $R^1$=methoxy, $R^2$=hydrogen;

Compound of Formula (III): A=3-indolylmethyl, B=D=E=H, $R^1$=methoxy, $R^2$=hydrogen;

Compound of Formula (III): A=4-thiazolylmethyl, B=D=E=H, $R^1$=methoxy, $R^2$=hydrogen;

Compound of Formula (III): A=4-iodobenzyl, B=D=E=H, $R^1$=methoxy, $R^2$=hydrogen;

Compound of Formula (III): A=4-fluorobenzyloxymethyl, B=D=E=H, $R^1$=methoxy, $R^2$=hydrogen;

Compound of Formula (III): A=3-fluorobenzyloxymethyl, B=D=E=H, $R^1$=methoxy, $R^2$=hydrogen;

Compound of Formula (III): A=2-fluorobenzyloxymethyl, B=D=E=H, $R^1$=methoxy, $R^2$=hydrogen;

Compound of Formula (III): A=B=E=H, D=(4-cyanobenzyloxy)methyl, $R^1$=methoxy, $R^2$=hydrogen;

Compound of Formula (III): A=B=E=H, D=(4-(t-butyloxycarbonyl)amino)benzyloxy)methyl, $R^1$=methoxy, $R^2$=hydrogen;

Compound of Formula (III): A=B=E=H, D=(4-(dimethylamino)benzyloxy)methyl, $R^1$=methoxy, $R^2$=hydrogen;

Compound of Formula (III): A=B=E=H, D=(4-pyridyl)methoxymethyl, $R^1$=methoxy, $R^2$=hydrogen;

Compound of Formula (III): A=B=E=H, D=(2-chloro)benzyloxymethyl, $R^1$=methoxy, $R^2$=hydrogen;

Compound of Formula (III): A=B=E=H, D=(4-chloro)benzyloxymethyl, $R^1$=methoxy, $R^2$=hydrogen;

Compound of Formula (III): A=B=E=H, D=(3-chloro)benzyloxymethyl, $R^1$=methoxy, $R^2$=hydrogen;

Compound of Formula (III): A=B=E=H, D=(2-pyridyl)methoxymethyl, $R^1$=methoxy, $R^2$=hydrogen;

Compound of Formula (III): A=B=E=H, D=(3-pyidyl)methoxymethyl, $R^1$=methoxy, $R^2$=hydrogen;

Compound of Formula (III): A=B=E=H, D=(4-methyl-2-quinolyl)methoxymethyl, $R^1$=methoxy, $R^2$=hydrogen;

Compound of Formula (III): A=B=E=H, D=(4-(methoxycarbonyl)benzyl)oxymethyl, $R^1$=methoxy, $R^2$=hydrogen;

Compound of Formula (III): A=B=E=H, D=(4-quinolyl)methoxymethyl, $R^1$=methoxy, $R^2$=hydrogen;

Compound of Formula (III): A=B=D=H, E=(4-pyridyl)methoxymethyl, $R^1$=methoxy, $R^2$=hydrogen;

Compound of Formula (III): A=B=E=H, D=(2-(N-morpholinyl)ethoxy)methyl, $R^1$=methoxy, $R^2$=hydrogen;

Compound of Formula (III): A=B=E=H, D=benzyloxymethyl, $R^1$=methoxy, $R^2$=hydrogen;

Compound of Formula (III): A=B=D=H, E=benzyloxymethyl, $R^1$=methoxy, $R^2$=hydrogen;

Compound of Formula (III): A=B=E=H, D=(4-methoxy)benzyloxymethyl, $R^1$=methoxy, $R^2$=hydrogen;

Compound of Formula (III): A=B=E=H, D=2-phenoxyethyl, $R^1$=methoxy, $R^2$=hydrogen;

Compound of Formula (III): A=B=E=H, D=2-(benzyloxy)ethyl, $R^1$=methoxy, $R^2$=hydrogen;

Compound of Formula (III): A=B=E=H, D=(4-methyl-1-piperazinyl)methyl, $R^1$=methoxy, $R^2$=hydrogen;

Compound of Formula (III): A=B=E=H, D=N-methyl-N-benzylaminomethyl, $R^1$=methoxy, $R^2$=hydrogen;

Compound of Formula (III): A=B=E=H, D=N-morpholinylmethyl, $R^1$=methoxy, $R^2$=hydrogen;

Compound of Formula (III): A=B=E=H, D=(1-piperidinyl)methyl, $R^1$=methoxy, $R^2$=hydrogen;

Compound of Formula (III): A=B=E=H, D=(N,N-dimethyl)aminomethyl, $R^1$=methoxy, $R^2$=hydrogen;

Compound of Formula (II): A=B=E=H, D=hydroxymethyl, $R^1$=methoxy, $R^2$=hydrogen;

Compound of Formula (III): A=B=E=H, D=(methylthioxy)methoxymethyl, $R^1$=methoxy, $R^2$=hydrogen;

Compound of Formula (III): A=B=E=H, D=3,5-dimethoxybenzyloxymethyl, $R^1$=methoxy, $R^2$=hydrogen;

Compound of Formula (III): A=B=E=H, D=4-fluorobenzyloxymethyl, $R^1$=methoxy, $R^2$=hydrogen;

Compound of Fonnula (III): A=B=E=H, D=2-fluorobenzyloxymethyl, $R^1$=methoxy, $R^2$=hydrogen;

Compound of Formula (III): A=B=E=H, D=4-bromobenzyloxymethyl, $R^1$=methoxy, $R^2$=hydrogen;

Compound of Formula (III): A=B=E=H, D=2-bromobenzyloxymethyl, $R^1$=methoxy, $R^2$=hydrogen;

Compound of Formula (III): A=B=E=H, D=3-bromobenzyloxymethyl, $R^1$=methoxy, $R^2$=hydrogen;

Compound of Formula (III): A=D=H; B and E taken together is —CH2CH2CH2CH2—, $R^1$=methoxy, $R^2$=hydrogen;

Compound of Formula (III): A=D=H; B and E taken together is —CH2CH2CH2—, $R^1$=methoxy, $R^2$=hydrogen;

Compound of Formula (III): A=D=H; B and E taken together is —CH2OCH2—, $R^1$=methoxy, $R^2$=hydrogen;

Compound of Formula (III): A=D=H; B and E taken together is —CH2—NH—CH2—, $R^1$=methoxy, $R^2$=hydrogen;

Compound of Formula (III): A=D=H; B and E taken together is —CH2—N(benzyl)-CH2—, $R^1$=methoxy, $R^2$=hydrogen;

Compound of Formula (III): A=D=H; B and E taken together is —CH2—N(phenyl-CH2—CH2—CH2—)—CH2—, $R^1$=methoxy, $R^2$=hydrogen;

Compound of Formula (III): B=E=H; A and D taken together is —CH2—N(phenyl-CH2—CH2—CH2—)—CH2—, $R^1$=methoxy, $R^2$=hydrogen;

Compound of Formula (III): B=E=H; A and D taken together is —CH2—N(phenyl-CH(CH3)—)—CH2—, $R^1$=methoxy, $R^2$=hydrogen;

Compound of Formula (III): B=E=H; A and D taken together is —CH2—N(CH3)—CH2—, $R^1$=methoxy, $R^2$=hydrogen;

Compound of Formula (III): B=E=H; A and D taken together is —CH2—N(CH3CH2—)—CH2—, $R^1$=methoxy, $R^2$=hydrogen;

Compound of Formula (III): B=E=H; A and D taken together is —CH2—N(allyl)-CH2—, $R^1$=methoxy, $R^2$=hydrogen;

Compound of Formula (III): B=E=H; A and D taken together is —CH2—N(propargyl)-CH2—, $R^1$=methoxy, $R^2$=hydrogen;

Compound of Formula (III): B=E=H; A and D taken together is —CH2—N(4-$NO_2$-phenyl-CH2—CH2—)—CH2—, $R^1$=methoxy, $R^2$=hydrogen;

Compound of Formula (III): B=E=H; A and D taken together is —CH2—N(2-$NO_2$-phenyl-CH2—CH2—)—CH2—, $R^1$=methoxy, $R^2$=hydrogen;

Compound of Formula (III): B=E=H; A and D taken together is —CH2—N(3-$NO_2$-phenyl-CH2—CH2—)—CH2—, $R^1$=methoxy, $R^2$=hydrogen;

Compound of Formula (III): B=E=H; A and D taken together is —CH2—N(4-$NH_2$-phenyl-CH2—CH2—)—CH2—, $R^1$=methoxy, $R^2$=hydrogen;

Compound of Formula (III): B=E=H; A and D taken together is —CH2—N(4-NH(acetyl)-phenyl-CH2—CH2—)—CH2—, $R^1$=methoxy, $R^2$=hydrogen;

Compound of Formula (III): B=E=H; A and D taken together is —CH2—N(2-$NO_2$-benzyl-SO2—)—CH2—, $R^1$=methoxy, $R^2$=hydrogen;

Compound of Formula (III): B=E=H; A and D taken together is —CH2—N(CHO)—CH2—, $R^1$=methoxy, $R^2$=hydrogen;

Compound of Formula (III): B=E=H; A and D taken together is —CH2—N(acetyl)-CH2—, $R^1$=methoxy, $R^2$=hydrogen;

Compound of Formula (III): B=E=H; A and D taken together is —CH2—N(2-methoxyethyl)-CH2—, $R^1$-methoxy, $R^2$=hydrogen;

Compound of Formula (III): B=E=H; A and D taken together is —CH2—N(2,2-dimethoxyethyl)-CH2—, $R^1$=methoxy, $R^2$=hydrogen;

Compound of Formula (III): B=E=H; A and D taken together is —CH2—N(2-phenoxyethyl)-CH2—, $R^1$=methoxy, $R^2$=hydrogen;

Compound of Formula (III): B=E=H; A and D taken together is —CH2—N(2-(dimethylamino)ethyl)-CH2—, $R^1$=methoxy, $R^2$=hydrogen;

Compound of Formula (III): B=E=H; A and D taken together is —CH2—N(2-(ethoxycarbonyl)ethyl)-CH2—, $R^1$=methoxy, $R^2$=hydrogen;

Compound of Formula (III): B=D=E=H, A=N-benzylaminomethyl, $R^1$=methoxy, $R^2$=hydrogen;

Compound of Formula (III): B=D=E=H, A=N-benzyl-N-methylaminomethyl, $R^1$=methoxy, $R^2$=hydrogen;

Compound of Formula (III): D=E=H, A=N-benzyl-N-methylaminomethyl, B=phenylthiomethyl, $R^1$=methoxy, $R^2$=hydrogen;

Compound of Formula (III): D=E=H, A=N-benzyl-N-methylaminomethyl, B=methyl, $R^1$=methoxy, $R^2$=hydrogen;

Compound of Formula (III): D=E=H, A=dimethylaminomethyl, B=phenylthiomethyl, $R^1$=methoxy, $R^2$=hydrogen;

Compound of Formula (III): D=E=H, A=dimethylaminomethyl, B=methyl, $R^1$=methoxy, $R^2$=hydrogen;

Compound of Formula (III): B=D=E=H, A=(4-quinolyl)carboxymethyl, $R^1$=methoxy, $R^2$=hydrogen;

Compound of Formula (III): B=D=E=H, A=(4-pyridyl)carboxymethyl, $R^1$=methoxy, $R^2$=hydrogen;

Compound of Formula (III): B=D=E=H, A=benzoyloxymethyl, $R^1$=methoxy, $R^2$=hydrogen;

Compound of Formula (III): B=D=E=H, A=4-chlorobenzoyloxymethyl, $R^1$=methoxy, $R^2$=hydrogen;

Compound of Formula (III): B=D=E=H, A=(2-quinolyl)carboxymethyl, $R^1$=metboxy, $R^2$=hydrogen;

Compound of Formula (III): B=D=E=H, A=(1-methyl-2-indolyl)carboxymethyl, $R^1$=methoxy, $R^2$=hydrogen;

Compound of Formula (III): B=D=E=H, A=(4-indolyl)carboxymethyl, $R^1$=methoxy, $R^2$=hydrogen;

Compound of Formula (III): B=D=H, A=E=benzyloxymethyl, $R^1$=methoxy, $R^2$=hydrogen;

Compound of Formula (III): A=E=H, B=D=(4-chloro)benzyloxymethyl, $R^1$=methoxy, $R^2$=hydrogen; and Compound of Formula (III): B=E=H, A=D=(4-chloro)benzyloxymethyl, $R^1$=methoxy, $R^2$=hydrogen.

11. A method for controlling a bacterial infection in a mammal comprising administering to an animal a therapeutically effective pharmaceutical composition containing a compound according to claim 10.

12. A pharmaceutical composition comprising a therapeutically effective amount of a compound of claim 1 in combination with a pharmaceutically acceptable carrier.

13. A method for controlling a bacterial infection in a mammal comprising administering to an animal a therapeutically-effective pharmaceutical composition containing compound according to claim 1.

14. A pharmaceutical composition comprising a therapeutically effective amount of a compound of claim 2 in combination with a pharmaceutically acceptable carrier.

15. A method for controlling a bacterial infection in a mammal comprising administering to an animal a therapeutically-effective pharmaceutical composition containing a compound according to claim 1.

16. A pharmaceutical composition comprising a therapeutically effective amount of a compound of claim 3 in combination with a pharmaceutically acceptable carrier.

17. A method for controlling a bacterial infection in a mammal comprising administering to an animal a therapeutically-effective pharmaceutical composition containing a compound according to claim 3.

18. A pharmaceutical composition comprising a therapeutically effective amount of a compound of claim 4 in combination with a pharmaceutically acceptable carrier.

19. A method for controlling a bacterial infection in a mammal comprising administering to an animal a therapeutically-effective pharmaceutical composition containing a compound according to claim 4.

20. A pharmaceutical composition comprising a therapeutically effective amount of a compound of claim 5 in combination with a pharmaceutically acceptable carrier.

21. A method for controlling a bacterial infection in a mammal comprising administering to an animal a therapeutically-effective pharmaceutical composition containing a compound according to claim 5.

22. A pharmaceutical composition comprising a therapeutically effective amount of a compound of claim 6 in combination with a pharmaceutically acceptable carrier.

23. A method for controlling a bacterial infection in a mammal comprising administering to an animal a therapeutically-effective pharmaceutical composition containing a compound according to claim 6.

24. A process according to claim 8 wherein:

in step (a) the aprotic solvent is dichloromethane, chloroform, DMF, tetrahydrofuran (THF), N-methyl pyrrolidinone or a mixture thereof, the reaction temperature is from 0° C. to room temperature, and the period of reaction is 1–8 hours;

in step (b) the reaction is run in a solvent aqueous acetonitrile, DMF or aqueous DMF;

in step (c) deprotecting said second intermediate compounds is by treatment with by methanol or ethanol when $OR^2$ is an ester or with fluoride in THF or acetonitrile when $R^2$ is a trialkylsilyl group, for a period from 1 to 24 hours; and in step (d) cyclizing said third intermediate compounds is by treatment with dilute acetic acid or HCl in ethanol or propanol for a period of from 4 hours to 10 days to give the desired compounds.

25. A pharmaceutical composition comprising a therapeutically effective amount of a compound of claim 2 in combination with a pharmaceutically acceptable carrier.

26. A method for controlling a bacterial infection in a mammal comprising administering to an animal a therapeutically effective pharmaceutical composition containing a compound according to claim 2.

27. A pharmaceutical composition comprising a therapeutically effective amount of a compound of claim 10 combination with a pharmaceutically acceptable carrier.

28. The process as in claim 8 wherein:

step (c) is replaced with a two-step sequence which comprises (1) reacting the hydroxy group of the bicyclic second intermediate compounds thereof with an alkyl or aryl sulfonyl chloride, an alkyl or aryl sulfonic anhydride or trifluoromethanesulfonic anhydride in an aprotic solvent at −78° C. to room temperature to give the corresponding sulfonate, and (2) reacting the said sulfonate with lithium azide or sodium azide in an aprotic solvent at 0° C. to 100° C. to give the third intermediate compound.

29. The process as in claim 8 wherein:

in step (a) the base is sodium hydride, lithium hydride, or potassium carbonate, the aprotic solvent is dichloromethane, chloroform, DMF, tetrahydrofuran (THF), N-methyl pyrrolidinone or a mixture thereof, the reaction temperature is from 0° C. to room temperature, and the reaction period is from 1–8 hours;

in step (b) the solvent is aqueous acetonitrile, DMF or aqueous DMF;

in step (c) the reagents are triphenylphosphine and diphenylphosphoryl azide, diethylazodi-carboxylate in tetrahydrofuran, under Mitsunobu reaction conditions;

in step (d) the reducing reagent is triphenylphosphine-water, hydrogen with a catalyst, sodium borohydride, or dialkylaluminum hydride; and in step (e) cyclizing said third intermediate compounds is by treatment with dilute acetic acid or HCl in ethanol or propanol or a period of from 4 hours to 10 days to give the desired compounds.

* * * * *